US012442043B2

(12) United States Patent
Taylor et al.

(10) Patent No.: US 12,442,043 B2
(45) **Date of Patent: *Oct. 14, 2025**

(54) DETECTING OVARIAN CANCER

(71) Applicants: Mayo Foundation for Medical Education and Research, Rochester, MN (US); Exact Sciences Corporation, Madison, WI (US)

(72) Inventors: William R. Taylor, Lake City, MN (US); John B. Kisiel, Rochester, MN (US); Douglas W. Mahoney, Elgin, MN (US); David A. Ahlquist, Rochester, MN (US); Hatim T. Allawi, Middleton, WI (US); Michael W. Kaiser, Stoughton, WI (US)

(73) Assignees: Mayo Foundation for Medical Education and Research, Rochester, MN (US); Exact Sciences Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/327,614

(22) Filed: Jun. 1, 2023

(65) Prior Publication Data

US 2024/0182976 A1 Jun. 6, 2024

Related U.S. Application Data

(63) Continuation of application No. 17/085,542, filed on Oct. 30, 2020, now Pat. No. 11,702,704.

(60) Provisional application No. 62/928,888, filed on Oct. 31, 2019, provisional application No. 63/065,081, filed on Aug. 13, 2020.

(51) Int. Cl.
*C12Q 1/6886* (2018.01)
*C12N 15/117* (2010.01)
*C12Q 1/6869* (2018.01)
*G01N 33/50* (2006.01)

(52) U.S. Cl.
CPC .......... *C12Q 1/6886* (2013.01); *C12N 15/117* (2013.01); *C12Q 1/6869* (2013.01); *G01N 33/50* (2013.01); *C12Q 2521/301* (2013.01); *C12Q 2523/125* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,965,188 | A | 10/1990 | Mullis et al. |
| 5,011,769 | A | 4/1991 | Duck et al. |
| 5,124,246 | A | 6/1992 | Urdea et al. |
| 5,288,609 | A | 2/1994 | Engelhardt et al. |
| 5,338,671 | A | 8/1994 | Scalice et al. |
| 5,403,711 | A | 4/1995 | Walder et al. |
| 5,409,818 | A | 4/1995 | Davey et al. |
| 5,494,810 | A | 2/1996 | Barany et al. |
| 5,508,169 | A | 4/1996 | Deugau et al. |
| 5,624,802 | A | 4/1997 | Urdea et al. |
| 5,639,611 | A | 6/1997 | Wallace et al. |
| 5,660,988 | A | 8/1997 | Duck et al. |
| 5,710,264 | A | 1/1998 | Urdea et al. |
| 5,773,258 | A | 6/1998 | Birch et al. |
| 5,786,146 | A | 7/1998 | Herman et al. |
| 5,792,614 | A | 8/1998 | Western et al. |
| 5,846,717 | A | 12/1998 | Brow et al. |
| 5,849,481 | A | 12/1998 | Urdea et al. |
| 5,851,770 | A | 12/1998 | Babon et al. |
| 5,882,867 | A | 3/1999 | Ullman et al. |
| 5,914,230 | A | 6/1999 | Liu et al. |
| 5,958,692 | A | 9/1999 | Cotton et al. |
| 5,965,408 | A | 10/1999 | Short |
| 5,985,557 | A | 11/1999 | Prudent et al. |
| 5,994,069 | A | 11/1999 | Hall et al. |
| 6,001,567 | A | 12/1999 | Brow et al. |
| 6,013,170 | A | 1/2000 | Meade |
| 6,063,573 | A | 5/2000 | Kayyem |
| 6,090,543 | A | 7/2000 | Prudent et al. |
| 6,110,677 | A | 8/2000 | Western et al. |
| 6,110,684 | A | 8/2000 | Kemper et al. |
| 6,121,001 | A | 9/2000 | Western et al. |
| 6,150,097 | A | 11/2000 | Tyagi et al. |
| 6,183,960 | B1 | 2/2001 | Lizardi |
| 6,210,884 | B1 | 4/2001 | Lizardi |

(Continued)

FOREIGN PATENT DOCUMENTS

| | | |
|---|---|---|
| CN | 109563546 A | 4/2019 |
| EP | 2899275 | 7/2015 |

(Continued)

OTHER PUBLICATIONS

Campan et al. PLoS One. 2011. 6(12):e28141 and Supporting Information. (Year: 2011).*

(Continued)

*Primary Examiner* — Joseph G. Dauner

(74) *Attorney, Agent, or Firm* — Casimir Jones, S.C.; Peter J. Schlueter

(57) ABSTRACT

Provided herein is technology for ovarian cancer screening and particularly, but not exclusively, to methods, compositions, and related uses for detecting the presence of ovarian cancer and sub-types of ovarian cancer (e.g., clear cell ovarian cancer, endometrioid ovarian cancer, mucinous ovarian cancer, serous ovarian cancer).

13 Claims, 24 Drawing Sheets

Specification includes a Sequence Listing.

(56) References Cited

U.S. PATENT DOCUMENTS

| | | | |
|---|---|---|---|
| 6,221,583 B1 | 4/2001 | Kayyem et al. | |
| 6,235,502 B1 | 5/2001 | Weissman et al. | |
| 6,248,229 B1 | 6/2001 | Meade | |
| 6,251,594 B1 | 6/2001 | Gonzalgo et al. | |
| 6,265,171 B1 | 7/2001 | Herman et al. | |
| 6,872,816 B1 | 3/2005 | Hall et al. | |
| 7,037,650 B2 | 5/2006 | Gonzalgo et al. | |
| 7,662,594 B2 | 2/2010 | Kong et al. | |
| 8,361,720 B2 | 1/2013 | Oldham-Haltom et al. | |
| 8,715,937 B2 | 5/2014 | Zou et al. | |
| 8,741,567 B2 | 6/2014 | He et al. | |
| 8,808,990 B2 | 8/2014 | Lidgard et al. | |
| 8,916,344 B2 | 12/2014 | Zou et al. | |
| 9,000,146 B2 | 4/2015 | Bruinsma et al. | |
| 9,096,893 B2 | 8/2015 | Allawi et al. | |
| 9,169,511 B2 | 10/2015 | Bruinsma et al. | |
| 9,212,392 B2 | 12/2015 | Allawi et al. | |
| 9,670,552 B2 | 6/2017 | An et al. | |
| 10,030,272 B2 | 7/2018 | Ahlquist et al. | |
| 10,370,726 B2 | 8/2019 | Ahlquist et al. | |
| 10,927,415 B2 | 2/2021 | Feinberg | |
| 11,702,704 B2 * | 7/2023 | Taylor | G01N 33/57449 435/6.14 |
| 2007/0202525 A1 | 8/2007 | Quake et al. | |
| 2009/0170087 A1 | 7/2009 | Budiman et al. | |
| 2012/0122088 A1 | 5/2012 | Zou et al. | |
| 2012/0122106 A1 | 5/2012 | Zou et al. | |
| 2012/0208180 A1 | 8/2012 | Duerst et al. | |
| 2012/0288868 A1 | 11/2012 | Bruinsma et al. | |
| 2013/0337439 A1 | 12/2013 | Goncalves Pereira Nobre et al. | |
| 2014/0199696 A1 | 7/2014 | Mansour et al. | |
| 2015/0275314 A1 | 10/2015 | Ahlquist et al. | |
| 2016/0010081 A1 | 1/2016 | Allawi et al. | |
| 2016/0017430 A1 | 1/2016 | Badosa | |
| 2016/0040246 A1 | 2/2016 | Ahlquist et al. | |
| 2016/0090634 A1 | 3/2016 | Kisiel et al. | |
| 2016/0194721 A1 | 7/2016 | Allawi et al. | |
| 2017/0121704 A1 | 5/2017 | Allawi et al. | |
| 2017/0314071 A1 | 11/2017 | Ehrich et al. | |
| 2017/0321286 A1 | 11/2017 | Allawi et al. | |
| 2018/0016643 A1 * | 1/2018 | An | C12Q 1/686 |
| 2018/0030547 A1 | 2/2018 | Hofmann et al. | |
| 2019/0161806 A1 | 5/2019 | Ahlquist et al. | |
| 2019/0177769 A1 | 6/2019 | Allawi et al. | |
| 2020/0024643 A1 | 1/2020 | Arensdorf et al. | |
| 2020/0377954 A1 | 12/2020 | Bitenc et al. | |
| 2020/0377956 A1 | 12/2020 | Vogelstein et al. | |
| 2021/0130907 A1 | 5/2021 | Taylor et al. | |
| 2022/0071605 A1 | 3/2022 | Eisele et al. | |
| 2022/0349009 A1 | 11/2022 | Taylor et al. | |

FOREIGN PATENT DOCUMENTS

| | | | |
|---|---|---|---|
| IT | TO20070201 A1 | 10/2007 | |
| JP | 2017514499 A | 6/2017 | |
| TW | 201632629 A * | 9/2016 | C12Q 1/6886 |
| WO | WO 95/00669 | 1/1995 | |
| WO | WO 95/15373 | 6/1995 | |
| WO | WO 97/46705 | 12/1997 | |
| WO | WO 99/28498 | 6/1999 | |
| WO | WO 00/26401 | 5/2000 | |
| WO | WO 05/023091 | 3/2005 | |
| WO | WO 2005/038051 | 4/2005 | |
| WO | WO 2007067695 | 6/2007 | |
| WO | WO-2007067695 A2 * | 6/2007 | A61K 31/7072 |
| WO | WO 2008/084219 | 7/2008 | |
| WO | WO 2009/102788 | 8/2009 | |
| WO | WO 2009/153667 | 12/2009 | |
| WO | WO-2009153667 A2 * | 12/2009 | C12Q 1/6886 |
| WO | WO 2010/089538 | 8/2010 | |
| WO | WO 2011/119934 | 9/2011 | |
| WO | WO 2012/104642 | 8/2012 | |
| WO | WO 2012/106525 | 8/2012 | |
| WO | WO 2012/150276 | 11/2012 | |
| WO | WO 2012/155072 | 11/2012 | |
| WO | WO 2013/070950 | 5/2013 | |
| WO | WO 2013/096661 | 6/2013 | |
| WO | WO 2013/103889 | 7/2013 | |
| WO | WO 2013/116375 | 8/2013 | |
| WO | WO 2013/142545 | 9/2013 | |
| WO | WO 2014/046200 | 3/2014 | |
| WO | WO 2014/159650 | 10/2014 | |
| WO | WO 2014/159652 | 10/2014 | |
| WO | WO 2015/066695 | 5/2015 | |
| WO | WO 2015/095689 | 6/2015 | |
| WO | WO 2015/116837 | 8/2015 | |
| WO | WO 2015/153283 | 10/2015 | |
| WO | WO 2015/153284 | 10/2015 | |
| WO | 2015169947 A1 | 11/2015 | |
| WO | WO 2016/094813 | 6/2016 | |
| WO | WO 2016/094839 | 6/2016 | |
| WO | WO 2016/160454 | 10/2016 | |
| WO | WO 2017/040627 | 3/2017 | |
| WO | WO 2017/075061 | 5/2017 | |
| WO | WO 2017/176630 | 10/2017 | |
| WO | WO 2017/180886 | 10/2017 | |
| WO | WO 2017192221 | 11/2017 | |
| WO | WO-2017192221 A1 * | 11/2017 | C12Q 1/6806 |
| WO | WO 2017/210372 | 12/2017 | |
| WO | WO 2018/017740 | 1/2018 | |
| WO | WO 2018/045322 | 3/2018 | |
| WO | WO 2018/140781 | 8/2018 | |
| WO | WO 2018/160576 | 9/2018 | |
| WO | WO 2019/108626 | 6/2019 | |
| WO | WO 2019/199696 | 10/2019 | |
| WO | WO 2020/089691 | 5/2020 | |
| WO | WO 2020/112869 | 6/2020 | |
| WO | WO 2020/115728 | 6/2020 | |
| WO | WO 2020/118274 | 6/2020 | |
| WO | WO 2020/154665 | 7/2020 | |
| WO | WO 2020/206256 | 10/2020 | |
| WO | WO 2020/227100 | 11/2020 | |
| WO | WO 2020/236939 | 11/2020 | |
| WO | WO 2020/264220 | 12/2020 | |
| WO | WO 2021/041726 | 3/2021 | |
| WO | WO 2021/076969 | 4/2021 | |
| WO | WO 2021/087275 | 5/2021 | |
| WO | WO 2021/212031 | 10/2021 | |
| WO | WO 2021/226071 | 11/2021 | |
| WO | WO 2021/226074 | 11/2021 | |
| WO | WO 2022/039904 | 2/2022 | |
| WO | WO 2022/040306 | 2/2022 | |
| WO | WO 2022/165247 | 8/2022 | |
| WO | WO 2022/187227 | 9/2022 | |
| WO | WO 2022/187695 | 9/2022 | |
| WO | WO 2023/081796 | 5/2023 | |

OTHER PUBLICATIONS

PE2E Search Machine translation of TW 201632629 A (Year: 2024).*

Brait et al. PLoS One. 2012. 7(9):e44951. (Year: 2012).*

Ahlquist et al., Next-generation stool DNA test accurately detects colorectal cancer and large adenomas. Gastroenterology. Feb. 2012; 142(2):248-56; quiz e25-6.

Ahn et al., Identification of novel DNA hypermethylation of the adenylate kinase 5 promoter in colorectal adenocarcinoma. Sci Rep. Jun. 16, 2021;11(1):12626.

Arafa et al., High frequency of RASSF1A and RARb2 gene promoter methylation in morphologically normal endometrium adjacent to endometrioid adenocarcinoma. Histopathology. Nov. 2008;53(5):525-32.

Bakkum-Gamez et al., Detection of endometrial cancer via molecular analysis of DNA collected with vaginal tampons. Gynecol Oncol. Apr. 2015;137(1):14-22.

Bakkum-Gamez et al., Detection of endometrial cancer using tampon-based collection and methylated DNA markers. Gynecol Oncol. Jul. 2023:174:11-20.

Banno et al., Relationship of the aberrant DNA hypermethylation of cancer-related genes with carcinogenesis of endometrial cancer. Oncol Rep. Dec. 2006;16(6):1189-96.

(56) References Cited

OTHER PUBLICATIONS

Bramblet et al., Methylated DNA Markers for Sporadic Colorectal and Endometrial Cancer Are Strongly Associated with Lynch Syndrome Cancers. Cancer Prev Res (Phila). Nov. 1, 2023;16(11):611-620.
Cancer Genome Atlas Research Network et al., Integrated genomic characterization of endometrial carcinoma. Nature. May 2, 2013;497(7447):67-73.
Chang et al., Increased epithelial stem cell traits in advanced endometrial endometrioid carcinoma. BMC Genomics. Dec. 16, 2009;10:613.
Chen et al., Quantitative DNA methylation analysis of selected genes in endometrial carcinogenesis. Taiwan J Obstet Gynecol. Oct. 2015;54(5):572-9.
Chen et al., Methods for identifying differentially methylated regions for sequence- and array-based data. Brief Funct Genomics. Nov. 2016;15(6):485-490.
Chin et al., The significance of atypical glandular cells on routine cervical cytologic testing in a community-based population. Am J Obstet Gynecol. Jun. 2000;182(6):1278-82.
Duffy et al., Methylated genes as new cancer biomarkers. Eur J Cancer. Feb. 2009;45(3):335-46.
Felix et al., Factors associated with Type I and Type II endometrial cancer. Cancer Causes Control. Nov. 2010;21(11):1851-6.
Fiegl et al., Methylated DNA collected by tampons—a new tool to detect endometrial cancer. Cancer Epidemiol Biomarkers Prev. May 2004;13(5):882-8.
Fridley et al., Self-contained gene-set analysis of expression data: an evaluation of existing and novel methods. PLoS One. Sep. 17, 2010;5(9):e12693. 9 pages.
GenBank Accession No. NC_000002.11, Aug. 13, 2013, 3 pages.
Grafstrom et al., The characteristics of DNA methylation in an in vitro DNA synthesizing system from mouse fibroblasts. Nucleic Acids Res. Apr. 25, 1985;13(8):2827-42.
Guida et al., Aberrant DNA hypermethylation of hMLH-1 and CDKN2A/p16 genes in benign, premalignant and malignant endometrial lesions. Eur J Gynaecol Oncol. 2009;30(3):267-70.
Horowitz et al., Microsatellite instability, MLH1 promoter methylation, and loss of mismatch repair in endometrial cancer and concomitant atypical hyperplasia. Gynecol Oncol. Jul. 2002;86(1):62-8.
Huang et al., Integrated Epigenomics Analysis Reveals a DNA Methylation Panel for Endometrial Cancer Detection Using Cervical Scrapings. Clin Cancer Res. Jan. 1, 2017;23(1):263-272.
Huang et al., Promoter hypermethylation of CIDEA, HAAO and RXFP3 associated with microsatellite instability in endometrial carcinomas. Gynecol Oncol. May 2010;117(2):239-47.
Hussein et al., The Genomic Heterogeneity of FIGO Grade 3 Endometrioid Carcinoma Impacts Diagnostic Accuracy and Reproducibility. Int J Gynecol Pathol. Jan. 2016;35(1):16-24.
Ito et al., Tet proteins can convert 5-methylcytosine to 5-formylcytosine and 5-carboxylcytosine. Science. Sep. 2, 2011;333(6047):1300-3.
Kinde et al., Evaluation of DNA from the Papanicolaou test to detect ovarian and endometrial cancers. Sci Transl Med. Jan. 9, 2013;5(167):167ra4. 21 pages.
Kisiel et al., New DNA Methylation Markers for Pancreatic Cancer: Discovery, Tissue Validation, and Pilot Testing in Pancreatic Juice. Clin Cancer Res. Oct. 1, 2015;21(19):4473-81.
Mariani et al., Prospective assessment of lymphatic dissemination in endometrial cancer: a paradigm shift in surgical staging. Gynecol Oncol. Apr. 2008;109(1):11-8.
Matsushita et al, DNA-friendly Cu(ii)/TEMPO-catalyzed 5-hydroxymethylcytosine-specific oxidation. hem Commun (Camb). May 23, 2017;53(42):5756-5759.
Moore et al., Uterine papillary serous carcinoma. Clin Obstet Gynecol. Jun. 2011;54(2):278-91.
Nelson et al., Key epigenetic changes associated with lung cancer development: results from dense methylation array profiling. Epigenetics. Jun. 1, 2012;7(6):559-66.
Okamoto et al., 5-Hydroxymethylcytosine-selective oxidation with peroxotungstate. Chem Commun (Camb). Oct. 28, 2011;47(40):11231-3.
Parkin et al., Global cancer statistics, 2002. CA Cancer J Clin. Mar.-Apr. 2005;55(2):74-108.
Pijnenborg et al., RASSF1A methylation and K-ras and B-raf mutations and recurrent endometrial cancer. Ann Oncol. Mar. 2007;18(3):491-7.
Robertson et al., The presence of 5-hydroxymethylcytosine at the gene promoter and not in the gene body negatively regulates gene expression. Biochem Biophys Res Commun. Jul. 22, 2011;411(1):40-3.
Sasaki et al., Hypermethylation can selectively silence multiple promoters of steroid receptors in cancers. Mol Cell Endocrinol. Apr. 28, 2003;202(1-2):201-7.
Sasaki et al., Progesterone receptor B gene inactivation and CpG hypermethylation in human uterine endometrial cancer. Cancer Res. Jan. 1, 2001;61(1):97-102.
Shi et al., Endogenous PAD4 in Breast Cancer Cells Mediates Cancer Extracellular Chromatin Network Formation and Promotes Lung Metastasis. Mol Cancer Res. May 2020;18(5):735-747.
Siegel et al., Cancer statistics, 2016. CA Cancer J Clin. Jan.-Feb. 2016;66(1):7-30.
Suehiro et al., Aneuploidy predicts outcome in patients with endometrial carcinoma and is related to lack of CDH13 hypermethylation. Clin Cancer Res. Jun. 1, 2008;14(11):3354-61.
Tao et al., DNA methylation in endometrial cancer. Epigenetics. Aug. 16, 2010;5(6):491-8.
Wentzensen et al., Discovery and validation of methylation markers for endometrial cancer. Int J Cancer. Oct. 15, 2014;135(8):1860-8.
Xiong et al., hMLH1 promoter methylation and silencing in primary endometrial cancers are associated with specific alterations in MBDs occupancy and histone modifications. Gynecol Oncol. Oct. 2006;103(1):321-8.
Xiong et al., Epigenetic-mediated upregulation of progesterone receptor B gene in endometrial cancer cell lines. Gynecol Oncol. Oct. 2005;99(1):135-41.
Zhang et al., Comparative DNA methylome analysis of endometrial carcinoma reveals complex and distinct deregulation of cancer promoters and enhancers. BMC Genomics. Oct. 6, 2014;15(1):868.
Zighelboim et al., Differential methylation hybridization array of endometrial cancers reveals two novel cancer-specific methylation markers. Clin Cancer Res. May 15, 2007;13(10):2882-9.
Zou et al., Quantification of methylated markers with a multiplex methylation-specific technology. Clin Chem. Feb. 2012;58(2):375-83.
Supplementary Partial European Search Report for EP 20744597. Dec. 23, 2022. 5 pages.
Supplementary Partial European Search Report for EP 20856304 Oct. 26, 2023. 13 pages.
International Search Report and Written Opinion for PCT/US20/15059. Mailed Jun. 22, 2020. 20 pages.
International Search Report and Written Opinion for PCT/US2022/019010. Mailed Jul. 22, 2022. 28 pages.
International Search Report and Written Opinion for PCT/US2020/058235. Mailed Mar. 22, 2021. 32 pages.
Antequera et al., High levels of de novo methylation and altered chromatin structure at CpG islands in cell lines. Cell. Aug. 10, 1990;62(3):503-14.
Ballabio et al., Screening for steroid sulfatase (STS) gene deletions by multiplex DNA amplification. Hum Genet. May 1990;84(6):571-3.
Baranay. Genetic disease detection and DNA amplification using cloned thermostable ligase. Proc. Natl. Acad. Sci USA 1991. vol. 88, 189-93.
Bustin. Absolute quantification of mRNA using real-time reverse transcription polymerase chain reaction assays. J Mol Endocrinol. Oct. 2000;25(2):169-93.
Chamberlain et al., Deletion screening of the Duchenne muscular dystrophy locus via multiplex DNA amplification. Nucleic Acids Res. Dec. 9, 1988;16(23):11141-56.

(56) References Cited

OTHER PUBLICATIONS

Chamberlin et al., New RNA polymerase from *Escherichia coli* infected with bacteriophage T7. Nature. Oct. 17, 1970;228(5268):227-31.
Don et al., 'Touchdown' PCR to circumvent spurious priming during gene amplification. Nucleic Acids Res. Jul. 25, 1991;19(14):4008.
Dowdy and Wearden, Statistics for Research, John Wiley & Sons, New York, 1983. TOC only. 6 pages.
Eads et al., CpG island hypermethylation in human colorectal tumors is not associated with DNA methyltransferase overexpression. Cancer Res. May 15, 1999;59(10):2302-6.
Egan. Signal Detection Theory and ROC Analysis, Academic Press, New York. 1975. TOC only. 9 pages.
Erlich (ed.), PCR Technology, Stockton Press. 1989. TOC only. 5 pages.
Feil et al., Methylation analysis on individual chromosomes: improved protocol for bisulphite genomic sequencing. Nucleic Acids Res. Feb. 25, 1994;22(4):695-6.
Frommer et al., A genomic sequencing protocol that yields a positive display of 5-methylcytosine residues in individual DNA strands. Proc Natl Acad Sci U S A. Mar. 1, 1992;89(5):1827-31.
Gardiner-Garden et al., CpG islands in vertebrate genomes. J Mol Biol. Jul. 20, 1987;196(2):261-82.
Gonzalgo et al., Rapid quantitation of methylation differences at specific sites using methylation-sensitive single nucleotide primer extension (Ms-SNuPE). Nucleic Acids Res. Jun. 15, 1997;25(12):2529-31.
Gonzalgo et al., Identification and characterization of differentially methylated regions of genomic DNA by methylation-sensitive arbitrarily primed PCR. Cancer Res. Feb. 15, 1997;57(4):594-9.
Grigg et al., Sequencing 5-methylcytosine residues in genomic DNA. Bioessays. Jun. 1994;16(6):431-6.
Grigg. Sequencing 5-methylcytosine residues by the bisulphite method. DNA Seq. 1996;6(4):189-98.
Gu et al., Genome-scale DNA methylation mapping of clinical samples at single-nucleotide resolution. Nat Methods. Feb. 2010;7(2):133-6.
Gu et al., Preparation of reduced representation bisulfite sequencing libraries for genome-scale DNA methylation profiling. Nat Protoc. Apr. 2011;6(4):468-81.
Guilfoyle et al., Ligation-mediated PCR amplification of specific fragments from a class-II restriction endonuclease total digest. Nucleic Acids Res. May 1, 1997;25(9):1854-8.
Hall et al., Sensitive detection of DNA polymorphisms by the serial invasive signal amplification reaction. Proc Natl Acad Sci U S A. Jul. 18, 2000;97(15):8272-7.
Hayden et al., Multiplex-ready PCR: a new method for multiplexed SSR and SNP genotyping. BMC Genomics. Feb. 18, 2008;9:80.
Hecker et al., High and low annealing temperatures increase both specificity and yield in touchdown and stepdown PCR. Biotechniques. Mar. 1996;20(3):478-85.
Herman et al., Methylation-specific PCR: a novel PCR assay for methylation status of CpG islands. Proc Natl Acad Sci U S A. Sep. 3, 1996;93(18):9821-6.
Higuchi et al., A general method of in vitro preparation and specific mutagenesis of DNA fragments: study of protein and DNA interactions. Nucleic Acids Res. Aug. 11, 1988;16(15):7351-67.
Higuchi et al., Kinetic PCR analysis: real-time monitoring of DNA amplification reactions. Biotechnology (N Y). Sep. 1993;11(9):1026-30.
Higuchi et al., Simultaneous amplification and detection of specific DNA sequences. Biotechnology (N Y). Apr. 1992;10(4):413-7.
In re Herz, 537 F.2d 549, 551-52, 190 USPQ 461, 463 (CCPA 1976) 4 pages.
Kacian et al., A replicating RNA molecule suitable for a detailed analysis of extracellular evolution and replication. Proc Natl Acad Sci U S A. Oct. 1972;69(10):3038-42.
Kalinina et al., Nanoliter scale PCR with TaqMan detection. Nucleic Acids Res. May 15, 1997;25(10):1999-2004.
Kawai et al., Comparison of DNA methylation patterns among mouse cell lines by restriction landmark genomic scanning. Mol Cell Biol. Nov. 1994;14(11):7421-7.
Kuppuswamy et al., Single nucleotide primer extension to detect genetic diseases: experimental application to hemophilia B (factor IX) and cystic fibrosis genes. Proc Natl Acad Sci U S A. Feb. 15, 1991;88(4):1143-7.
Laird. Principles and challenges of genomewide DNA methylation analysis. Nat Rev Genet. Mar. 2010;11(3):191-203.
Li et al., MethPrimer: designing primers for methylation PCRs. Bioinformatics. Nov. 2002;18(11):1427-31.
Lyamichev et al., Polymorphism identification and quantitative detection of genomic DNA by invasive cleavage of oligonucleotide probes. Nat Biotechnol. Mar. 1999;17(3):292-6.
Martin et al., Genomic sequencing indicates a correlation between DNA hypomethylation in the 5' region of the pS2 gene and its expression in human breast cancer cell lines. Gene. May 19, 1995;157(1-2):261-4.
Meissner et al., Genome-scale DNA methylation maps of pluripotent and differentiated cells. Nature. Aug. 7, 2008;454(7205):766-70.
Meissner et al., Reduced representation bisulfite sequencing for comparative high-resolution DNA methylation analysis. Nucleic Acids Res. Oct. 13, 2005;33(18):5868-77.
Nyce et al., Variable effects of DNA-synthesis inhibitors upon DNA methylation in mammalian cells. Nucleic Acids Res. May 27, 1986;14(10):4353-67.
Olek et al., A modified and improved method for bisulphite based cytosine methylation analysis. Nucleic Acids Res. Dec. 15, 1996;24(24):5064-6.
Olek et al., The pre-implantation ontogeny of the H19 methylation imprint. Nat Genet. Nov. 1997;17(3):275-6.
Ozols et al., Epithelial ovarian cancer. Principles and Practice of Gynecologic Oncology. Lippincott Williams & Wilkins; Philadelphia, PA, USA: 2000. pp. 981-1057.
Ramsahoye et al., Non-CpG methylation is prevalent in embryonic stem cells and may be mediated by DNA methyltransferase 3a. Proc Natl Acad Sci U S A. May 9, 2000;97(10):5237-42.
Rein et al., Identifying 5-methylcytosine and related modifications in DNA genomes. Nucleic Acids Res. May 15, 1998;26(10):2255-64.
Roux. Using mismatched primer-template pairs in touchdown PCR. Biotechniques. May 1994;16(5):812-4.
Sadri et al., Rapid analysis of DNA methylation using new restriction enzyme sites created by bisulfite modification. Nucleic Acids Res. Dec. 15, 1996;24(24):5058-9.
Salomon et al., Methylation of mouse DNA in vivo: di- and tripyrimidine sequences containing 5-methylcytosine. Biochim Biophys Acta. Apr. 15, 1970;204(2):340-51.
Schouten et al., Relative quantification of 40 nucleic acid sequences by multiplex ligation-dependent probe amplification. Nucleic Acids Res. Jun. 15, 2002;30(12):e57. 13 pages.
Singer-Sam et al., A quantitative Hpall-PCR assay to measure methylation of DNA from a small number of cells. Nucleic Acids Res. Feb. 11, 1990;18(3):687.
Singer-Sam et al., A sensitive, quantitative assay for measurement of allele-specific transcripts differing by a single nucleotide. PCR Methods Appl. Feb. 1992;1(3):160-3.
Szabo et al., Allele-specific expression and total expression levels of imprinted genes during early mouse development: implications for imprinting mechanisms. Genes Dev. Dec. 15, 1995;9(24):3097-108.
Toyota et al., Identification of differentially methylated sequences in colorectal cancer by methylated CpG island amplification. Cancer Res. May 15, 1999;59(10):2307-12.
Triglia et al., A procedure for in vitro amplification of DNA segments that lie outside the boundaries of known sequences. Nucleic Acids Res. Aug. 25, 1988;16(16):8186.
Vogelstein et al., Digital PCR. Proc Natl Acad Sci U S A. Aug. 3, 1999;96(16):9236-41.
Woodcock et al., The majority of methylated deoxycytidines in human DNA are not in the CpG dinucleotide. Biochem Biophys Res Commun. Jun. 15, 1987;145(2):888-94.

(56) References Cited

OTHER PUBLICATIONS

Wu et al., The ligation amplification reaction (LAR)—amplification of specific DNA sequences using sequential rounds of template-dependent ligation. Genomics. May 1989;4(4):560-9.
Xiong et al., COBRA: a sensitive and quantitative DNA methylation assay. Nucleic Acids Res. Jun. 15, 1997;25(12):2532-4.
Zeschnigk et al., Imprinted segments in the human genome: different DNA methylation patterns in the Prader-Willi/Angelman syndrome region as determined by the genomic sequencing method. Hum Mol Genet. Mar. 1997;6(3):387-95.
Zhang et al., DNA methylation analysis of chromosome 21 gene promoters at single base pair and single allele resolution. PLoS Genet. Mar. 2009;5(3):e1000438. 15 pages.
Zou et al, Highly methylated genes in colorectal neoplasia: implications for screening. Cancer Epidemiol Biomarkers Prev. Dec. 2007;16(12):2686-96.
Zou et al., Sensitive quantification of methylated markers with a novel methylation specific technology. Clin Chem 2010. 56: A199 abstract D-144. 1 page.
Calin et al. Blood. 2009. 114(23): 4761-4770.
Li et al. Chemico-Biological Interactions. 2022. 361: 109967, 14 pages.
Talukdar et al. Cancer Res. 2021. 81:2612-2624.
Earp et al. Genomics. 2015. 106: 311-321.
He et al. Scientific Reports. 2016. 6: 24706, 11 pages.
Marinelli et al. Gynecologic Oncology. 2022. 165: 568-576.
Sundararajan et al. Scientific Reports. 2019. 9: 8295, 9 pages.
Bakkum-Gamez et al. Journal of Clinical Oncology. 2020. 28 (15 suppl): 6072-6072.
Liu et al., Bisulfite-free direct detection of 5-methylcytosine and 5-hydroxymethylcytosine at base resolution. Nat Biotechnol. Apr. 2019;37(4):424-429.
Wu et al., Analysis of methylation profiling data of hyperplasia and primary and metastatic endometrial cancers. Eur J Obstet Gynecol Reprod Biol. Oct. 2017:217:161-166.
International Search Report and Written Opinion for PCT/US2023/031831, mailed Jan. 30, 2024, 16 pages.
Extended European Search Report for European Application No. 20744597.4, mailed Apr. 17, 2023, 09 Pages.
Extended European Search Report for European Application No. 20881481.4, mailed Nov. 3, 2023, 12 Pages.
Farkas S.A., et al., "Genome-wide DNA Methylation Assay Reveals Novel Candidate Biomarker Genes in Cervical Cancer", Epigenetics, vol. 8, No. 11, Nov. 1, 2013, pp. 1213-1225, XP055203588, ISSN: 1559-2294, DOI: 10.4161/epi.26346, abstract, p. 1222, right-hand column, paragraph 3, figures 1,3.
Gasperov N.M., et al., "Methylated Host Cell Gene Promoters and Human Papillomavirus Type 16 and 18 Predicting Cervical Lesions and Cancer", PLoS One, vol. 10, No. 6, Jun. 9, 2015, e0129452, pp. 1-14, XP055401782, DOI: 10.1371/journal.pone.0129452, abstract, p. 10, paragraph 3-paragraph 4.
Lai H-C., et al., "Identification of Novel DNA Methylation Markers in Cervical Cancer", International Journal of Cancer, John Wiley & Sons, Inc, US, vol. 123, No. 1, Apr. 8, 2008, pp. 161-167, XP071285244, ISSN: 0020-7136, DOI: 10.1002/IJC.23519, abstract, p. 162, left-hand column, last paragraph-right-hand column, paragraph 1.
Supplementary Partial European Search Report in European Patent Application No. 22764185.9, dated Dec. 23, 2024, 15 Pages.
Vasiljevic N., et al., "Credentialing of DNA Methylation Assays for Human Genes As Diagnostic Biomarkers of Cervical Intraepithelial Neoplasia in High-risk HPV Positive Women", Gynecologic Oncology, vol. 132, No. 3, Feb. 6, 2014, pp. 709-714, XP028633070, ISSN: 0090-8258, DOI: 10.1016/J.YGYNO.2014.02.001, abstract p. 710, left-hand column, paragraph 1-right-hand column, paragraph 3.
Wang R., et al., "Genome-wide Methylome Analysis Using MethylCap-seq Uncovers 4 Hypermethylated Markers with High Sensitivity for Both Adeno- and Squamous-cell Cervical Carcinoma", Oncotarget, vol. 7, No. 49, Dec. 6, 2016, pp. 80735-80750, XP055462413, DOI: 10.18632/oncotarget.12598, abstract, p. 80745, left-hand column, paragraph 1-p. 80746, left-hand column, paragraph 1.
Yang H-J., et al., "Differential DNA Methylation Profiles in Gynecological Cancers and Correlation with Clinico-pathological Data", BMC Cancer, Biomed Central, London, GB, vol. 6, No. 1, Aug. 23, 2006, 212, pp. 1-10, XP021016209, ISSN: 1471-2407, DOI: 10.1186/1471-2407-6-212, abstract, p. 3, left-hand column, last paragraph.
Supplementary European Search Report for European Application No. 22764185.9, dated Apr. 23, 2025, 18 Pages.

* cited by examiner

FIG. 1

AGRN_8794
>hg19_dna range=chr1:968670-968849 5'pad=0 3'pad=10 strand=+
repeatMasking=none WT
GCGCCGCACCTGGGGCCCTCCCCCACCTACGCCCCGCCAGGGCGGGGCCGCGGGCGCAGACACTCGCGGGCACAC
GCACGACGACGCGCACACGCGGTCGCACGCGGCCCCCCGAGCCCCCTGCGGCGACTCCGATTCACCCCCGCGGGT
GCGGGGCGCGGACCCGCCCGGCCCAGCTCC (SEQ ID NO:284)

BST

GCGTCGTATTTGGGGTTTTTTTTATTTACGTTTCGTTAGGGCGGGGTCGCGGGCGTAGATATTCGCGGGTATAC

GTACGACGACGCGTATACGCGGTCGTACGCGGTTTTTCGAGTTTTTTGCGGCGATTTCGATTTATTTTCGCGGGT

GCGGGGCGCGGATTCGTTCGGTTTAGTTTT (SEQ ID NO:285)

AGRN_8794_FP GCGGTTTTTCGAGTTTTTTGCG (SEQ ID NO:137)

AGRN_8794_RP GAACGAATCCGCGCC (SEQ ID NO:138)

AGRN_8794_Pb_A5 AGGCCACGGACG GGCGATTTCGATTTATTTTCG/3C6/ (SEQ ID NO:235)

---

BCAT1_6015

>hg19_dna range=chr12:25055940-25056138 5'pad=0 3'pad=10 strand=+
repeatMasking=none WT
GCGGGGCTGCAGAGAGCGGCAGTGGCACGGAGCGCGCGGCTGGAAGCGAAAGCAGGCGGTGTGGCCAAGCCCCGG
CGCACGGCCCATAGGGCGCTGGGTACCACGACCTGGGGCCGCGCGCCAGGGCCAGGCGCAGGGTACGACGCAACC
CCTCCAGCATCCCTTGGGGAGGAGCCTCCAACCGTCTCGTCCCAGTCTG (SEQ ID NO:286)

BST
GCGGGGTTGTAGAGAGCGGTAGTGGTACGGAGCGCGCGGTTGGAAGCGAAAGTAGGCGGTGTGGTTAAGTTTCGG

CGTACGGTTTATAGGGCGTTGGGTATTACGATTTGGGGTCGCGCGTTAGGGTTAGGCGTAGGGTACGACGTAATT

TTTTTAGTATTTTTTGGGGAGGAGTTTTTAATCGTTTCGTTTTAGTTTG (SEQ ID NO:287)

BCAT1_6015_FP GCGGTGTGGTTAAGTTTCGG (SEQ ID NO:139)

BCAT1_6015_RP CGCGACCCCAAATCGTA (SEQ ID NO:140)

BCAT1_6015_Pb_A1 CGCGCCGAGG GCGTACGGTTTATAGGGC/3C6/ (SEQ ID NO:236)

---

BHLHE23_8339

>hg19_dna range=chr20:61638294-61638506 5'pad=0 3'pad=0 strand=+
repeatMasking=none WT
GCGACGCGCAGGGGGCGGGCTCTACCTCCCCCTCGCCCCCGCTTCGGTTTTAAGCCGCGGAGGCGCCCGGTGGGA
CCTCGCTGCTGTCCAATCAGGGGGGACCGGGTGAGCTCCTCTTCCTGGAGCCGGGCTCCACCAGCGCCGCAGGCT
CACAGGCCGGGGGTGGGGGCTCTGGACCGAGGGGCGGCGCGGGGCGGCGCGGGGCGGCGCGCG (SEQ ID
NO:288)

FIG. 1 (CONT'D)

GCGACGCGTAGGGGGCGGGTTTTATTTTTTTTTCGTTTTCGTTTCGGTTTTAAGTCGCGGAGGCGTTCGGTGGGATTTCGTTGTTGTTTAATTAGGGGGGATCGGGTGAGTTTTTTTTTTGGAGTCGGGTTTTATTAGCGTCGTAGGTTTATAGGTCGGGGGTGGGGGTTTTGGATCGAGGGGCGGCGCGGGGCGGCGCGGGGCGGCGCGCG (SEQ ID NO:289)

BHLHE23_8339_FP CGGGTTTTATTTTTTTTTCGTTTTCGTTTC (SEQ ID NO:141)

BHLHE23_8339_RP AACGAAATCCCACCGAACG (SEQ ID NO:142)

BHLHE23_8339_Pb_A1 CGCGCCGAGG CGGTTTTAAGTCGCGGA/3C6/ (SEQ ID NO:237)

ELMO1_9100

>hg19_dna range=chr7:37488054-37488165 5'pad=10 3'pad=2 strand=+ repeatMasking=none

WT

AACTGCAGAGCGCCCCGACGCGCCCGCAGCCCTCACCCTGCCGAGCGCGGCGGCCACCCCCGCCCGAGCCGCGGCGCCCCCAGGGAGGAAACAAAAGTGTCTCCGCGGCGCC (SEQ ID NO:290)

BST

AATTGTAGAGCGTTTCGACGCGTTCGTAGTTTTTATTTTGTCGAGCGCGGCGGTTATTTTCGTTCGAGTCGCGGCGTTTTTAGGGAGGAAATAAAAGTGTTTTCGCGGCGTT (SEQ ID NO:291)

ELMO1_9100_FP GTAGAGCGTTTCGACGCG (SEQ ID NO:143)

ELMO1_9100_RP TCGAACGAAAATAACCGCCG (SEQ ID NO:144)

ELMO1_9100_Pb_A5 AGGCCACGGACG GCGCTCGACAAAATAAAAAC/3C6/ (SEQ ID NO:238)

---

EPS8L2

>hg19_dna range=chr11:726397-726519 5'pad=10 3'pad=3 strand=- repeatMasking=none

WT

GCCCGGGCCCCAGCTCATCCCCCGCCCCCGCTCACCGCGGGCTGAAGGCCTTGGCTTCCAGCCAGGCGCGGACCTCGTCCGGACCCGACTCGTAGGTGAGCGGCTGGCTCACGGGCTGGCTGC (SEQ ID NO:292)

BST

GTTCGGGTTTTAGTTTATTTTTCGTTTTCGTTTATCGCGGGTTGAAGGTTTTGGTTTTTAGTTAGGCGCGGATTTCGTTCGGATTCGATTCGTAGGTGAGCGGTTGGTTTACGGGTTGGTTGT (SEQ ID NO:293)

---

FIG. 1 (CONT'D)

EPS8L2_FP GTTTTTAGTTAGGCGCGGATTTC (SEQ ID NO:145)

EPS8L2_RP AACCCGTAAACCAACCGC (SEQ ID NO:146)

EPS8L2_Pb_A1 CGCGCCGAGG CGTTCGGATTCGATTCGT/3C6/ (SEQ ID NO:239)

---

JAM3

>hg19_dna range=chr11:133938908-133939011 5'pad=0 3'pad=0 strand=- repeatMasking=none

WT

GAGCCGGAGTCGCGGTGGCCGCCTCAGCGCCATGTCGAGGGTTGCTGAGGGGCCAGCGGCAGCGCGGCGCGGCTTGTAGTCCCCGCGCGCATGCGCCCAGCCTG (SEQ ID NO:294)

BST

Existing design

GAGTCGGAGTCGCGGTGGTCGTTTTAGCGTTATGTCGAGGGTTGTTGAGGGGTTAGCGGTAGCGCGGCGCGGTTTGTAGTTTTCGCGCGTATGCGTTTAGTTTG (SEQ ID NO:295)

JAM3_FP TGGTCGTTTTAGCGTTATGTCG (SEQ ID NO:147)

JAM3_RP CGAAAACTACAAACCGCGC (SEQ ID NO:148)

JAM3_Pb_A5_LQ AGGCCACGGACG CCGCGCTACCGCTA/3C6/ (SEQ ID NO:240)

KCNA3_7320

>hg19_dna range=chr1:111217250-111217357 5'pad=10 3'pad=6 strand=+ repeatMasking=none

WT

AGGTGGTCCCCGGGCACCACGGTCATGTCGGGCGGCAGCTCGCGGCCTGCGGCGGGCTCCGCGTAGCCGTGGTTCACCAGCGTGTGGGCACCGCCGCTGCTCGCTGGG (SEQ ID NO:296)

BST

AGGTGGTTTTCGGGTATTACGGTTATGTCGGGCGGTAGTTCGCGGTTTGCGGCGGGTTTCGCGTAGTCGTGGTTTATTAGCGTGTGGGTATCGTCGTTGTTCGTTGGG (SEQ ID NO:297)

KCNA3_7320_FP CGGTTATGTCGGGCGG (SEQ ID NO:149)

KCNA3_7320_RP CAACGACGATACCCACACG (SEQ ID NO:150)

KCNA3_7320_Pb_A1 CGCGCCGAGG GCTAATAAACCACGACTACG/3C6/ (SEQ ID NO:241)

---

KCNA3_7518 Chr1:111217487-111217673

>hg19_dna range=chr1:111217481-111217679 5'pad=6 3'pad=6 strand=+ repeatMasking=none

WT

CTCCCCGCCCTTTCGCCGCCTCCGCCCCCGAGCCGAGCCCACCGCCTGTTGCAGCCAAAGCCGCGATGCTCTGTCTGGGTCTGGCGCGGTCAGCCGGGCTCCCGCACGGGGACGCCTCCTCCCTCCTTCTCGCGCTCTCCGCCCCCTCCCCTGCGGGGCGCGCGCCCGCCTCCGCGTCCCCTTAGGATTCCCGCCCACC (SEQ ID NO:298)

FIG. 1 (CONT'D)

BST

TTTTTCGTTTTTTCGTCGTTTTCGTTTTCGAGTCGAGTTTATCGTTTGTTGTAGTTAAAGTCGCGATGTTTTGTT
TGGGTTTGGCGCGGTTAGTCGGGTTTTCGTACGGGGACGTTTTTTTTTTTTTTTCGCGTTTTTCGTTTTTTTTT
TTGCGGGGCGCGCGTTCGTTTTCGCGTTTTTTTAGGATTTTCGTTTATT (SEQ ID NO:299)

KCNA3_7518_FP TCGTTTTTTCGTCGTTTTCGTTTTC (SEQ ID NO:151)
KCNA3_7518_RP CCCGTACGAAAACCCGA (SEQ ID NO:152)
KCNA3_7518_Pb_A5 AGGCCACGGACG CGAGTCGAGTTTATCGTTTG/3C6/ (SEQ ID NO:242)

---

MDFI_6321

>hg19_dna range=chr6:41606064-41606357 5'pad=10 3'pad=6 strand=-
repeatMasking=none

WT

GATCCCCGCGCGGGGCCCGCCATGCGCGCCTGCTCCGGGCGCCCCTGCCCAGGTCCCGCTGGCTCCCGGGTGCTC
GCCTGGCGCCCCTTCCCCTCTCACTCGCTGCTTTCTCCCATTTCGGCGCCAGCTCACGCCGTTCGCCCCTTCCTT
CTTCCTTCTCTCCCTCCAGCCCCCCTCGCTCCTCCCCTACTCGCCTCTCCCCTCCCCTCTTCCCTGGCCCACCCT
CTCCCCGCCCCCTCCTCGCCTTCTCAGTCGCCCCTCTGCGGGTCCCCTCCCCCGCGCCGGGCTTGGCCC (SEQ
ID NO:300)

BST

GATTTTCGCGCGGGGTTCGTTATGCGCGTTTGTTTCGGGCGTTTTTGTTTAGGTTTCGTTGGTTTTCGGGTGTTC
GTTTGGCGTTTTTTTTTTTTTTTATTCGTTGTTTTTTTTTATTTCGGCGTTAGTTTACGTCGTTCGTTTTTTTTTT
TTTTTTTTTTTTTTTTAGTTTTTTTCGTTTTTTTTTTATTCGTTTTTTTTTTTTTTTTTTTTTTTGGTTTATTTT
TTTTTCGTTTTTTTTTCGTTTTTTTAGTCGTTTTTTTGCGGGTTTTTTTTTCGCGTCGGGTTTGGTTT (SEQ
ID NO:301)

MDFI_6321_BST plasmid sequence

GATTTTCGCGCGGGGTTCGTTATGCGCGTTTGTTTCGGGCGTTTTTGTTTAGGTTTCGTTGGTTTTCGGGTGTTC
GTTTGGCGTTTTTTTTTTTTTTTATTCGTTGTTTTTTTTTATTTCGGCGTTAGTTTACGTCGTTCGTTTTTTTTTT
TTTTTTTTTTTTTTTTAG (SEQ ID NO:302)

MDFI_6321_FP GTTCGTTATGCGCGTTTGTTTC (SEQ ID NO:153)
MDFI_6321_RP GAACACCCGAAAACCAACGA (SEQ ID NO:154)
MDFI_6321_Pb_A1 CGCGCCGAGG CGGGCGTTTTTGTTTAGG/3C6/ (SEQ ID NO:243)

---

RASSF1_8293 chr3:50378182-50378372

>hg19_dna range=chr3:50378172-50378382 5'pad=10 3'pad=10 strand=-
repeatMasking=none

FIG. 1 (CONT'D)

WT
TTTCCATTGCGCGGCTCTCCTCAGCTCCTTCCCGCCGCCCAGTCTGGATCCTGGGGGAGGCGCTGAAGTCGGGGC
CCGCCCTGTGGCCCCGCCCGGCCCGCGCTTGCTAGCGCCCAAAGCCAGCGAAGCACGGGCCCAACCGGGCCATGT
CGGGGGAGCCTGAGCTCATTGAGCTGCGGGAGCTGGCACCCGCTGGGCGCGCTGGGAAGGG (SEQ ID NO:303)

BST
TTTTTATTGCGCGGTTTTTTTTAGTTTTTTTTCGTCGTTTAGTTTGGATTTTGGGGGAGGCGTTGAAGTCGGGGT
TCGTTTTGTGGTTTCGTTCGGTTCGCGTTTGTTAGCGTTTAAAGTTAGCGAAGTACGGGTTTAATCGGGTTATGT
CGGGGGAGTTTGAGTTTATTGAGTTGCGGGAGTTGGTATTCGTTGGGCGCGTTGGGAAGGG (SEQ ID NO:304)

RASSF1_8293_FP GTTTTGTGGTTTCGTTCGGTTC (SEQ ID NO:155)
RASSF1_8293_RP CCGATTAAACCCGTACTTCGC (SEQ ID NO:156)
RASSF1_8293_Pb_A5 AGGCCACGGACG CGCGTTTGTTAGCGTTTAAA/3C6/ (SEQ ID NO:244)

---

SFMBT2_2363 chr10:7451790-7452428
>hg19_dna range=chr10:7451780-7452430 5'pad=10 3'pad=2 strand=- repeatMasking=none WT
GCCGCCCACCTTCCTCGTTTCTGCACTCATTTTAGCGACGCAGCCGCCGCTGCTACCTACCCCGCGCTCCCGCGT
CTCCTCCGCGCTGGGGTCTCCCCTTTCTTTTGGTTTGGGTGGGAGAAAAAGATGGTGAGGACGGGGAATCGGAGA
CCGGCATGGGGGTAAAAATCGTGCAGACATTCGGAATCGCTCCCTTGGAAACATTTGCCTGAGCAACTGAAATAA
AATTGGCAGTAGTAGTTTTGGAGCGTGCTCCAGCGAGGATGGTCTTTTTGTTCATTATTTTCTCTTTAAAGTAAT
ATCCTGTCACTTAGGGGCTTTCCGGTTGTCTCCTCTTATTCGACCCCCTTTCAAAATTGCTGACTTGAGCTGGTT
CTGGAGTTTATTTTTTAATATGCGTGCGTGGGTATGTGTATGTGTGTGTATGTTTTGCAGAAATCCGCCAAAATG
CAACTGTAGGAACTGCGAGATGTATTTATTGATTTTGACCAGGGGCGGTGGGAAGGGGCTGGAGGGAGCTGGGGG
ATCCTGGAGGGTGGGAAGTGGCTGATTCTCGGTGGCCGGACACTCATCCAGAGCCTGATCCGTACTCGTGTTTTC
TTGGAAGCGCCACAACTGCGGGGAAGGAGTCTTTAGAAACCGTGCCAGTTT (SEQ ID NO:305)

BST
GTCGTTTATTTTTTTCGTTTTTGTATTTATTTTAGCGACGTAGTCGTCGTTGTTATTTATTTCGCGTTTTCGCGT
TTTTTTCGCGTTGGGGTTTTTTTTTTTTTTTGGTTTGGGTGGGAGAAAAAGATGGTGAGGACGGGGAATCGGAGA
TCGGTATGGGGGTAAAAATCGTGTAGATATTCGGAATCGTTTTTTTGGAAATATTTGTTTGAGTAATTGAAATAA
AATTGGTAGTAGTAGTTTTGGAGCGTGTTTTAGCGAGGATGGTTTTTTTGTTTATTATTTTTTTTTAAAGTAAT
ATTTTGTTATTTAGGGGTTTTTCGGTTGTTTTTTTTTATTCGATTTTTTTTTAAAATTGTTGATTTGAGTTGGTT
TTGGAGTTTATTTTTTAATATGCGTGCGTGGGTATGTGTATGTGTGTGTATGTTTTGTAGAAATTCGTTAAAATG
TAATTGTAGGAATTGCGAGATGTATTTATTGATTTTGATTAGGGGCGGTGGGAAGGGGTTGGAGGGAGTTGGGGG
ATTTTGGAGGGTGGGAAGTGGTTGATTTTCGGTGGTCGGATATTTATTTAGAGTTTGATTCGTATTCGTGTTTTT
TTGGAAGCGTTATAATTGCGGGGAAGGAGTTTTTAGAAATCGTGTTAGTTT (SEQ ID NO:306)

FIG. 1 (CONT'D)

SFMBT2_2363_BST plasmid sequence

GTCGTTTATTTTTTTCGTTTTTGTATTTATTTTAGCGACGTAGTCGTCGTTGTTATTTATTTCGCGTTTTCGCGTTTTTTTCGCGTTGGGGTTT (SEQ ID NO:307)

SFMBT2_1839_BST plasmid sequence

GAAGTGGCTGATTCTCGGTGGCCGGACACTCATCCAGAGCCTGATCCGTACTCGTGTTTTCTTGGAAGCGCCACAACTGCGGGGAAGGAGTCTTTAGAAACCGTGCCAGTTT (SEQ ID NO:308)

SFMBT2_2363_FP TTTCGTTTTTGTATTTATTTTAGCGACGT (SEQ ID NO:157)

SFMBT2_2363_RP ACGCGAAAAAAACGCGAAAACG (SEQ ID NO:158)

SFMBT2_2363_Pb_A1 CGCGCCGAGG GCGAAATAAATAACAACGACGA/3C6/ (SEQ ID NO:245)

SFMBT2_1839_FP CTGATTCTCGGTGGCCG (SEQ ID NO:309)

SFMBT2_1839_RP GGCGCTTCCAAGAAAACACG (SEQ ID NO:310)

SFMBT2_1839_Pb_A5 AGGCCACGGACG CGAGTACGGATCAGGCT/3C6/ (SEQ ID NO:311)

---

SKI_2465 Chr1:2222218-2222508

>hg19_dna range=chr1:2222208-2222518 5'pad=10 3'pad=10 strand=+ repeatMasking=none

WT

CCTGTAAAGCCGGGGATGGCAGGACGCATTGTCACCCCCTCCTGCCGCTCTTACGAAACACTCTTAATTGAGTCCGATTCTTGGTGAATCAGCCTTCCAAGAACCGCGACCGCAGCATCCTGTGCCGCTTCTGTGTTCCGCATTTTTCTCTTTCTGCAGCGTTTCCTCTCATTCTGGATGGAAAGGCCTGTTTGTCTCCCTCAATCTTTGGCGAGGGTGGCAGGCAGCCAGGCGGCCATTACGGGCCGCGCCTCCCACCAGCCAGTCGCTGGCAGGAGCGTCCGGGGAGGGAGCAGACCCCGTTCACCCTC (SEQ ID NO:312)

BST

TTTGTAAAGTCGGGGATGGTAGGACGTATTGTTATTTTTTTTGTCGTTTTTACGAAATATTTTTAATTGAGTTCGATTTTTGGTGAATTAGTTTTTTAAGAATCGCGATCGTAGTATTTTGTGTCGTTTTTGTGTTTCGTATTTTTTTTTTTTGTAGCGTTTTTTTTTATTTTGGATGGAAAGGTTTGTTTGTTTTTTTTAATTTTTGGCGAGGGTGGTAGGTAGTTAGGCGGTTATTACGGGTCGCGTTTTTTATTAGTTAGTCGTTGGTAGGAGCGTTCGGGGAGGGAGTAGATTTCGTTTATTTTT (SEQ ID NO:313)

SKI_2465_BST plasmid sequence

GTAGGTAGTTAGGCGGTTATTACGGGTCGCGTTTTTTATTAGTTAGTCGTTGGTAGGAGCGTTCGGGGAGGGAGTAGATTTCGTTTATTTTT (SEQ ID NO:314)

SKI_2465_FP GTTAGGCGGTTATTACGGGTC (SEQ ID NO:159)

SKI_2465_RP GAAATCTACTCCCTCCCCGA (SEQ ID NO:160)

SKI_2465_Pb_A5 AGGCCACGGACG CGCGTTTTTTATTAGTTAGTCGTT/3C6/ (SEQ ID NO:246)

FIG. 1 (CONT'D)

---

SPOCK2_7433 chr10:73847355-73847446

>hg19_dna range=chr10:73847345-73847456 5'pad=10 3'pad=10 strand=+ repeatMasking=none WT
CCCAGAGCCCCGGTCACACTCCCGTCCCATGCTGTCCCCCTCCCGCAAAGCCCACGGTGGGAACAGAGGGCACCG
CGCGAGCCGATGCCACCCTCACTGCCGGCCCCACCCA (SEQ ID NO:315)

BST
TTTAGAGTTTCGGTTATATTTTCGTTTTATGTTGTTTTTTTTTCGTAAAGTTTACGGTGGGAATAGAGGGTATCG
CGCGAGTCGATGTTATTTTTATTGTCGGTTTTATTTA (SEQ ID NO:316)

SPOCK2_7433_FP TATGTTGTTTTTTTTTCGTAAAGTTTACGGT (SEQ ID NO:161)
SPOCK2_7433_RP CCGACAATAAAAATAACATCGACTCG (SEQ ID NO:162)
SPOCK2_7433_Pb_A1 CGCGCCGAGG GCGCGATACCCTCTATTC/3C6/ (SEQ ID NO:247)

---

VIPR2 chr7:158937203-158937476

>hg19_dna range=chr7:158937193-158937479 5'pad=10 3'pad=3 strand=+ repeatMasking=none WT
CCTCCCAACCCGAGTCCCGCAACCCGGCGGGACCGGAGCTCAGCGCTTCACGCTCTCCGGGAGGAAGCTCCGGAC
CCCGGGCGACCCCGCTCCCTCTCCCGGACCCCGCCCGCGCTCCAGCACCCGGGAGGAAGGCGAAGACCGGCGGGA
GGAGCGCTCTTCTCGGAAGGGGAGAACCGGGTCCGAGGCGCCGTGGGGCGGGGGTCGCGGGCGCACTCACGGGGG
CGAGCAGCCAGCAGGTCAGCAGCGCGGGAGGCAGCAGCGTCCGCATCCCGAGCTCAGCGTGC (SEQ ID NO:317)

BST
TTTTTTAATTCGAGTTTCGTAATTCGGCGGGATCGGAGTTTAGCGTTTTACGTTTTTCGGGAGGAAGTTTCGGAT
TTCGGGCGATTTCGTTTTTTTTTTCGGATTTCGTTCGCGTTTTAGTATTCGGGAGGAAGGCGAAGATCGGCGGGA
GGAGCGTTTTTTTCGGAAGGGGAGAATCGGGTTCGAGGCGTCGTGGGGCGGGGGTCGCGGGCGTATTTACGGGGG
CGAGTAGTTAGTAGGTTAGTAGCGCGGGAGGTAGTAGCGTTCGTATTTCGAGTTTAGCGTGT (SEQ ID NO:318)

VIPR_FP TCGTTCGCGTTTTAGTATTCGG (SEQ ID NO:163)
VIPR_RP CGAAAAAAACGCTCCTCCCG (SEQ ID NO:164)
VIPR_Pb_A5 AGGCCACGGACG GCCGATCTTCGCCTT/3C6/ (SEQ ID NO:248)

---

ZMIZ1 chr10:81002589-81002797

>hg19_dna range=chr10:81002587-81002801 5'pad=2 3'pad=4 strand=+ repeatMasking=none

FIG. 1 (CONT'D)

WT
GTCGGGTCGTGCGTTCGCTCGGCAGCGGCGTGCACCAGCACCACCCCTGCGTGCAAGTTTGAAATGTGAGCTGCC
TCCGATTCATACTCGCTCGCGCTCCCTCGCAGCGAAGTGGCTGGGCTGACGGTCTGCGCGCGCGAGTGAGTGCGG
GCGGCGGGCTGGGGGGCGGGGTGCGGACGGCGAGGCTCGCGGGGCGGGGAGGGCGCGCGCGAGCC (SEQ ID NO:319)

BST
GTCGGGTCGTGCGTTCGTTCGGTAGCGGCGTGTATTAGTATTATTTTTGCGTGTAAGTTTGAAATGTGAGTTGTT
TTCGATTTATATTCGTTCGCGTTTTTTCGTAGCGAAGTGGTTGGGTTGACGGTTTGCGCGCGCGAGTGAGTGCGG
GCGGCGGGTTGGGGGGCGGGGTGCGGACGGCGAGGTTCGCGGGGCGGGGAGGGCGCGCGCGAGTT (SEQ ID NO:320)

ZMIZ1_2684_FP GTTCGTTCGGTAGCGGC (SEQ ID NO:165)
ZMIZ1_2684_RP ACCACTTCGCTACGAAAAAACG (SEQ ID NO:166)
ZMIZ1_2684_Pb_A1 CGCGCCGAGG GCGAACGAATATAAATCGAAAAC/3C6/ (SEQ ID NO:249)

---

ZNF382 chr19:37096085-37096209

>hg19_dna range=chr19:37096075-37096214 5'pad=10 3'pad=5 strand=+ repeatMasking=none WT
TGGCAGAAGCGTAGTGCCAGCCGCAATAGGGCGGCCGTGGGTGCAAACGGAGGGGAGCGCCGGCAGCTAGCACCG
CGCGGCGACTAACGGGCCGCCCCGGAGACTCCTGGGAGCTCAGGCCCACGCGCGAGTGCGCAGGC (SEQ ID NO:321)

BST
TGGTAGAAGCGTAGTGTTAGTCGTAATAGGGCGGTCGTGGGTGTAAACGGAGGGGAGCGTCGGTAGTTAGTATCG
CGCGGCGATTAACGGGTCGTTTCGGAGATTTTTGGGAGTTTAGGTTTACGCGCGAGTGCGTAGGT (SEQ ID NO:322)

ZNF382_FP TAGTCGTAATAGGGCGGTCG (SEQ ID NO:167)
ZNF382_RP CCGAAACGACCCGTTAATCG (SEQ ID NO:168)
ZNF382_Pb_A5 AGGCCACGGACG GCCGCGCGATACTAA/3C6/ (SEQ ID NO:250)

---

GYPC_3753 chr2:127413592-127413887

>hg19_dna range=chr2:127413582-127413897 5'pad=10 3'pad=10 strand=+ repeatMasking=none WT
AGAAGTGGGCGGGTGTGTGTTTAAAAAAAAAAAAGGGGGTGGAAACCCCACCAGCCAAGTCTGCAGAAAAAAAAT
AAATGAAGTCTGCCTATCTCCGGGCCAGAGCCCCTCCCCTCGGCCCGCGCGGGAGGAGTGTGACCCAGGTGCCGC
TTCCTCTCGCCGCCGAGGGTCAGGAGCCCGGGAGCGCGACCCTCCCCCGGCCCGGCCTGGCCCGGCCTGGCCAGT
CCCCGCGGTCTCTGCCCGGGCTGACGCCCAGGAATGTGGTCGACGAGAAGCCCCAACAGCACGGCGTGGCCTCTC
AGCCTCGGTGAGTACC (SEQ ID NO:323)

FIG. 1 (CONT'D)

BST

AGAAGTGGGCGGGTGTGTGTTTAAAAAAAAAAAAGGGGGTGGAAATTTTATTAGTTAAGTTTGTAGAAAAAAAAT
AAATGAAGTTTGTTTATTTTCGGGTTAGAGTTTTTTTTTCGGTTCGCGCGGGAGGAGTGTGATTTAGGTGTCGT
TTTTTTTCGTCGTCGAGGGTTAGGAGTTCGGGAGCGCGATTTTTTTTCGGTTCGGTTTGGTTCGGTTTGGTTAGT
TTTCGCGGTTTTTGTTCGGGTTGACGTTTAGGAATGTGGTCGACGAGAAGTTTTAATAGTACGGCGTGGTTTTTT
AGTTTCGGTGAGTATT (SEQ ID NO:324)

GYPC_3753_BST plasmid sequnce

GGAGTGTGATTTAGGTGTCGTTTTTTTTCGTCGTCGAGGGTTAGGAGTTCGGGAGCGCGATTTTTTTTCGGTTCG
GT (SEQ ID NO:325)

GYPC_3753_FP TGATTTAGGTGTCGTTTTTTTTCGTC (SEQ ID NO:169)
GYPC_3753_RP GAAAAAAAATCGCGCTCCCG (SEQ ID NO:170)
GYPC_3753_Pb_A5 AGGCCACGGACG CGTCGAGGGTTAGGAGT/3C6/ (SEQ ID NO:251)

---

GYPC chr2:127413898-127413988

>hg19_dna range=chr2:127413888-127413992 5'pad=10 3'pad=4 strand=+
repeatMasking=none WT
GGTGAGTACCCGCCGTGGGGAAGGGTCCTGGGGACCCACTGGAGGCCGCGGCCCGCAGCAGCCAGGGGCCGAGCC
ACGGCCACGGACGCCCTGGTGTCCCGGTCC (SEQ ID NO:326)

BST

GGTGAGTATTCGTCGTGGGGAAGGGTTTTGGGGATTTATTGGAGGTCGCGGTTCGTAGTAGTTAGGGGTCGAGTT
ACGGTTACGGACGTTTTGGTGTTTCGGTTT (SEQ ID NO:327)

GYPC_3981_FP ATTTATTGGAGGTCGCGGTTC (SEQ ID NO:171)
GYPC_3981_RP CCGAAACACCAAAACGTCCG (SEQ ID NO:172)
GYPC_3981_Pb_A1 CGCGCCGAGG GTAACCGTAACTCGACCC/3C6/ (SEQ ID NO:252)

---

RFTN1 chr3:16554329-16554496

>hg19_dna range=chr3:16554319-16554502 5'pad=10 3'pad=6 strand=+
repeatMasking=none WT
GGGGACTCTCGGCACCCGCGTCCCTGTGCTTCTGGTGGTTCCGGCGCTTCCTCGGAGCGCGCGGCATGTCTGCTC
CTACACGTCCAGCACCTCTGTCCCCAGAGCAAACCCACCTCCCAGGGCACACGCAGAGGGGCAGTCAGGCACCGC
CTCCACCCTGCCCCACCCAGGCCGCGCGCACCCC (SEQ ID NO:328)

FIG. 1 (CONT'D)

BST

GGGGATTTTCGGTATTCGCGTTTTTGTGTTTTTGGTGGTTTCGGCGTTTTTTCGGAGCGCGCGGTATGTTTGTTT
TTATACGTTTAGTATTTTTGTTTTTAGAGTAAATTTATTTTTTAGGGTATACGTAGAGGGGTAGTTAGGTATCGT
TTTTATTTTGTTTTATTTAGGTCGCGCGTATTTT (SEQ ID NO:329)

RFTN1_FP_V2 GTGTTTTTGGTGGTTTCGGC (SEQ ID NO:173)

RFTN1_RP ATACTAAACGTATAAAAACAAACATACCGC (SEQ ID NO:174)

RFTN1_Pb_A5 AGGCCACGGACG CGCGCTCCGAAAAAAC/3C6/ (SEQ ID NO:253)

---

PARP15 chr3:122296692-122296851

>hg19_dna range=chr3:122296682-122296861 5'pad=10 3'pad=10 strand=+ repeatMasking=none WT
CTCTTCCTCCCGGAGTATGGTGAGGAGCGCGGGGGACGGGTGCGGGAAGGGGACAGCAGGGCTGAGCCTGGGGCC
CGCAAGACCCAGCAGCCCGAGCGGGCGCAGAGACCCCACGCCACGCACAACCCTCTCTTCTAGGGGGCGCCGACT
ACACTGACTTCCCTGTTCCGGAAGAGGGGG (SEQ ID NO:330)

BST

TTTTTTTTTTCGGAGTATGGTGAGGAGCGCGGGGGACGGGTGCGGGAAGGGGATAGTAGGGTTGAGTTTGGGGTT
CGTAAGATTTAGTAGTTCGAGCGGGCGTAGAGATTTTACGTTACGTATAATTTTTTTTTTAGGGGGCGTCGATT
ATATTGATTTTTTTGTTTCGGAAGAGGGGG (SEQ ID NO:331)

PARP15_6789_FP GGTTCGTAAGATTTAGTAGTTCGAGC (SEQ ID NO:175)

PARP15_6789_RP CGAAACAAAAAAATCAATATAATCGACGC (SEQ ID NO:176)

PARP15_6789_Pb_A1 CGCGCCGAGG CGGGCGTAGAGATTTTACG/3C6/ (SEQ ID NO:254)

---

GP5 chr3:194118822-194118924

>hg19_dna range=chr3:194118812-194118934 5'pad=10 3'pad=10 strand=+ repeatMasking=none WT
CTCTGCAGGACGCCGCGGCCCATTCCGAAGAGCAGGATGTGCGTGAGGTTGGTGGGCAGGCCTAGCGCGGAGATG
CGCGCCACGTCGCCCCCCGAGCACTGCGCGGCGTCCCGGAAGACACAC (SEQ ID NO:332)

BST

TTTTGTAGGACGTCGCGGTTTATTTCGAAGAGTAGGATGTGCGTGAGGTTGGTGGGTAGGTTTAGCGCGGAGATG
CGCGTTACGTCGTTTTTCGAGTATTGCGCGGCGTTTCGGAAGATATAT (SEQ ID NO:333)

GP5_8905_FP TAGGACGTCGCGGTTTATTTC (SEQ ID NO:177)

GP5_8905_RP CGCAATACTCGAAAAACGACG(SEQ ID NO:178)

GP5_8905_Pb_A5 AGGCCACGGACG GTAACGCGCATCTCCG/3C6/ (SEQ ID NO:255)

---

FIG. 1 (CONT'D)

GPRIN1 chr5:176023887-176023974

>hg19_dna range=chr5:176023884-176023984 5'pad=3 3'pad=10 strand=- repeatMasking=none WT
GCCAAGGGGCGCCCGCGCCGCCGCCCGCCGCCCGTGCCGGCCCCGGCCGTTCGGGCTCGGTGCGCACCGCGCCCC
CAGATGGCGCCGCCAAGCGTCCGCCC (SEQ ID NO:334)

BST
GTTAAGGGGCGTTCGCGTCGTCGTTCGTCGTTCGTGTCGGTTTCGGTCGTTCGGGTTCGGTGCGTATCGCGTTTT
TAGATGGCGTCGTTAAGCGTTCGTTT (SEQ ID NO:335)

GPRIN1_FP TCGCGTCGTCGTTCGT (SEQ ID NO:179)
GPRIN1_RP GACGCCATCTAAAAACGCGA (SEQ ID NO:180)
GPRIN1_Pb_A1 CGCGCCGAGG TCGTTCGTGTCGGTTTC/3C6/ (SEQ ID NO:256)

---

HCG4_0331 chr6:29760284-29760410

>hg19_dna range=chr6:29760274-29760420 5'pad=10 3'pad=10 strand=+ repeatMasking=none WT
GCTTCCTCTCCGTGGGCGACGTGGACGACACGCAGTGCGTGCGGCTCGACAGCGACGCCACGAGTCCCAGGATGG
AGCCGCGGGCGCCGTGGATGGAGCAGGAGGGGCCGGAATATTGGGAAGAGGAGACAGGGACCGCCAAGGCCA
(SEQ ID NO:336)

BST
GTTTTTTTTTCGTGGGCGACGTGGACGATACGTAGTGCGTGCGGTTCGATAGCGACGTTACGAGTTTTAGGATGG
AGTCGCGGGCGTCGTGGATGGAGTAGGAGGGGTCGGAATATTGGGAAGAGGAGATAGGGATCGTTAAGGTTA
(SEQ ID NO:337)

HCG4_0331_FP GGCGACGTGGACGATAC (SEQ ID NO:181)
HCG4_0331_RP CTAAAACTCGTAACGTCGCTATCG (SEQ ID NO:182
HCG4_0331_Pb_A5 AGGCCACGGACG GAACCGCACGCACTA/3C6/ (SEQ ID NO:257)

---

HCG4_0556 chr6:29760436-29760577

>hg19_dna range=chr6:29760426-29760578 5'pad=10 3'pad=1 strand=+ repeatMasking=none WT
CAGTTTTACCGAGTGAACCTGCGGACCCTGAGCGGCTACTACAACCAGAGTGAGGCCTGTGAGTGACACCGGCCG
GGGGCGCAGGTCACTACCCCTCCACATCCCCCACGGACCGCCCGGGTCTCCCCGAGTCTCTGGGTCCGAGATCCA
CGC (SEQ ID NO:338)

FIG. 1 (CONT'D)

BST

TAGTTTTATCGAGTGAATTTGCGGATTTTGAGCGGTTATTATAATTAGAGTGAGGTTTGTGAGTGATATCGGTCG
GGGGCGTAGGTTATTATTTTTTTATATTTTTTACGGATCGTTCGGGTTTTTTCGAGTTTTTGGGTTCGAGATTTA
CGT (SEQ ID NO:339)

HCG4_0556_FP GGTTTGTGAGTGATATCGGTCG (SEQ ID NO:183)

HCG4_0556_RP CGAACCCAAAAACTCGAAAAAACC (SEQ ID NO:184)

HCG4_0556_Pb_A1 CGCGCCGAGG CCGAACGATCCGTAAAAAATATAA/3C6/ (SEQ ID NO:258)

---

NKX2-6_4159 chr8:23564076-23564193

>hg19_dna range=chr8:23564066-23564203 5'pad=10 3'pad=10 strand=+ repeatMasking=none

WT

TGTCCTTGACCGAGAAGGGGGTGGAGGTGACGGGGCTCAGCAGCATCCCGAAGGCGGATGGGGCGGGGCCGAGGA
GGTCCGGGTGAGGAGCGGCACCCTGAACTTCCCGTCTTGTCGCTGCAGGCCCCGCAGACAGAC (SEQ ID NO:340)

BST

TGTTTTTGATCGAGAAGGGGGTGGAGGTGACGGGGTTTAGTAGTATTTCGAAGGCGGATGGGGCGGGGTCGAGGA
GGTTCGGGTGAGGAGCGGTATTTTGAATTTTTCGTTTTGTCGTTGTAGGTTTCGTAGATAGAT (SEQ ID NO:341)

NKX2-6_4159_FP GGGTTTAGTAGTATTTCGAAGGCG (SEQ ID NO:185)

NKX2-6_4159_RP GAAAAATTCAAAATACCGCTCCTCAC (SEQ ID NO:186)

NKX2-6_4159_Pb_A5 AGGCCACGGACG CCCGAACCTCCTCGA/3C6/ (SEQ ID NO:259)

---

C1QL3 chr10:16562562-16562645

>hg19_dna range=chr10:16562552-16562655 5'pad=10 3'pad=10 strand=- repeatMasking=none

WT

ATGAAGGCTACGAGGTGCTCAAGTTCGACGACGTGGTCACCAACCTCGGAAACCACTACGACCCCACCACCGGCA
AGTTCACCTGCTCCATCCCGGGCATCTAC (SEQ ID NO:342)

BST

ATGAAGGTTACGAGGTGTTTAAGTTCGACGACGTGGTTATTAATTTCGGAAATTATTACGATTTTATTATCGGTA
AGTTTATTTGTTTTATTTCGGGTATTTAT (SEQ ID NO:343)

C1QL3_FP GAAGGTTACGAGGTGTTTAAGTTCG (SEQ ID NO:187)

C1QL3_RP AACAAATAAACTTACCGATAATAAAATCGTAATAATTTC (SEQ ID NO:188)

C1QL3_Pb_A1 CGCGCCGAGG GACGACGTGGTTATTAATTTCG/3C6/ (SEQ ID NO:260)

---

FIG. 1 (CONT'D)

FAIM2 Chr12:50297643-50297814

>hg19_dna range=chr12:50297633-50297817 5'pad=10 3'pad=3 strand=+ repeatMasking=none WT
AGCCTGCCTGCGTCTCTTCCTTCCTCCGCGTGGGTTCTAGCAACATCCACTGCAGCCGGGCCAGGCGAGCCGGCG
CGTACCATCGGCGCGGGGGGAGGAGAGGGCCGGGCCTGGGAAGATGCTGCGGAGGACGCTGCGGATTCGCGAGCC
CGGGGTAAGGCGGCGGCGCACCGCCCCCTCCCGCC (SEQ ID NO:344)

BST

AGTTTGTTTGCGTTTTTTTTTTTTTTCGCGTGGGTTTTAGTAATATTTATTGTAGTCGGGTTAGGCGAGTCGGCG

CGTATTATCGGCGCGGGGGGAGGAGAGGGTCGGGTTTGGGAAGATGTTGCGGAGGACGTTGCGGATTCGCGAGTT

CGGGGTAAGGCGGCGGCGTATCGTTTTTTTTCGTT (SEQ ID NO:345)

FAIM2_FP TTGCGGAGGACGTTGC (SEQ ID NO:189)

FAIM2_RP GAAAAAAAACGATACGCCGCC (SEQ ID NO:190)

FAIM2_Pb_A1 CGCGCCGAGG CGGATTCGCGAGTTCG/3C6/ (SEQ ID NO:261)

---

LOC100131366 chr14:103655515-103655633

>hg19_dna range=chr14:103655508-103655639 5'pad=7 3'pad=6 strand=- repeatMasking=none

WT
GGGGGGCGGGGCTGGGGAGAGGGTGGCCCCTGCACACTAGTCCCCTCCCCTCGACCCCGCAGCCCCGCGGCGCGT

TTCCTGAGGCGCCCCCGCCACGTCCCGCGAGTCTCTGCCAAGTTCCCGCGCGGGTGC (SEQ ID NO:346)

BST

GGGGGGCGGGGTTGGGGAGAGGGTGGTTTTTGTATATTAGTTTTTTTTTTTCGATTTCGTAGTTTCGCGGCGCGT

TTTTTGAGGCGTTTTCGTTACGTTTCGCGAGTTTTTGTTAAGTTTTCGCGCGGGTGT (SEQ ID NO:347)

LOC100131366_FP TTTCGATTTCGTAGTTTCGCGG (SEQ ID NO:191)

LOC100131366_RP CTCGCGAAACGTAACGAAAAC (SEQ ID NO:192)

LOC100131366_Pb_A5 AGGCCACGGACG GCGCGTTTTTTGAGGC/3C6/ (SEQ ID NO:262)

---

NTN1 chr17:9143164-9143445

>hg19_dna range=chr17:9143154-9143455 5'pad=10 3'pad=10 strand=- repeatMasking=none

WT
GGGGAGGGGCCGCCGAGGGTCCCGCCCCCCGCGCCGTGCGGCCCCGCCCCCTCCCTCCCCCCACCTGGGAAAGCC

CTCGCGGGCCAAGTCCGCGGCGGCCGGGCCAAGGCGCCCGCTCTCGCTCGGCCCCGCCCTGGCGCCCGCCCGCCC

GCCCGCCCGCTGCCTCGGCGCTAGGCCTTCTTGCACTTGCCCTTCTTCTCACGCTGCTGGAACTTGCGCAGCCGC

CGCGCCCACGTGTCCCGCCACTGGATCACCAGGCTGCTTTTATCGGCCACGATGCCGCTCTGGTCCGGAGAGTCC

TC (SEQ ID NO:348)

FIG. 1 (CONT'D)

BST

GGGGAGGGGTCGTCGAGGGTTTCGTTTTTCGCGTCGTGCGGTTTCGTTTTTTTTTTTTTTTTATTTGGGAAAGTT
TTCGCGGGTTAAGTTCGCGGCGGTCGGGTTAAGGCGTTCGTTTTCGTTCGGTTTCGTTTTGGCGTTCGTTCGTTC
GTTCGTTCGTTGTTTCGGCGTTAGGTTTTTTTGTATTTGTTTTTTTTTTTACGTTGTTGGAATTTGCGTAGTCGT
CGCGTTTACGTGTTTCGTTATTGGATTATTAGGTTGTTTTTATCGGTTACGATGTCGTTTTGGTTCGGAGAGTTT
TT (SEQ ID NO:349)

NTN1_BST plasmid sequence

GTTAAGGCGTTCGTTTTCGTTCGGTTTCGTTTTGGCGTTCGTTCGTTCGTTCGTTCGTTGTTTCGGCGTTAGGTT
TTTTTGT (SEQ ID NO:350)

NTN1_FP CGTTCGTTTTCGTTCGGTTTC (SEQ ID NO:193)

NTN1_RP ACCTAACGCCGAAACAACG (SEQ ID NO:194)

NTN1_Pb_A1 CGCGCCGAGG CGTTTTGGCGTTCGTTC/3C6/ (SEQ ID NO:263)

---

ARL5C_1519 chr17:37321484-37321627

>hg19_dna range=chr17:37321474-37321631 5'pad=10 3'pad=4 strand=-
repeatMasking=none

WT

GCCCCGGGCCTTTCAGACACTTTTCTGGAATGTGAAGGGAGGTGGGGGCTCAGCTGTCTTTTCCACCGTCCCGGA
GTGGGGCAGGTGTCGGAGCTGGGTGGGAAGCAGACGCGGTACGGTGGGCAGAGGTCCCCAGCCTGCGGGGAGCGC
TATCTCCT (SEQ ID NO:351)

BST

GTTTCGGGTTTTTTAGATATTTTTTTGGAATGTGAAGGGAGGTGGGGGTTTAGTTGTTTTTTTTATCGTTTCGGA
GTGGGGTAGGTGTCGGAGTTGGGTGGGAAGTAGACGCGGTACGGTGGGTAGAGGTTTTTAGTTTGCGGGGAGCGT
TATTTTTT (SEQ ID NO:352)

ARL5C_1519_FP GTTGTTTTTTTTATCGTTTCGGAGTG (SEQ ID NO:195)

ARL5C_1519_RP CCTCTACCCACCGTACCG (SEQ ID NO:196)

ARL5C_1519_Pb_A5 AGGCCACGGACG GCGTCTACTTCCCACC/3C6/ (SEQ ID NO:264)

---

C17orf64 chr17:58498720-58498794

>hg19_dna range=chr17:58498713-58498798 5'pad=7 3'pad=4 strand=+
repeatMasking=none

WT

GGGCCTCCGGGCTACCCCTACTTGAAGCCGCTATGCCCCTCTCCTGTGCCCGAGGTGGCCGCTGGGTGGCAGGGG
AGGCCCGGGCC (SEQ ID NO:353)

FIG. 1 (CONT'D)

BST

GGGTTTTCGGGTTATTTTTATTTGAAGTCGTTATGTTTTTTTTTTGTGTTCGAGGTGGTCGTTGGGTGGTAGGGG
AGGTTCGGGTT (SEQ ID NO:354)

C17orf64_8780_FP GTTTTCGGGTTATTTTTATTTGAAGTCG (SEQ ID NO:197)

C17orf64_8780_RP TCCCCTACCACCCAACG (SEQ ID NO:198)

C17orf64_8780_Pb_A1 CGCGCCGAGG GACCACCTCGAACACAAA/3C6/ (SEQ ID NO:265)

---

OXT Chr20:3052753-3052884

>hg19_dna range=chr20:3052743-3052891 5'pad=10 3'pad=7 strand=+ repeatMasking=none WT
GGGCAAAGGCCGCTGCTTCGGGCCCAATATCTGCTGCGCGGAAGAGCTGGGCTGCTTCGTGGGCACCGCCGAAGC
GCTGCGCTGCCAGGAGGAGAACTACCTGCCGTCGCCCTGCCAGTCCGGCCAGAAGGCGTGCGGGAGCGGGGGCC
(SEQ ID NO:355)

BST

GGGTAAAGGTCGTTGTTTCGGGTTTAATATTTGTTGCGCGGAAGAGTTGGGTTGTTTCGTGGGTATCGTCGAAGC
GTTGCGTTGTTAGGAGGAGAATTATTTGTCGTCGTTTTGTTAGTTCGGTTAGAAGGCGTGCGGGAGCGGGGGTT
(SEQ ID NO:356)

OXT_FP GGGTTTAATATTTGTTGCGCGG (SEQ ID NO:199)

OXT_RP CGAAGCGTTGCGTTGTTAG (SEQ ID NO:200)

OXT_Pb_A5 AGGCCACGGACG GACGATACCCACGAAACAA/3C6/ (SEQ ID NO:266)

---

PEAR1 Chr1:156863357-156863488

>hg19_dna range=chr1:156863347-156863492 5'pad=10 3'pad=4 strand=+ repeatMasking=none TTTCCCTCCCGGGCGCCTGGATCTCCCCTCCCCCGGCTCCTGTTTCCTTGTCAAAACTTCCTGCCTTGGCGAGGG
CCCGAGTTCCCACCCCCTTCCTGCCCCCCGCCCCTCGGCGCCCCTCCCGGCCCTGCGATCAGCAGCGTCCC
(SEQ ID NO:357)

BST

TTTTTTTTTCGGGCGTTTGGATTTTTTTTTTTTCGGTTTTTGTTTTTTTGTTAAAATTTTTTGTTTTGGCGAGGG
TTCGAGTTTTTATTTTTTTTTTGTTTTTCGTTTTTCGGCGTTTTTTTCGGTTTTGCGATTAGTAGCGTTTT
(SEQ ID NO:358)

PEAR1_FP TTGGCGAGGGTTCGAGT (SEQ ID NO:201)

PEAR1_RP CTAATCGCAAAACCGAAAAAAACG (SEQ ID NO:202)

PEAR1_Pb_A1 CGCGCCGAGG GCCGAAAAACGAAAAACAAAAA/3C6/ (SEQ ID NO:267)

---

FIG. 1 (CONT'D)

ATP10A
>hg19_dna range=chr15:26108540-26108828 5'pad=10 3'pad=10 strand=+ repeatMasking=none WT
CGGTGGCCACGGCCCCGCCCTCGTTCCGCGCCCGGACTGGGCCACGCCGGATAGCGGGAAACAAAAAAAGCCCGA
GCTGGAAACTTCAGAGAGGTTTAGTTTCGTTTCCCAGAAGCATCAGTTCGGTCCCAAAACGCTGCAAACGCGCGC
TGCCTGCAGTAGGAGAGAGGAAACCGCGAAGCGCGAGAAAAGGCGCCCCCGTCCCCAAGCAGCCCGCGCGCCCTT
CCAGGGGCCAGACCTGCTCCATCCTGGACGGCGAAACGACCTCGGGAGACCCCGGTTAGGACCT (SEQ ID NO:359)

BST

CGGTGGTTACGGTTTCGTTTTCGTTTCGCGTTCGGATTGGGTTACGTCGGATAGCGGGAAATAAAAAAAGTTCGA
GTTGGAAATTTTAGAGAGGTTTAGTTTCGTTTTTAGAAGTATTAGTTCGGTTTTAAAACGTTGTAAACGCGCGT
TGTTTGTAGTAGGAGAGAGGAAATCGCGAAGCGCGAGAAAAGGCGTTTTCGTTTTTAAGTAGTTCGCGCGTTTTT
TTAGGGGTTAGATTTGTTTTATTTTGGACGGCGAAACGATTTCGGGAGATTTCGGTTAGGATTT (SEQ ID NO:360)

ATP10A_FP GAGAGGAAATCGCGAAGCG (SEQ ID NO:203)

ATP10A_RP CCCCTAAAAAAACGCGCGA (SEQ ID NO:204)

ATP10A_Pb_A5 AGGCCACGGACG GCGAGAAAAGGCGTTTTC/3C6/ (SEQ ID NO:268)

CELF2 10:11207221-11207812

>hg19_dna range=chr10:11207212-11207819 5'pad=9 3'pad=7 strand=- repeatMasking=none

WT

GGGGGTGCGGGGAGGAGTCGGGAGCAGCCCCTGGAGCACAGGGGCCGCCAGCACCGGCTGCTTCCAGCCCTCCTG
CCTACCCGCCCTTCCTCCTGCAGGCTGGGGGCTCGGACAGCCCCAGTGCCCCGCGACGCCCACCTGGACGCCTGG
CGACCCCCGCCCCGCGCTCTGTACCTTTACTCTGCGGAGGGTTCTGACTCCGGTCCCGGAGGACGTTGATCTGGT
AGACGGCTCCGTAAGGCTCAAAAAGTTCTTTCAGCTCCTTTTCCGACCATGACCGGGGGATCTGTCCGACAAACA
TCTTAATGGCATCTGGGTCTGGTTGGTCTGAGTGATCCAAAGCTCCGTTCATCTTGTTGGCTGTGCCGTTACTGT
CAAAAACGGAACCGGGAGCCAGAGTTAGGGCGGCACGATGAGGGACAGGAAGAAAAAATAGTGGGGGTGGGGGAG
CGGGGAGGCGGAAGGAGGAGGAAGAAGAGCAGTGGCAAAGTGCCTAATGAGTCGTAGAAATTTGATGAACTAAAA
CAAAGCGGAGGCACCATGAGTTGCTCCTCGGCGGCGGCGAGGCTCTCACTGCGTGCTGCTGTCGAGCAGAGCCGG
GGGAGCAC (SEQ ID NO:361)

BST

GGGGGTGCGGGGAGGAGTCGGGAGTAGTTTTTGGAGTATAGGGGTCGTTAGTATCGGTTGTTTTTAGTTTTTTTG
TTTATTCGTTTTTTTTTTTGTAGGTTGGGGGTTCGGATAGTTTTAGTGTTTCGCGACGTTTATTTGGACGTTTGG
CGATTTTCGTTTCGCGTTTTGTATTTTTATTTTGCGGAGGGTTTTGATTTCGGTTTCGGAGGACGTTGATTTGGT
AGACGGTTTCGTAAGGTTTAAAAAGTTTTTTTAGTTTTTTTTTCGATTATGATCGGGGGATTTGTTCGATAAATA
TTTTAATGGTATTTGGGTTTGGTTGGTTTGAGTGATTTAAAGTTTCGTTTATTTTGTTGGTTGTGTCGTTATTGT
TAAAAACGGAATCGGGAGTTAGAGTTAGGGCGGTACGATGAGGGATAGGAAGAAAAAATAGTGGGGGTGGGGGAG
CGGGGAGGCGGAAGGAGGAGGAAGAAGAGTAGTGGTAAAGTGTTTAATGAGTCGTAGAAATTTGATGAATTAAAA

FIG. 1 (CONT'D)

TAAAGCGGAGGTATTATGAGTTGTTTTTCGGCGGCGGCGAGGTTTTTATTGCGTGTTGTTGTCGAGTAGAGTCGG
GGGAGTAT (SEQ ID NO:362)

CELF2_BST plasmid sequence
GTTTTAGTGTTTCGCGACGTTTATTTGGACGTTTGGCGATTTTCGTTTCGCGTTTTGTATTTTTATTTTGCGGAG
GGTTTTGATTTCGGTTTCGGA (SEQ ID NO:363)

CELF2_FP GACGTTTATTTGGACGTTTGGC (SEQ ID NO:205)
CELF2_RP ACCGAAATCAAAACCCTCCG (SEQ ID NO:206)
CELF2_Pb_A1 CGCGCCGAGG CGATTTTCGTTTCGCGTT/3C6/ (SEQ ID NO:269)

CELF2_FP_V2 GTTTCGCGACGTTTATTTGGAC (SEQ ID NO:207)
CELF2_RP ACCGAAATCAAAACCCTCCG (SEQ ID NO:208)
CELF2_Pb_A1_V2 CGCGCCGAGG CGTTTGGCGATTTTCGTT/3C6/ (SEQ ID NO:270)

CAPN2
>hg19_dna range=chr1:223936858-223937009 5'pad=10 3'pad=5 strand=-
repeatMasking=none
WT
GCACCCGGCGCCCGAGCTGCGAAAGGGACGCCCTTCTCCTCCCGCGCGGAACTTCAGGAGTGCGGGGCCCGAGTG
TAAACTGGACCACCGTGGGGCCGCGCGGGCCCCTGGGCATCACCACAAACTGTGCCTGTGGCCATCGTGTCAGGA
CA (SEQ ID NO:364)
BST
GTATTCGGCGTTCGAGTTGCGAAAGGGACGTTTTTTTTTTTCGCGCGGAATTTTAGGAGTGCGGGGTTCGAGTG
TAAATTGGATTATCGTGGGGTCGCGCGGGTTTTTGGGTATTATTATAAATTGTGTTTGTGGTTATCGTGTTAGGA
TA (SEQ ID NO:365)

CAPN2_Reg2_FP GCGCGGAATTTTAGGAGTGC (SEQ ID NO:209)
CAPN2_Reg2_RP CGCGACCCCACGATAATC (SEQ ID NO:210)
CAPN2_Reg2_Pb_A5 AGGCCACGGACG CGGGGTTCGAGTGTAAAT/3C6/ (SEQ ID NO:271)

---

DSCR6 21:38378492-38378858
>hg19_dna range=chr21:38378483-38378866 5'pad=9 3'pad=8 strand=+
repeatMasking=none
WT
GGAGAAGCCGGGACTCCTCACATCCCACATCCGGCAGGGGAAGCCCAGCAGGTGAGCGCAGGTCCCCCCAGTCCC
CGAGGGAGTGCGCCCGACGGAAACGCCCCTAGCCCGCGGGCCTCGCTTTCCTCTCCCGGGTTCCTGGGTCACTTC
CCGCTGTCTCCAGCCCGAGCTCGTGGCCCCAATCCCTGGTACCTCCATCCTCTGGTCACCCCTTCTCTGGTGCCC

FIG. 1 (CONT'D)

CCTCCCCGACTTTTCTTTGTCCCGTCCCCACCCTTGCCCGGGCCTGCCGGACCCCCCTCCTTGACACCCGGCGCC
ACCTCCTTGAGCTTTTCTCGTCTCCTCCCCATCCCCGGCTCCCTGGTCCCCTCCCGGAACTTCTCTGGTCCCCTC
CGCTCCTCC (SEQ ID NO:366)

BST

GGAGAAGTCGGGATTTTTTATATTTATATTCGGTAGGGGAAGTTTAGTAGGTGAGCGTAGGTTTTTTAGTTTT
CGAGGGAGTGCGTTCGACGGAAACGTTTTTAGTTCGCGGGTTTCGTTTTTTTTTTTCGGGTTTTTGGGTTATTTT
TCGTTGTTTTTAGTTCGAGTTCGTGGTTTTAATTTTTGGTATTTTTATTTTTTGGTTATTTTTTTTTTGGTGTTT
TTTTTTCGATTTTTTTTTGTTTCGTTTTTATTTTTGTTCGGGTTTGTCGGATTTTTTTTTTGATATTCGGCGTT
ATTTTTTTGAGTTTTTTTCGTTTTTTTTTTTATTTTCGGTTTTTTGGTTTTTTTTCGGAATTTTTTTGGTTTTTTT
CGTTTTTTT (SEQ ID NO:367)

DSCR6_BST plasmid sequence

GTTTTTTTAGTTTTCGAGGGAGTGCGTTCGACGGAAACGTTTTTAGTTCGCGGGTTTCGTTTTTTTTTTTCGGGT
(SEQ ID NO:368)

DSCR6_FP GTTTTCGAGGGAGTGCGTTC (SEQ ID NO:211)

DSCR6_RP CGAAAAAAAAAAACGAAACCCGC (SEQ ID NO:212)

DSCR6_Pb_A1 CGCGCCGAGG CGACGGAAACGTTTTTAGTTC/3C6/ (SEQ ID NO:272)

---

NR2F6 19:17346347-17346780

>hg19_dna range=chr19:17346337-17346783 5'pad=10 3'pad=3 strand=+
repeatMasking=none

WT

CAGCCATACTCGGCCGAGTCGACCTGCAGGCGGCCCAGCTTGTCCACCTGCTCCTGGAAGGCGCGCACCTGGTCC
ATGAAAGCCACGGCGCGCTCGGCGGCCATAGGCGCGGCGTGGAGGCCGGCGGCGGCCAGTAGCGGCGCCGTGTGC
AGGGGCAGCGCCGCCTGCGCCGCGTTCAGCACGAAGAGCTCGCTCCAGCTCAGGCGCAGCAGCGCCACCTGGTCG
GCCACCGGCAGCTCGGGGAAGAAGGGCGCGTGGCGCGCCCACTCCACGGTGCTGAAGAGCAGCCGCGCCGCCAGC
TCGCACACGTTGTCGATGCCCAGCACCGCGCCCGCCGCGCCGCCCCCTGCGCCGAAGCGTCCGGCCGCCGCAGGG
TAGGGCTCAGCGCGCAGCAGCTGCGCGATCAGTTCGGACACCGGCTGCCCCGGGAAGAGGTCTCCGCCGCTC
(SEQ ID NO:369)

BST

TAGTTATATTCGGTCGAGTCGATTTGTAGGCGGTTTAGTTTGTTTATTTGTTTTTGGAAGGCGCGTATTTGGTTT
ATGAAAGTTACGGCGCGTTCGGCGGTTATAGGCGCGGCGTGGAGGTCGGCGGCGGTTAGTAGCGGCGTCGTGTGT
AGGGGTAGCGTCGTTTGCGTCGCGTTTAGTACGAAGAGTTCGTTTTAGTTTAGGCGTAGTAGCGTTATTTGGTCG
GTTATCGGTAGTTCGGGGAAGAAGGGCGCGTGGCGCGTTTATTTTACGGTGTTGAAGAGTAGTCGCGTCGTTAGT
TCGTATACGTTGTCGATGTTTAGTATCGCGTTCGTCGCGTCGTTTTTGCGTCGAAGCGTTCGGTCGTCGTAGGG
TAGGGTTTAGCGCGTAGTAGTTGCGCGATTAGTTCGGATATCGGTTGTTTCGGGAAGAGGTTTTCGTCGTTT
(SEQ ID NO:370)

FIG. 1 (CONT'D)

NR2F6_BST plasmid sequence

GTTTATTTTACGGTGTTGAAGAGTAGTCGCGTCGTTAGTTCGTATACGTTGTCGATGTTTAGTATCGCGTTCGTC
GCGTCGTTTTTTGCGTCGAAGCG (SEQ ID NO:371)

NR2F6_FP GGTGTTGAAGAGTAGTCGCGT (SEQ ID NO:213)
NR2F6_RP CGACGCAAAAAACGACGC (SEQ ID NO:214)
NR2F6_Pb_A5 AGGCCACGGACG TCGTTAGTTCGTATACGTTGTC/3C6/ (SEQ ID NO:273)

---

CDO1 5:115152022-115152432

>hg19_dna range=chr5:115152020-115152435 5'pad=2 3'pad=3 strand=+ repeatMasking=none

WT

GCCGGCAAAGAGCTGGTGCAGGATGCGGATCAGATCAGCCAGGGTCCGTGGCTTCAGCACTTCGGTCTGTTCCAT
CTCGTGGGGAGCTGGCTGCGCGCGCGTCTCACTGCTGGGCTGCGGTGGAGGAGCTGAGCGAGCCAAGGAGCTGGG
GGCGAGGGAGCCTAACAGCCCGCTAGACCGCTAAGCAGACACACACGCACAAACCCAGCATTAGAGTGCCGAAAC
GTAAGGATGTCGTCGCAGAGACAGCAAGAGACCCACCCCCAGGCCCCTGGCAGCGCAGTGGATCCGGGATCGCTG
GAGACGCGGTGCACACACAAATCAGGTTCAGATCTGTGGGGTTCATCCTCCCGGGCCCCTTTTAAGCGCTTGGAG
TCACTAGGAATGTACCAACGGCCCTCGGAGGGAGGACGAGG (SEQ ID NO:372)

BST

GTCGGTAAAGAGTTGGTGTAGGATGCGGATTAGATTAGTTAGGGTTCGTGGTTTTAGTATTTCGGTTTGTTTTAT
TTCGTGGGGAGTTGGTTGCGCGCGCGTTTTATTGTTGGGTTGCGGTGGAGGAGTTGAGCGAGTTAAGGAGTTGGG
GGCGAGGGAGTTTAATAGTTCGTTAGATCGTTAAGTAGATATATACGTATAAATTTAGTATTAGAGTGTCGAAAC
GTAAGGATGTCGTCGTAGAGATAGTAAGAGATTTATTTTTAGGTTTTTGGTAGCGTAGTGGATTCGGGATCGTTG
GAGACGCGGTGTATATATAAATTAGGTTTAGATTTGTGGGGTTTATTTTTTCGGGTTTTTTTAAGCGTTTGGAG
TTATTAGGAATGTATTAACGGTTTTCGGAGGGAGGACGAGG (SEQ ID NO:373)

CDO1_BST plasmid sequence

GAGTGTCGAAACGTAAGGATGTCGTCGTAGAGATAGTAAGAGATTTATTTTTAGGTTTTTGGTAGCGTAGTGGAT
TCGGGATCGTTGGAGACGCGGTGTATATATAAATTAGGTTTAGA (SEQ ID NO:374)

CDO1_FP CGAAACGTAAGGATGTCGTCG (SEQ ID NO:215)
CDO1_RP AATTTATATATACACCGCGTCTCCAAC (SEQ ID NO:216)
CDO1_Pb_A1 CGCGCCGAGG CGATCCCGAATCCACTAC/3C6/ (SEQ ID NO:274)

---

DNMT3A 2:25500046-25500305

>hg19_dna range=chr2:25500041-25500307 5'pad=5 3'pad=2 strand=+ repeatMasking=none

FIG. 1 (CONT'D)

WT

GCACTCGCCAGCGCTTTGTTCGTGACCGGCCTTTTAAGGGCTGTCTCACCCATCTTGTCTGGCTCTGCCTCCCTG
TTTCCTTTCCGTCCTCTCTCCCACCACAGCCAGCTCCCCACTTTTTTCGCGGGGGCCCCCTCCAGCCTGTCCGGG
GCCTCCCCGTTCCCAGGCCAGGGCTTCCCCCTCCTCCCAGACCTCGTTGCTCTGCCCGGTGAGGCCCCGGGCTCC
CAGCAGGGGGCGCCTGCTCGCGATCAGGTGGCGGCCTGGGGG (SEQ ID NO:375)

BST

GTATTCGTTAGCGTTTTGTTCGTGATCGGTTTTTAAGGGTTGTTTTATTTATTTTGTTTGGTTTTGTTTTTTTG
TTTTTTTTTCGTTTTTTTTTTTATTATAGTTAGTTTTTATTTTTTTCGCGGGGGTTTTTTTAGTTTGTTCGGG
GTTTTTTCGTTTTTAGGTTAGGGTTTTTTTTTTTTTTAGATTTCGTTGTTTTGTTCGGTGAGGTTTCGGGTTTT
TAGTAGGGGGCGTTTGTTCGCGATTAGGTGGCGGTTTGGGGG (SEQ ID NO:376)

DNMT3A_Reg2 plasmid sequence

GATTTCGTTGTTTTGTTCGGTGAGGTTTCGGGTTTTTAGTAGGGGGCGTTTGTTCGCGATTAGGTGGCGGTTTGG
GGG (SEQ ID NO:377)

DNMT3A_Reg2_FP TGTTTTGTTCGGTGAGGTTTCG (SEQ ID NO:217)
DNMT3A_Reg2_RP CAAACCGCCACCTAATCGC (SEQ ID NO:218)
DNMT3A_Reg2_Pb_A5 AGGCCACGGACG CGAACAAACGCCCCC/3C6/ (SEQ ID NO:275)

---

SIM2 21:38076892-38077026

WT

>hg19_dna range=chr21:38076882-38077036 5'pad=10 3'pad=10 strand=+
repeatMasking=none GAGGGGACCTGGATCCCTGAACCCCGGGGCGGAAAGGGAGCCTCCGGGCGGCTGTGGGTGCCGCGCTCCTCGGAG
CCAGCAGCTGCTGGGGCGGCGTCCGAACTCCCCAGGTCTGCGCACGGCAATGGGGGCACCGGGCCTTCTGTCTGT
CCTCA (SEQ ID NO:378)

BST

GAGGGGATTTGGATTTTTGAATTTCGGGGCGGAAAGGGAGTTTTCGGGCGGTTGTGGGTGTCGCGTTTTTCGGAG
TTAGTAGTTGTTGGGGCGGCGTTCGAATTTTTTAGGTTTGCGTACGGTAATGGGGGTATCGGGTTTTTTGTTTGT
TTTTA (SEQ ID NO:379)

SIM2 prostate sequence:

GAATTCGGGTTTAGCGCGGGTTTTTCGCGGTAGTGGTCGTAGTTCGGGAAGTTCGGGGGCGCGGTGTTTT
CGTGAATTC (SEQ ID NO:380)

SIM2_Reg2_FP AAAGGGAGTTTTCGGGCG (SEQ ID NO:219)
SIM2_Reg2_RP ACCCGATACCCCCATTACC (SEQ ID NO:220)
SIM2_Reg2_Pb_A1 CGCGCCGAGG CGTACGCAAACCTAAAAAATTC/3C6/ (SEQ ID NO:276)

FIG. 1 (CONT'D)

CMTM3
>hg19_dna range=chr16:66638172-66638351 5'pad=10 3'pad=10 strand=+ repeatMasking=none
CGGGGACAGGAGGGGTGGCCAAGAAAGTCGCAAGAAAACTCCGGCCCCCAAGAAAAAGAGAGGGCATGGGTTGCG
GAGCCGACATCACGGCCGGGGTCTTTGCTGTTTAGACGCCTGGGTTCCCGGATCCCAGACACGCGCACGGGCAGG
AAGTTAGACC (SEQ ID NO:381)

CGGGGATAGGAGGGGTGGTTAAGAAAGTCGTAAGAAAATTTCGGTTTTTAAGAAAAAGAGAGGGTATGGGTTGCG
GAGTCGATATTACGGTCGGGGTTTTTGTTGTTTAGACGTTTGGGTTTTCGGATTTTAGATACGCGTACGGGTAGG
AAGTTAGATT (SEQ ID NO:382)

CMTM3_FP GGTGGTTAAGAAAGTCGTAAGAAAATTTCG (SEQ ID NO:221)
CMTM3_RP TCTAAACAACAAAAACCCCGACC (SEQ ID NO:222)
CMTM3_Pb_A5 AGGCCACGGACG CGTAATATCGACTCCGCAA/3C6/ (SEQ ID NO:277)

---

SRC
>hg19_dna range=chr20:36013121-36013303 5'pad=10 3'pad=10 strand=+ repeatMasking=none
GTTGCCTGGGTCCGCCCAGAGATGAGTCGGGACGCGCGGCCCACGTGCGGCGGAGGGGCAGCTGGGTCGCTCGGG
GAACGGGGCACCGGATGGCCCCGGTTGGGCCCGCGCCAGGATGCGCCCCTGCGCCCTCTGCTGGCGCTCTGCGGT
CACCGCAGCCCCG (SEQ ID NO:383)

GTTGTTTGGGTTCGTTTAGAGATGAGTCGGGACGCGCGGTTTACGTGCGGCGGAGGGGTAGTTGGGTCGTTCGGG
GAACGGGGTATCGGATGGTTTCGGTTGGGTTCGCGTTAGGATGCGTTTTTGCGTTTTTTGTTGGCGTTTTGCGGT
TATCGTAGTTTCG (SEQ ID NO:384)

SRC_FP GGATGGTTTCGGTTGGGTTC (SEQ ID NO:223)
SRC_RP GCAAAACGCCAACAAAAAACG (SEQ ID NO:224)
SRC_Pb_A5 AGGCCACGGACG CGCGTTAGGATGCGT/3C6/ (SEQ ID NO:278)

---

LRRC41_9559
>hg19_dna range=chr1:46769340-46769650 5'pad=0 3'pad=0 strand=- repeatMasking=none CGGACGAATTCTGGGGAAAGGTCGAGGGAACTAGAGCTCCCGACTATGCAAACCCTAGAGGGTAAACTGGGGGCT
AAGAGGGCCCCGTGCGTGTTTTGGCGGGCTAGGTCCTGGGCTTCAGGGCAGAGAAGAGGGCCGAGTGGATCGCCT
TGCCTTACCTCCTCAGGATCTCCGGATTCGGTAAGCATCTTTTGCTCGTCCTCCAGTCCCATGTCTGGCTACGGT
TCTAGATTCAACACGAGCAGCAACAGCGGCACCTAACCCAGTTCAGGATCAAGAAGGACTTGTAAGGGTCACTCA
GCGGAAATCCG (SEQ ID NO:385)

CGGACGAATTTTGGGGAAAGGTCGAGGGAATTAGAGTTTTCGATTATGTAAATTTTAGAGGGTAAATTGGGGGTT
AAGAGGGTTTCGTGCGTGTTTTGGCGGGTTAGGTTTTGGGTTTTAGGGTAGAGAAGAGGGTCGAGTGGATCGTTT
TGTTTTATTTTTTTAGGATTTTCGGATTCGGTAAGTATTTTTTGTTCGTTTTTTAGTTTTATGTTTGGTTACGGT

FIG. 1 (CONT'D)

TTTAGATTTAATACGAGTAGTAATAGCGGTATTTAATTTAGTTTAGGATTAAGAAGGATTTGTAAGGGTTATTTA
GCGGAAATTCG (SEQ ID NO:386)

LRRC41 plasmid sequence

CGGACGAATTTTGGGGAAAGGTCGAGGGAATTAGAGTTTTCGATTATGTAAATTTTAGAGGGTAAATTGGGGGTT
AAGAGGGTTTCGTGCGTGTTTTGGCGGGTTAGGTTTTGGGTTTTAGGGTAGAGAAGAGGGTCGAGTGGATCGTTT
TGTT (SEQ ID NO:387)

LRRC41_9559_FP GGTCGAGGGAATTAGAGTTTTCG (SEQ ID NO:225)
LRRC41_9559_RP AACCTAACCCGCCAAAACAC (SEQ ID NO:226)
LRRC41_9559_Pb_A1 CGCGCCGAGG CGCACGAAACCCTCTTA/3C6/ (SEQ ID NO:279)

---

TSHZ3
>hg19_dna range=chr19:31839415-31840120 5'pad=0 3'pad=0 strand=+
repeatMasking=none
WT
CGTCCCAGAACTAAGTGCTATGCGGAGATGAGGGTGGGAGCAGCAGTACAAGGAGGGGGTGGGGGCGAGGAAACA
CAAACAGGGGAGAAGGAAACGCCAGCATCTAACATGGACTTGACAGTCATCTGACAATACCCAGACCCTGTGCGC
TCCGGGTTCCACCGCTGTGCCCAGTTTGGGCCCAAGAAATGAGGAATCAATCGTGTTAGTACTAAGGTGGCCGAG
GGGACCGGCTCGCTCACTCGTTCGCGCTCCCTGGCTCGGCGGACACCAGGCAGTCCCCCGGCGGTCGGCCGCTCG
GAGGACGCGGAAGATGTCCCGGGGAACTCAGGTGACCCCGCCCGCCACCCACAGAAAGAGCCAGGCCGGGGTTGC
TTCCCATTCCCTCTGCAGCCGGAGAGCTGAGGAGGTAGGGACCTGGCGCGGCTCAGCGCGCTCCGCGAGCGGCTC
CCCAAATGGGTGCGAGAGGGAAGAGGGCAGAGCGCGGCGGGGCGTCCGGGGGGCGCCCGGTACCCGAGGCGGGCG
CACGCACCCAAACAGGAGAGCGGCGCCCGGAGTTACTCAGTGCGGGCAGAAGAGCGGGGCGAGGAGCGGGGTCGC
GCCCGCTGGAGGCGCGGGGCGAGCGGAGGAAGAGGAGGAGGAGAGCAGAAGGAAGGGGAAGCGGCTCGTACCTGC
TGCGCGCCGGGGCGCCTGCTGCTTCCTCCTC (SEQ ID NO:388)

BST

CGTTTTAGAATTAAGTGTTATGCGGAGATGAGGGTGGGAGTAGTAGTATAAGGAGGGGGTGGGGGCGAGGAAATA
TAAATAGGGGAGAAGGAAACGTTAGTATTTAATATGGATTTGATAGTTATTTGATAATATTTAGATTTTGTGCGT
TTCGGGTTTTATCGTTGTGTTTAGTTTGGGTTTAAGAAATGAGGAATTAATCGTGTTAGTATTAAGGTGGTCGAG
GGGATCGGTTCGTTTATTCGTTCGCGTTTTTTGGTTCGGCGGATATTAGGTAGTTTTTCGGCGGTCGGTCGTTCG
GAGGACGCGGAAGATGTTTCGGGGAATTTAGGTGATTTCGTTCGTTATTTATAGAAAGAGTTAGGTCGGGGTTGT
TTTTTATTTTTTTTGTAGTCGGAGAGTTGAGGAGGTAGGGATTTGGCGCGGTTTAGCGCGTTTCGCGAGCGGTTT
TTTAAATGGGTGCGAGAGGGAAGAGGGTAGAGCGCGGCGGGGCGTTCGGGGGGCGTTCGGTATTCGAGGCGGGCG
TACGTATTTAAATAGGAGAGCGGCGTTCGGAGTTATTTAGTGCGGGTAGAAGAGCGGGGCGAGGAGCGGGGTCGC
GTTCGTTGGAGGCGCGGGGCGAGCGGAGGAAGAGGAGGAGGAGAGTAGAAGGAAGGGGAAGCGGTTCGTATTTGT
TGCGCGTCGGGGCGTTTGTTGTTTTTTTTTT (SEQ ID NO:389)

FIG. 1 (CONT'D)

TSHZ3 plasmid sequence
GAATTAATCGTGTTAGTATTAAGGTGGTCGAGGGGATCGGTTCGTTTATTCGTTCGCGTTTTTTGGTTCGGCGGA
TATTAGGTAGTTTTTCGGCGGTCGGTCGTTCGGAGGACGCGGAAGATGTTTCGGGGAATTTAGGTGATTTCGTTC
GTTA (SEQ ID NO:390)

TSHZ3_FP GGGATCGGTTCGTTTATTCGTTC (SEQ ID NO:227)
TSHZ3_RP CCCGAAACATCTTCCGCG (SEQ ID NO:228)
TSHZ3_Pb_A5 AGGCCACGGACG CGCGTTTTTTGGTTCGG/3C6/ (SEQ ID NO:280)

---

HDGFRP3
>hg19_dna range=chr15:83875827-83875946 5'pad=0 3'pad=0 strand=+ repeatMasking=none
CGTCGGGCCTGCGGGGGCCGGACCCGCCTTCGAAAGTGGGCGGAAGGATGGCCGCCCTGGCGGAGTGCGGGCGAG
GCCGGGAGCCCTTGCCTCAGCCCCGGCCCGGTCTTCTTCGTGCCG (SEQ ID NO:391)

CGTCGGGTTTGCGGGGGTCGGATTCGTTTTCGAAAGTGGGCGGAAGGATGGTCGTTTTGGCGGAGTGCGGGCGAG
GTCGGGAGTTTTTGTTTTAGTTTCGGTTCGGTTTTTTTCGTGTCG (SEQ ID NO:392)

HDGFRP3_FP GATTCGTTTTCGAAAGTGGGC (SEQ ID NO:229)
HDGFRP3_RP TAAAACAAAAACTCCCGACCTCG (SEQ ID NO:230)
HDGFRP3_Pb_A1 CGCGCCGAGG CGGAAGGATGGTCGTTTT/3C6/ (SEQ ID NO:281)

---

TACC2
>hg19_dna range=chr10:123922953-123923142 5'pad=0 3'pad=0 strand=- repeatMasking=none
CGGTGTGGTCCGAAAGGCTCTTCTCTTAAACCCCCCGGCAGCCGGCTCCTGTGTGTGACACGATGATGTCATCAT
CGCCGAGCAGCCCCAACGCCTGCATCTTCACAAAGCTCCATCGCGGGCTCCGGAAACGGGGCTGGGGGTGGGGAG
GCGAAGACCCTCCCTCTGCCCCGGCCCCTCCCGCCTCGCC (SEQ ID NO:393)

CGGTGTGGTTCGAAAGGTTTTTTTTTAAATTTTTCGGTAGTCGGTTTTTGTGTGTGATACGATGATGTTATTAT
CGTCGAGTAGTTTTAACGTTTGTATTTTTATAAAGTTTTATCGCGGGTTTCGGAAACGGGGTTGGGGGTGGGGAG
GCGAAGATTTTTTTTTGTTTCGGTTTTTTTCGTTTCGTT (SEQ ID NO:394)

TACC2_FP GTTTTTGTGTGTGATACGATGATGTTATTATC (SEQ ID NO:231)
TACC2_RP GTTTCCGAAACCCGCGA (SEQ ID NO:232)
TACC2_Pb_A5 AGGCCACGGACG CGTCGAGTAGTTTTAACGTTTG/3C6/ (SEQ ID NO:282)

---

FIG. 1 (CONT'D)

LBH

>hg19_dna range=chr2:30453651-30453973 5'pad=0 3'pad=0 strand=+
repeatMasking=none
CGGGCGTATGTGTGTCTCCAATGGAAAAATCCTACCCAGGACGACACCACATCCTTGCTCCCACAAATAAAACCT
TCCACGGAACTCAGGGCTGCAGACCAGCCCTTCGCAAGCCAACGCGCCCCGTGGGCACTCGGTCCCCCGGCTCCG
CGTCTCTGCCACCTTCCCACCGCTTCTTCTTTAACCATGCTCTTGTTTCCCCTCGCTGATCGCAAGGCTGCGGGC
GAGGATTCCAGAGAGAGGCCTAGTATGGGGAACAAACGCTTCAGAGGGGTCCGAGGTGGGCTGGGGACAGCCAGT
GGATGGGAAGGAGGGCGCTGGCG (SEQ ID NO:395)

CGGGCGTATGTGTGTTTTTAATGGAAAAATTTTATTTAGGACGATATTATATTTTTGTTTTTATAAATAAAATTT
TTTACGGAATTTAGGGTTGTAGATTAGTTTTTCGTAAGTTAACGCGTTTCGTGGGTATTCGGTTTTTCGGTTTCG
CGTTTTTGTTATTTTTTTATCGTTTTTTTTTAATTATGTTTTTGTTTTTTTTCGTTGATCGTAAGGTTGCGGGC
GAGGATTTTAGAGAGAGGTTTAGTATGGGGAATAAACGTTTTAGAGGGGTTCGAGGTGGGTTGGGGATAGTTAGT
GGATGGGAAGGAGGGCGTTGGCG (SEQ ID NO:396)

LBH plasmid sequence

TACGGAATTTAGGGTTGTAGATTAGTTTTTCGTAAGTTAACGCGTTTCGTGGGTATTCGGTTTTTCGGTTTCGCG

TTTTTGTTATTTTTTTATCGTTTTTTTTTAATTATGTTTTTGTTTTTTTTCGTTGATCGTAAGGTTGCGGGCGA

GGATTTTAGAGAGAGGTTTAGTATGGG (SEQ ID NO:397)

LBH_FP TAGTTTTTCGTAAGTTAACGCGTTTC (SEQ ID NO:233)

LBH_RP CCCGCAACCTTACGATCAAC (SEQ ID NO:234)

LBH_Pb_A1 CGCGCCGAGG CGTGGGTATTCGGTTTTTC/3C6/ (SEQ ID NO:283)

SEQUENCE LISTING

```
Sequence total quantity: 397
SEQ ID NO: 1           moltype = DNA  length = 26
FEATURE                Location/Qualifiers
source                 1..26
                       mol_type = other DNA
                       organism = Synthetic construct
SEQUENCE: 1
gaggagtttt aatattttta tagcgg                                          26

SEQ ID NO: 2           moltype = DNA  length = 25
FEATURE                Location/Qualifiers
source                 1..25
                       mol_type = other DNA
                       organism = Synthetic construct
SEQUENCE: 2
aacaaacttc aataaacccg acgca                                           25

SEQ ID NO: 3           moltype = DNA  length = 24
FEATURE                Location/Qualifiers
source                 1..24
                       mol_type = other DNA
                       organism = Synthetic construct
SEQUENCE: 3
ggcgacggcg aggaggagtt ttac                                            24

SEQ ID NO: 4           moltype = DNA  length = 23
FEATURE                Location/Qualifiers
source                 1..23
                       mol_type = other DNA
                       organism = Synthetic construct
SEQUENCE: 4
gcaacccttc gacgctaaac ccg                                             23

SEQ ID NO: 5           moltype = DNA  length = 25
FEATURE                Location/Qualifiers
source                 1..25
                       mol_type = other DNA
                       organism = Synthetic construct
SEQUENCE: 5
gatatgttgt cggggttcgt tacga                                           25

SEQ ID NO: 6           moltype = DNA  length = 25
FEATURE                Location/Qualifiers
source                 1..25
                       mol_type = other DNA
                       organism = Synthetic construct
SEQUENCE: 6
caaaataccc gataaaacaa tcgaa                                           25

SEQ ID NO: 7           moltype = DNA  length = 30
FEATURE                Location/Qualifiers
source                 1..30
                       mol_type = other DNA
```

```
                       organism = Synthetic construct
SEQUENCE: 7
cgttagtcgt ttttattttt aatttatcgt                                   30

SEQ ID NO: 8           moltype = DNA  length = 21
FEATURE                Location/Qualifiers
source                 1..21
                       mol_type = other DNA
                       organism = Synthetic construct
SEQUENCE: 8
cttcaaaaac tccaacgcgt c                                            21

SEQ ID NO: 9           moltype = DNA  length = 25
FEATURE                Location/Qualifiers
source                 1..25
                       mol_type = other DNA
                       organism = Synthetic construct
SEQUENCE: 9
gattagatta gattcggagt ttcgt                                        25

SEQ ID NO: 10          moltype = DNA  length = 25
FEATURE                Location/Qualifiers
source                 1..25
                       mol_type = other DNA
                       organism = Synthetic construct
SEQUENCE: 10
accaactaaa atcctcctcc cccgc                                        25

SEQ ID NO: 11          moltype = DNA  length = 27
FEATURE                Location/Qualifiers
source                 1..27
                       mol_type = other DNA
                       organism = Synthetic construct
SEQUENCE: 11
tagtttggtt aaagggtgcg aattcga                                      27

SEQ ID NO: 12          moltype = DNA  length = 33
FEATURE                Location/Qualifiers
source                 1..33
                       mol_type = other DNA
                       organism = Synthetic construct
SEQUENCE: 12
cgaaactctt ccgaactaaa taatacaccc gct                               33

SEQ ID NO: 13          moltype = DNA  length = 25
FEATURE                Location/Qualifiers
source                 1..25
                       mol_type = other DNA
                       organism = Synthetic construct
SEQUENCE: 13
tttgttggga gttcggggtt ttatc                                        25

SEQ ID NO: 14          moltype = DNA  length = 23
FEATURE                Location/Qualifiers
source                 1..23
                       mol_type = other DNA
                       organism = Synthetic construct
SEQUENCE: 14
aacctatccg aaacctcccc gtt                                          23

SEQ ID NO: 15          moltype = DNA  length = 26
FEATURE                Location/Qualifiers
source                 1..26
                       mol_type = other DNA
                       organism = Synthetic construct
SEQUENCE: 15
ttgcgtatag gttagtttag gatcgt                                       26

SEQ ID NO: 16          moltype = DNA  length = 24
FEATURE                Location/Qualifiers
source                 1..24
                       mol_type = other DNA
                       organism = Synthetic construct
SEQUENCE: 16
cttacacccg ccccgctaaa ttcg                                         24

SEQ ID NO: 17          moltype = DNA  length = 25
FEATURE                Location/Qualifiers
source                 1..25
```

```
                        mol_type = other DNA
                        organism = Synthetic construct
SEQUENCE: 17
tcgttggtta tcgtacgttt ttcgt                                          25

SEQ ID NO: 18           moltype = DNA  length = 25
FEATURE                 Location/Qualifiers
source                  1..25
                        mol_type = other DNA
                        organism = Synthetic construct
SEQUENCE: 18
actaaaccta tcccgaaatc ccgat                                          25

SEQ ID NO: 19           moltype = DNA  length = 28
FEATURE                 Location/Qualifiers
source                  1..28
                        mol_type = other DNA
                        organism = Synthetic construct
SEQUENCE: 19
ggttgttttt gtagtgttta taggacgg                                       28

SEQ ID NO: 20           moltype = DNA  length = 25
FEATURE                 Location/Qualifiers
source                  1..25
                        mol_type = other DNA
                        organism = Synthetic construct
SEQUENCE: 20
aaaacaaaat atactacccg ccgaa                                          25

SEQ ID NO: 21           moltype = DNA  length = 25
FEATURE                 Location/Qualifiers
source                  1..25
                        mol_type = other DNA
                        organism = Synthetic construct
SEQUENCE: 21
ggggaggagt ttttaatcgt ttcgt                                          25

SEQ ID NO: 22           moltype = DNA  length = 25
FEATURE                 Location/Qualifiers
source                  1..25
                        mol_type = other DNA
                        organism = Synthetic construct
SEQUENCE: 22
aaacaaccgc ttcgatttta acgac                                          25

SEQ ID NO: 23           moltype = DNA  length = 28
FEATURE                 Location/Qualifiers
source                  1..28
                        mol_type = other DNA
                        organism = Synthetic construct
SEQUENCE: 23
cggtagggga agtttagtag gtgagcgt                                       28

SEQ ID NO: 24           moltype = DNA  length = 27
FEATURE                 Location/Qualifiers
source                  1..27
                        mol_type = other DNA
                        organism = Synthetic construct
SEQUENCE: 24
gaactaaaaa cgtttccgtc gaacgca                                        27

SEQ ID NO: 25           moltype = DNA  length = 27
FEATURE                 Location/Qualifiers
source                  1..27
                        mol_type = other DNA
                        organism = Synthetic construct
SEQUENCE: 25
ggtagttagg cggttattac gggtcgc                                        27

SEQ ID NO: 26           moltype = DNA  length = 25
FEATURE                 Location/Qualifiers
source                  1..25
                        mol_type = other DNA
                        organism = Synthetic construct
SEQUENCE: 26
aaaatctact ccctccccga acgct                                          25

SEQ ID NO: 27           moltype = DNA  length = 23
FEATURE                 Location/Qualifiers
```

```
source                  1..23
                        mol_type = other DNA
                        organism = Synthetic construct
SEQUENCE: 27
cgcgcgtttt attgttgggt tgc                                          23

SEQ ID NO: 28           moltype = DNA  length = 24
FEATURE                 Location/Qualifiers
source                  1..24
                        mol_type = other DNA
                        organism = Synthetic construct
SEQUENCE: 28
aacgaactat taaactccct cgcc                                         24

SEQ ID NO: 29           moltype = DNA  length = 25
FEATURE                 Location/Qualifiers
source                  1..25
                        mol_type = other DNA
                        organism = Synthetic construct
SEQUENCE: 29
gttagtagtt gttggggcgg cgttc                                        25

SEQ ID NO: 30           moltype = DNA  length = 25
FEATURE                 Location/Qualifiers
source                  1..25
                        mol_type = other DNA
                        organism = Synthetic construct
SEQUENCE: 30
aacccgatac ccccattacc gtacg                                        25

SEQ ID NO: 31           moltype = DNA  length = 28
FEATURE                 Location/Qualifiers
source                  1..28
                        mol_type = other DNA
                        organism = Synthetic construct
SEQUENCE: 31
cgcgtagtag taggggtgag tagagggc                                     28

SEQ ID NO: 32           moltype = DNA  length = 28
FEATURE                 Location/Qualifiers
source                  1..28
                        mol_type = other DNA
                        organism = Synthetic construct
SEQUENCE: 32
gaatctaacc caaaaattaa cacgcgct                                     28

SEQ ID NO: 33           moltype = DNA  length = 25
FEATURE                 Location/Qualifiers
source                  1..25
                        mol_type = other DNA
                        organism = Synthetic construct
SEQUENCE: 33
cgggatcgga gttagaattt ttcgt                                        25

SEQ ID NO: 34           moltype = DNA  length = 23
FEATURE                 Location/Qualifiers
source                  1..23
                        mol_type = other DNA
                        organism = Synthetic construct
SEQUENCE: 34
acctaaacgc ctaacgaccc ccg                                          23

SEQ ID NO: 35           moltype = DNA  length = 24
FEATURE                 Location/Qualifiers
source                  1..24
                        mol_type = other DNA
                        organism = Synthetic construct
SEQUENCE: 35
tatttcgggg gagggttaag ggcg                                         24

SEQ ID NO: 36           moltype = DNA  length = 22
FEATURE                 Location/Qualifiers
source                  1..22
                        mol_type = other DNA
                        organism = Synthetic construct
SEQUENCE: 36
gctacgaatt cgcgaacccg aa                                           22

SEQ ID NO: 37           moltype = DNA  length = 30
```

```
FEATURE                Location/Qualifiers
source                 1..30
                       mol_type = other DNA
                       organism = Synthetic construct
SEQUENCE: 37
gggttgttta gaaagtgatt tttcgggagc                                      30

SEQ ID NO: 38          moltype = DNA  length = 25
FEATURE                Location/Qualifiers
source                 1..25
                       mol_type = other DNA
                       organism = Synthetic construct
SEQUENCE: 38
aaaaccgaaa caaaacgaaa acgca                                           25

SEQ ID NO: 39          moltype = DNA  length = 31
FEATURE                Location/Qualifiers
source                 1..31
                       mol_type = other DNA
                       organism = Synthetic construct
SEQUENCE: 39
tgttttttta ttttattttt agtttttttcg t                                   31

SEQ ID NO: 40          moltype = DNA  length = 33
FEATURE                Location/Qualifiers
source                 1..33
                       mol_type = other DNA
                       organism = Synthetic construct
SEQUENCE: 40
aatttctcat taccgacttt tcttccaacc gaa                                  33

SEQ ID NO: 41          moltype = DNA  length = 29
FEATURE                Location/Qualifiers
source                 1..29
                       mol_type = other DNA
                       organism = Synthetic construct
SEQUENCE: 41
ggcgcgtatt tggtttatga aagttacgg                                       29

SEQ ID NO: 42          moltype = DNA  length = 25
FEATURE                Location/Qualifiers
source                 1..25
                       mol_type = other DNA
                       organism = Synthetic construct
SEQUENCE: 42
caaacgacgc tacccctaca cacga                                           25

SEQ ID NO: 43          moltype = DNA  length = 33
FEATURE                Location/Qualifiers
source                 1..33
                       mol_type = other DNA
                       organism = Synthetic construct
SEQUENCE: 43
ggcgttagtt ttttatttat ttttaggggg cgc                                  33

SEQ ID NO: 44          moltype = DNA  length = 25
FEATURE                Location/Qualifiers
source                 1..25
                       mol_type = other DNA
                       organism = Synthetic construct
SEQUENCE: 44
ccaacccata cttctacccg ccgac                                           25

SEQ ID NO: 45          moltype = DNA  length = 25
FEATURE                Location/Qualifiers
source                 1..25
                       mol_type = other DNA
                       organism = Synthetic construct
SEQUENCE: 45
acgaaatatt tttaattgag ttcga                                           25

SEQ ID NO: 46          moltype = DNA  length = 25
FEATURE                Location/Qualifiers
source                 1..25
                       mol_type = other DNA
                       organism = Synthetic construct
SEQUENCE: 46
aaaaaatacg aaacacaaaa acgac                                           25
```

```
SEQ ID NO: 47          moltype = DNA  length = 25
FEATURE                Location/Qualifiers
source                 1..25
                       mol_type = other DNA
                       organism = Synthetic construct
SEQUENCE: 47
ttggcgtatt ataataagcg ttcga                                        25

SEQ ID NO: 48          moltype = DNA  length = 25
FEATURE                Location/Qualifiers
source                 1..25
                       mol_type = other DNA
                       organism = Synthetic construct
SEQUENCE: 48
gaaaaacaac aaacgcacga ccgtc                                        25

SEQ ID NO: 49          moltype = DNA  length = 32
FEATURE                Location/Qualifiers
source                 1..32
                       mol_type = other DNA
                       organism = Synthetic construct
SEQUENCE: 49
acgtagttga agatttttg ttagtttttc ga                                 32

SEQ ID NO: 50          moltype = DNA  length = 25
FEATURE                Location/Qualifiers
source                 1..25
                       mol_type = other DNA
                       organism = Synthetic construct
SEQUENCE: 50
acctcatacg ccgcttaaaa tcgcc                                        25

SEQ ID NO: 51          moltype = DNA  length = 25
FEATURE                Location/Qualifiers
source                 1..25
                       mol_type = other DNA
                       organism = Synthetic construct
SEQUENCE: 51
tagtagggtt gagtttgggg ttcgt                                        25

SEQ ID NO: 52          moltype = DNA  length = 24
FEATURE                Location/Qualifiers
source                 1..24
                       mol_type = other DNA
                       organism = Synthetic construct
SEQUENCE: 52
gtaaaatctc tacgcccgct cgaa                                         24

SEQ ID NO: 53          moltype = DNA  length = 23
FEATURE                Location/Qualifiers
source                 1..23
                       mol_type = other DNA
                       organism = Synthetic construct
SEQUENCE: 53
cgttcgagtt gcgaaaggga cgt                                          23

SEQ ID NO: 54          moltype = DNA  length = 23
FEATURE                Location/Qualifiers
source                 1..23
                       mol_type = other DNA
                       organism = Synthetic construct
SEQUENCE: 54
gcactcctaa aattccgcgc gaa                                          23

SEQ ID NO: 55          moltype = DNA  length = 31
FEATURE                Location/Qualifiers
source                 1..31
                       mol_type = other DNA
                       organism = Synthetic construct
SEQUENCE: 55
ggtaaaattt acgttgtgta gaattaggcg g                                 31

SEQ ID NO: 56          moltype = DNA  length = 25
FEATURE                Location/Qualifiers
source                 1..25
                       mol_type = other DNA
                       organism = Synthetic construct
SEQUENCE: 56
acgtaaaaat ccacgccgaa aacgc                                        25
```

```
SEQ ID NO: 57           moltype = DNA  length = 25
FEATURE                 Location/Qualifiers
source                  1..25
                        mol_type = other DNA
                        organism = Synthetic construct
SEQUENCE: 57
ttatttttgg attagcgatc gacga                                          25

SEQ ID NO: 58           moltype = DNA  length = 24
FEATURE                 Location/Qualifiers
source                  1..24
                        mol_type = other DNA
                        organism = Synthetic construct
SEQUENCE: 58
gcgctaacta ttctcgatta cgcc                                           24

SEQ ID NO: 59           moltype = DNA  length = 25
FEATURE                 Location/Qualifiers
source                  1..25
                        mol_type = other DNA
                        organism = Synthetic construct
SEQUENCE: 59
cgtttaggtt atcgttattt ttcgt                                          25

SEQ ID NO: 60           moltype = DNA  length = 22
FEATURE                 Location/Qualifiers
source                  1..22
                        mol_type = other DNA
                        organism = Synthetic construct
SEQUENCE: 60
gaaccgccga acatcctacg at                                             22

SEQ ID NO: 61           moltype = DNA  length = 30
FEATURE                 Location/Qualifiers
source                  1..30
                        mol_type = other DNA
                        organism = Synthetic construct
SEQUENCE: 61
gggggcggga gatattcgaa gttatttatc                                     30

SEQ ID NO: 62           moltype = DNA  length = 24
FEATURE                 Location/Qualifiers
source                  1..24
                        mol_type = other DNA
                        organism = Synthetic construct
SEQUENCE: 62
aaacgctatc gcccgaaaaa accg                                           24

SEQ ID NO: 63           moltype = DNA  length = 25
FEATURE                 Location/Qualifiers
source                  1..25
                        mol_type = other DNA
                        organism = Synthetic construct
SEQUENCE: 63
ttttgggtag gaaggatagt agcgt                                          25

SEQ ID NO: 64           moltype = DNA  length = 20
FEATURE                 Location/Qualifiers
source                  1..20
                        mol_type = other DNA
                        organism = Synthetic construct
SEQUENCE: 64
caaaaacgaa cgacgacgac                                                20

SEQ ID NO: 65           moltype = DNA  length = 23
FEATURE                 Location/Qualifiers
source                  1..23
                        mol_type = other DNA
                        organism = Synthetic construct
SEQUENCE: 65
gcgagtcggg gttttttgga gac                                            23

SEQ ID NO: 66           moltype = DNA  length = 24
FEATURE                 Location/Qualifiers
source                  1..24
                        mol_type = other DNA
                        organism = Synthetic construct
SEQUENCE: 66
```

```
cacccaccct acgtataccc gcgt                                            24

SEQ ID NO: 67           moltype = DNA  length = 20
FEATURE                 Location/Qualifiers
source                  1..20
                        mol_type = other DNA
                        organism = Synthetic construct
SEQUENCE: 67
gatttggcgc ggtttagcgc                                                 20

SEQ ID NO: 68           moltype = DNA  length = 26
FEATURE                 Location/Qualifiers
source                  1..26
                        mol_type = other DNA
                        organism = Synthetic construct
SEQUENCE: 68
ccctctcgca cccatttaaa aaaccg                                          26

SEQ ID NO: 69           moltype = DNA  length = 25
FEATURE                 Location/Qualifiers
source                  1..25
                        mol_type = other DNA
                        organism = Synthetic construct
SEQUENCE: 69
tgaatgttaa ttaagattgc gttcg                                           25

SEQ ID NO: 70           moltype = DNA  length = 23
FEATURE                 Location/Qualifiers
source                  1..23
                        mol_type = other DNA
                        organism = Synthetic construct
SEQUENCE: 70
aacaccctca cgaaaaaccc gcg                                             23

SEQ ID NO: 71           moltype = DNA  length = 27
FEATURE                 Location/Qualifiers
source                  1..27
                        mol_type = other DNA
                        organism = Synthetic construct
SEQUENCE: 71
ttgtagttgt tgttttttgg cggtcgc                                         27

SEQ ID NO: 72           moltype = DNA  length = 25
FEATURE                 Location/Qualifiers
source                  1..25
                        mol_type = other DNA
                        organism = Synthetic construct
SEQUENCE: 72
aaaccgaacg aatttcgctt tcccg                                           25

SEQ ID NO: 73           moltype = DNA  length = 25
FEATURE                 Location/Qualifiers
source                  1..25
                        mol_type = other DNA
                        organism = Synthetic construct
SEQUENCE: 73
tggcggcgtc gtatattttt tacgt                                           25

SEQ ID NO: 74           moltype = DNA  length = 20
FEATURE                 Location/Qualifiers
source                  1..20
                        mol_type = other DNA
                        organism = Synthetic construct
SEQUENCE: 74
accgctataa cgcccccgaa                                                 20

SEQ ID NO: 75           moltype = DNA  length = 25
FEATURE                 Location/Qualifiers
source                  1..25
                        mol_type = other DNA
                        organism = Synthetic construct
SEQUENCE: 75
tagttaaaga gtatattgga ggcgg                                           25

SEQ ID NO: 76           moltype = DNA  length = 25
FEATURE                 Location/Qualifiers
source                  1..25
                        mol_type = other DNA
                        organism = Synthetic construct
```

```
SEQUENCE: 76
ctctatccta aaaacgaaaa acgaa                                         25

SEQ ID NO: 77          moltype = DNA  length = 25
FEATURE                Location/Qualifiers
source                 1..25
                       mol_type = other DNA
                       organism = Synthetic construct
SEQUENCE: 77
aggggtagcg tgtgagtagt atcga                                         25

SEQ ID NO: 78          moltype = DNA  length = 25
FEATURE                Location/Qualifiers
source                 1..25
                       mol_type = other DNA
                       organism = Synthetic construct
SEQUENCE: 78
taccctttcc caaaataacg tcgaa                                         25

SEQ ID NO: 79          moltype = DNA  length = 25
FEATURE                Location/Qualifiers
source                 1..25
                       mol_type = other DNA
                       organism = Synthetic construct
SEQUENCE: 79
gttagttttc gcggtttttg ttcgg                                         25

SEQ ID NO: 80          moltype = DNA  length = 28
FEATURE                Location/Qualifiers
source                 1..28
                       mol_type = other DNA
                       organism = Synthetic construct
SEQUENCE: 80
cgccgtacta ttaaaacttc tcgtcgac                                      28

SEQ ID NO: 81          moltype = DNA  length = 25
FEATURE                Location/Qualifiers
source                 1..25
                       mol_type = other DNA
                       organism = Synthetic construct
SEQUENCE: 81
tttttggttg ggttaagttc ggcgc                                         25

SEQ ID NO: 82          moltype = DNA  length = 25
FEATURE                Location/Qualifiers
source                 1..25
                       mol_type = other DNA
                       organism = Synthetic construct
SEQUENCE: 82
gccttctcaa tcgcccctct acgaa                                         25

SEQ ID NO: 83          moltype = DNA  length = 25
FEATURE                Location/Qualifiers
source                 1..25
                       mol_type = other DNA
                       organism = Synthetic construct
SEQUENCE: 83
ttagtttcgt tttcggagtt cgcga                                         25

SEQ ID NO: 84          moltype = DNA  length = 34
FEATURE                Location/Qualifiers
source                 1..34
                       mol_type = other DNA
                       organism = Synthetic construct
SEQUENCE: 84
ctcctatata taacacgata atatcatcat cgcc                               34

SEQ ID NO: 85          moltype = DNA  length = 25
FEATURE                Location/Qualifiers
source                 1..25
                       mol_type = other DNA
                       organism = Synthetic construct
SEQUENCE: 85
tttttagttt ttttcgtttt cgcgg                                         25

SEQ ID NO: 86          moltype = DNA  length = 27
FEATURE                Location/Qualifiers
source                 1..27
                       mol_type = other DNA
```

```
                       organism = Synthetic construct
SEQUENCE: 86
acgacttcct ttatctctac tcccgcc                                            27

SEQ ID NO: 87          moltype = DNA  length = 25
FEATURE                Location/Qualifiers
source                 1..25
                       mol_type = other DNA
                       organism = Synthetic construct
SEQUENCE: 87
cggaaaatta gtaatattag ggcgt                                              25

SEQ ID NO: 88          moltype = DNA  length = 25
FEATURE                Location/Qualifiers
source                 1..25
                       mol_type = other DNA
                       organism = Synthetic construct
SEQUENCE: 88
cgaacccgac tcgtaaataa acgac                                              25

SEQ ID NO: 89          moltype = DNA  length = 22
FEATURE                Location/Qualifiers
source                 1..22
                       mol_type = other DNA
                       organism = Synthetic construct
SEQUENCE: 89
gtcgtacgta tcgggtggac ga                                                 22

SEQ ID NO: 90          moltype = DNA  length = 20
FEATURE                Location/Qualifiers
source                 1..20
                       mol_type = other DNA
                       organism = Synthetic construct
SEQUENCE: 90
ccctaactaa cgcgaacccg                                                    20

SEQ ID NO: 91          moltype = DNA  length = 25
FEATURE                Location/Qualifiers
source                 1..25
                       mol_type = other DNA
                       organism = Synthetic construct
SEQUENCE: 91
ggaggggcga atagagtttt tttcg                                              25

SEQ ID NO: 92          moltype = DNA  length = 24
FEATURE                Location/Qualifiers
source                 1..24
                       mol_type = other DNA
                       organism = Synthetic construct
SEQUENCE: 92
aaaacgaccc cttcctctct cgcc                                               24

SEQ ID NO: 93          moltype = DNA  length = 25
FEATURE                Location/Qualifiers
source                 1..25
                       mol_type = other DNA
                       organism = Synthetic construct
SEQUENCE: 93
tttggttagg aagtagcgga atcgg                                              25

SEQ ID NO: 94          moltype = DNA  length = 29
FEATURE                Location/Qualifiers
source                 1..29
                       mol_type = other DNA
                       organism = Synthetic construct
SEQUENCE: 94
gcaataacct aaactccaac atcaacgta                                          29

SEQ ID NO: 95          moltype = DNA  length = 25
FEATURE                Location/Qualifiers
source                 1..25
                       mol_type = other DNA
                       organism = Synthetic construct
SEQUENCE: 95
ataattttaa gggggaaacg ttcgt                                              25

SEQ ID NO: 96          moltype = DNA  length = 26
FEATURE                Location/Qualifiers
source                 1..26
```

```
                       mol_type = other DNA
                       organism = Synthetic construct
SEQUENCE: 96
ccaatataac cgacttctta aacgct                                           26

SEQ ID NO: 97          moltype = DNA  length = 25
FEATURE                Location/Qualifiers
source                 1..25
                       mol_type = other DNA
                       organism = Synthetic construct
SEQUENCE: 97
gattaattag gcggttcggt agcgg                                            25

SEQ ID NO: 98          moltype = DNA  length = 32
FEATURE                Location/Qualifiers
source                 1..32
                       mol_type = other DNA
                       organism = Synthetic construct
SEQUENCE: 98
caattaaaac ctatcattaa cttcccctcg ac                                    32

SEQ ID NO: 99          moltype = DNA  length = 28
FEATURE                Location/Qualifiers
source                 1..28
                       mol_type = other DNA
                       organism = Synthetic construct
SEQUENCE: 99
ggttgtaagg gtttttggtt ttcgacgc                                         28

SEQ ID NO: 100         moltype = DNA  length = 23
FEATURE                Location/Qualifiers
source                 1..23
                       mol_type = other DNA
                       organism = Synthetic construct
SEQUENCE: 100
aacgaattca tacgtccccc gaa                                              23

SEQ ID NO: 101         moltype = DNA  length = 28
FEATURE                Location/Qualifiers
source                 1..28
                       mol_type = other DNA
                       organism = Synthetic construct
SEQUENCE: 101
cgtttcgtta gtagttatcg attttcgt                                         28

SEQ ID NO: 102         moltype = DNA  length = 22
FEATURE                Location/Qualifiers
source                 1..22
                       mol_type = other DNA
                       organism = Synthetic construct
SEQUENCE: 102
aaacgaaccc cctccttcgc gt                                               22

SEQ ID NO: 103         moltype = DNA  length = 23
FEATURE                Location/Qualifiers
source                 1..23
                       mol_type = other DNA
                       organism = Synthetic construct
SEQUENCE: 103
gtttacgcgc gagagcgtgt tgc                                              23

SEQ ID NO: 104         moltype = DNA  length = 25
FEATURE                Location/Qualifiers
source                 1..25
                       mol_type = other DNA
                       organism = Synthetic construct
SEQUENCE: 104
gcccgaaccc gacctaatat tcgat                                            25

SEQ ID NO: 105         moltype = DNA  length = 34
FEATURE                Location/Qualifiers
source                 1..34
                       mol_type = other DNA
                       organism = Synthetic construct
SEQUENCE: 105
ggatgtttgt gtttttaatt taatttttga gttc                                  34

SEQ ID NO: 106         moltype = DNA  length = 25
FEATURE                Location/Qualifiers
```

```
source                  1..25
                        mol_type = other DNA
                        organism = Synthetic construct
SEQUENCE: 106
aaatactact accccgaacg acgct                                              25

SEQ ID NO: 107          moltype = DNA  length = 34
FEATURE                 Location/Qualifiers
source                  1..34
                        mol_type = other DNA
                        organism = Synthetic construct
SEQUENCE: 107
acatatacac acatatcctt ccttccccaa cgat                                    34

SEQ ID NO: 108          moltype = DNA  length = 25
FEATURE                 Location/Qualifiers
source                  1..25
                        mol_type = other DNA
                        organism = Synthetic construct
SEQUENCE: 108
ttttgtaaag ttttcgcggt tgcga                                              25

SEQ ID NO: 109          moltype = DNA  length = 25
FEATURE                 Location/Qualifiers
source                  1..25
                        mol_type = other DNA
                        organism = Synthetic construct
SEQUENCE: 109
tcgtcggtta cgttttttac gtgac                                              25

SEQ ID NO: 110          moltype = DNA  length = 20
FEATURE                 Location/Qualifiers
source                  1..20
                        mol_type = other DNA
                        organism = Synthetic construct
SEQUENCE: 110
cgaaaccgac tccaaacgct                                                    20

SEQ ID NO: 111          moltype = DNA  length = 24
FEATURE                 Location/Qualifiers
source                  1..24
                        mol_type = other DNA
                        organism = Synthetic construct
SEQUENCE: 111
gggtgtcgaa gtcggatttt acga                                               24

SEQ ID NO: 112          moltype = DNA  length = 27
FEATURE                 Location/Qualifiers
source                  1..27
                        mol_type = other DNA
                        organism = Synthetic construct
SEQUENCE: 112
aaccacaaaa aaacatttcc tccccgc                                            27

SEQ ID NO: 113          moltype = DNA  length = 27
FEATURE                 Location/Qualifiers
source                  1..27
                        mol_type = other DNA
                        organism = Synthetic construct
SEQUENCE: 113
gagtttcggc ggtttttcga aagtagc                                            27

SEQ ID NO: 114          moltype = DNA  length = 25
FEATURE                 Location/Qualifiers
source                  1..25
                        mol_type = other DNA
                        organism = Synthetic construct
SEQUENCE: 114
ccacgaacaa cgacactacg acgct                                              25

SEQ ID NO: 115          moltype = DNA  length = 25
FEATURE                 Location/Qualifiers
source                  1..25
                        mol_type = other DNA
                        organism = Synthetic construct
SEQUENCE: 115
tgtttttcg tttttggtcg tcggc                                               25

SEQ ID NO: 116          moltype = DNA  length = 24
```

```
FEATURE                Location/Qualifiers
source                 1..24
                       mol_type = other DNA
                       organism = Synthetic construct
SEQUENCE: 116
aaccccaaat tccctccata cgaa                                          24

SEQ ID NO: 117         moltype = DNA  length = 23
FEATURE                Location/Qualifiers
source                 1..23
                       mol_type = other DNA
                       organism = Synthetic construct
SEQUENCE: 117
gggaggcgtt taggaatcgt cgc                                           23

SEQ ID NO: 118         moltype = DNA  length = 21
FEATURE                Location/Qualifiers
source                 1..21
                       mol_type = other DNA
                       organism = Synthetic construct
SEQUENCE: 118
cctatatccc gaaaactcgc a                                             21

SEQ ID NO: 119         moltype = DNA  length = 25
FEATURE                Location/Qualifiers
source                 1..25
                       mol_type = other DNA
                       organism = Synthetic construct
SEQUENCE: 119
aggagtgttt gagtaggggt ttcgg                                         25

SEQ ID NO: 120         moltype = DNA  length = 25
FEATURE                Location/Qualifiers
source                 1..25
                       mol_type = other DNA
                       organism = Synthetic construct
SEQUENCE: 120
tttttcctct acaccgaatt acgaa                                         25

SEQ ID NO: 121         moltype = DNA  length = 25
FEATURE                Location/Qualifiers
source                 1..25
                       mol_type = other DNA
                       organism = Synthetic construct
SEQUENCE: 121
tagggttagt aggcggttta ggcgc                                         25

SEQ ID NO: 122         moltype = DNA  length = 29
FEATURE                Location/Qualifiers
source                 1..29
                       mol_type = other DNA
                       organism = Synthetic construct
SEQUENCE: 122
cgaactccaa ctttaaaaaa taccgcgta                                     29

SEQ ID NO: 123         moltype = DNA  length = 25
FEATURE                Location/Qualifiers
source                 1..25
                       mol_type = other DNA
                       organism = Synthetic construct
SEQUENCE: 123
gatttatttt cggcgagggg ttcgc                                         25

SEQ ID NO: 124         moltype = DNA  length = 27
FEATURE                Location/Qualifiers
source                 1..27
                       mol_type = other DNA
                       organism = Synthetic construct
SEQUENCE: 124
cgctttcccg ataaaaacga cgacgta                                       27

SEQ ID NO: 125         moltype = DNA  length = 28
FEATURE                Location/Qualifiers
source                 1..28
                       mol_type = other DNA
                       organism = Synthetic construct
SEQUENCE: 125
agtagtagtt gttggagtag aatcgcgt                                      28
```

```
SEQ ID NO: 126         moltype = DNA  length = 26
FEATURE                Location/Qualifiers
source                 1..26
                       mol_type = other DNA
                       organism = Synthetic construct
SEQUENCE: 126
gcccgaaacg ataaaaataa tcgcgc                                        26

SEQ ID NO: 127         moltype = DNA  length = 25
FEATURE                Location/Qualifiers
source                 1..25
                       mol_type = other DNA
                       organism = Synthetic construct
SEQUENCE: 127
ttttattttc gaggtcggaa atcgg                                         25

SEQ ID NO: 128         moltype = DNA  length = 25
FEATURE                Location/Qualifiers
source                 1..25
                       mol_type = other DNA
                       organism = Synthetic construct
SEQUENCE: 128
caaatcaaaa acgcgaacgc tctcg                                         25

SEQ ID NO: 129         moltype = DNA  length = 25
FEATURE                Location/Qualifiers
source                 1..25
                       mol_type = other DNA
                       organism = Synthetic construct
SEQUENCE: 129
ttagttgcgg gaagatagtg atcgg                                         25

SEQ ID NO: 130         moltype = DNA  length = 25
FEATURE                Location/Qualifiers
source                 1..25
                       mol_type = other DNA
                       organism = Synthetic construct
SEQUENCE: 130
aacgcctacc gaacaaatac ccgaa                                         25

SEQ ID NO: 131         moltype = DNA  length = 20
FEATURE                Location/Qualifiers
source                 1..20
                       mol_type = other DNA
                       organism = Synthetic construct
SEQUENCE: 131
tcgtgtttac gtggggacgg                                               20

SEQ ID NO: 132         moltype = DNA  length = 25
FEATURE                Location/Qualifiers
source                 1..25
                       mol_type = other DNA
                       organism = Synthetic construct
SEQUENCE: 132
cgcgaacaaa attaaacgaa tcgta                                         25

SEQ ID NO: 133         moltype = DNA  length = 26
FEATURE                Location/Qualifiers
source                 1..26
                       mol_type = other DNA
                       organism = Synthetic construct
SEQUENCE: 133
tagacgttag gagtgagggt cggggc                                        26

SEQ ID NO: 134         moltype = DNA  length = 29
FEATURE                Location/Qualifiers
source                 1..29
                       mol_type = other DNA
                       organism = Synthetic construct
SEQUENCE: 134
taaaacgaat acgaaaatcg cgaaacgaa                                     29

SEQ ID NO: 135         moltype = DNA  length = 25
FEATURE                Location/Qualifiers
source                 1..25
                       mol_type = other DNA
                       organism = Synthetic construct
SEQUENCE: 135
tttaggtggg tagtcgcgta ttcgg                                         25
```

```
SEQ ID NO: 136         moltype = DNA  length = 25
FEATURE                Location/Qualifiers
source                 1..25
                       mol_type = other DNA
                       organism = Synthetic construct
SEQUENCE: 136
ctaacgataa cccgtaatct ccgca                                           25

SEQ ID NO: 137         moltype = DNA  length = 22
FEATURE                Location/Qualifiers
source                 1..22
                       mol_type = other DNA
                       organism = Synthetic construct
SEQUENCE: 137
gcggtttttc gagtttttg cg                                               22

SEQ ID NO: 138         moltype = DNA  length = 15
FEATURE                Location/Qualifiers
source                 1..15
                       mol_type = other DNA
                       organism = Synthetic construct
SEQUENCE: 138
gaacgaatcc gcgcc                                                      15

SEQ ID NO: 139         moltype = DNA  length = 20
FEATURE                Location/Qualifiers
source                 1..20
                       mol_type = other DNA
                       organism = Synthetic construct
SEQUENCE: 139
gcggtgtggt taagtttcgg                                                 20

SEQ ID NO: 140         moltype = DNA  length = 17
FEATURE                Location/Qualifiers
source                 1..17
                       mol_type = other DNA
                       organism = Synthetic construct
SEQUENCE: 140
cgcgacccca aatcgta                                                    17

SEQ ID NO: 141         moltype = DNA  length = 30
FEATURE                Location/Qualifiers
source                 1..30
                       mol_type = other DNA
                       organism = Synthetic construct
SEQUENCE: 141
cgggttttat tttttttcg ttttcgtttc                                       30

SEQ ID NO: 142         moltype = DNA  length = 19
FEATURE                Location/Qualifiers
source                 1..19
                       mol_type = other DNA
                       organism = Synthetic construct
SEQUENCE: 142
aacgaaatcc caccgaacg                                                  19

SEQ ID NO: 143         moltype = DNA  length = 18
FEATURE                Location/Qualifiers
source                 1..18
                       mol_type = other DNA
                       organism = Synthetic construct
SEQUENCE: 143
gtagagcgtt tcgacgcg                                                   18

SEQ ID NO: 144         moltype = DNA  length = 20
FEATURE                Location/Qualifiers
source                 1..20
                       mol_type = other DNA
                       organism = Synthetic construct
SEQUENCE: 144
tcgaacgaaa ataaccgccg                                                 20

SEQ ID NO: 145         moltype = DNA  length = 23
FEATURE                Location/Qualifiers
source                 1..23
                       mol_type = other DNA
                       organism = Synthetic construct
SEQUENCE: 145
```

```
gtttttagtt aggcgcggat ttc                                               23

SEQ ID NO: 146         moltype = DNA  length = 18
FEATURE                Location/Qualifiers
source                 1..18
                       mol_type = other DNA
                       organism = Synthetic construct
SEQUENCE: 146
aacccgtaaa ccaaccgc                                                     18

SEQ ID NO: 147         moltype = DNA  length = 22
FEATURE                Location/Qualifiers
source                 1..22
                       mol_type = other DNA
                       organism = Synthetic construct
SEQUENCE: 147
tggtcgtttt agcgttatgt cg                                                22

SEQ ID NO: 148         moltype = DNA  length = 19
FEATURE                Location/Qualifiers
source                 1..19
                       mol_type = other DNA
                       organism = Synthetic construct
SEQUENCE: 148
cgaaaactac aaaccgcgc                                                    19

SEQ ID NO: 149         moltype = DNA  length = 16
FEATURE                Location/Qualifiers
source                 1..16
                       mol_type = other DNA
                       organism = Synthetic construct
SEQUENCE: 149
cggttatgtc gggcgg                                                       16

SEQ ID NO: 150         moltype = DNA  length = 19
FEATURE                Location/Qualifiers
source                 1..19
                       mol_type = other DNA
                       organism = Synthetic construct
SEQUENCE: 150
caacgacgat acccacacg                                                    19

SEQ ID NO: 151         moltype = DNA  length = 25
FEATURE                Location/Qualifiers
source                 1..25
                       mol_type = other DNA
                       organism = Synthetic construct
SEQUENCE: 151
tcgtttttc gtcgttttcg ttttc                                              25

SEQ ID NO: 152         moltype = DNA  length = 17
FEATURE                Location/Qualifiers
source                 1..17
                       mol_type = other DNA
                       organism = Synthetic construct
SEQUENCE: 152
cccgtacgaa aacccga                                                      17

SEQ ID NO: 153         moltype = DNA  length = 22
FEATURE                Location/Qualifiers
source                 1..22
                       mol_type = other DNA
                       organism = Synthetic construct
SEQUENCE: 153
gttcgttatg cgcgtttgtt tc                                                22

SEQ ID NO: 154         moltype = DNA  length = 20
FEATURE                Location/Qualifiers
source                 1..20
                       mol_type = other DNA
                       organism = Synthetic construct
SEQUENCE: 154
gaacacccga aaaccaacga                                                   20

SEQ ID NO: 155         moltype = DNA  length = 22
FEATURE                Location/Qualifiers
source                 1..22
                       mol_type = other DNA
                       organism = Synthetic construct
```

```
SEQUENCE: 155
gttttgtggt ttcgttcggt tc                                            22

SEQ ID NO: 156          moltype = DNA  length = 21
FEATURE                 Location/Qualifiers
source                  1..21
                        mol_type = other DNA
                        organism = Synthetic construct
SEQUENCE: 156
ccgattaaac ccgtacttcg c                                             21

SEQ ID NO: 157          moltype = DNA  length = 29
FEATURE                 Location/Qualifiers
source                  1..29
                        mol_type = other DNA
                        organism = Synthetic construct
SEQUENCE: 157
tttcgttttt gtatttattt tagcgacgt                                     29

SEQ ID NO: 158          moltype = DNA  length = 22
FEATURE                 Location/Qualifiers
source                  1..22
                        mol_type = other DNA
                        organism = Synthetic construct
SEQUENCE: 158
acgcgaaaaa aacgcgaaaa cg                                            22

SEQ ID NO: 159          moltype = DNA  length = 21
FEATURE                 Location/Qualifiers
source                  1..21
                        mol_type = other DNA
                        organism = Synthetic construct
SEQUENCE: 159
gttaggcggt tattacgggt c                                             21

SEQ ID NO: 160          moltype = DNA  length = 20
FEATURE                 Location/Qualifiers
source                  1..20
                        mol_type = other DNA
                        organism = Synthetic construct
SEQUENCE: 160
gaaatctact ccctccccga                                               20

SEQ ID NO: 161          moltype = DNA  length = 31
FEATURE                 Location/Qualifiers
source                  1..31
                        mol_type = other DNA
                        organism = Synthetic construct
SEQUENCE: 161
tatgttgttt ttttttcgta aagtttacgg t                                  31

SEQ ID NO: 162          moltype = DNA  length = 26
FEATURE                 Location/Qualifiers
source                  1..26
                        mol_type = other DNA
                        organism = Synthetic construct
SEQUENCE: 162
ccgacaataa aaataacatc gactcg                                        26

SEQ ID NO: 163          moltype = DNA  length = 22
FEATURE                 Location/Qualifiers
source                  1..22
                        mol_type = other DNA
                        organism = Synthetic construct
SEQUENCE: 163
tcgttcgcgt tttagtattc gg                                            22

SEQ ID NO: 164          moltype = DNA  length = 20
FEATURE                 Location/Qualifiers
source                  1..20
                        mol_type = other DNA
                        organism = Synthetic construct
SEQUENCE: 164
cgaaaaaaac gctcctcccg                                               20

SEQ ID NO: 165          moltype = DNA  length = 17
FEATURE                 Location/Qualifiers
source                  1..17
                        mol_type = other DNA
```

```
                        organism = Synthetic construct
SEQUENCE: 165
gttcgttcgg tagcggc                                          17

SEQ ID NO: 166          moltype = DNA  length = 22
FEATURE                 Location/Qualifiers
source                  1..22
                        mol_type = other DNA
                        organism = Synthetic construct
SEQUENCE: 166
accacttcgc tacgaaaaaa cg                                    22

SEQ ID NO: 167          moltype = DNA  length = 20
FEATURE                 Location/Qualifiers
source                  1..20
                        mol_type = other DNA
                        organism = Synthetic construct
SEQUENCE: 167
tagtcgtaat agggcggtcg                                       20

SEQ ID NO: 168          moltype = DNA  length = 20
FEATURE                 Location/Qualifiers
source                  1..20
                        mol_type = other DNA
                        organism = Synthetic construct
SEQUENCE: 168
ccgaaacgac ccgttaatcg                                       20

SEQ ID NO: 169          moltype = DNA  length = 26
FEATURE                 Location/Qualifiers
source                  1..26
                        mol_type = other DNA
                        organism = Synthetic construct
SEQUENCE: 169
tgatttaggt gtcgtttttt ttcgtc                                26

SEQ ID NO: 170          moltype = DNA  length = 20
FEATURE                 Location/Qualifiers
source                  1..20
                        mol_type = other DNA
                        organism = Synthetic construct
SEQUENCE: 170
gaaaaaaaat cgcgctcccg                                       20

SEQ ID NO: 171          moltype = DNA  length = 21
FEATURE                 Location/Qualifiers
source                  1..21
                        mol_type = other DNA
                        organism = Synthetic construct
SEQUENCE: 171
atttattgga ggtcgcggtt c                                     21

SEQ ID NO: 172          moltype = DNA  length = 20
FEATURE                 Location/Qualifiers
source                  1..20
                        mol_type = other DNA
                        organism = Synthetic construct
SEQUENCE: 172
ccgaaacacc aaaacgtccg                                       20

SEQ ID NO: 173          moltype = DNA  length = 20
FEATURE                 Location/Qualifiers
source                  1..20
                        mol_type = other DNA
                        organism = Synthetic construct
SEQUENCE: 173
gtgtttttgg tggtttcggc                                       20

SEQ ID NO: 174          moltype = DNA  length = 30
FEATURE                 Location/Qualifiers
source                  1..30
                        mol_type = other DNA
                        organism = Synthetic construct
SEQUENCE: 174
atactaaacg tataaaaaca aacataccgc                            30

SEQ ID NO: 175          moltype = DNA  length = 26
FEATURE                 Location/Qualifiers
source                  1..26
```

```
                        mol_type = other DNA
                        organism = Synthetic construct
SEQUENCE: 175
ggttcgtaag atttagtagt tcgagc                                              26

SEQ ID NO: 176          moltype = DNA  length = 29
FEATURE                 Location/Qualifiers
source                  1..29
                        mol_type = other DNA
                        organism = Synthetic construct
SEQUENCE: 176
cgaaacaaaa aaatcaatat aatcgacgc                                           29

SEQ ID NO: 177          moltype = DNA  length = 21
FEATURE                 Location/Qualifiers
source                  1..21
                        mol_type = other DNA
                        organism = Synthetic construct
SEQUENCE: 177
taggacgtcg cggtttattt c                                                   21

SEQ ID NO: 178          moltype = DNA  length = 21
FEATURE                 Location/Qualifiers
source                  1..21
                        mol_type = other DNA
                        organism = Synthetic construct
SEQUENCE: 178
cgcaatactc gaaaaacgac g                                                   21

SEQ ID NO: 179          moltype = DNA  length = 16
FEATURE                 Location/Qualifiers
source                  1..16
                        mol_type = other DNA
                        organism = Synthetic construct
SEQUENCE: 179
tcgcgtcgtc gttcgt                                                         16

SEQ ID NO: 180          moltype = DNA  length = 20
FEATURE                 Location/Qualifiers
source                  1..20
                        mol_type = other DNA
                        organism = Synthetic construct
SEQUENCE: 180
gacgccatct aaaaacgcga                                                     20

SEQ ID NO: 181          moltype = DNA  length = 17
FEATURE                 Location/Qualifiers
source                  1..17
                        mol_type = other DNA
                        organism = Synthetic construct
SEQUENCE: 181
ggcgacgtgg acgatac                                                        17

SEQ ID NO: 182          moltype = DNA  length = 24
FEATURE                 Location/Qualifiers
source                  1..24
                        mol_type = other DNA
                        organism = Synthetic construct
SEQUENCE: 182
ctaaaactcg taacgtcgct atcg                                                24

SEQ ID NO: 183          moltype = DNA  length = 22
FEATURE                 Location/Qualifiers
source                  1..22
                        mol_type = other DNA
                        organism = Synthetic construct
SEQUENCE: 183
ggtttgtgag tgatatcggt cg                                                  22

SEQ ID NO: 184          moltype = DNA  length = 24
FEATURE                 Location/Qualifiers
source                  1..24
                        mol_type = other DNA
                        organism = Synthetic construct
SEQUENCE: 184
cgaacccaaa aactcgaaaa aacc                                                24

SEQ ID NO: 185          moltype = DNA  length = 24
FEATURE                 Location/Qualifiers
```

```
source                 1..24
                       mol_type = other DNA
                       organism = Synthetic construct
SEQUENCE: 185
gggtttagta gtatttcgaa ggcg                                          24

SEQ ID NO: 186         moltype = DNA  length = 26
FEATURE                Location/Qualifiers
source                 1..26
                       mol_type = other DNA
                       organism = Synthetic construct
SEQUENCE: 186
gaaaaattca aaataccgct cctcac                                        26

SEQ ID NO: 187         moltype = DNA  length = 25
FEATURE                Location/Qualifiers
source                 1..25
                       mol_type = other DNA
                       organism = Synthetic construct
SEQUENCE: 187
gaaggttacg aggtgtttaa gttcg                                         25

SEQ ID NO: 188         moltype = DNA  length = 39
FEATURE                Location/Qualifiers
source                 1..39
                       mol_type = other DNA
                       organism = Synthetic construct
SEQUENCE: 188
aacaaataaa cttaccgata ataaaatcgt aataatttc                          39

SEQ ID NO: 189         moltype = DNA  length = 16
FEATURE                Location/Qualifiers
source                 1..16
                       mol_type = other DNA
                       organism = Synthetic construct
SEQUENCE: 189
ttgcggagga cgttgc                                                   16

SEQ ID NO: 190         moltype = DNA  length = 21
FEATURE                Location/Qualifiers
source                 1..21
                       mol_type = other DNA
                       organism = Synthetic construct
SEQUENCE: 190
gaaaaaaaac gatacgccgc c                                             21

SEQ ID NO: 191         moltype = DNA  length = 22
FEATURE                Location/Qualifiers
source                 1..22
                       mol_type = other DNA
                       organism = Synthetic construct
SEQUENCE: 191
tttcgatttc gtagtttcgc gg                                            22

SEQ ID NO: 192         moltype = DNA  length = 21
FEATURE                Location/Qualifiers
source                 1..21
                       mol_type = other DNA
                       organism = Synthetic construct
SEQUENCE: 192
ctcgcgaaac gtaacgaaaa c                                             21

SEQ ID NO: 193         moltype = DNA  length = 21
FEATURE                Location/Qualifiers
source                 1..21
                       mol_type = other DNA
                       organism = Synthetic construct
SEQUENCE: 193
cgttcgtttt cgttcggttt c                                             21

SEQ ID NO: 194         moltype = DNA  length = 19
FEATURE                Location/Qualifiers
source                 1..19
                       mol_type = other DNA
                       organism = Synthetic construct
SEQUENCE: 194
acctaacgcc gaaacaacg                                                19

SEQ ID NO: 195         moltype = DNA  length = 26
```

```
FEATURE                Location/Qualifiers
source                 1..26
                       mol_type = other DNA
                       organism = Synthetic construct
SEQUENCE: 195
gttgtttttt ttatcgtttc ggagtg                                            26

SEQ ID NO: 196         moltype = DNA  length = 18
FEATURE                Location/Qualifiers
source                 1..18
                       mol_type = other DNA
                       organism = Synthetic construct
SEQUENCE: 196
cctctaccca ccgtaccg                                                     18

SEQ ID NO: 197         moltype = DNA  length = 28
FEATURE                Location/Qualifiers
source                 1..28
                       mol_type = other DNA
                       organism = Synthetic construct
SEQUENCE: 197
gttttcgggt tatttttatt tgaagtcg                                          28

SEQ ID NO: 198         moltype = DNA  length = 17
FEATURE                Location/Qualifiers
source                 1..17
                       mol_type = other DNA
                       organism = Synthetic construct
SEQUENCE: 198
tcccctacca cccaacg                                                      17

SEQ ID NO: 199         moltype = DNA  length = 22
FEATURE                Location/Qualifiers
source                 1..22
                       mol_type = other DNA
                       organism = Synthetic construct
SEQUENCE: 199
gggtttaata tttgttgcgc gg                                                22

SEQ ID NO: 200         moltype = DNA  length = 19
FEATURE                Location/Qualifiers
source                 1..19
                       mol_type = other DNA
                       organism = Synthetic construct
SEQUENCE: 200
cgaagcgttg cgttgttag                                                    19

SEQ ID NO: 201         moltype = DNA  length = 17
FEATURE                Location/Qualifiers
source                 1..17
                       mol_type = other DNA
                       organism = Synthetic construct
SEQUENCE: 201
ttggcgaggg ttcgagt                                                      17

SEQ ID NO: 202         moltype = DNA  length = 24
FEATURE                Location/Qualifiers
source                 1..24
                       mol_type = other DNA
                       organism = Synthetic construct
SEQUENCE: 202
ctaatcgcaa aaccgaaaaa aacg                                              24

SEQ ID NO: 203         moltype = DNA  length = 19
FEATURE                Location/Qualifiers
source                 1..19
                       mol_type = other DNA
                       organism = Synthetic construct
SEQUENCE: 203
gagaggaaat cgcgaagcg                                                    19

SEQ ID NO: 204         moltype = DNA  length = 19
FEATURE                Location/Qualifiers
source                 1..19
                       mol_type = other DNA
                       organism = Synthetic construct
SEQUENCE: 204
cccctaaaaa aacgcgcga                                                    19
```

```
SEQ ID NO: 205          moltype = DNA  length = 22
FEATURE                 Location/Qualifiers
source                  1..22
                        mol_type = other DNA
                        organism = Synthetic construct
SEQUENCE: 205
gacgtttatt tggacgtttg gc                                              22

SEQ ID NO: 206          moltype = DNA  length = 20
FEATURE                 Location/Qualifiers
source                  1..20
                        mol_type = other DNA
                        organism = Synthetic construct
SEQUENCE: 206
accgaaatca aaaccctccg                                                 20

SEQ ID NO: 207          moltype = DNA  length = 22
FEATURE                 Location/Qualifiers
source                  1..22
                        mol_type = other DNA
                        organism = Synthetic construct
SEQUENCE: 207
gtttcgcgac gtttatttgg ac                                              22

SEQ ID NO: 208          moltype = DNA  length = 20
FEATURE                 Location/Qualifiers
source                  1..20
                        mol_type = other DNA
                        organism = Synthetic construct
SEQUENCE: 208
accgaaatca aaaccctccg                                                 20

SEQ ID NO: 209          moltype = DNA  length = 20
FEATURE                 Location/Qualifiers
source                  1..20
                        mol_type = other DNA
                        organism = Synthetic construct
SEQUENCE: 209
gcgcggaatt ttaggagtgc                                                 20

SEQ ID NO: 210          moltype = DNA  length = 18
FEATURE                 Location/Qualifiers
source                  1..18
                        mol_type = other DNA
                        organism = Synthetic construct
SEQUENCE: 210
cgcgacccca cgataatc                                                   18

SEQ ID NO: 211          moltype = DNA  length = 20
FEATURE                 Location/Qualifiers
source                  1..20
                        mol_type = other DNA
                        organism = Synthetic construct
SEQUENCE: 211
gttttcgagg gagtgcgttc                                                 20

SEQ ID NO: 212          moltype = DNA  length = 23
FEATURE                 Location/Qualifiers
source                  1..23
                        mol_type = other DNA
                        organism = Synthetic construct
SEQUENCE: 212
cgaaaaaaaa aaacgaaacc cgc                                             23

SEQ ID NO: 213          moltype = DNA  length = 21
FEATURE                 Location/Qualifiers
source                  1..21
                        mol_type = other DNA
                        organism = Synthetic construct
SEQUENCE: 213
ggtgttgaag agtagtcgcg t                                               21

SEQ ID NO: 214          moltype = DNA  length = 18
FEATURE                 Location/Qualifiers
source                  1..18
                        mol_type = other DNA
                        organism = Synthetic construct
SEQUENCE: 214
cgacgcaaaa aacgacgc                                                   18
```

```
SEQ ID NO: 215          moltype = DNA  length = 21
FEATURE                 Location/Qualifiers
source                  1..21
                        mol_type = other DNA
                        organism = Synthetic construct
SEQUENCE: 215
cgaaacgtaa ggatgtcgtc g                                             21

SEQ ID NO: 216          moltype = DNA  length = 27
FEATURE                 Location/Qualifiers
source                  1..27
                        mol_type = other DNA
                        organism = Synthetic construct
SEQUENCE: 216
aatttatata tacaccgcgt ctccaac                                       27

SEQ ID NO: 217          moltype = DNA  length = 22
FEATURE                 Location/Qualifiers
source                  1..22
                        mol_type = other DNA
                        organism = Synthetic construct
SEQUENCE: 217
tgttttgttc ggtgaggttt cg                                            22

SEQ ID NO: 218          moltype = DNA  length = 19
FEATURE                 Location/Qualifiers
source                  1..19
                        mol_type = other DNA
                        organism = Synthetic construct
SEQUENCE: 218
caaaccgcca cctaatcgc                                                19

SEQ ID NO: 219          moltype = DNA  length = 18
FEATURE                 Location/Qualifiers
source                  1..18
                        mol_type = other DNA
                        organism = Synthetic construct
SEQUENCE: 219
aaagggagtt ttcgggcg                                                 18

SEQ ID NO: 220          moltype = DNA  length = 19
FEATURE                 Location/Qualifiers
source                  1..19
                        mol_type = other DNA
                        organism = Synthetic construct
SEQUENCE: 220
acccgatacc cccattacc                                                19

SEQ ID NO: 221          moltype = DNA  length = 30
FEATURE                 Location/Qualifiers
source                  1..30
                        mol_type = other DNA
                        organism = Synthetic construct
SEQUENCE: 221
ggtggttaag aaagtcgtaa gaaaatttcg                                    30

SEQ ID NO: 222          moltype = DNA  length = 23
FEATURE                 Location/Qualifiers
source                  1..23
                        mol_type = other DNA
                        organism = Synthetic construct
SEQUENCE: 222
tctaaacaac aaaaaccccg acc                                           23

SEQ ID NO: 223          moltype = DNA  length = 20
FEATURE                 Location/Qualifiers
source                  1..20
                        mol_type = other DNA
                        organism = Synthetic construct
SEQUENCE: 223
ggatggtttc ggttgggttc                                               20

SEQ ID NO: 224          moltype = DNA  length = 21
FEATURE                 Location/Qualifiers
source                  1..21
                        mol_type = other DNA
                        organism = Synthetic construct
SEQUENCE: 224
```

```
gcaaaacgcc aacaaaaaac g                                              21

SEQ ID NO: 225         moltype = DNA  length = 23
FEATURE                Location/Qualifiers
source                 1..23
                       mol_type = other DNA
                       organism = Synthetic construct
SEQUENCE: 225
ggtcgaggga attagagttt tcg                                            23

SEQ ID NO: 226         moltype = DNA  length = 20
FEATURE                Location/Qualifiers
source                 1..20
                       mol_type = other DNA
                       organism = Synthetic construct
SEQUENCE: 226
aacctaaccc gccaaaacac                                                20

SEQ ID NO: 227         moltype = DNA  length = 23
FEATURE                Location/Qualifiers
source                 1..23
                       mol_type = other DNA
                       organism = Synthetic construct
SEQUENCE: 227
gggatcggtt cgtttattcg ttc                                            23

SEQ ID NO: 228         moltype = DNA  length = 18
FEATURE                Location/Qualifiers
source                 1..18
                       mol_type = other DNA
                       organism = Synthetic construct
SEQUENCE: 228
cccgaaacat cttccgcg                                                  18

SEQ ID NO: 229         moltype = DNA  length = 21
FEATURE                Location/Qualifiers
source                 1..21
                       mol_type = other DNA
                       organism = Synthetic construct
SEQUENCE: 229
gattcgtttt cgaaagtggg c                                              21

SEQ ID NO: 230         moltype = DNA  length = 23
FEATURE                Location/Qualifiers
source                 1..23
                       mol_type = other DNA
                       organism = Synthetic construct
SEQUENCE: 230
taaaacaaaa actcccgacc tcg                                            23

SEQ ID NO: 231         moltype = DNA  length = 32
FEATURE                Location/Qualifiers
source                 1..32
                       mol_type = other DNA
                       organism = Synthetic construct
SEQUENCE: 231
gtttttgtgt gtgatacgat gatgttatta tc                                  32

SEQ ID NO: 232         moltype = DNA  length = 17
FEATURE                Location/Qualifiers
source                 1..17
                       mol_type = other DNA
                       organism = Synthetic construct
SEQUENCE: 232
gtttccgaaa cccgcga                                                   17

SEQ ID NO: 233         moltype = DNA  length = 26
FEATURE                Location/Qualifiers
source                 1..26
                       mol_type = other DNA
                       organism = Synthetic construct
SEQUENCE: 233
tagtttttcg taagttaacg cgtttc                                         26

SEQ ID NO: 234         moltype = DNA  length = 20
FEATURE                Location/Qualifiers
source                 1..20
                       mol_type = other DNA
                       organism = Synthetic construct
```

```
SEQUENCE: 234
cccgcaacct tacgatcaac                                        20

SEQ ID NO: 235          moltype = DNA  length = 33
FEATURE                 Location/Qualifiers
source                  1..33
                        mol_type = other DNA
                        organism = Synthetic construct
SEQUENCE: 235
aggccacgga cgggcgattt cgatttattt tcg                         33

SEQ ID NO: 236          moltype = DNA  length = 28
FEATURE                 Location/Qualifiers
source                  1..28
                        mol_type = other DNA
                        organism = Synthetic construct
SEQUENCE: 236
cgcgccgagg gcgtacggtt tatagggc                               28

SEQ ID NO: 237          moltype = DNA  length = 27
FEATURE                 Location/Qualifiers
source                  1..27
                        mol_type = other DNA
                        organism = Synthetic construct
SEQUENCE: 237
cgcgccgagg cggttttaag tcgcgga                                27

SEQ ID NO: 238          moltype = DNA  length = 32
FEATURE                 Location/Qualifiers
source                  1..32
                        mol_type = other DNA
                        organism = Synthetic construct
SEQUENCE: 238
aggccacgga cggcgctcga caaaataaaa ac                          32

SEQ ID NO: 239          moltype = DNA  length = 28
FEATURE                 Location/Qualifiers
source                  1..28
                        mol_type = other DNA
                        organism = Synthetic construct
SEQUENCE: 239
cgcgccgagg cgttcggatt cgattcgt                               28

SEQ ID NO: 240          moltype = DNA  length = 26
FEATURE                 Location/Qualifiers
source                  1..26
                        mol_type = other DNA
                        organism = Synthetic construct
SEQUENCE: 240
aggccacgga cgccgcgcta ccgcta                                 26

SEQ ID NO: 241          moltype = DNA  length = 30
FEATURE                 Location/Qualifiers
source                  1..30
                        mol_type = other DNA
                        organism = Synthetic construct
SEQUENCE: 241
cgcgccgagg gctaataaac cacgactacg                             30

SEQ ID NO: 242          moltype = DNA  length = 32
FEATURE                 Location/Qualifiers
source                  1..32
                        mol_type = other DNA
                        organism = Synthetic construct
SEQUENCE: 242
aggccacgga cgcgagtcga gtttatcgtt tg                          32

SEQ ID NO: 243          moltype = DNA  length = 28
FEATURE                 Location/Qualifiers
source                  1..28
                        mol_type = other DNA
                        organism = Synthetic construct
SEQUENCE: 243
cgcgccgagg cgggcgtttt tgtttagg                               28

SEQ ID NO: 244          moltype = DNA  length = 32
FEATURE                 Location/Qualifiers
source                  1..32
                        mol_type = other DNA
```

```
                        organism = Synthetic construct
SEQUENCE: 244
aggccacgga cgcgcgtttg ttagcgttta aa                             32

SEQ ID NO: 245          moltype = DNA  length = 32
FEATURE                 Location/Qualifiers
source                  1..32
                        mol_type = other DNA
                        organism = Synthetic construct
SEQUENCE: 245
cgcgccgagg gcgaaataaa taacaacgac ga                             32

SEQ ID NO: 246          moltype = DNA  length = 36
FEATURE                 Location/Qualifiers
source                  1..36
                        mol_type = other DNA
                        organism = Synthetic construct
SEQUENCE: 246
aggccacgga cgcgcgtttt ttattagtta gtcgtt                         36

SEQ ID NO: 247          moltype = DNA  length = 28
FEATURE                 Location/Qualifiers
source                  1..28
                        mol_type = other DNA
                        organism = Synthetic construct
SEQUENCE: 247
cgcgccgagg gcgcgatacc ctctattc                                  28

SEQ ID NO: 248          moltype = DNA  length = 27
FEATURE                 Location/Qualifiers
source                  1..27
                        mol_type = other DNA
                        organism = Synthetic construct
SEQUENCE: 248
aggccacgga cggccgatct tcgcctt                                   27

SEQ ID NO: 249          moltype = DNA  length = 33
FEATURE                 Location/Qualifiers
source                  1..33
                        mol_type = other DNA
                        organism = Synthetic construct
SEQUENCE: 249
cgcgccgagg gcgaacgaat ataaatcgaa aac                            33

SEQ ID NO: 250          moltype = DNA  length = 27
FEATURE                 Location/Qualifiers
source                  1..27
                        mol_type = other DNA
                        organism = Synthetic construct
SEQUENCE: 250
aggccacgga cggccgcgcg atactaa                                   27

SEQ ID NO: 251          moltype = DNA  length = 29
FEATURE                 Location/Qualifiers
source                  1..29
                        mol_type = other DNA
                        organism = Synthetic construct
SEQUENCE: 251
aggccacgga cgcgtcgagg gttaggagt                                 29

SEQ ID NO: 252          moltype = DNA  length = 28
FEATURE                 Location/Qualifiers
source                  1..28
                        mol_type = other DNA
                        organism = Synthetic construct
SEQUENCE: 252
cgcgccgagg gtaaccgtaa ctcgaccc                                  28

SEQ ID NO: 253          moltype = DNA  length = 28
FEATURE                 Location/Qualifiers
source                  1..28
                        mol_type = other DNA
                        organism = Synthetic construct
SEQUENCE: 253
aggccacgga cgcgcgctcc gaaaaaac                                  28

SEQ ID NO: 254          moltype = DNA  length = 29
FEATURE                 Location/Qualifiers
source                  1..29
```

```
                         mol_type = other DNA
                         organism = Synthetic construct
SEQUENCE: 254
cgcgccgagg cgggcgtaga gattttacg                                        29

SEQ ID NO: 255           moltype = DNA  length = 28
FEATURE                  Location/Qualifiers
source                   1..28
                         mol_type = other DNA
                         organism = Synthetic construct
SEQUENCE: 255
aggccacgga cggtaacgcg catctccg                                         28

SEQ ID NO: 256           moltype = DNA  length = 27
FEATURE                  Location/Qualifiers
source                   1..27
                         mol_type = other DNA
                         organism = Synthetic construct
SEQUENCE: 256
cgcgccgagg tcgttcgtgt cggtttc                                          27

SEQ ID NO: 257           moltype = DNA  length = 27
FEATURE                  Location/Qualifiers
source                   1..27
                         mol_type = other DNA
                         organism = Synthetic construct
SEQUENCE: 257
aggccacgga cggaaccgca cgcacta                                          27

SEQ ID NO: 258           moltype = DNA  length = 34
FEATURE                  Location/Qualifiers
source                   1..34
                         mol_type = other DNA
                         organism = Synthetic construct
SEQUENCE: 258
cgcgccgagg ccgaacgatc cgtaaaaaat ataa                                  34

SEQ ID NO: 259           moltype = DNA  length = 27
FEATURE                  Location/Qualifiers
source                   1..27
                         mol_type = other DNA
                         organism = Synthetic construct
SEQUENCE: 259
aggccacgga cgcccgaacc tcctcga                                          27

SEQ ID NO: 260           moltype = DNA  length = 32
FEATURE                  Location/Qualifiers
source                   1..32
                         mol_type = other DNA
                         organism = Synthetic construct
SEQUENCE: 260
cgcgccgagg gacgacgtgg ttattaattt cg                                    32

SEQ ID NO: 261           moltype = DNA  length = 26
FEATURE                  Location/Qualifiers
source                   1..26
                         mol_type = other DNA
                         organism = Synthetic construct
SEQUENCE: 261
cgcgccgagg cggattcgcg agttcg                                           26

SEQ ID NO: 262           moltype = DNA  length = 28
FEATURE                  Location/Qualifiers
source                   1..28
                         mol_type = other DNA
                         organism = Synthetic construct
SEQUENCE: 262
aggccacgga cggcgcgttt tttgaggc                                         28

SEQ ID NO: 263           moltype = DNA  length = 27
FEATURE                  Location/Qualifiers
source                   1..27
                         mol_type = other DNA
                         organism = Synthetic construct
SEQUENCE: 263
cgcgccgagg cgttttggcg ttcgttc                                          27

SEQ ID NO: 264           moltype = DNA  length = 28
FEATURE                  Location/Qualifiers
```

```
source                  1..28
                        mol_type = other DNA
                        organism = Synthetic construct
SEQUENCE: 264
aggccacgga cggcgtctac ttcccacc                                      28

SEQ ID NO: 265          moltype = DNA  length = 28
FEATURE                 Location/Qualifiers
source                  1..28
                        mol_type = other DNA
                        organism = Synthetic construct
SEQUENCE: 265
cgcgccgagg gaccacctcg aacacaaa                                      28

SEQ ID NO: 266          moltype = DNA  length = 31
FEATURE                 Location/Qualifiers
source                  1..31
                        mol_type = other DNA
                        organism = Synthetic construct
SEQUENCE: 266
aggccacgga cggacgatac ccacgaaaca a                                  31

SEQ ID NO: 267          moltype = DNA  length = 32
FEATURE                 Location/Qualifiers
source                  1..32
                        mol_type = other DNA
                        organism = Synthetic construct
SEQUENCE: 267
cgcgccgagg gccgaaaaac gaaaaacaaa aa                                 32

SEQ ID NO: 268          moltype = DNA  length = 30
FEATURE                 Location/Qualifiers
source                  1..30
                        mol_type = other DNA
                        organism = Synthetic construct
SEQUENCE: 268
aggccacgga cggcgagaaa aggcgttttc                                    30

SEQ ID NO: 269          moltype = DNA  length = 28
FEATURE                 Location/Qualifiers
source                  1..28
                        mol_type = other DNA
                        organism = Synthetic construct
SEQUENCE: 269
cgcgccgagg cgattttcgt ttcgcgtt                                      28

SEQ ID NO: 270          moltype = DNA  length = 28
FEATURE                 Location/Qualifiers
source                  1..28
                        mol_type = other DNA
                        organism = Synthetic construct
SEQUENCE: 270
cgcgccgagg cgtttggcga ttttcgtt                                      28

SEQ ID NO: 271          moltype = DNA  length = 30
FEATURE                 Location/Qualifiers
source                  1..30
                        mol_type = other DNA
                        organism = Synthetic construct
SEQUENCE: 271
aggccacgga cgcggggttc gagtgtaaat                                    30

SEQ ID NO: 272          moltype = DNA  length = 31
FEATURE                 Location/Qualifiers
source                  1..31
                        mol_type = other DNA
                        organism = Synthetic construct
SEQUENCE: 272
cgcgccgagg cgacggaaac gtttttagtt c                                  31

SEQ ID NO: 273          moltype = DNA  length = 34
FEATURE                 Location/Qualifiers
source                  1..34
                        mol_type = other DNA
                        organism = Synthetic construct
SEQUENCE: 273
aggccacgga cgtcgttagt tcgtatacgt tgtc                               34

SEQ ID NO: 274          moltype = DNA  length = 28
```

```
FEATURE                 Location/Qualifiers
source                  1..28
                        mol_type = other DNA
                        organism = Synthetic construct
SEQUENCE: 274
cgcgccgagg cgatcccgaa tccactac                                    28

SEQ ID NO: 275          moltype = DNA  length = 27
FEATURE                 Location/Qualifiers
source                  1..27
                        mol_type = other DNA
                        organism = Synthetic construct
SEQUENCE: 275
aggccacgga cgcgaacaaa cgccccc                                     27

SEQ ID NO: 276          moltype = DNA  length = 32
FEATURE                 Location/Qualifiers
source                  1..32
                        mol_type = other DNA
                        organism = Synthetic construct
SEQUENCE: 276
cgcgccgagg cgtacgcaaa cctaaaaaat tc                               32

SEQ ID NO: 277          moltype = DNA  length = 31
FEATURE                 Location/Qualifiers
source                  1..31
                        mol_type = other DNA
                        organism = Synthetic construct
SEQUENCE: 277
aggccacgga cgcgtaatat cgactccgca a                                31

SEQ ID NO: 278          moltype = DNA  length = 27
FEATURE                 Location/Qualifiers
source                  1..27
                        mol_type = other DNA
                        organism = Synthetic construct
SEQUENCE: 278
aggccacgga cgcgcgttag gatgcgt                                     27

SEQ ID NO: 279          moltype = DNA  length = 27
FEATURE                 Location/Qualifiers
source                  1..27
                        mol_type = other DNA
                        organism = Synthetic construct
SEQUENCE: 279
cgcgccgagg cgcacgaaac cctctta                                     27

SEQ ID NO: 280          moltype = DNA  length = 29
FEATURE                 Location/Qualifiers
source                  1..29
                        mol_type = other DNA
                        organism = Synthetic construct
SEQUENCE: 280
aggccacgga cgcgcgtttt ttggttcgg                                   29

SEQ ID NO: 281          moltype = DNA  length = 28
FEATURE                 Location/Qualifiers
source                  1..28
                        mol_type = other DNA
                        organism = Synthetic construct
SEQUENCE: 281
cgcgccgagg cggaaggatg gtcgtttt                                    28

SEQ ID NO: 282          moltype = DNA  length = 34
FEATURE                 Location/Qualifiers
source                  1..34
                        mol_type = other DNA
                        organism = Synthetic construct
SEQUENCE: 282
aggccacgga cgcgtcgagt agttttaacg tttg                             34

SEQ ID NO: 283          moltype = DNA  length = 29
FEATURE                 Location/Qualifiers
source                  1..29
                        mol_type = other DNA
                        organism = Synthetic construct
SEQUENCE: 283
cgcgccgagg cgtgggtatt cggtttttc                                   29
```

```
SEQ ID NO: 284          moltype = DNA  length = 180
FEATURE                 Location/Qualifiers
source                  1..180
                        mol_type = genomic DNA
                        organism = Homo sapiens
SEQUENCE: 284
gcgccgcacc tggggccctc ccccacctac gccccgccag ggcggggccg cgggcgcaga  60
cactcgcggg cacacgcacg acgacgcgca cacgcggtcg cacgcggccc cccgagcccc  120
ctgcggcgac tccgattcac ccccgcgggt gcggggcgcg gacccgcccg gcccagctcc  180

SEQ ID NO: 285          moltype = DNA  length = 180
FEATURE                 Location/Qualifiers
source                  1..180
                        mol_type = other DNA
                        organism = Synthetic construct
SEQUENCE: 285
gcgtcgtatt tggggttttt ttttatttac gtttcgttag ggcggggtcg cgggcgtaga  60
tattcgcggg tatacgtacg acgacgcgta tacgcggtcg tacgcggttt ttcgagtttt  120
ttgcggcgat ttcgatttat tttcgcgggt gcggggcgcg gattcgttcg gtttagtttt  180

SEQ ID NO: 286          moltype = DNA  length = 199
FEATURE                 Location/Qualifiers
source                  1..199
                        mol_type = genomic DNA
                        organism = Homo sapiens
SEQUENCE: 286
gcggggctgc agagagcggc agtggcacgg agcgcgcggc tggaagcgaa agcaggcggt  60
gtggccaagc cccggcgcac ggcccatagg gcgctgggta ccacgacctg gggccgcgcg  120
ccagggccag gcgcagggta cgacgcaacc cctccagcat cccttgggga ggagcctcca  180
accgtctcgt cccagtctg                                               199

SEQ ID NO: 287          moltype = DNA  length = 199
FEATURE                 Location/Qualifiers
source                  1..199
                        mol_type = other DNA
                        organism = Synthetic construct
SEQUENCE: 287
gcggggttgt agagagcggt agtggtacgg agcgcgcggt tggaagcgaa agtaggcggt  60
gtggttaagt ttcggcgtac ggtttatagg gcgttgggta ttacgatttg gggtcgcgcg  120
ttagggttag gcgtagggta cgacgtaatt tttttagtat tttttgggga ggagttttta  180
atcgtttcgt tttagtttg                                               199

SEQ ID NO: 288          moltype = DNA  length = 213
FEATURE                 Location/Qualifiers
source                  1..213
                        mol_type = genomic DNA
                        organism = Homo sapiens
SEQUENCE: 288
gcgacgcgca gggggcgggc tctacctccc cctcgccccc gcttcggttt taagccgcgg  60
aggcgcccgg tgggacctcg ctgctgtcca atcagggggg accgggtgag ctcctcttcc  120
tggagccggg ctccaccagc gccgcaggct cacaggccgg gggtgggggc tctggaccga  180
ggggcggcgc ggggcggcgc ggggcggcgc gcg                               213

SEQ ID NO: 289          moltype = DNA  length = 213
FEATURE                 Location/Qualifiers
source                  1..213
                        mol_type = other DNA
                        organism = Synthetic construct
SEQUENCE: 289
gcgacgcgta gggggcgggt tttatttttt tttcgttttc gtttcggttt taagtcgcgg  60
aggcgttcgg tgggatttcg ttgttgttta attagggggg atcgggtgag tttttttttt  120
tggagtcggg ttttattagc gtcgtaggtt tataggtcgg gggtgggggt tttggatcga  180
ggggcggcgc ggggcggcgc ggggcggcgc gcg                               213

SEQ ID NO: 290          moltype = DNA  length = 112
FEATURE                 Location/Qualifiers
source                  1..112
                        mol_type = genomic DNA
                        organism = Homo sapiens
SEQUENCE: 290
aactgcagag cgccccgacg cgcccgcagc cctcaccctg ccgagcgcgg cggccacccc  60
cgcccgagcc gcggcgcccc cagggaggaa acaaaagtgt ctccgcggcg cc          112

SEQ ID NO: 291          moltype = DNA  length = 112
FEATURE                 Location/Qualifiers
source                  1..112
                        mol_type = other DNA
                        organism = Synthetic construct
SEQUENCE: 291
```

```
aattgtagag cgtttcgacg cgttcgtagt ttttattttg tcgagcgcgg cggttatttt  60
cgttcgagtc gcggcgtttt tagggaggaa ataaaagtgt tttcgcggcg tt          112

SEQ ID NO: 292         moltype = DNA  length = 123
FEATURE                Location/Qualifiers
source                 1..123
                       mol_type = genomic DNA
                       organism = Homo sapiens
SEQUENCE: 292
gcccgggccc cagctcatcc cccgcccccg ctcaccgcgg gctgaaggcc ttggcttcca  60
gccaggcgcg gacctcgtcc ggacccgact cgtaggtgag cggctggctc acgggctggc  120
tgc                                                                123

SEQ ID NO: 293         moltype = DNA  length = 123
FEATURE                Location/Qualifiers
source                 1..123
                       mol_type = other DNA
                       organism = Synthetic construct
SEQUENCE: 293
gttcgggttt tagtttattt ttcgttttcg tttatcgcgg gttgaaggtt ttggttttta  60
gttaggcgcg gatttcgttc ggattcgatt cgtaggtgag cggttggttt acgggttggt  120
tgt                                                                123

SEQ ID NO: 294         moltype = DNA  length = 104
FEATURE                Location/Qualifiers
source                 1..104
                       mol_type = genomic DNA
                       organism = Homo sapiens
SEQUENCE: 294
gagccggagt cgcggtggcc gcctcagcgc catgtcgagg gttgctgagg ggccagcggc  60
agcgcggcgc ggcttgtagt ccccgcgcgc atgcgcccag cctg                   104

SEQ ID NO: 295         moltype = DNA  length = 104
FEATURE                Location/Qualifiers
source                 1..104
                       mol_type = other DNA
                       organism = Synthetic construct
SEQUENCE: 295
gagtcggagt cgcggtggtc gttttagcgt tatgtcgagg gttgttgagg ggttagcggt  60
agcgcggcgc ggtttgtagt tttcgcgcgt atgcgtttag tttg                   104

SEQ ID NO: 296         moltype = DNA  length = 108
FEATURE                Location/Qualifiers
source                 1..108
                       mol_type = genomic DNA
                       organism = Homo sapiens
SEQUENCE: 296
aggtggtccc cgggcaccac ggtcatgtcg ggcggcagct cgcggcctgc ggcgggctcc  60
gcgtagccgt ggttcaccag cgtgtgggca ccgccgctgc tcgctggg               108

SEQ ID NO: 297         moltype = DNA  length = 108
FEATURE                Location/Qualifiers
source                 1..108
                       mol_type = other DNA
                       organism = Synthetic construct
SEQUENCE: 297
aggtggtttt cgggtattac ggttatgtcg ggcggtagtt cgcggtttgc ggcgggtttc  60
gcgtagtcgt ggtttattag cgtgtgggta tcgtcgttgt tcgttggg               108

SEQ ID NO: 298         moltype = DNA  length = 199
FEATURE                Location/Qualifiers
source                 1..199
                       mol_type = genomic DNA
                       organism = Homo sapiens
SEQUENCE: 298
ctccccgccc tttcgccgcc tccgcccccg agccgagccc accgcctgtt gcagccaaag  60
ccgcgatgct ctgtctgggt ctggcgcggt cagccgggct cccgcacggg gacgcctcct  120
ccctccttct cgcgctctcc gccccctccc ctgcggggcg cgcgcccgcc tccgcgtccc  180
cttaggattc ccgcccacc                                               199

SEQ ID NO: 299         moltype = DNA  length = 199
FEATURE                Location/Qualifiers
source                 1..199
                       mol_type = other DNA
                       organism = Synthetic construct
SEQUENCE: 299
tttttcgttt tttcgtcgtt ttcgttttcg agtcgagttt atcgtttgtt gtagttaaag  60
tcgcgatgtt ttgtttgggt ttggcgcggt tagtcgggtt ttcgtacggg gacgtttttt  120
ttttttttt cgcgttttc gttttttttt ttgcggggcg cgcgttcgtt ttcgcgtttt   180
```

```
tttaggattt tcgtttatt                                         199

SEQ ID NO: 300         moltype = DNA  length = 294
FEATURE                Location/Qualifiers
source                 1..294
                       mol_type = genomic DNA
                       organism = Homo sapiens
SEQUENCE: 300
gatccccgcg cggggcccgc catgcgcgcc tgctccgggc gcccctgccc aggtcccgct  60
ggctcccggg tgctcgcctg gcgccccttc ccctctcact cgctgctttc tcccatttcg  120
gcgccagctc acgccgttcg ccccttcctt cttccttctc tccctccagc ccccctcgct  180
cctcccctac tcgcctctcc cctcccctct tccctggccc accctctccc cgccccctcc  240
tcgccttctc agtcgcccct ctgcgggtcc cctcccccgc gccgggcttg gccc        294

SEQ ID NO: 301         moltype = DNA  length = 294
FEATURE                Location/Qualifiers
source                 1..294
                       mol_type = other DNA
                       organism = Synthetic construct
SEQUENCE: 301
gattttcgcg cggggttcgt tatgcgcgtt tgtttcgggc gtttttgttt aggtttcgtt  60
ggttttcggg tgttcgtttg gcgttttttt ttttttatt cgttgttttt ttttatttcg  120
gcgttagttt acgtcgttcg ttttttttt ttttttttt tttttttagt ttttttcgtt  180
tttttttat tcgtttttt ttttttttt tttttggttt attttttttt cgtttttttt  240
tcgttttttt agtcgttttt ttgcgggttt ttttttcgc gtcgggtttg gttt        294

SEQ ID NO: 302         moltype = DNA  length = 169
FEATURE                Location/Qualifiers
source                 1..169
                       mol_type = other DNA
                       organism = Synthetic construct
SEQUENCE: 302
gattttcgcg cggggttcgt tatgcgcgtt tgtttcgggc gtttttgttt aggtttcgtt  60
ggttttcggg tgttcgtttg gcgttttttt ttttttatt cgttgttttt ttttatttcg  120
gcgttagttt acgtcgttcg ttttttttt ttttttttt ttttttag               169

SEQ ID NO: 303         moltype = DNA  length = 211
FEATURE                Location/Qualifiers
source                 1..211
                       mol_type = genomic DNA
                       organism = Homo sapiens
SEQUENCE: 303
tttccattgc gcggctctcc tcagctcctt cccgccgccc agtctggatc ctgggggagg  60
cgctgaagtc ggggcccgcc ctgtggcccc gcccggcccg cgcttgctag cgcccaaagc  120
cagcgaagca cgggcccaac cgggccatgt cgggggagcc tgagctcatt gagctgcggg  180
agctggcacc cgctgggcgc gctgggaagg g                                211

SEQ ID NO: 304         moltype = DNA  length = 211
FEATURE                Location/Qualifiers
source                 1..211
                       mol_type = other DNA
                       organism = Synthetic construct
SEQUENCE: 304
tttttattgc gcggtttttt ttagtttttt ttcgtcgttt agtttggatt ttgggggagg  60
cgttgaagtc ggggttcgtt ttgtggtttc gttcggttcg cgtttgttag cgtttaaagt  120
tagcgaagta cgggtttaat cgggttatgt cgggggagtt tgagtttatt gagttgcggg  180
agttggtatt cgttgggcgc gttgggaagg g                                211

SEQ ID NO: 305         moltype = DNA  length = 651
FEATURE                Location/Qualifiers
source                 1..651
                       mol_type = genomic DNA
                       organism = Homo sapiens
SEQUENCE: 305
gccgcccacc ttcctcgttt ctgcactcat tttagcgacg cagccgccgc tgctacctac  60
cccgcgctcc cgcgtctcct ccgcgctggg gtctcccctt tcttttggtt tgggtgggag  120
aaaaagatgg tgaggacggg gaatcggaga ccggcatggg ggtaaaaatc gtgcagacat  180
tcggaatcgc tcccttggaa acatttgcct gagcaactga aataaaattg gcagtagtag  240
ttttggagcg tgctccagcg aggatggtct ttttgttcat tattttctct ttaaagtaat  300
atcctgtcac ttaggggctt tccggttgtc tcctcttatt cgaccccctt tcaaaattgc  360
tgacttgagc tggttctgga gtttattttt taatatgcgt gcgtgggtat gtgtatgtgt  420
gtgtatgttt tgcagaaatc cgccaaaatg caactgtagg aactgcgaga tgtatttatt  480
gattttgacc aggggcggtg ggaaggggct ggagggagct gggggatcct ggagggtggg  540
aagtggctga ttctcggtgg ccggacactc atccagagcc tgatccgtac tcgtgttttc  600
ttggaagcgc cacaactgcg gggaaggagt ctttagaaac cgtgccagtt t           651

SEQ ID NO: 306         moltype = DNA  length = 651
FEATURE                Location/Qualifiers
source                 1..651
```

```
                        mol_type = other DNA
                        organism = Synthetic construct
SEQUENCE: 306
gtcgtttatt tttttcgttt ttgtatttat tttagcgacg tagtcgtcgt tgttatttat  60
ttcgcgtttt cgcgtttttt tcgcgttggg gttttttttt ttttttggtt tgggtgggag  120
aaaaagatgg tgaggacggg gaatcggaga tcggtatggg ggtaaaaatc gtgtagatat  180
tcggaatcgt ttttttggaa atatttgttt gagtaattga aataaaattg gtagtagtag  240
ttttggagcg tgttttagcg aggatggttt ttttgtttat tatttttttt ttaaagtaat  300
attttgttat ttaggggttt ttcggttgtt ttttttttatt cgattttttt ttaaaattgt  360
tgatttgagt tggttttgga gtttattttt taatatgcgt gcgtgggtat gtgtatgtgt  420
gtgtatgttt tgtagaaatt cgttaaaatg taattgtagg aattgcgaga tgtatttatt  480
gattttgatt aggggcggtg ggaaggggtt ggagggagtt gggggatttt ggagggtggg  540
aagtggttga ttttcggtgg tcggatattt atttagagtt tgattcgtat tcgtgttttt  600
ttggaagcgt tataattgcg gggaaggagt ttttagaaat cgtgttagtt t           651

SEQ ID NO: 307          moltype = DNA  length = 94
FEATURE                 Location/Qualifiers
source                  1..94
                        mol_type = other DNA
                        organism = Synthetic construct
SEQUENCE: 307
gtcgtttatt tttttcgttt ttgtatttat tttagcgacg tagtcgtcgt tgttatttat  60
ttcgcgtttt cgcgtttttt tcgcgttggg gttt                              94

SEQ ID NO: 308          moltype = DNA  length = 112
FEATURE                 Location/Qualifiers
source                  1..112
                        mol_type = other DNA
                        organism = Synthetic construct
SEQUENCE: 308
gaagtggctg attctcggtg gccggacact catccagagc ctgatccgta ctcgtgtttt  60
cttggaagcg ccacaactgc ggggaaggag tctttagaaa ccgtgccagt tt          112

SEQ ID NO: 309          moltype = DNA  length = 17
FEATURE                 Location/Qualifiers
source                  1..17
                        mol_type = other DNA
                        organism = Synthetic construct
SEQUENCE: 309
ctgattctcg gtggccg                                                 17

SEQ ID NO: 310          moltype = DNA  length = 20
FEATURE                 Location/Qualifiers
source                  1..20
                        mol_type = other DNA
                        organism = Synthetic construct
SEQUENCE: 310
ggcgcttcca agaaaacacg                                              20

SEQ ID NO: 311          moltype = DNA  length = 29
FEATURE                 Location/Qualifiers
source                  1..29
                        mol_type = other DNA
                        organism = Synthetic construct
SEQUENCE: 311
aggccacgga cgcgagtacg gatcaggct                                    29

SEQ ID NO: 312          moltype = DNA  length = 311
FEATURE                 Location/Qualifiers
source                  1..311
                        mol_type = genomic DNA
                        organism = Homo sapiens
SEQUENCE: 312
cctgtaaagc cggggatggc aggacgcatt gtcacccccct cctgccgctc ttacgaaaca  60
ctcttaattg agtccgattc ttggtgaatc agccttccaa gaaccgcgac cgcagcatcc  120
tgtgccgctt ctgtgttccg catttttctc tttctgcagc gtttcctctc attctggatg  180
gaaaggcctg tttgtctccc tcaatctttg gcgagggtgg caggcagcca ggcggccatt  240
acgggccgcg cctcccacca gccagtcgct ggcaggagcg tccggggagg gagcagaccc  300
cgttcaccct c                                                       311

SEQ ID NO: 313          moltype = DNA  length = 311
FEATURE                 Location/Qualifiers
source                  1..311
                        mol_type = other DNA
                        organism = Synthetic construct
SEQUENCE: 313
tttgtaaagt cggggatggt aggacgtatt gttatttttt tttgtcgttt ttacgaaata  60
tttttaattg agttcgattt ttggtgaatt agtttttttaa gaatcgcgat cgtagtattt  120
tgtgtcgttt ttgtgtttcg tatttttttt tttttgtagc gttttttttt attttggatg  180
```

```
gaaaggtttg tttgtttttt ttaatttttg gcgagggtgg taggtagtta ggcggttatt  240
acgggtcgcg ttttttatta gttagtcgtt ggtaggagcg ttcggggagg gagtagattt  300
cgtttatttt t                                                       311

SEQ ID NO: 314         moltype = DNA  length = 92
FEATURE                Location/Qualifiers
source                 1..92
                       mol_type = other DNA
                       organism = Synthetic construct
SEQUENCE: 314
gtaggtagtt aggcggttat tacgggtcgc gttttttatt agttagtcgt tggtaggagc  60
gttcggggag ggagtagatt tcgtttattt tt                                92

SEQ ID NO: 315         moltype = DNA  length = 112
FEATURE                Location/Qualifiers
source                 1..112
                       mol_type = genomic DNA
                       organism = Homo sapiens
SEQUENCE: 315
cccagagccc cggtcacact cccgtcccat gctgtccccc tcccgcaaag cccacggtgg  60
gaacagaggg caccgcgcga gccgatgcca ccctcactgc cggcccccacc ca          112

SEQ ID NO: 316         moltype = DNA  length = 112
FEATURE                Location/Qualifiers
source                 1..112
                       mol_type = other DNA
                       organism = Synthetic construct
SEQUENCE: 316
tttagagttt cggttatatt ttcgttttat gttgtttttt tttcgtaaag tttacggtgg  60
gaatagaggg tatcgcgcga gtcgatgtta tttttattgt cggttttatt ta          112

SEQ ID NO: 317         moltype = DNA  length = 287
FEATURE                Location/Qualifiers
source                 1..287
                       mol_type = genomic DNA
                       organism = Homo sapiens
SEQUENCE: 317
cctcccaacc cgagtcccgc aacccggcgg gaccggagct cagcgcttca cgctctccgg  60
gaggaagctc cggaccccgg gcgacccccgc tccctctccc ggaccccgcc cgcgctccag  120
cacccgggag gaaggcgaag accggcggga ggagcgctct tctcggaagg ggagaaccgg  180
gtccgaggcg ccgtggggcg ggggtcgcgg gcgcactcac gggggcgagc agccagcagg  240
tcagcagcgc gggaggcagc agcgtccgca tcccgagctc agcgtgc                287

SEQ ID NO: 318         moltype = DNA  length = 287
FEATURE                Location/Qualifiers
source                 1..287
                       mol_type = other DNA
                       organism = Synthetic construct
SEQUENCE: 318
ttttttaatt cgagtttcgt aattcggcgg gatcggagtt tagcgtttta cgtttttcgg  60
gaggaagttt cggatttcgg gcgatttcgt tttttttttc ggatttcgtt cgcgttttag  120
tattcgggag gaaggcgaag atcggcggga ggagcgtttt tttcggaagg ggagaatcgg  180
gttcgaggcg tcgtggggcg ggggtcgcgg gcgtatttac gggggcgagt agttagtagg  240
ttagtagcgc gggaggtagt agcgttcgta tttcgagttt agcgtgt                287

SEQ ID NO: 319         moltype = DNA  length = 215
FEATURE                Location/Qualifiers
source                 1..215
                       mol_type = genomic DNA
                       organism = Homo sapiens
SEQUENCE: 319
gtcgggtcgt gcgttcgctc ggcagcggcg tgcaccagca ccacccctgc gtgcaagttt  60
gaaatgtgag ctgcctccga ttcatactcg ctcgcgctcc ctcgcagcga agtggctggg  120
ctgacggtct gcgcgcgcga gtgagtgcgg gcggcgggct gggggcggg gtgcggacgg  180
cgaggctcgc ggggcgggga gggcgcgcgc gagcc                             215

SEQ ID NO: 320         moltype = DNA  length = 215
FEATURE                Location/Qualifiers
source                 1..215
                       mol_type = other DNA
                       organism = Synthetic construct
SEQUENCE: 320
gtcgggtcgt gcgttcgttc ggtagcggcg tgtattagta ttatttttgc gtgtaagttt  60
gaaatgtgag ttgttttcga tttatattcg ttcgcgtttt ttcgtagcga agtggttggg  120
ttgacggttt gcgcgcgcga gtgagtgcgg gcggcgggtt gggggcggg gtgcggacgg  180
cgaggttcgc ggggcgggga gggcgcgcgc gagtt                             215

SEQ ID NO: 321         moltype = DNA  length = 140
FEATURE                Location/Qualifiers
```

```
source                  1..140
                        mol_type = genomic DNA
                        organism = Homo sapiens
SEQUENCE: 321
tggcagaagc gtagtgccag ccgcaatagg gcggccgtgg gtgcaaacgg aggggagcgc  60
cggcagctag caccgcgcgg cgactaacgg gccgccccgg agactcctgg gagctcaggc  120
ccacgcgcga gtgcgcaggc                                              140

SEQ ID NO: 322          moltype = DNA  length = 140
FEATURE                 Location/Qualifiers
source                  1..140
                        mol_type = other DNA
                        organism = Synthetic construct
SEQUENCE: 322
tggtagaagc gtagtgttag tcgtaatagg gcggtcgtgg gtgtaaacgg aggggagcgt  60
cggtagttag tatcgcgcgg cgattaacgg gtcgtttcgg agatttttgg gagtttaggt  120
ttacgcgcga gtgcgtaggt                                              140

SEQ ID NO: 323          moltype = DNA  length = 316
FEATURE                 Location/Qualifiers
source                  1..316
                        mol_type = genomic DNA
                        organism = Homo sapiens
SEQUENCE: 323
agaagtgggc gggtgtgtgt ttaaaaaaaa aaaagggggt ggaaacccca ccagccaagt  60
ctgcagaaaa aaaataaatg aagtctgcct atctccgggc cagagcccct cccctcggcc  120
cgcgcgggag gagtgtgacc caggtgccgc ttcctctcgc cgccgagggt caggagcccg  180
ggagcgcgac cctcccccgg cccggcctgg cccggcctgg ccagtccccg cggtctctgc  240
ccgggctgac gcccaggaat gtggtcgacg agaagcccca acagcacggc gtggcctctc  300
agcctcggtg agtacc                                                  316

SEQ ID NO: 324          moltype = DNA  length = 316
FEATURE                 Location/Qualifiers
source                  1..316
                        mol_type = other DNA
                        organism = Synthetic construct
SEQUENCE: 324
agaagtgggc gggtgtgtgt ttaaaaaaaa aaaagggggt ggaaatttta ttagttaagt  60
ttgtagaaaa aaaataaatg aagtttgttt attttcgggt tagagttttt tttttcggtt  120
cgcgcgggag gagtgtgatt taggtgtcgt ttttttttcgt cgtcgagggt taggagttcg  180
ggagcgcgat tttttttcgg ttcggtttgg ttcggtttgg ttagttttcg cggtttttgt  240
tcgggttgac gtttaggaat gtggtcgacg agaagtttta atagtacggc gtggtttttt  300
agtttcggtg agtatt                                                  316

SEQ ID NO: 325          moltype = DNA  length = 77
FEATURE                 Location/Qualifiers
source                  1..77
                        mol_type = other DNA
                        organism = Synthetic construct
SEQUENCE: 325
ggagtgtgat ttaggtgtcg ttttttttcg tcgtcgaggg ttaggagttc gggagcgcga  60
ttttttttcg gttcggt                                                 77

SEQ ID NO: 326          moltype = DNA  length = 105
FEATURE                 Location/Qualifiers
source                  1..105
                        mol_type = genomic DNA
                        organism = Homo sapiens
SEQUENCE: 326
ggtgagtacc cgccgtgggg aagggtcctg gggacccact ggaggccgcg gcccgcagca  60
gccaggggcc gagccacggc cacggacgcc ctggtgtccc ggtcc                  105

SEQ ID NO: 327          moltype = DNA  length = 105
FEATURE                 Location/Qualifiers
source                  1..105
                        mol_type = other DNA
                        organism = Synthetic construct
SEQUENCE: 327
ggtgagtatt cgtcgtgggg aagggttttg gggatttatt ggaggtcgcg gttcgtagta  60
gttaggggtc gagttacggt tacggacgtt ttggtgtttc ggttt                  105

SEQ ID NO: 328          moltype = DNA  length = 184
FEATURE                 Location/Qualifiers
source                  1..184
                        mol_type = genomic DNA
                        organism = Homo sapiens
SEQUENCE: 328
ggggactctc ggcacccgcg tccctgtgct tctggtggtt ccggcgcttc ctcggagcgc  60
gcggcatgtc tgctcctaca cgtccagcac ctctgtcccc agagcaaacc cacctcccag  120
```

```
ggcacacgca gaggggcagt caggcaccgc ctccaccctg ccccacccag gccgcgcgca  180
cccc                                                              184

SEQ ID NO: 329          moltype = DNA  length = 184
FEATURE                 Location/Qualifiers
source                  1..184
                        mol_type = other DNA
                        organism = Synthetic construct
SEQUENCE: 329
ggggatttc ggtattcgcg tttttgtgtt tttggtggtt tcggcgtttt ttcggagcgc  60
gcggtatgtt tgtttttata cgtttagtat ttttgttttt agagtaaatt tattttttag  120
ggtatacgta gaggggtagt taggtatcgt ttttattttg ttttatttag gtcgcgcgta  180
tttt                                                              184

SEQ ID NO: 330          moltype = DNA  length = 180
FEATURE                 Location/Qualifiers
source                  1..180
                        mol_type = genomic DNA
                        organism = Homo sapiens
SEQUENCE: 330
ctcttcctcc cggagtatgg tgaggagcgc gggggacggg tgcgggaagg ggacagcagg  60
gctgagcctg gggcccgcaa gacccagcag cccgagcggg cgcagagacc ccacgccacg  120
cacaaccctc tcttctaggg ggcgccgact acactgactt ccctgttccg gaagaggggg  180

SEQ ID NO: 331          moltype = DNA  length = 180
FEATURE                 Location/Qualifiers
source                  1..180
                        mol_type = other DNA
                        organism = Synthetic construct
SEQUENCE: 331
tttttttttt cggagtatgg tgaggagcgc gggggacggg tgcgggaagg ggatagtagg  60
gttgagtttg gggttcgtaa gatttagtag ttcgagcggg cgtagagatt ttacgttacg  120
tataattttt ttttttaggg ggcgtcgatt atattgattt ttttgtttcg gaagaggggg  180

SEQ ID NO: 332          moltype = DNA  length = 123
FEATURE                 Location/Qualifiers
source                  1..123
                        mol_type = genomic DNA
                        organism = Homo sapiens
SEQUENCE: 332
ctctgcagga cgccgcggcc cattccgaag agcaggatgt gcgtgaggtt ggtgggcagg  60
cctagcgcgg agatgcgcgc cacgtcgccc cccgagcact gcgcggcgtc ccggaagaca  120
cac                                                               123

SEQ ID NO: 333          moltype = DNA  length = 123
FEATURE                 Location/Qualifiers
source                  1..123
                        mol_type = other DNA
                        organism = Synthetic construct
SEQUENCE: 333
ttttgtagga cgtcgcggtt tatttcgaag agtaggatgt gcgtgaggtt ggtgggtagg  60
tttagcgcgg agatgcgcgt tacgtcgttt ttcgagtatt gcgcggcgtt tcggaagata  120
tat                                                               123

SEQ ID NO: 334          moltype = DNA  length = 101
FEATURE                 Location/Qualifiers
source                  1..101
                        mol_type = genomic DNA
                        organism = Homo sapiens
SEQUENCE: 334
gccaaggggc gcccgcgccg ccgcccgccg cccgtgccgg ccccggccgt tcgggctcgg  60
tgcgcaccgc gcccccagat ggcgccgcca agcgtccgcc c                     101

SEQ ID NO: 335          moltype = DNA  length = 101
FEATURE                 Location/Qualifiers
source                  1..101
                        mol_type = other DNA
                        organism = Synthetic construct
SEQUENCE: 335
gttaaggggc gttcgcgtcg tcgttcgtcg ttcgtgtcgg tttcggtcgt tcgggttcgg  60
tgcgtatcgc gtttttagat ggcgtcgtta agcgttcgtt t                     101

SEQ ID NO: 336          moltype = DNA  length = 147
FEATURE                 Location/Qualifiers
source                  1..147
                        mol_type = genomic DNA
                        organism = Homo sapiens
SEQUENCE: 336
gcttcctctc cgtgggcgac gtggacgaca cgcagtgcgt gcggctcgac agcgacgcca  60
```

```
cgagtcccag gatggagccg cgggcgccgt ggatggagca ggaggggccg gaatattggg  120
aagaggagac agggaccgcc aaggcca                                      147

SEQ ID NO: 337         moltype = DNA  length = 147
FEATURE                Location/Qualifiers
source                 1..147
                       mol_type = other DNA
                       organism = Synthetic construct
SEQUENCE: 337
gttttttttt cgtgggcgac gtggacgata cgtagtgcgt gcggttcgat agcgacgtta  60
cgagttttag gatggagtcg cgggcgtcgt ggatggagta ggaggggtcg gaatattggg  120
aagaggagat agggatcgtt aaggtta                                      147

SEQ ID NO: 338         moltype = DNA  length = 153
FEATURE                Location/Qualifiers
source                 1..153
                       mol_type = genomic DNA
                       organism = Homo sapiens
SEQUENCE: 338
cagttttacc gagtgaacct gcggaccctg agcggctact acaaccagag tgaggcctgt  60
gagtgacacc ggccgggggc gcaggtcact acccctccac atcccccacg gaccgcccgg  120
gtctccccga gtctctgggt ccgagatcca cgc                              153

SEQ ID NO: 339         moltype = DNA  length = 153
FEATURE                Location/Qualifiers
source                 1..153
                       mol_type = other DNA
                       organism = Synthetic construct
SEQUENCE: 339
tagttttatc gagtgaattt gcggattttg agcggttatt ataattagag tgaggtttgt  60
gagtgatatc ggtcgggggc gtaggttatt atttttttat attttttacg gatcgttcgg  120
gtttttcga gtttttgggt tcgagattta cgt                                153

SEQ ID NO: 340         moltype = DNA  length = 138
FEATURE                Location/Qualifiers
source                 1..138
                       mol_type = genomic DNA
                       organism = Homo sapiens
SEQUENCE: 340
tgtccttgac cgagaagggg gtggaggtga cggggctcag cagcatcccg aaggcggatg  60
gggcggggcc gaggaggtcc gggtgaggag cggcaccctg aacttcccgt cttgtcgctg  120
caggccccgc agacagac                                                138

SEQ ID NO: 341         moltype = DNA  length = 138
FEATURE                Location/Qualifiers
source                 1..138
                       mol_type = other DNA
                       organism = Synthetic construct
SEQUENCE: 341
tgtttttgat cgagaagggg gtggaggtga cggggtttag tagtatttcg aaggcggatg  60
gggcggggtc gaggaggttc gggtgaggag cggtattttg aatttttcgt tttgtcgttg  120
taggtttcgt agatagat                                                138

SEQ ID NO: 342         moltype = DNA  length = 104
FEATURE                Location/Qualifiers
source                 1..104
                       mol_type = genomic DNA
                       organism = Homo sapiens
SEQUENCE: 342
atgaaggcta cgaggtgctc aagttcgacg acgtggtcac caacctcgga aaccactacg  60
accccaccac cggcaagttc acctgctcca tcccgggcat ctac                  104

SEQ ID NO: 343         moltype = DNA  length = 104
FEATURE                Location/Qualifiers
source                 1..104
                       mol_type = other DNA
                       organism = Synthetic construct
SEQUENCE: 343
atgaaggtta cgaggtgttt aagttcgacg acgtggttat taatttcgga aattattacg  60
attttattat cggtaagttt atttgtttta tttcgggtat ttat                  104

SEQ ID NO: 344         moltype = DNA  length = 185
FEATURE                Location/Qualifiers
source                 1..185
                       mol_type = genomic DNA
                       organism = Homo sapiens
SEQUENCE: 344
agcctgcctg cgtctcttcc ttcctccgcg tgggttctag caacatccac tgcagccggg  60
ccaggcgagc cggcgcgtac catcggcgcg gggggaggag agggccgggc ctgggaagat  120
```

```
gctgcggagg acgctgcgga ttcgcgagcc cggggtaagg cggcggcgca ccgccccctc  180
ccgcc                                                              185

SEQ ID NO: 345         moltype = DNA  length = 185
FEATURE                Location/Qualifiers
source                 1..185
                       mol_type = other DNA
                       organism = Synthetic construct
SEQUENCE: 345
agtttgtttg cgtttttttt ttttttcgcg tgggttttag taatatttat tgtagtcggg  60
ttaggcgagt cggcgcgtat tatcggcgcg gggggaggag agggtcgggt ttgggaagat  120
gttgcggagg acgttgcgga ttcgcgagtt cggggtaagg cggcggcgta tcgttttttt  180
tcgtt                                                              185

SEQ ID NO: 346         moltype = DNA  length = 132
FEATURE                Location/Qualifiers
source                 1..132
                       mol_type = genomic DNA
                       organism = Homo sapiens
SEQUENCE: 346
ggggggcggg gctggggaga gggtggcccc tgcacactag tcccctcccc tcgaccccgc  60
agccccgcgg cgcgtttcct gaggcgcccc cgccacgtcc cgcgagtctc tgccaagttc  120
ccgcgcgggt gc                                                      132

SEQ ID NO: 347         moltype = DNA  length = 132
FEATURE                Location/Qualifiers
source                 1..132
                       mol_type = other DNA
                       organism = Synthetic construct
SEQUENCE: 347
ggggggcggg gttggggaga gggtggtttt tgtatattag tttttttttt tcgatttcgt  60
agtttcgcgg cgcgtttttt gaggcgtttt cgttacgttt cgcgagtttt tgttaagttt  120
tcgcgcgggt gt                                                      132

SEQ ID NO: 348         moltype = DNA  length = 302
FEATURE                Location/Qualifiers
source                 1..302
                       mol_type = genomic DNA
                       organism = Homo sapiens
SEQUENCE: 348
ggggaggggc cgccgagggt cccgcccccc gcgccgtgcg gccccgcccc ctccctcccc  60
ccacctggga aagccctcgc gggccaagtc cgcggcggcc gggccaaggc gcccgctctc  120
gctcggcccc gccctggcgc ccgcccgccc gcccgcccgc tgcctcggcg ctaggccttc  180
ttgcacttgc ccttcttctc acgctgctgg aacttgcgca gccgccgcgc ccacgtgtcc  240
cgccactgga tcaccaggct gcttttatcg gccacgatgc cgctctggtc cggagagtcc  300
tc                                                                 302

SEQ ID NO: 349         moltype = DNA  length = 302
FEATURE                Location/Qualifiers
source                 1..302
                       mol_type = other DNA
                       organism = Synthetic construct
SEQUENCE: 349
ggggaggggt cgtcgagggt ttcgttttttc gcgtcgtgcg gtttcgtttt tttttttttt  60
ttatttggga aagttttcgc gggttaagtt cgcggcggtc gggttaaggc gttcgttttc  120
gttcggtttc gttttggcgt tcgttcgttc gttcgttcgt tgtttcggcg ttaggttttt  180
ttgtatttgt tttttttttt acgttgttgg aatttgcgta gtcgtcgcgt ttacgtgttt  240
cgttattgga ttattaggtt gtttttatcg gttacgatgt cgttttggtt cggagagttt  300
tt                                                                 302

SEQ ID NO: 350         moltype = DNA  length = 82
FEATURE                Location/Qualifiers
source                 1..82
                       mol_type = other DNA
                       organism = Synthetic construct
SEQUENCE: 350
gttaaggcgt tcgttttcgt tcggtttcgt tttggcgttc gttcgttcgt tcgttcgttg  60
tttcggcgtt aggttttttt gt                                           82

SEQ ID NO: 351         moltype = DNA  length = 158
FEATURE                Location/Qualifiers
source                 1..158
                       mol_type = genomic DNA
                       organism = Homo sapiens
SEQUENCE: 351
gccccgggcc tttcagacac ttttctggaa tgtgaaggga ggtgggggct cagctgtctt  60
ttccaccgtc ccggagtggg gcaggtgtcg gagctgggtg ggaagcagac gcggtacggt  120
gggcagaggt ccccagcctg cggggagcgc tatctcct                          158
```

```
SEQ ID NO: 352         moltype = DNA  length = 158
FEATURE                Location/Qualifiers
source                 1..158
                       mol_type = other DNA
                       organism = Synthetic construct
SEQUENCE: 352
gtttcgggtt ttttagatat ttttttggaa tgtgaaggga ggtgggggtt tagttgtttt  60
ttttatcgtt tcggagtggg gtaggtgtcg gagttgggtg ggaagtagac gcggtacggt  120
gggtagaggt ttttagtttg cggggagcgt tatttttt                          158

SEQ ID NO: 353         moltype = DNA  length = 86
FEATURE                Location/Qualifiers
source                 1..86
                       mol_type = genomic DNA
                       organism = Homo sapiens
SEQUENCE: 353
gggcctccgg gctacccccta cttgaagccg ctatgcccct ctcctgtgcc cgaggtggcc  60
gctgggtggc aggggaggcc cgggcc                                       86

SEQ ID NO: 354         moltype = DNA  length = 86
FEATURE                Location/Qualifiers
source                 1..86
                       mol_type = other DNA
                       organism = Synthetic construct
SEQUENCE: 354
gggttttcgg gttattttta tttgaagtcg ttatgttttt tttttgtgtt cgaggtggtc  60
gttgggtggt aggggaggtt cgggtt                                       86

SEQ ID NO: 355         moltype = DNA  length = 149
FEATURE                Location/Qualifiers
source                 1..149
                       mol_type = genomic DNA
                       organism = Homo sapiens
SEQUENCE: 355
gggcaaaggc cgctgcttcg ggcccaatat ctgctgcgcg gaagagctgg gctgcttcgt  60
gggcaccgcc gaagcgctgc gctgccagga ggagaactac ctgccgtcgc cctgccagtc  120
cggccagaag gcgtgcggga gcgggggcc                                    149

SEQ ID NO: 356         moltype = DNA  length = 149
FEATURE                Location/Qualifiers
source                 1..149
                       mol_type = other DNA
                       organism = Synthetic construct
SEQUENCE: 356
gggtaaaggt cgttgtttcg ggtttaatat ttgttgcgcg gaagagttgg gttgtttcgt  60
gggtatcgtc gaagcgttgc gttgttagga ggagaattat ttgtcgtcgt tttgttagtt  120
cggttagaag gcgtgcggga gcgggggtt                                    149

SEQ ID NO: 357         moltype = DNA  length = 146
FEATURE                Location/Qualifiers
source                 1..146
                       mol_type = genomic DNA
                       organism = Homo sapiens
SEQUENCE: 357
tttccctccc gggcgcctgg atctccccctc ccccggctcc tgtttccttg tcaaaacttc  60
ctgccttggc gagggcccga gttcccaccc ccttcctgcc ccccgcccct cggcgcccct  120
cccggccctg cgatcagcag cgtccc                                       146

SEQ ID NO: 358         moltype = DNA  length = 146
FEATURE                Location/Qualifiers
source                 1..146
                       mol_type = other DNA
                       organism = Synthetic construct
SEQUENCE: 358
tttttttttc gggcgtttgg attttttttt tttcggtttt tgttttttttg ttaaaatttt  60
ttgttttggc gagggttcga gtttttattt tttttttgtt tttcgttttt cggcgttttt  120
ttcggttttg cgattagtag cgtttt                                       146

SEQ ID NO: 359         moltype = DNA  length = 289
FEATURE                Location/Qualifiers
source                 1..289
                       mol_type = genomic DNA
                       organism = Homo sapiens
SEQUENCE: 359
cggtggccac ggccccgccc tcgttccgcg cccggactgg gccacgccgg atagcgggaa  60
acaaaaaaag cccgagctgg aaacttcaga gaggtttagt ttcgtttccc agaagcatca  120
gttcggtccc aaaacgctgc aaacgcgcgc tgcctgcagt aggagagagg aaaccgcgaa  180
gcgcgagaaa aggcgccccc gtccccaagc agcccgcgcg cccttccagg ggccagacct  240
gctccatcct ggacggcgaa acgacctcgg gagaccccgg ttaggacct              289
```

```
SEQ ID NO: 360          moltype = DNA  length = 289
FEATURE                 Location/Qualifiers
source                  1..289
                        mol_type = other DNA
                        organism = Synthetic construct
SEQUENCE: 360
cggtggttac ggtttcgttt tcgtttcgcg ttcggattgg gttacgtcgg atagcgggaa  60
ataaaaaaag ttcgagttgg aaattttaga gaggtttagt ttcgtttttt agaagtatta  120
gttcggtttt aaaacgttgt aaacgcgcgt tgtttgtagt aggagagagg aaatcgcgaa  180
gcgcgagaaa aggcgttttc gtttttaagt agttcgcgcg tttttttagg ggttagattt  240
gttttatttt ggacggcgaa acgatttcgg gagatttcgg ttaggattt              289

SEQ ID NO: 361          moltype = DNA  length = 608
FEATURE                 Location/Qualifiers
source                  1..608
                        mol_type = genomic DNA
                        organism = Homo sapiens
SEQUENCE: 361
gggggtgcgg ggaggagtcg ggagcagccc ctggagcaca ggggccgcca gcaccggctg  60
cttccagccc tcctgcctac ccgcccttcc tcctgcaggc tgggggctcg gacagcccca  120
gtgccccgcg acgcccacct ggacgcctgg cgacccccgc cccgcgctct gtacctttac  180
tctgcggagg gttctgactc cggtcccgga ggacgttgat ctggtagacg gctccgtaag  240
gctcaaaaag ttctttcagc tccttttccg accatgaccg gggatctgt ccgacaaaca  300
tcttaatggc atctgggtct ggttggtctg agtgatccaa agctccgttc atcttgttgg  360
ctgtgccgtt actgtcaaaa acggaaccgg gagccagagt tagggcggca cgatgaggga  420
caggaagaaa aaatagtggg ggtgggggag cggggaggcg gaaggaggag gaagaagagc  480
agtggcaaag tgcctaatga gtcgtagaaa tttgatgaac taaaacaaag cggaggcacc  540
atgagttgct cctcggcggc ggcgaggctc tcactgcgtg ctgctgtcga gcagagccgg  600
gggagcac                                                           608

SEQ ID NO: 362          moltype = DNA  length = 608
FEATURE                 Location/Qualifiers
source                  1..608
                        mol_type = other DNA
                        organism = Synthetic construct
SEQUENCE: 362
gggggtgcgg ggaggagtcg ggagtagttt ttggagtata ggggtcgtta gtatcggttg  60
tttttagttt ttttgtttat tcgttttttt ttttgtaggt tgggggttcg gatagtttta  120
gtgtttcgcg acgtttattt ggacgtttgg cgattttcgt ttcgcgtttt gtatttttat  180
tttgcggagg gttttgattt cggtttcgga ggacgttgat ttggtagacg gtttcgtaag  240
gtttaaaaag ttttttagt tttttttcg attatgatcg gggatttgt tcgataaata  300
ttttaatggt atttgggttt ggttggtttg agtgatttaa agtttcgttt attttgttgg  360
ttgtgtcgtt attgttaaaa acggaatcgg gagttagagt tagggcggta cgatgaggga  420
taggaagaaa aaatagtggg ggtgggggag cggggaggcg gaaggaggag gaagaagagt  480
agtggtaaag tgtttaatga gtcgtagaaa tttgatgaat taaaataaag cggaggtatt  540
atgagttgtt tttcggcggc ggcgaggttt ttattgcgtg ttgttgtcga gtagagtcgg  600
gggagtat                                                           608

SEQ ID NO: 363          moltype = DNA  length = 96
FEATURE                 Location/Qualifiers
source                  1..96
                        mol_type = other DNA
                        organism = Synthetic construct
SEQUENCE: 363
gttttagtgt ttcgcgacgt ttatttggac gtttggcgat tttcgtttcg cgttttgtat  60
ttttattttg cggagggttt tgatttcggt ttcgga                           96

SEQ ID NO: 364          moltype = DNA  length = 152
FEATURE                 Location/Qualifiers
source                  1..152
                        mol_type = genomic DNA
                        organism = Homo sapiens
SEQUENCE: 364
gcacccggcg cccgagctgc gaaagggacg cccttctcct cccgcgcgga acttcaggag  60
tgcggggccc gagtgtaaac tggaccaccg tggggccgcg cgggcccctg ggcatcacca  120
caaactgtgc ctgtggccat cgtgtcagga ca                               152

SEQ ID NO: 365          moltype = DNA  length = 152
FEATURE                 Location/Qualifiers
source                  1..152
                        mol_type = other DNA
                        organism = Synthetic construct
SEQUENCE: 365
gtattcggcg ttcgagttgc gaaagggacg tttttttttt ttcgcgcgga attttaggag  60
tgcggggttc gagtgtaaat tggattatcg tggggtcgcg cgggtttttg ggtattatta  120
taaattgtgt ttgtggttat cgtgttagga ta                               152

SEQ ID NO: 366          moltype = DNA  length = 384
```

```
FEATURE                Location/Qualifiers
source                 1..384
                       mol_type = genomic DNA
                       organism = Homo sapiens
SEQUENCE: 366
ggagaagccg ggactcctca catcccacat ccggcagggg aagcccagca ggtgagcgca  60
ggtcccccca gtccccgagg gagtgcgccc gacggaaacg cccctagccc gcgggcctcg  120
ctttcctctc ccgggttcct gggtcacttc ccgctgtctc cagcccgagc tcgtggcccc  180
aatccctggt acctccatcc tctggtcacc ccttctctgg tgccccctcc ccgacttttc  240
tttgtcccgt ccccaccctt gcccgggcct gccggacccc cctccttgac acccggcgcc  300
acctccttga gcttttctcg tctcctcccc atccccggct ccctggtccc ctcccggaac  360
ttctctggtc ccctccgctc ctcc                                          384

SEQ ID NO: 367         moltype = DNA  length = 384
FEATURE                Location/Qualifiers
source                 1..384
                       mol_type = other DNA
                       organism = Synthetic construct
SEQUENCE: 367
ggagaagtcg ggatttttta tattttatat tcggtagggg aagtttagta ggtgagcgta  60
ggttttttta gttttcgagg gagtgcgttc gacggaaacg tttttagttc gcgggtttcg  120
ttttttttt tcgggttttt gggttatttt tcgttgtttt tagttcgagt tcgtggtttt  180
aatttttggt atttttattt tttggttatt ttttttttgg tgtttttttt tcgatttttt  240
tttgtttcgt ttttattttt gttcgggttt gtcggatttt ttttttgat attcggcgtt  300
attttttga gtttttttcg tttttttttt attttcggtt ttttggtttt ttttcggaat  360
tttttggtt tttttcgttt tttt                                           384

SEQ ID NO: 368         moltype = DNA  length = 75
FEATURE                Location/Qualifiers
source                 1..75
                       mol_type = other DNA
                       organism = Synthetic construct
SEQUENCE: 368
gtttttttag ttttcgaggg agtgcgttcg acggaaacgt ttttagttcg cgggtttcgt  60
tttttttttt cgggt                                                    75

SEQ ID NO: 369         moltype = DNA  length = 447
FEATURE                Location/Qualifiers
source                 1..447
                       mol_type = genomic DNA
                       organism = Homo sapiens
SEQUENCE: 369
cagccatact cggccgagtc gacctgcagg cggcccagct tgtccacctg ctcctggaag  60
gcgcgcacct ggtccatgaa agccacggcg cgctcggcgg ccataggcgc ggcgtggagg  120
ccggcggcgg ccagtagcgg cgccgtgtgc aggggcagcg ccgcctgcgc cgcgttcagc  180
acgaagagct cgctccagct caggcgcagc agcgccacct ggtcggccac cggcagctcg  240
gggaagaagg gcgcgtggcg cgcccactcc acggtgctga agagcagccg cgccgccagc  300
tcgcacacgt tgtcgatgcc cagcaccgcg cccgccgcgc cgccccctgc gccgaagcgt  360
ccggccgccg cagggtaggg ctcagcgcgc agcagctgcg cgatcagttc ggacaccggc  420
tgccccggga agaggtctcc gccgctc                                       447

SEQ ID NO: 370         moltype = DNA  length = 447
FEATURE                Location/Qualifiers
source                 1..447
                       mol_type = other DNA
                       organism = Synthetic construct
SEQUENCE: 370
tagttatatt cggtcgagtc gatttgtagg cggtttagtt tgtttatttg tttttggaag  60
gcgcgtattt ggtttatgaa agttacggcg cgttcggcgg ttataggcgc ggcgtggagg  120
tcggcggcgg ttagtagcgg cgtcgtgtgt aggggtagcg tcgtttgcgt cgcgtttagt  180
acgaagagtt cgttttagtt taggcgtagt agcgttattt ggtcggttat cggtagttcg  240
gggaagaagg gcgcgtggcg cgtttatttt acggtgttga agagtagtcg cgtcgttagt  300
tcgtatacgt tgtcgatgtt tagtatcgcg ttcgtcgcgt cgttttttgc gtcgaagcgt  360
tcggtcgtcg tagggtaggg tttagcgcgt agtagttgcg cgattagttc ggatatcggt  420
tgtttcggga agaggttttc gtcgttt                                       447

SEQ ID NO: 371         moltype = DNA  length = 98
FEATURE                Location/Qualifiers
source                 1..98
                       mol_type = other DNA
                       organism = Synthetic construct
SEQUENCE: 371
gtttatttta cggtgttgaa gagtagtcgc gtcgttagtt cgtatacgtt gtcgatgttt  60
agtatcgcgt tcgtcgcgtc gttttttgcg tcgaagcg                           98

SEQ ID NO: 372         moltype = DNA  length = 416
FEATURE                Location/Qualifiers
source                 1..416
                       mol_type = genomic DNA
```

```
                        organism = Homo sapiens
SEQUENCE: 372
gccggcaaag agctggtgca ggatgcggat cagatcagcc agggtccgtg gcttcagcac  60
ttcggtctgt tccatctcgt ggggagctgg ctgcgcgcgc gtctcactgc tgggctgcgg  120
tggaggagct gagcgagcca aggagctggg ggcgagggag cctaacagcc cgctagaccg  180
ctaagcagac acacacgcac aaacccagca ttagagtgcc gaaacgtaag gatgtcgtcg  240
cagagacagc aagagaccca cccccaggcc cctggcagcg cagtggatcc gggatcgctg  300
gagacgcggt gcacacacaa atcaggttca gatctgtggg gttcatcctc ccgggcccct  360
tttaagcgct tggagtcact aggaatgtac caacggccct cggagggagg acgagg      416

SEQ ID NO: 373          moltype = DNA  length = 416
FEATURE                 Location/Qualifiers
source                  1..416
                        mol_type = other DNA
                        organism = Synthetic construct
SEQUENCE: 373
gtcggtaaag agttggtgta ggatgcggat tagattagtt agggttcgtg gttttagtat  60
ttcggtttgt tttatttcgt ggggagttgg ttgcgcgcgc gttttattgt tgggttgcgg  120
tggaggagtt gagcgagtta aggagttggg ggcgagggag tttaatagtt cgttagatcg  180
ttaagtagat atatacgtat aaatttagta ttagagtgtc gaaacgtaag gatgtcgtcg  240
tagagatagt aagagattta tttttaggtt tttggtagcg tagtggattc gggatcgttg  300
gagacgcggt gtatatataa attaggttta gatttgtggg gtttattttt tcgggttttt  360
tttaagcgtt tggagttatt aggaatgtat taacggtttt cggagggagg acgagg      416

SEQ ID NO: 374          moltype = DNA  length = 119
FEATURE                 Location/Qualifiers
source                  1..119
                        mol_type = other DNA
                        organism = Synthetic construct
SEQUENCE: 374
gagtgtcgaa acgtaaggat gtcgtcgtag agatagtaag agatttattt ttaggttttt  60
ggtagcgtag tggattcggg atcgttggag acgcggtgta tatataaatt aggtttaga   119

SEQ ID NO: 375          moltype = DNA  length = 267
FEATURE                 Location/Qualifiers
source                  1..267
                        mol_type = genomic DNA
                        organism = Homo sapiens
SEQUENCE: 375
gcactcgcca gcgctttgtt cgtgaccggc cttttaaggg ctgtctcacc catcttgtct  60
ggctctgcct ccctgtttcc tttccgtcct ctctcccacc acagccagct ccccactttt  120
ttcgcggggg ccccctccag cctgtccggg gcctccccgt tcccaggcca gggcttcccc  180
ctcctcccag acctcgttgc tctgcccggt gaggccccgg gctcccagca gggggcgcct  240
gctcgcgatc aggtggcggc ctgggggg                                    267

SEQ ID NO: 376          moltype = DNA  length = 267
FEATURE                 Location/Qualifiers
source                  1..267
                        mol_type = other DNA
                        organism = Synthetic construct
SEQUENCE: 376
gtattcgtta gcgttttgtt cgtgatcggt tttttaaggg ttgttttatt tattttgttt  60
ggttttgttt ttttgttttt ttttcgtttt tttttttatt atagttagtt ttttattttt  120
ttcgcggggg tttttttttag tttgttcggg gttttttcgt ttttaggtta gggttttttt  180
ttttttttag atttcgttgt tttgttcggt gaggtttcgg gtttttagta gggggcgttt  240
gttcgcgatt aggtggcggt ttgggggg                                    267

SEQ ID NO: 377          moltype = DNA  length = 78
FEATURE                 Location/Qualifiers
source                  1..78
                        mol_type = other DNA
                        organism = Synthetic construct
SEQUENCE: 377
gatttcgttg ttttgttcgg tgaggtttcg ggtttttagt agggggcgtt tgttcgcgat  60
taggtggcgg tttggggg                                                78

SEQ ID NO: 378          moltype = DNA  length = 155
FEATURE                 Location/Qualifiers
source                  1..155
                        mol_type = genomic DNA
                        organism = Homo sapiens
SEQUENCE: 378
gaggggacct ggatccctga accccggggc ggaaagggag cctccgggcg gctgtgggtg  60
ccgcgctcct cggagccagc agctgctggg gcggcgtccg aactccccag gtctgcgcac  120
ggcaatgggg gcaccgggcc ttctgtctgt cctca                             155

SEQ ID NO: 379          moltype = DNA  length = 155
FEATURE                 Location/Qualifiers
source                  1..155
```

```
                         mol_type = other DNA
                         organism = Synthetic construct
SEQUENCE: 379
gaggggattt ggatttttga atttcggggc ggaaagggag ttttcgggcg gttgtgggtg  60
tcgcgttttt cggagttagt agttgttggg gcggcgttcg aattttttag gtttgcgtac  120
ggtaatgggg gtatcgggtt ttttgtttgt tttta                             155

SEQ ID NO: 380           moltype = DNA  length = 79
FEATURE                  Location/Qualifiers
source                   1..79
                         mol_type = other DNA
                         organism = Synthetic construct
SEQUENCE: 380
gaattcgggt ttagcgcggg tttttcgcgg tagtggtcgt agttcgggaa gttcgggggc  60
gcggtgtttt cgtgaattc                                               79

SEQ ID NO: 381           moltype = DNA  length = 160
FEATURE                  Location/Qualifiers
source                   1..160
                         mol_type = genomic DNA
                         organism = Homo sapiens
SEQUENCE: 381
cggggacagg aggggtggcc aagaaagtcg caagaaaact ccggccccca agaaaaagag  60
agggcatggg ttgcggagcc gacatcacgg ccggggtctt tgctgtttag acgcctgggt  120
tcccggatcc cagacacgcg cacgggcagg aagttagacc                        160

SEQ ID NO: 382           moltype = DNA  length = 160
FEATURE                  Location/Qualifiers
source                   1..160
                         mol_type = other DNA
                         organism = Synthetic construct
SEQUENCE: 382
cggggatagg aggggtggtt aagaaagtcg taagaaaatt tcggttttta agaaaaagag  60
agggtatggg ttgcggagtc gatattacgg tcggggtttt tgttgtttag acgtttgggt  120
tttcggattt tagatacgcg tacgggtagg aagttagatt                        160

SEQ ID NO: 383           moltype = DNA  length = 163
FEATURE                  Location/Qualifiers
source                   1..163
                         mol_type = genomic DNA
                         organism = Homo sapiens
SEQUENCE: 383
gttgcctggg tccgcccaga gatgagtcgg gacgcgcggc ccacgtgcgg cggaggggca  60
gctgggtcgc tcggggaacg gggcaccgga tggccccggt tgggcccgcg ccaggatgcg  120
cccctgcgcc ctctgctggc gctctgcggt caccgcagcc ccg                    163

SEQ ID NO: 384           moltype = DNA  length = 163
FEATURE                  Location/Qualifiers
source                   1..163
                         mol_type = other DNA
                         organism = Synthetic construct
SEQUENCE: 384
gttgtttggg ttcgtttaga gatgagtcgg gacgcgcggt ttacgtgcgg cggaggggta  60
gttgggtcgt tcggggaacg gggtatcgga tggtttcggt tgggttcgcg ttaggatgcg  120
tttttgcgtt ttttgttggc gttttgcggt tatcgtagtt tcg                    163

SEQ ID NO: 385           moltype = DNA  length = 311
FEATURE                  Location/Qualifiers
source                   1..311
                         mol_type = genomic DNA
                         organism = Homo sapiens
SEQUENCE: 385
cggacgaatt ctggggaaag gtcgagggaa ctagagctcc cgactatgca aaccctagag  60
ggtaaactgg gggctaagag ggccccgtgc gtgttttggc gggctaggtc ctgggcttca  120
gggcagagaa gagggccgag tggatcgcct tgccttacct cctcaggatc tccggattcg  180
gtaagcatct tttgctcgtc ctccagtccc atgtctggct acggttctag attcaacacg  240
agcagcaaca gcggcaccta acccagttca ggatcaagaa ggacttgtaa gggtcactca  300
gcggaaatcc g                                                       311

SEQ ID NO: 386           moltype = DNA  length = 311
FEATURE                  Location/Qualifiers
source                   1..311
                         mol_type = other DNA
                         organism = Synthetic construct
SEQUENCE: 386
cggacgaatt ttggggaaag gtcgagggaa ttagagtttt cgattatgta aattttagag  60
ggtaaattgg gggttaagag ggtttcgtgc gtgttttggc gggttaggtt ttgggtttta  120
gggtagagaa gagggtcgag tggatcgttt tgttttattt ttttaggatt ttcggattcg  180
gtaagtattt tttgttcgtt ttttagtttt atgtttggtt acggttttag atttaatacg  240
```

```
agtagtaata gcggtattta atttagttta ggattaagaa ggatttgtaa gggttattta  300
gcggaaattc g                                                       311

SEQ ID NO: 387         moltype = DNA  length = 154
FEATURE                Location/Qualifiers
source                 1..154
                       mol_type = other DNA
                       organism = Synthetic construct
SEQUENCE: 387
cggacgaatt ttggggaaag gtcgagggaa ttagagtttt cgattatgta aattttagag  60
ggtaaattgg gggttaagag ggtttcgtgc gtgttttggc gggttaggtt ttgggtttta  120
gggtagagaa gagggtcgag tggatcgttt tgtt                              154

SEQ ID NO: 388         moltype = DNA  length = 706
FEATURE                Location/Qualifiers
source                 1..706
                       mol_type = genomic DNA
                       organism = Homo sapiens
SEQUENCE: 388
cgtcccagaa ctaagtgcta tgcggagatg agggtgggag cagcagtaca aggagggggt  60
gggggcgagg aaacacaaac aggggagaag gaaacgccag catctaacat ggacttgaca  120
gtcatctgac aatacccaga ccctgtgcgc tccgggttcc accgctgtgc ccagtttggg  180
cccaagaaat gaggaatcaa tcgtgttagt actaaggtgg ccgaggggac cggctcgctc  240
actcgttcgc gctccctggc tcggcggaca ccaggcagtc ccccggcggt cggccgctcg  300
gaggacgcgg aagatgtccc ggggaactca ggtgaccccg cccgccaccc acagaaagag  360
ccaggccggg gttgcttccc attccctctg cagccggaga gctgaggagg tagggacctg  420
gcgcggctca gcgcgctccg cgagcggctc cccaaatggg tgcgagaggg aagagggcag  480
agcgcggcgg ggcgtccggg gggcgcccgg tacccgaggc gggcgcacgc acccaaacag  540
gagagcggcg cccggagtta ctcagtgcgg gcagaagagc ggggcgagga gcggggtcgc  600
gcccgctgga ggcgcggggc gagcggagga agaggaggag gagagcagaa ggaaggggaa  660
gcggctcgta cctgctgcgc gccggggcgc ctgctgcttc ctcctc                  706

SEQ ID NO: 389         moltype = DNA  length = 706
FEATURE                Location/Qualifiers
source                 1..706
                       mol_type = other DNA
                       organism = Synthetic construct
SEQUENCE: 389
cgttttagaa ttaagtgtta tgcggagatg agggtgggag tagtagtata aggagggggt  60
gggggcgagg aaatataaat aggggagaag gaaacgttag tatttaatat ggatttgata  120
gttatttgat aatatttaga ttttgtgcgt ttcgggtttt atcgttgtgt ttagtttggg  180
tttaagaaat gaggaattaa tcgtgttagt attaaggtgg tcgaggggat cggttcgttt  240
attcgttcgc gtttttggt tcggcggata ttaggtagtt tttcggcggt cggtcgttcg  300
gaggacgcgg aagatgtttc ggggaattta ggtgatttcg ttcgttattt atagaaagag  360
ttaggtcggg gttgtttttt attttttttg tagtcggaga gttgaggagg tagggatttg  420
gcgcggttta gcgcgtttcg cgagcggttt tttaaatggg tgcgagaggg aagagggtag  480
agcgcggcgg ggcgttcggg gggcgttcgg tattcgaggc gggcgtacgt atttaaatag  540
gagagcggcg ttcggagtta tttagtgcgg gtagaagagc ggggcgagga gcggggtcgc  600
gttcgttgga ggcgcggggc gagcggagga agaggaggag gagagtagaa ggaaggggaa  660
gcggttcgta tttgttgcgc gtcggggcgt ttgttgtttt tttttt                  706

SEQ ID NO: 390         moltype = DNA  length = 154
FEATURE                Location/Qualifiers
source                 1..154
                       mol_type = other DNA
                       organism = Synthetic construct
SEQUENCE: 390
gaattaatcg tgttagtatt aaggtggtcg aggggatcgg ttcgtttatt cgttcgcgtt  60
ttttggttcg gcggatatta ggtagttttt cggcggtcgg tcgttcggag gacgcggaag  120
atgtttcggg gaatttaggt gatttcgttc gtta                              154

SEQ ID NO: 391         moltype = DNA  length = 120
FEATURE                Location/Qualifiers
source                 1..120
                       mol_type = genomic DNA
                       organism = Homo sapiens
SEQUENCE: 391
cgtcgggcct gcgggggccg gacccgcctt cgaaagtggg cggaaggatg gccgccctgg  60
cggagtgcgg gcgaggccgg gagcccttgc ctcagccccg gcccggtctt cttcgtgccg  120

SEQ ID NO: 392         moltype = DNA  length = 120
FEATURE                Location/Qualifiers
source                 1..120
                       mol_type = other DNA
                       organism = Synthetic construct
SEQUENCE: 392
cgtcgggttt gcgggggtcg gattcgtttt cgaaagtggg cggaaggatg gtcgttttgg  60
cggagtgcgg gcgaggtcgg gagtttttgt tttagtttcg gttcggtttt tttcgtgtcg  120
```

-continued

```
SEQ ID NO: 393          moltype = DNA  length = 190
FEATURE                 Location/Qualifiers
source                  1..190
                        mol_type = genomic DNA
                        organism = Homo sapiens
SEQUENCE: 393
cggtgtggtc cgaaaggctc ttctcttaaa ccccccggca gccggctcct gtgtgtgaca  60
cgatgatgtc atcatcgccg agcagcccca acgcctgcat cttcacaaag ctccatcgcg  120
ggctccggaa acggggctgg gggtggggag gcgaagaccc tccctctgcc ccggcccctc  180
ccgcctcgcc                                                         190

SEQ ID NO: 394          moltype = DNA  length = 190
FEATURE                 Location/Qualifiers
source                  1..190
                        mol_type = other DNA
                        organism = Synthetic construct
SEQUENCE: 394
cggtgtggtt cgaaaggttt ttttttaaa tttttcggta gtcggttttt gtgtgtgata  60
cgatgatgtt attatcgtcg agtagtttta acgtttgtat ttttataaag ttttatcgcg  120
ggtttcggaa acggggttgg gggtggggag gcgaagattt tttttttgtt tcggtttttt  180
tcgtttcgtt                                                         190

SEQ ID NO: 395          moltype = DNA  length = 323
FEATURE                 Location/Qualifiers
source                  1..323
                        mol_type = genomic DNA
                        organism = Homo sapiens
SEQUENCE: 395
cgggcgtatg tgtgtctcca atggaaaaat cctacccagg acgacaccac atccttgctc  60
ccacaaataa aaccttccac ggaactcagg gctgcagacc agcccttcgc aagccaacgc  120
gccccgtggg cactcggtcc cccggctccg cgtctctgcc accttcccac cgcttcttct  180
ttaaccatgc tcttgtttcc cctcgctgat cgcaaggctg cgggcgagga ttccagagag  240
aggcctagta tggggaacaa acgcttcaga ggggtccgag gtgggctggg gacagccagt  300
ggatgggaag gagggcgctg gcg                                          323

SEQ ID NO: 396          moltype = DNA  length = 323
FEATURE                 Location/Qualifiers
source                  1..323
                        mol_type = other DNA
                        organism = Synthetic construct
SEQUENCE: 396
cgggcgtatg tgtgttttta atggaaaaat tttatttagg acgatattat atttttgttt  60
ttataaataa aattttttac ggaatttagg gttgtagatt agtttttcgt aagttaacgc  120
gtttcgtggg tattcggttt ttcggtttcg cgtttttgtt attttttat cgtttttttt  180
ttaattatgt ttttgttttt tttcgttgat cgtaaggttg cgggcgagga ttttagagag  240
aggtttagta tggggaataa acgttttaga ggggttcgag gtgggttggg gatagttagt  300
ggatgggaag gagggcgttg gcg                                          323

SEQ ID NO: 397          moltype = DNA  length = 177
FEATURE                 Location/Qualifiers
source                  1..177
                        mol_type = other DNA
                        organism = Synthetic construct
SEQUENCE: 397
tacggaattt agggttgtag attagttttt cgtaagttaa cgcgtttcgt gggtattcgg  60
tttttcggtt tcgcgttttt gttatttttt tatcgttttt tttttaatta tgtttttgtt  120
ttttttcgtt gatcgtaagg ttgcgggcga ggattttaga gagaggttta gtatggg     177
```

DETECTING OVARIAN CANCER

CROSS-REFERENCE TO RELATED APPLICATIONS

This application is a continuation of U.S. patent application Ser. No. 17/085,542, filed Oct. 30, 2020, which claims the priority benefit of U.S. Provisional Application No. 62/928,888, filed Oct. 31, 2019 and U.S. Provisional Application No. 63/065,081, filed Aug. 13, 2020, which are incorporated herein by reference in their entireties.

SEQUENCE LISTING

The text of the computer readable sequence listing filed herewith, titled "38034_ 304_SequenceListing" created May 24, 2023, having a file size of 373,093 bytes, is hereby incorporated by reference in its entirety.

FIELD OF INVENTION

Provided herein is technology for ovarian cancer screening and particularly, but not exclusively, to methods, compositions, and related uses for detecting the presence of ovarian cancer and sub-types of ovarian cancer (e.g., clear cell ovarian cancer, endometrioid ovarian cancer, mucinous ovarian cancer, serous ovarian cancer).

BACKGROUND

Ovarian cancer is among the most lethal gynecologic malignancies in developed countries. In the United States, approximately 23,000 women are diagnosed with the disease and almost 14,000 women die from it each year. There are three main types of ovarian cancer: epithelial, germ cell, and sex cord stromal. About 90% of ovarian cancers start in the epithelium tissue, which is the lining on the outside of the ovary. This type of ovarian cancer is divided into serous, mucinous, endometrioid, clear cell, transitional and undifferentiated types. The risk of epithelial ovarian cancer increases with age, especially after the age of 50. Germ cell tumors account for about 5% of ovarian cancers. They begin in the egg-producing cells. This type of ovarian cancer can occur in women of any age, but about 80% are found in women under the age of 30. The main subtypes are teratoma, dysgerminoma, endodermal sinus tumor and choriocarcinoma. Sex cord stromal tumors, about 5% of ovarian cancers, grow in the connective tissue that holds the ovary together and makes estrogen and progesterone. Most are found in older women.

Despite progress in cancer therapy, ovarian cancer mortality has remained virtually unchanged over the past two decades. Given the steep survival gradient relative to the stage at which the disease is diagnosed, early detection remains the most important factor in improving long-term survival of ovarian cancer patients.

Improved methods for detecting ovarian cancer and various subtypes of ovarian cancer (e.g., clear cell ovarian cancer, endometrioid ovarian cancer, mucinous ovarian cancer, and serous ovarian cancer) are needed.

The present invention addresses these needs.

SUMMARY

As noted, ovarian cancer (OC) is the foremost cause of gynecological cancer death and is overall one of the most frequent causes of fatal malignancy in women (see, Ozor R. F., et al., Epithelial ovarian cancer. In: Hoskin W. J., Perez C. A., Young R. C., editors. Principles and Practice of Gynecologic Oncology. Lippincott Williams & Wilkins; Philadelphia, PA, USA: 2000. pp. 981-1057). The symptoms are often nonspecific, hampering early detection, so the majority of patients present with advanced-stage disease.

Recently, the characteristics of several subtypes of OC have been elucidated by the findings from histopathological, molecular, and genetic studies. The main histotypes are epithelial in origin and include serous ovarian cancer (serous OC), Clear Cell Carcinoma (clear cell OC), Endometrioid Carcinoma (endometrioid OC), and Mucinous Carcinoma (mucinous OC). Serous OC is the most malignant form of ovarian cancer and accounts for up to 70% of all ovarian cancer cases. Clear cell OC is the second most common histotype accounting for about 10-13% of women diagnosed with ovarian cancer. Endometrioid OC is the third most common histotype of ovarian cancer and like clear cell carcinoma is believed to arise from endometriosis. Mucinous OC account for 4% of ovarian carcinomas and are commonly diagnosed at a low stage.

To lessen the heavy toll of OC and its various subtypes (e.g., clear cell OC, serous OC, endometrioid OC, mucinous OC), effective screening approaches are urgently needed. There is an imperative for innovation that will deliver accurate, affordable, and safe screening tools for the presymptomatic detection of earliest stage cancer and advanced precancer.

The present invention addresses such needs. Indeed, the present invention provides novel methylated DNA markers that discriminate cases of OC and its various subtypes (e.g., clear cell OC, serous OC, endometrioid OC, mucinous OC).

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (Laird (2010) Nat Rev Genet 11: 191-203). Furthermore, in other cancers like sporadic colon cancer, methylation markers offer excellent specificity and are more broadly informative and sensitive than are individual DNA mutations (Zou et al (2007) Cancer Epidemiol Biomarkers Prev 16: 2686-96).

Analysis of CpG islands has yielded important findings when applied to animal models and human cell lines. For example, Zhang and colleagues found that amplicons from different parts of the same CpG island may have different levels of methylation (Zhang et al. (2009) PLoS Genet 5: e1000438). Further, methylation levels were distributed bi-modally between highly methylated and unmethylated sequences, further supporting the binary switch-like pattern of DNA methyltransferase activity (Zhang et al. (2009) PLoS Genet 5: e1000438). Analysis of murine tissues in vivo and cell lines in vitro demonstrated that only about 0.3% of high CpG density promoters (HCP, defined as having >7% CpG sequence within a 300 base pair region) were methylated, whereas areas of low CpG density (LCP, defined as having <5% CpG sequence within a 300 base pair region) tended to be frequently methylated in a dynamic tissue-specific pattern (Meissner et al. (2008) Nature 454: 766-70). HCPs include promoters for ubiquitous housekeeping genes and highly regulated developmental genes. Among the HCP sites methylated at >50% were several established markers such as Wnt 2, NDRG2, SFRP2, and BMP3 (Meissner et al. (2008) Nature 454: 766-70).

Epigenetic methylation of DNA at cytosine-phosphate-guanine (CpG) island sites by DNA methyltransferases has been studied as a potential class of biomarkers in the tissues of most tumor types. In a biologically attractive mechanism, acquired methylation events in promotor regions of tumor suppressor genes are thought to silence expression, contributing to oncogenesis. DNA methylation may be a more chemically and biologically stable diagnostic tool than RNA or protein expression. Furthermore, in other cancers like sporadic colon cancer, aberrant methylation markers are more broadly informative and sensitive than are individual DNA mutations and offer excellent specificity.

Several methods are available to search for novel methylation markers. While microarray based interrogation of CpG methylation is a reasonable, high-throughput approach, this strategy is biased towards known regions of interest, mainly established tumor suppressor promotors. Alternative methods for genome-wide analysis of DNA methylation have been developed in the last decade. There are three basic approaches. The first employs digestion of DNA by restriction enzymes which recognize specific methylated sites, followed by several possible analytic techniques which provide methylation data limited to the enzyme recognition site or the primers used to amplify the DNA in quantification steps (such as methylation-specific PCR; MSP). A second approach enriches methylated fractions of genomic DNA using anti-bodies directed to methyl-cytosine or other methylation-specific binding domains followed by microarray analysis or sequencing to map the fragment to a reference genome. This approach does not provide single nucleotide resolution of all methylated sites within the fragment. A third approach begins with bisulfate treatment of the DNA to convert all unmethylated cytosines to uracil, followed by restriction enzyme digestion and complete sequencing of all fragments after coupling to an adapter ligand. The choice of restriction enzymes can enrich the fragments for CpG dense regions, reducing the number of redundant sequences which may map to multiple gene positions during analysis.

RRBS yields CpG methylation status data at single nucleotide resolution of 80-90% of all CpG islands and a majority of tumor suppressor promoters at medium to high read coverage. In cancer case—control studies, analysis of these reads results in the identification of differentially methylated regions (DMRs). In previous RRBS analysis of pancreatic cancer specimens, hundreds of DMRs were uncovered, many of which had never been associated with carcinogenesis and many of which were unannotated. Further validation studies on independent tissue samples sets confirmed marker CpGs which were 100% sensitive and specific in terms of performance.

Provided herein is technology for OC and various OC subtypes (e.g., clear cell OC, endometrioid OC, mucinous OC, serous OC) screening and particularly, but not exclusively, to methods, compositions, and related uses for detecting the presence of OC and various OC subtypes (e.g., clear cell OC, endometrioid OC, mucinous OC, serous OC).

Indeed, as described in Examples I and II, experiments conducted during the course for identifying embodiments for the present invention identified a novel set of differentially methylated regions (DMRs) for discriminating 1) cancer of the ovary derived DNA from non-neoplastic control DNA, 2) DNA derived from clear cell OC tissue from non-neoplastic control DNA, 3) DNA derived from endometrioid OC tissue from non-neoplastic control DNA, 4) DNA derived from mucinous OC tissue from non-neoplastic control DNA, and 5) DNA derived from serous OC tissue from non-neoplastic control DNA.

Such experiments list and describe 560 novel DNA methylation markers distinguishing OC tissue from benign tissue (see, Tables 1A, 1B, 3, 4A, 6A, and 8A; Examples I and II), clear cell OC tissue from benign tissue (see, Tables 1A, 1B, 2A, 4B, 5B, 6A, 8B; Examples I and II), endometrioid OC tissue from benign tissue (see, Tables 1A, 1B, 2B, 4C, 5C, 6A, and 8C; Examples I and II), mucinous OC tissue from benign tissue (see, Tables 1A, 1B, 2C, 4D, 5D, 6A, and 8D; Examples I and II), serous OC tissue from benign tissue (see, Tables 1A, 1B, 2D, 4E, 5A, 6A, and 8E; Examples I and II), and detecting OC (e.g., OC, clear cell OC, endometrioid OC, mucinous OC, serous OC) within a blood sample (see, Table 9; Example III).

From these 560 novel DNA methylation markers, further experiments identified the following markers and/or panels of markers capable of distinguishing ovarian cancer tissue from benign tissue:

AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A; Example I);

MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I);

PALLD, PRDM14, MAX.chr1.147790358-147790381, BCAT1, MAML3_A, SKI, DNMT3A_A, and C2CD4D (see, Table 4A; Example I); and BCAT1_6015, SKI, SIM2_B, DNMT3A_A, CDO1_A, and DSCR6 (see, Table 8A; Example II).

From these 560 novel DNA methylation markers, further experiments identified the following markers and/or panels of markers for detecting ovarian cancer (e.g., OC, clear cell OC, endometrioid OC, mucinous OC, serous OC) in blood samples (e.g., plasma samples, whole blood samples, leukocyte samples, serum samples):

GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g.,

GYPC_A, GYPC_B, GYPC_C), CAPN2 (e.g., CAPN2_A, CAPN2_B), and BCAT1 (see, Table 9; Example III); and ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III).

From these 560 novel DNA methylation markers, further experiments identified the following markers and/or panels of markers for detecting ovarian cancer (e.g., OC, clear cell OC, endometrioid OC, mucinous OC, serous OC) in blood samples (e.g., plasma samples, whole blood samples, leukocyte samples, serum samples) in combination with increased levels of cancer antigen 125 (CA-125) in the blood sample:

CA-125 and ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, and SIM2_A (see, Tables 11, 12 and 13, Example III).

From these 560 novel DNA methylation markers, further experiments identified the following markers and/or panels of markers capable of distinguishing clear cell OC tissue from ovarian tissue:

TACC2_A, LRRC41_A, EPS8L2, LBH, LIME1_B, MDFI, FAIM2_A, GYPC_A, AGRN_B, and ZBED4 (see, Table 2A; Example I);

MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I);

NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I); and AGRN 8794, BHLHE23_8339, EPS8L2_F, RASSF1_8293, MDFI 6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II).

From these 560 novel DNA methylation markers, further experiments identified the following markers and/or panels of markers capable of distinguishing endometrioid OC tissue from benign tissue:

PARP15, GPRIN1_A, GYPC1_A, FLJ34208, MAX.chr1.147790358-147790381, FAIM2_A, SH2B3, KCNQ5, IRF4, and BCAT1 (see, Table 2B; Example I);

NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I);

NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I); and BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II).

From these 560 novel DNA methylation markers, further experiments identified the following markers and/or panels of markers capable of distinguishing mucinous OC tissue from benign tissue:

CMTM3_A, ATP10A_C, TSHZ3, ZMIZ1_B, ATP10A_B, ELMO1_B, TACC2_A, LRRC4, VIM, and ZNF382_A (see, Table 2C; Example I);

NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I);

NCOR2, PALLD, TACC2_A, BCAT1, AGRN_B, SKI, SLC12A8, ZMIZ1_B, and BCL2L11 (see, Table 5D; Example I); and BCAT1_6015, ELMO1_9100, KCNA3_7518, KCNA3_7320, MDFI 6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II).

From these 560 novel DNA methylation markers, further experiments identified the following markers and/or panels of markers capable of distinguishing serous OC tissue from benign tissue:

MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I);

PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I);

NCOR2, MAX.chr1.147790358-147790381, MAX.chr6.10382190-10382225, IFFO1_A, GDF6, and C2CD4D (see, Table 5A; Example I); and SKI, PEAR1_B, CAPN2_B, SIM2_B, DNMT3A_A, CDO1_A, and NR2F6 (see, Table 8E; Example II).

As described herein, the technology provides a number of methylated DNA markers and subsets thereof (e.g., sets of 2, 3, 4, 5, 6, 7, or 8 markers) with high discrimination for ovarian cancer overall and various types of ovarian cancer (e.g., clear cell OC, endometrioid OC, mucinous OC, serous OC). Experiments applied a selection filter to candidate markers to identify markers that provide a high signal to noise ratio and a low background level to provide high specificity for purposes of ovarian cancer screening or diagnosis.

In some embodiments, the technology is related to assessing the presence of and methylation state of one or more of the markers identified herein in a biological sample (e.g., ovarian tissue, plasma sample). These markers comprise one or more differentially methylated regions (DMR) as discussed herein, e.g., as provided in Tables 1A and 6A. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) *Mol. Cell. Biol.* 14: 7421-7427) and another example involves methylation-sensitive arbitrarily primed PCR (Gonzalgo et al. (1997) *Cancer Res.* 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes or methylation-dependent restriction enzymes prior to PCR amplification (Singer-Sam et al. (1990) *Nucl. Acids Res.* 18: 687). In addition, other techniques have been reported that utilize bisulfite treatment of DNA as a starting point for methylation analysis. These include methylation-specific PCR (MSP) (Herman et al. (1992) *Proc. Natl. Acad. Sci. USA* 93: 9821-9826) and restriction enzyme digestion of PCR products amplified from bisulfite-converted DNA (Sadri and Hornsby (1996) *Nucl. Acids Res.* 24: 5058-5059; and Xiong and Laird (1997) *Nucl. Acids Res.* 25: 2532-2534). PCR techniques have been developed for detection of gene mutations (Kuppuswamy et al. (1991) *Proc. Natl. Acad. Sci. USA* 88: 1143-1147) and quantification of allelic-specific expression (Szabo and Mann (1995) *Genes Dev.* 9: 3097-3108; and Singer-Sam et al. (1992) *PCR Methods Appl.* 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. No. 8,361,720; and U.S. Pat. Appl. Pub. Nos. 2012/0122088 and 2012/0122106, incorporated herein by reference).

For example, in some embodiments, methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits contain a reagent capable of modifying DNA in a methylation-specific manner (e.g., a methylation-sensitive restriction enzyme, a methylation-dependent restriction enzyme, and a bisulfite reagent). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining a methylation state (e.g., of one or more DMR, e.g., DMR 1-560 as provided in Tables 1A and 6A); comparing methylation states (e.g., of one or more DMR, e.g., DMR 1-560 as provided in Tables 1A and 6A); generating standard curves; determining a Ct value; calculating a fraction, frequency, or percentage of methylation (e.g., of one or more DMR, e.g., DMR 1-560 as provided in Tables 1A and 6A); identifying a CpG island; determining a specificity and/or sensitivity of an assay or marker; calculating an ROC curve and an associated AUC; sequence analysis; all as described herein or is known in the art.

In some embodiments, a microprocessor or computer uses methylation state data in an algorithm to predict a site of a cancer.

In some embodiments, a software or hardware component receives the results of multiple assays and determines a single value result to report to a user that indicates a cancer risk based on the results of the multiple assays (e.g., determining the methylation state of multiple DMR, e.g., as provided in Tables 1A and 6A). Related embodiments calculate a risk factor based on a mathematical combination (e.g., a weighted combination, a linear combination) of the results from multiple assays, e.g., determining the methylation states of multiple markers (such as multiple DMR, e.g., as provided in Tables 1A and 6A). In some embodiments, the methylation state of a DMR defines a dimension and may have values in a multidimensional space and the coordinate defined by the methylation states of multiple DMR is a result, e.g., to report to a user, e.g., related to a cancer risk.

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, California and Motorola Corporation of Schaumburg, Illinois. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

Accordingly, provided herein is technology related to a method of screening for ovarian cancer and/or various forms of ovarian cancer (e.g., clear cell OC, endometrioid OC, mucinous OC, serous OC) in a sample obtained from a subject, the method comprising assaying a methylation state of a marker in a sample obtained from a subject (e.g., ovarian tissue) (e.g., plasma sample) and identifying the subject as having OC and/or a specific form of OC (e.g., clear cell OC, endometrioid OC, mucinous OC, serous OC) when the methylation state of the marker is different than a methylation state of the marker assayed in a subject that does not have such cancer, wherein the marker comprises a base in a differentially methylated region (DMR) selected from a group consisting of DMR 1-560 as provided in Tables 1A and 6A.

In some embodiments wherein the sample obtained from the subject is ovarian tissue and the methylation state of one or more of the following markers is different than a methylation state of the one or more markers assayed in a subject that does not have ovarian cancer indicates the subject has ovarian cancer: AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A; Example I).

In some embodiments wherein the sample obtained from the subject is ovarian tissue and the methylation state of one or more of the following markers is different than a methylation state of the one or more markers assayed in a subject that does not have ovarian cancer indicates the subject has ovarian cancer: MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I).

In some embodiments wherein the sample obtained from the subject is ovarian tissue and the methylation state of one or more of the following markers is different than a methylation state of the one or more markers assayed in a subject that does not have ovarian cancer indicates the subject has ovarian cancer: PALLD, PRDM14, MAX.chr1.147790358-147790381, BCAT1, MAML3_A, SKI, DNMT3A_A, and C2CD4D (see, Table 4A; Example I).

In some embodiments wherein the sample obtained from the subject is ovarian tissue and the methylation state of one or more of the following markers is different than a methylation state of the one or more markers assayed in a subject that does not have ovarian cancer indicates the subject has ovarian cancer: BCAT1_6015, SKI, SIM2_B, DNMT3A_A, CDO1_A, and DSCR6 (see, Table 8A; Example II).

In some embodiments wherein the sample obtained from the subject is ovarian tissue and the methylation state of one or more of the following markers is different than a methylation state of the one or more markers assayed in a subject that does not have ovarian cancer indicates the subject has clear cell ovarian cancer: TACC2_A, LRRC41_A, EPS8L2, LBH, LIME1_B, MDFI, FAIM2_A, GYPC_A, AGRN_B, and ZBED4 (see, Table 2A; Example I).

In some embodiments wherein the sample obtained from the subject is ovarian tissue and the methylation state of one or more of the following markers is different than a methylation state of the one or more markers assayed in a subject that does not have ovarian cancer indicates the subject has clear cell ovarian cancer: MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I).

In some embodiments wherein the sample obtained from the subject is ovarian tissue and the methylation state of one or more of the following markers is different than a methylation state of the one or more markers assayed in a subject that does not have ovarian cancer indicates the subject has clear cell ovarian cancer: NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I).

In some embodiments wherein the sample obtained from the subject is ovarian tissue and the methylation state of one or more of the following markers is different than a methylation state of the one or more markers assayed in a subject that does not have ovarian cancer indicates the subject has clear cell ovarian cancer: AGRN_8794, BHLHE23_8339, EPS8L2_F, RASSF1_8293, MDFI 6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II).

In some embodiments wherein the sample obtained from the subject is ovarian tissue and the methylation state of one or more of the following markers is different than a methylation state of the one or more markers assayed in a subject that does not have ovarian cancer indicates the subject has endometrioid ovarian cancer: PARP15, GPRIN1_A, GYPC1_A, FLJ34208, MAX.chr1.147790358-147790381, FAIM2_A, SH2B3, KCNQ5, IRF4, and BCAT1 (see, Table 2B; Example I).

In some embodiments wherein the sample obtained from the subject is ovarian tissue and the methylation state of one or more of the following markers is different than a methylation state of the one or more markers assayed in a subject that does not have ovarian cancer indicates the subject has endometrioid ovarian cancer: NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I).

In some embodiments wherein the sample obtained from the subject is ovarian tissue and the methylation state of one or more of the following markers is different than a methylation state of the one or more markers assayed in a subject that does not have ovarian cancer indicates the subject has endometrioid ovarian cancer: NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I).

In some embodiments wherein the sample obtained from the subject is ovarian tissue and the methylation state of one or more of the following markers is different than a methylation state of the one or more markers assayed in a subject that does not have ovarian cancer indicates the subject has endometrioid ovarian cancer: BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II).

In some embodiments wherein the sample obtained from the subject is ovarian tissue and the methylation state of one or more of the following markers is different than a methylation state of the one or more markers assayed in a subject that does not have ovarian cancer indicates the subject has mucinous ovarian cancer: CMTM3_A, ATP10A_C, TSHZ3, ZMIZ1_B, ATP10A_B, ELMO1_B, TACC2_A, LRRC4, VIM, and ZNF382_A (see, Table 2C; Example I).

In some embodiments wherein the sample obtained from the subject is ovarian tissue and the methylation state of one or more of the following markers is different than a methylation state of the one or more markers assayed in a subject that does not have ovarian cancer indicates the subject has mucinous ovarian cancer: NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I).

In some embodiments wherein the sample obtained from the subject is ovarian tissue and the methylation state of one or more of the following markers is different than a methylation state of the one or more markers assayed in a subject that does not have ovarian cancer indicates the subject has mucinous ovarian cancer: NCOR2, PALLD, TACC2_A, BCAT1, AGRN_B, SKI, SLC12A8, ZMIZ1_B, and BCL2L11 (see, Table 5D; Example I).

In some embodiments wherein the sample obtained from the subject is ovarian tissue and the methylation state of one or more of the following markers is different than a methylation state of the one or more markers assayed in a subject that does not have ovarian cancer indicates the subject has mucinous ovarian cancer: BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II).

In some embodiments wherein the sample obtained from the subject is ovarian tissue and the methylation state of one or more of the following markers is different than a methylation state of the one or more markers assayed in a subject that does not have ovarian cancer indicates the subject has serous ovarian cancer: MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I).

In some embodiments wherein the sample obtained from the subject is ovarian tissue and the methylation state of one or more of the following markers is different than a methylation state of the one or more markers assayed in a subject that does not have ovarian cancer indicates the subject has serous ovarian cancer: PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I).

In some embodiments wherein the sample obtained from the subject is ovarian tissue and the methylation state of one or more of the following markers is different than a methylation state of the one or more markers assayed in a subject that does not have ovarian cancer indicates the subject has serous ovarian cancer: NCOR2, MAX.chr1.147790358-147790381, MAX.chr6.10382190-10382225, IFFO1_A, GDF6, and C2CD4D (see, Table 5A; Example I).

In some embodiments wherein the sample obtained from the subject is ovarian tissue and the methylation state of one or more of the following markers is different than a methylation state of the one or more markers assayed in a subject that does not have ovarian cancer indicates the subject has serous ovarian cancer: SKI, PEAR1_B, CAPN2_B, SIM2_B, DNMT3A_A, CDO1_A, and NR2F6 (see, Table 8E; Example II).

In some embodiments wherein the sample obtained from the subject is a blood sample (e.g., plasma sample, whole blood sample, leukocyte sample, serum sample) and the methylation state of one or more of the following markers is different than a methylation state of the one or more markers assayed in a subject that does not have OC indicates the subject has OC: GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1 (see, Table 9; Example III).

In some embodiments wherein the sample obtained from the subject is a blood sample (e.g., plasma sample, whole blood sample, leukocyte sample, serum sample) and the methylation state of one or more of the following markers is different than a methylation state of the one or more markers assayed in a subject that does not have OC indicates the subject has OC: ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, SIM2_A, AGRN 8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III).

In some embodiments wherein the sample obtained from the subject is a blood sample (e.g., plasma sample, whole blood sample, leukocyte sample, serum sample) and 1) increased levels of CA-125 are detected, and 2) the methylation state of one or more of the following markers is different than a methylation state of the one or more markers assayed in a subject that does not have OC indicates the subject has OC: ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, and SIM2_A (see, Table 11-13, Example III).

The technology is related to identifying and discriminating ovarian cancer and/or various forms of ovarian cancer (e.g., clear cell OC, endometrioid OC, mucinous OC, serous OC). Some embodiments provide methods comprising assaying a plurality of markers, e.g., comprising assaying 1, 2, 3, 2 to 11 to 100 or 120 or 375 or 560 markers (e.g., 1-4, 1-6, 1-7, 1-8, 1-9, 1-10, 1-11, 1-12, 1-13, 1-14, 1-15, 1-16, 1-17, 1-18, 1-19, 1-20, 1-25, 1-50, 1-75, 1-100, 1-200, 1-300, 1-400, 1-500, 1-560) (e.g., 2-4, 2-6, 2-7, 2-8, 2-9, 2-10, 2-11, 2-12, 2-13, 2-14, 2-15, 2-16, 2-17, 2-18, 2-19, 2-20, 2-25, 2-50, 2-75, 2-100, 2-200, 2-300, 2-400, 2-500, 2-560) (e.g., 3-4, 3-6, 3-7, 3-8, 3-9, 3-10, 3-11, 3-12, 3-13, 3-14, 3-15, 3-16, 3-17, 3-18, 3-19, 3-20, 3-25, 3-50, 3-75, 3-100, 3-200, 3-300, 3-400, 3-500, 3-560) (e.g., 4-5, 4-6, 4-7, 4-8, 4-9, 4-10, 4-11, 4-12, 4-13, 4-14, 4-15, 4-16, 4-17, 4-18, 4-19, 4-20, 4-25, 4-50, 4-75, 4-100, 4-200, 4-300, 4-400, 4-500, 4-560) (e.g., 5-6, 5-7, 5-8, 5-9, 5-10, 5-11, 5-12, 5-13, 5-14, 5-15, 5-16, 5-17, 5-18, 5-19, 5-20, 5-25, 5-50, 5-75, 5-100, 5-200, 5-300, 5-400, 5-500, 5-560).

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a stool sample, a tissue sample (e.g., ovarian tissue sample), a blood sample (e.g., plasma, serum, whole blood), an excretion, or a urine sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a DMR, e.g., in some embodiments are provided a set of oligonucleotides comprising the sequences provided by SEQ ID NO: 1-283 (see, Tables 1C and 6B). In some embodiments are provided an oligonucleotide comprising a sequence complementary to a chromosomal region having a base in a DMR, e.g., an oligonucleotide sensitive to methylation state of a DMR.

The technology provides various panels of markers use for identifying ovarian cancer, e.g., in some embodiments the marker comprises a chromosomal region having an annotation that is AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A, 6B; Example I).

The technology provides various panels of markers use for identifying ovarian cancer, e.g., in some embodiments the marker comprises a chromosomal region having an annotation that is MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I).

The technology provides various panels of markers use for identifying ovarian cancer, e.g., in some embodiments the marker comprises a chromosomal region having an annotation that is PALLD, PRDM14, MAX.chr1.147790358-147790381, BCAT1, MAML3_A, SKI, DNMT3A_A, and C2CD4D (see, Table 4A; Example I).

The technology provides various panels of markers use for identifying ovarian cancer, e.g., in some embodiments the marker comprises a chromosomal region having an annotation that is BCAT1_6015, SKI, SIM2_B, DNMT3A_A, CDO1_A, and DSCR6 (see, Table 8A; Example II).

The technology provides various panels of markers use for identifying clear cell ovarian cancer, e.g., in some embodiments the marker comprises a chromosomal region having an annotation that is TACC2_A, LRRC41_A, EPS8L2, LBH, LIME1_B, MDFI, FAIM2_A, GYPC_A, AGRN_B, and ZBED4 (see, Table 2A; Example I).

The technology provides various panels of markers use for identifying clear cell ovarian cancer, e.g., in some embodiments the marker comprises a chromosomal region having an annotation that is MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I).

The technology provides various panels of markers use for identifying clear cell ovarian cancer, e.g., in some embodiments the marker comprises a chromosomal region having an annotation that is NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I).

The technology provides various panels of markers use for identifying clear cell ovarian cancer, e.g., in some embodiments the marker comprises a chromosomal region having an annotation that is AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II).

The technology provides various panels of markers use for identifying endometrioid ovarian cancer, e.g., in some embodiments the marker comprises a chromosomal region having an annotation that is PARP15, GPRIN1_A, GYPC1_A, FLJ34208, MAX.chr1.147790358-147790381, FAIM2_A, SH2B3, KCNQ5, IRF4, and BCAT1 (see, Table 2B; Example I).

The technology provides various panels of markers use for identifying endometrioid ovarian cancer, e.g., in some embodiments the marker comprises a chromosomal region having an annotation that is NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I).

The technology provides various panels of markers use for identifying endometrioid ovarian cancer, e.g., in some embodiments the marker comprises a chromosomal region having an annotation that is NCOR2, PALLD, PRDM14, MAX.chr1.147790358-147790381, MAX.chr11.14926602-

14926671, DSCR6, GPRIN1_A, CDO1_A, SIM2_A, IFFO1_A, and C2CD4D (see, Table 5C; Example I).

The technology provides various panels of markers use for identifying endometrioid ovarian cancer, e.g., in some embodiments the marker comprises a chromosomal region having an annotation that is BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II).

The technology provides various panels of markers use for identifying mucinous ovarian cancer, e.g., in some embodiments the marker comprises a chromosomal region having an annotation that is CMTM3_A, ATP10A_C, TSHZ3, ZMIZ1_B, ATP10A_B, ELMO1_B, TACC2_A, LRRC4, VIM, and ZNF382_A (see, Table 2C; Example I).

The technology provides various panels of markers use for identifying mucinous ovarian cancer, e.g., in some embodiments the marker comprises a chromosomal region having an annotation that is NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I).

The technology provides various panels of markers use for identifying mucinous ovarian cancer, e.g., in some embodiments the marker comprises a chromosomal region having an annotation that is NCOR2, PALLD, TACC2_A, BCAT1, AGRN_B, SKI, SLC12A8, ZMIZ1_B, and BCL2L11 (see, Table 5D; Example I).

The technology provides various panels of markers use for identifying mucinous ovarian cancer, e.g., in some embodiments the marker comprises a chromosomal region having an annotation that is BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II).

The technology provides various panels of markers use for identifying serous ovarian cancer, e.g., in some embodiments the marker comprises a chromosomal region having an annotation that is MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I).

The technology provides various panels of markers use for identifying serous ovarian cancer, e.g., in some embodiments the marker comprises a chromosomal region having an annotation that is PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I).

The technology provides various panels of markers use for identifying serous ovarian cancer, e.g., in some embodiments the marker comprises a chromosomal region having an annotation that is NCOR2, MAX.chr1.147790358-147790381, MAX.chr6.10382190-10382225, IFFO1_A, GDF6, and C2CD4D (see, Table 5A; Example I).

The technology provides various panels of markers use for identifying serous ovarian cancer, e.g., in some embodiments the marker comprises a chromosomal region having an annotation that is SKI, PEAR1_B, CAPN2_B, SIM2_B, DNMT3A_A, CDO1_A, and NR2F6 (see, Table 8E; Example II).

The technology provides various panels of markers use for identifying ovarian cancer, e.g., in some embodiments the marker comprises a chromosomal region having an annotation that is GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1 (see, Table 9; Example III).

The technology provides various panels of markers use for identifying ovarian cancer, e.g., in some embodiments the marker comprises a chromosomal region having an annotation that is ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, SIM2_A, AGRN 8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III).

The technology provides various panels of markers use for identifying ovarian cancer, e.g., in some embodiments the marker comprises a chromosomal region having an annotation that is ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, SIM2_A, AGRN 8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III).

Kit embodiments are provided, e.g., a kit comprising a reagent capable of modifying DNA in a methylation-specific manner (e.g., a methylation-sensitive restriction enzyme, a methylation-dependent restriction enzyme, and a bisulfite reagent); and a control nucleic acid comprising a sequence from a DMR selected from a group consisting of DMR 1-560 (from Tables 1A and 6A) and having a methylation state associated with a subject who does not have ovarian cancer or a subtype of OC (e.g., clear cell OC, endometrioid OC, mucinous OC, serous OC). In some embodiments, kits comprise a bisulfite reagent and an oligonucleotide as described herein. In some embodiments, kits comprise a reagent capable of modifying DNA in a methylation-specific manner (e.g., a methylation-sensitive restriction enzyme, a methylation-dependent restriction enzyme, and a bisulfite reagent); and a control nucleic acid comprising a sequence from a DMR selected from a group consisting of DMR 1-560 (from Tables 1A and 6A) and having a methylation state associated with a subject who has ovarian cancer or a subtype of ovarian cancer (e.g., clear cell OC, endometrioid OC, mucinous OC, serous OC). Some kit embodiments comprise a sample collector for obtaining a sample from a subject (e.g., a stool sample; ovarian tissue sample; plasma sample, serum sample, whole blood sample); a reagent capable of modifying DNA in a methylation-specific manner (e.g., a methylation-sensitive restriction enzyme, a methylation-dependent restriction enzyme, and a bisulfite reagent); and an oligonucleotide as described herein.

The technology is related to embodiments of compositions (e.g., reaction mixtures). In some embodiments are provided a composition comprising a nucleic acid comprising a DMR and a reagent capable of modifying DNA in a methylation-specific manner (e.g., a methylation-sensitive restriction enzyme, a methylation-dependent restriction enzyme, and a bisulfite reagent). Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

Additional related method embodiments are provided for screening for ovarian cancer and/or various forms of ovarian cancer (e.g., clear cell OC, endometrioid OC, mucinous OC, serous OC) in a sample obtained from a subject (e.g., ovarian tissue sample; plasma sample; stool sample), e.g., a method comprising determining a methylation state of a marker in the sample comprising a base in a DMR that is one or more of DMR 1-506 (from Tables 1A and 6A); comparing the methylation state of the marker from the subject sample to a methylation state of the marker from a normal control sample from a subject who does not have ovarian cancer (e.g., ovarian cancer and/or a form of ovarian cancer: clear cell OC, endometrioid OC, mucinous OC, serous OC); and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a DMR with a reagent capable of modifying nucleic acid in a methylation-specific manner (e.g., a methylation-sensitive restriction enzyme, a methylation-dependent restriction enzyme, and a bisulfite reagent) to produce, for example, nucleic acid modified in a methylation-specific manner; sequencing the nucleic acid modified in a methylation-specific manner to provide a nucleotide sequence of the nucleic acid modified in a methylation-specific manner; comparing the nucleotide sequence of the nucleic acid modified in a methylation-specific manner with a nucleotide sequence of a nucleic acid comprising the DMR from a subject who does not have ovarian cancer and/or a form of ovarian cancer to identify differences in the two sequences; and identifying the subject as having ovarian cancer and/or a form of ovarian cancer (e.g., clear cell OC, endometrioid OC, mucinous OC, serous OC) when a difference is present.

Systems for screening for ovarian cancer in a sample obtained from a subject are provided by the technology. Exemplary embodiments of systems include, e.g., a system for screening for ovarian cancer and/or types of ovarian cancer (e.g., clear cell OC, endometrioid OC, mucinous OC, serous OC) in a sample obtained from a subject (e.g., ovarian tissue sample; plasma sample; stool sample), the system comprising an analysis component configured to determine the methylation state of a sample, a software component configured to compare the methylation state of the sample with a control sample or a reference sample methylation state recorded in a database, and an alert component configured to alert a user of a ovarian-cancer-associated methylation state. An alert is determined in some embodiments by a software component that receives the results from multiple assays (e.g., determining the methylation states of multiple markers, e.g., DMR, e.g., as provided in Tables 1A and 6A) and calculating a value or result to report based on the multiple results. Some embodiments provide a database of weighted parameters associated with each DMR provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of a cancer risk in a subject.

In some embodiments of systems, a sample comprises a nucleic acid comprising a DMR. In some embodiments the system further comprises a component for isolating a nucleic acid, a component for collecting a sample such as a component for collecting a stool sample. In some embodiments, the system comprises nucleic acid sequences comprising a DMR. In some embodiments the database comprises nucleic acid sequences from subjects who do not have ovarian cancer and/or specific types of ovarian cancer (e.g., clear cell OC, endometrioid OC, mucinous OC, serous OC). Also provided are nucleic acids, e.g., a set of nucleic acids, each nucleic acid having a sequence comprising a DMR. In some embodiments the set of nucleic acids wherein each nucleic acid has a sequence from a subject who does not have ovarian cancer and/or specific types of ovarian cancer. Related system embodiments comprise a set of nucleic acids as described and a database of nucleic acid sequences associated with the set of nucleic acids. Some embodiments further comprise a reagent capable of modifying DNA in a methylation-specific manner (e.g., a methylation-sensitive restriction enzyme, a methylation-dependent restriction enzyme, and a bisulfite reagent). And, some embodiments further comprise a nucleic acid sequencer.

In certain embodiments, methods for characterizing a sample (e.g., ovarian tissue sample; plasma sample; whole blood sample; serum sample; stool sample) from a human patient are provided. For example, in some embodiments such embodiments comprise obtaining DNA from a sample of a human patient; assaying a methylation state of a DNA methylation marker comprising a base in a differentially methylated region (DMR) selected from a group consisting of DMR 1-560 from Tables 1A and 6A; and comparing the assayed methylation state of the one or more DNA methylation markers with methylation level references for the one or more DNA methylation markers for human patients not having ovarian cancer and/or specific types of ovarian cancer (e.g., clear cell OC, endometrioid OC, mucinous OC, serous OC).

Such methods are not limited to a particular type of sample from a human patient. In some embodiments, the sample is a ovarian tissue sample. In some embodiments, the sample is a plasma sample. In some embodiments, the sample is a stool sample, a tissue sample, an ovarian tissue sample, a blood sample (e.g., plasma sample, whole blood sample, serum sample), or a urine sample.

In some embodiments, such methods comprise assaying a plurality of DNA methylation markers (e.g., 1-4, 1-6, 1-7, 1-8, 1-9, 1-10, 1-11, 1-12, 1-13, 1-14, 1-15, 1-16, 1-17, 1-18, 1-19, 1-20, 1-25, 1-50, 1-75, 1-100, 1-200, 1-300, 1-400, 1-500, 1-560) (e.g., 2-4, 2-6, 2-7, 2-8, 2-9, 2-10, 2-11, 2-12, 2-13, 2-14, 2-15, 2-16, 2-17, 2-18, 2-19, 2-20, 2-25, 2-50, 2-75, 2-100, 2-200, 2-300, 2-400, 2-500, 2-560) (e.g., 3-4, 3-6, 3-7, 3-8, 3-9, 3-10, 3-11, 3-12, 3-13, 3-14, 3-15, 3-16, 3-17, 3-18, 3-19, 3-20, 3-25, 3-50, 3-75, 3-100, 3-200, 3-300, 3-400, 3-500, 3-560) (e.g., 4-5, 4-6, 4-7, 4-8, 4-9, 4-10, 4-11, 4-12, 4-13, 4-14, 4-15, 4-16, 4-17, 4-18, 4-19, 4-20, 4-25, 4-50, 4-75, 4-100, 4-200, 4-300, 4-400, 4-500, 4-560) (e.g., 5-6, 5-7, 5-8, 5-9, 5-10, 5-11, 5-12, 5-13, 5-14, 5-15, 5-16, 5-17, 5-18, 5-19, 5-20, 5-25, 5-50, 5-75, 5-100, 5-200, 5-300, 5-400, 5-500, 5-560). In some embodiments, such methods comprise assaying 2 to 11 DNA methylation markers. In some embodiments, such methods comprise assaying 12 to 120 DNA methylation markers. In some embodiments, such methods comprise assaying 2 to 375 DNA methylation markers. In some embodiments, such methods comprise assaying the methylation state of the one or more DNA methylation markers in the sample comprises determining the methylation state of one base. In some embodiments, such methods comprise assaying the methylation state of the one or more DNA methylation markers in the sample comprises determining the extent of methylation at a plurality of bases. In some embodiments, such methods comprise assaying a methylation state of a forward strand or assaying a methylation state of a reverse strand.

In some embodiments, the DNA methylation marker is a region of 100 or fewer bases. In some embodiments, the DNA methylation marker is a region of 500 or fewer bases. In some embodiments, the DNA methylation marker is a region of 1000 or fewer bases. In some embodiments, the DNA methylation marker is a region of 5000 or fewer bases. In some embodiments, the DNA methylation marker is one base. In some embodiments, the DNA methylation marker is in a high CpG density promoter.

In some embodiments, the assaying comprises using methylation specific polymerase chain reaction, nucleic acid sequencing, mass spectrometry, methylation specific nuclease, mass-based separation, or target capture.

In some embodiments, the assaying comprises use of a methylation specific oligonucleotide. In some embodiments, the methylation specific oligonucleotide is selected from the group consisting of SEQ ID NO: 1-283 (Tables 1C, 6B).

In some embodiments, a chromosomal region having an annotation selected from the group consisting of AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A, 6B; Example I) comprises the DNA methylation marker.

In some embodiments, a chromosomal region having an annotation selected from the group consisting of MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I) comprises the DNA methylation marker.

In some embodiments, a chromosomal region having an annotation selected from the group consisting of PALLD, PRDM14, MAX.chr1.147790358-147790381, BCAT1, MAML3_A, SKI, DNMT3A_A, and C2CD4D (see, Table 4A; Example I) comprises the DNA methylation marker.

In some embodiments, a chromosomal region having an annotation selected from the group consisting of BCAT1_6015, SKI, SIM2_B, DNMT3A_A, CDO1_A, and DSCR6 (see, Table 8A; Example II) comprises the DNA methylation marker.

In some embodiments, a chromosomal region having an annotation selected from the group consisting of TACC2_A, LRRC41_A, EPS8L2, LBH, LIME1_B, MDFI, FAIM2_A, GYPC_A, AGRN_B, and ZBED4 (see, Table 2A; Example I) comprises the DNA methylation marker.

In some embodiments, a chromosomal region having an annotation selected from the group consisting of MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I) comprises the DNA methylation marker.

In some embodiments, a chromosomal region having an annotation selected from the group consisting of NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I) comprises the DNA methylation marker.

In some embodiments, a chromosomal region having an annotation selected from the group consisting of AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II) comprises the DNA methylation marker.

In some embodiments, a chromosomal region having an annotation selected from the group consisting of PARP15, GPRIN1_A, GYPC1_A, FLJ34208, MAX.chr1.147790358-147790381, FAIM2_A, SH2B3, KCNQ5, IRF4, and BCAT1 (see, Table 2B; Example I) comprises the DNA methylation marker.

In some embodiments, a chromosomal region having an annotation selected from the group consisting of NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I) comprises the DNA methylation marker.

In some embodiments, a chromosomal region having an annotation selected from the group consisting of NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I) comprises the DNA methylation marker.

In some embodiments, a chromosomal region having an annotation selected from the group consisting of BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II) comprises the DNA methylation marker.

In some embodiments, a chromosomal region having an annotation selected from the group consisting of CMTM3_A, ATP10A_C, TSHZ3, ZMIZ1_B, ATP10A_B, ELMO1_B, TACC2_A, LRRC4, VIM, and ZNF382_A (see, Table 2C; Example I) comprises the DNA methylation marker.

In some embodiments, a chromosomal region having an annotation selected from the group consisting of NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I) comprises the DNA methylation marker.

In some embodiments, a chromosomal region having an annotation selected from the group consisting of NCOR2, PALLD, TACC2_A, BCAT1, AGRN_B, SKI, SLC12A8, ZMIZ1_B, and BCL2L11 (see, Table 5D; Example I) comprises the DNA methylation marker.

In some embodiments, a chromosomal region having an annotation selected from the group consisting of BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II) comprises the DNA methylation marker.

In some embodiments, a chromosomal region having an annotation selected from the group consisting of MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I) comprises the DNA methylation marker.

In some embodiments, a chromosomal region having an annotation selected from the group consisting of PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I) comprises the DNA methylation marker.

In some embodiments, a chromosomal region having an annotation selected from the group consisting of NCOR2, MAX.chr1.147790358-147790381, MAX.chr6.10382190-10382225, IFFO1_A, GDF6, and C2CD4D (see, Table 5A; Example I) comprises the DNA methylation marker.

In some embodiments, a chromosomal region having an annotation selected from the group consisting of SKI, PEAR1_B, CAPN2_B, SIM2_B, DNMT3A_A, CDO1_A, and NR2F6 (see, Table 8E; Example II) comprises the DNA methylation marker.

In some embodiments, a chromosomal region having an annotation selected from the group consisting of GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1 (see, Table 9; Example III) comprises the DNA methylation marker.

In some embodiments, a chromosomal region having an annotation selected from the group consisting of ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, SIM2_A, AGRN 8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III) comprises the DNA methylation marker.

In some embodiments, such methods comprise determining the methylation state of two DNA methylation markers. In some embodiments, such methods comprise determining the methylation state of a pair of DNA methylation markers provided in Tables 1A and/or 6A.

In certain embodiments, the technology provides methods for characterizing a sample (e.g., ovarian tissue sample; plasma sample; whole blood sample; serum sample; stool sample) obtained from a human patient. In some embodiments, such methods comprise determining a methylation state of a DNA methylation marker in the sample comprising a base in a DMR selected from a group consisting of DMR 1-560 from Tables 1A and 6A; comparing the methylation state of the DNA methylation marker from the patient sample to a methylation state of the DNA methylation marker from a normal control sample from a human subject who does not have a ovarian cancer and/or a specific form of ovarian cancer (e.g., clear cell OC, endometrioid OC, mucinous OC, serous OC); and determining a confidence interval and/or a p value of the difference in the methylation state of the human patient and the normal control sample. In some embodiments, the confidence interval is 90%, 95%, 97.5%, 98%, 99%, 99.5%, 99.9% or 99.99% and thep value is 0.1, 0.05, 0.025, 0.02, 0.01, 0.005, 0.001, or 0.0001.

In certain embodiments, the technology provides methods for characterizing a sample obtained from a human subject (e.g., ovarian tissue sample; plasma sample; whole blood sample; serum sample; stool sample), the method comprising reacting a nucleic acid comprising a DMR with a reagent capable of modifying DNA in a methylation-specific manner (e.g., a methylation-sensitive restriction enzyme, a methylation-dependent restriction enzyme, and a bisulfite reagent) to produce nucleic acid modified in a methylation-specific manner; sequencing the nucleic acid modified in a methylation-specific manner to provide a nucleotide sequence of the nucleic acid modified in a methylation-specific manner; comparing the nucleotide sequence of the nucleic acid modified in a methylation-specific manner with a nucleotide sequence of a nucleic acid comprising the DMR from a subject who does not have ovarian cancer to identify differences in the two sequences.

In certain embodiments, the technology provides systems for characterizing a sample obtained from a human subject (e.g., ovarian tissue sample; plasma sample; stool sample), the system comprising an analysis component configured to determine the methylation state of a sample, a software component configured to compare the methylation state of the sample with a control sample or a reference sample methylation state recorded in a database, and an alert component configured to determine a single value based on a combination of methylation states and alert a user of a ovarian cancer-associated methylation state. In some embodiments, the sample comprises a nucleic acid comprising a DMR.

In some embodiments, such systems further comprise a component for isolating a nucleic acid. In some embodiments, such systems further comprise a component for collecting a sample.

In some embodiments, the sample is a stool sample, a tissue sample, a ovarian tissue sample, a blood sample (e.g., plasma sample, whole blood sample, serum sample), or a urine sample.

In some embodiments, the database comprises nucleic acid sequences comprising a DMR. In some embodiments, the database comprises nucleic acid sequences from subjects who do not have a ovarian cancer.

Additional embodiments will be apparent to persons skilled in the relevant art based on the teachings contained herein.

BRIEF DESCRIPTION OF THE DRAWINGS

FIG. 1: Marker chromosomal regions used for various methylated DNA markers recited in Table 1A and 6A and related primer and probe information. Shown are naturally occurring sequences (WT) and bisulfite-modified sequences (BST) from PCR target regions.

DEFINITIONS

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, a "nucleic acid" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the terms "locus" or "region" of a nucleic acid refer to a subregion of a nucleic acid, e.g., a gene on a chromosome, a single nucleotide, a CpG island, etc.

The terms "complementary" and "complementarity" refer to nucleotides (e.g., 1 nucleotide) or polynucleotides (e.g., a sequence of nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of an RNA, or of a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and poly adenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene. In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-beta replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al, Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics 4:560). Finally, thermostable template-dependent DNA polymerases (e.g., Taq and Pfu DNA polymerases), by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and U.S. Pat. No. 9,096,893, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

The term "amplifiable nucleic acid" refers to a nucleic acid that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as, e.g., a nucleic acid fragment from a restriction digest, or produced synthetically, that is capable of acting as a point of initiation of synthesis when placed under conditions in which synthesis of a primer extension product that is complementary to a nucleic acid template strand is induced, (e.g., in the presence of nucleotides and an inducing agent such as a DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," as used herein refers to a nucleic acid sought to be sorted out from other nucleic acids, e.g., by probe binding, amplification, isolation, capture, etc. For example, when used in reference to the polymerase chain reaction, "target" refers to the region of nucleic acid bounded by the primers used for polymerase chain reaction, while when used in an assay in which target DNA is not amplified, e.g., in some embodiments of an invasive cleavage assay, a target comprises the site at which a probe and invasive oligonucleotides (e.g., INVADER oligonucleotide) bind to form an invasive cleavage structure, such that the presence of the target nucleic acid can be detected. A "segment" is defined as a region of nucleic acid within the target sequence.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) J Mol. Biol. 196: 261-281. For example, the observed CpG frequency over expected frequency can be calculated according to the formula $R=(A\times B)/(C\times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) Proc. Natl. Acad. Sci. USA 97: 5237-5242; Salmon and Kaye (1970) Biochim. Biophys. Acta. 204: 340-351; Grafstrom (1985) Nucleic Acids Res. 13: 2827-2842; Nyce (1986) Nucleic Acids Res. 14: 4353-4367; Woodcock (1987) Biochem. Biophys. Res. Commun. 145: 888-894).

As used herein, a "methylation-specific reagent" refers to a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such methods can be applied in a manner in which unmethylated nucleotides (e.g., each unmethylated cytosine) is modified to a different nucleotide. For example, in some embodiments, such a reagent can deaminate unmethylated cytosine nucleotides to produce deoxy uracil residues. Examples of such reagents include, but are not limited to, a methylation-sensitive restriction enzyme, a methylation-dependent restriction enzyme, and a bisulfite reagent.

A change in the nucleic acid nucleotide sequence by a methylation-specific reagent can also result in a nucleic acid molecule in which each methylated nucleotide is modified to a different nucleotide.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) *Cancer Research* 57: 594-599.

The term "MethyLight™" refers to the art-recognized fluorescence-based real-time PCR technique described by Eads et al. (1999) *Cancer Res.* 59: 2302-2306.

The term "HeavyMethyl™" refers to an assay wherein methylation specific blocking probes (also referred to herein as blockers) covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones (1997) *Nucleic Acids Res.* 25: 2529-2531.

The term "MSP" (Methylation-specific PCR) refers to the art-recognized methylation assay described by Herman et al. (1996) *Proc. Natl. Acad. Sci. USA* 93: 9821-9826, and by U.S. Pat. No. 5,786,146.

The term "COBRA" (Combined Bisulfite Restriction Analysis) refers to the art-recognized methylation assay described by Xiong & Laird (1997) *Nucleic Acids Res.* 25: 2532-2534.

The term "MCA" (Methylated CpG Island Amplification) refers to the methylation assay described by Toyota et al. (1999) *Cancer Res.* 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The term "methylation-specific restriction enzyme" refers to a restriction enzyme that selectively digests a nucleic acid dependent on the methylation state of its recognition site. In the case of a restriction enzyme that specifically cuts if the recognition site is not methylated or is hemi-methylated (a methylation-sensitive enzyme), the cut will not take place (or will take place with a significantly reduced efficiency) if the recognition site is methylated on one or both strands. In the case of a restriction enzyme that specifically cuts only if the recognition site is methylated (a methylation-dependent enzyme), the cut will not take place (or will take place with a significantly reduced efficiency) if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A. As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A, or T and, therefore, when C is the selected nucleotide, G is a nucleotide complementary to the selected nucleotide.

As used herein, the "sensitivity" of a given marker (or set of markers used together) refers to the percentage of samples that report a DNA methylation value above a threshold value that distinguishes between neoplastic and non-neoplastic samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker (or set of markers used together) refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity, therefore, reflects the probability that a DNA methylation measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) *Signal Detection Theory and ROC Analysis*, Academic Press, New York).

The term "neoplasm" as used herein refers to any new and abnormal growth of tissue. Thus, a neoplasm can be a premalignant neoplasm or a malignant neoplasm.

The term "neoplasm-specific marker," as used herein, refers to any biological material or element that can be used to indicate the presence of a neoplasm. Examples of biological materials include, without limitation, nucleic acids, polypeptides, carbohydrates, fatty acids, cellular components (e.g., cell membranes and mitochondria), and whole cells. In some instances, markers are particular nucleic acid regions (e.g., genes, intragenic regions, specific loci, etc.). Regions of nucleic acid that are markers may be referred to, e.g., as "marker genes," "marker regions," "marker sequences," "marker loci," etc.

As used herein, the term "adenoma" refers to a benign tumor of glandular origin. Although these growths are benign, over time they may progress to become malignant.

The term "pre-cancerous" or "pre-neoplastic" and equivalents thereof refer to any cellular proliferative disorder that is undergoing malignant transformation.

A "site" of a neoplasm, adenoma, cancer, etc. is the tissue, organ, cell type, anatomical area, body part, etc. in a subject's body where the neoplasm, adenoma, cancer, etc. is located.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject contracting a neoplasm or the likelihood that such a subject will respond favorably to a compound (e.g., a pharmaceutical, e.g., a drug) or other treatment.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded). An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample. The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution containing salts (e.g., NaCl), detergents (e.g., SDS), and other components (e.g., Denhardt's solution, dry milk, salmon sperm DNA, etc.).

The term "sample" is used in its broadest sense. In one sense it can refer to an animal cell or tissue. In another sense, it refers to a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, a "remote sample" as used in some contexts relates to a sample indirectly collected from a site that is not the cell, tissue, or organ source of the sample. For instance, when sample material originating from the pancreas is assessed in a stool sample (e.g., not from a sample taken directly from an ovary), the sample is a remote sample.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human. Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; pinnipeds; and horses. Thus, also provided is the diagnosis and treatment of livestock, including, but not limited to, domesticated swine, ruminants, ungulates, horses (including race horses), and the like. The presently-disclosed subject matter further includes a system for diagnosing a lung cancer in a subject. The system can be provided, for example, as a commercial kit that can be used to screen for a risk of lung cancer or diagnose a lung cancer in a subject from whom a biological sample has been collected. An exemplary system provided in accordance with the present technology includes assessing the methylation state of a marker described herein.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520 (e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "ovarian cancer" refers to any cancerous growth arising from the ovary, which includes, but is not limited to, traditionally diagnosed ovarian, fallopian tube and primary peritoneal cancers. In some embodiments, ovarian cancer is a type of cancer that forms in tissues of the ovary. In other embodiments, ovarian cancer is either ovarian epithelial carcinomas (cancer that begins in the cells on the surface of the ovary) or malignant germ cell tumors (cancer that begins in egg cells).

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DETAILED DESCRIPTION

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

Provided herein is technology for ovarian cancer screening and particularly, but not exclusively, to methods, compositions, and related uses for detecting the presence of ovarian cancer and/or specific forms of ovarian cancer (e.g., clear cell OC, endometrioid OC, mucinous OC, serous OC). As the technology is described herein, the section headings used are for organizational purposes only and are not to be construed as limiting the subject matter in any way.

Indeed, as described in Examples I, II, and III, experiments conducted during the course for identifying embodiments for the present invention identified a novel set of 560 differentially methylated regions (DMRs) for discriminating cancer of the ovarian derived DNA from non-neoplastic control DNA. From these 560 novel DNA methylation markers, further experiments identified markers capable of distinguishing different types of ovarian cancer from normal tissue and from plasma samples. For example, separate sets of DMRs were identified capable of distinguishing 1) clear cell ovarian cancer tissue from normal tissue, 2) endometrioid ovarian cancer tissue from normal tissue, 3) mucinous ovarian cancer tissue from normal tissue, 4) serous ovarian cancer tissue from normal tissue, and 5) ovarian cancer in blood samples.

Although the disclosure herein refers to certain illustrated embodiments, it is to be understood that these embodiments are presented by way of example and not by way of limitation.

In particular aspects, the present technology provides compositions and methods for identifying, determining, and/or classifying a cancer such as ovarian cancer and/or a sub-type of ovarian cancer (e.g., clear cell OC, endometrioid OC, mucinous OC, serous OC). The methods comprise determining the methylation status of at least one methylation marker in a biological sample isolated from a subject (e.g., stool sample, ovarian tissue sample, plasma sample), wherein a change in the methylation state of the marker is indicative of the presence, class, or site of ovarian cancer and/or a sub-type thereof. Particular embodiments relate to markers comprising a differentially methylated region (DMR, e.g., DMR 1-560, see Tables 1A and 6A) that are used for diagnosis (e.g., screening) of ovarian cancer and various types of ovarian cancer (e.g., clear cell OC, endometrioid OC, mucinous OC, serous OC).

In addition to embodiments wherein the methylation analysis of at least one marker, a region of a marker, or a base of a marker comprising a DMR (e.g., DMR, e.g., DMR 1-560) provided herein and listed in Tables 1A and 6A is analyzed, the technology also provides panels of markers comprising at least one marker, region of a marker, or base of a marker comprising a DMR with utility for the detection of cancers, in particular ovarian cancer.

Some embodiments of the technology are based upon the analysis of the CpG methylation status of at least one marker, region of a marker, or base of a marker comprising a DMR.

In some embodiments, the present technology provides for the use of a reagent that modifies DNA in a methylation-specific manner (e.g., a methylation-sensitive restriction enzyme, a methylation-dependent restriction enzyme, and a bisulfite reagent) in combination with one or more methylation assays to determine the methylation status of CpG dinucleotide sequences within at least one marker comprising a DMR (e.g., DMR 1-560, see Tables 1A and 6A). Genomic CpG dinucleotides can be methylated or unmethylated (alternatively known as up- and down-methylated respectively). However, the methods of the present invention are suitable for the analysis of biological samples of a heterogeneous nature, e.g., a low concentration of tumor cells, or biological materials therefrom, within a background of a remote sample (e.g., blood, organ effluent, or stool). Accordingly, when analyzing the methylation status of a CpG position within such a sample one may use a quantitative assay for determining the level (e.g., percent, fraction, ratio, proportion, or degree) of methylation at a particular CpG position.

According to the present technology, determination of the methylation status of CpG dinucleotide sequences in markers comprising a DMR has utility both in the diagnosis and characterization of cancers such as ovarian cancer.

Combinations of Markers

In some embodiments, the technology relates to assessing the methylation state of combinations of markers comprising a DMR from Tables 1A and 6A (e.g., DMR Nos. 1-560). In some embodiments, assessing the methylation state of more than one marker increases the specificity and/or sensitivity of a screen or diagnostic for identifying a neoplasm in a subject (e.g., ovarian cancer).

Various cancers are predicted by various combinations of markers, e.g., as identified by statistical techniques related to specificity and sensitivity of prediction. The technology provides methods for identifying predictive combinations and validated predictive combinations for some cancers.

Methods for Assaying Methylation State

In certain embodiments, methods for analyzing a nucleic acid for the presence of 5-methylcytosine involves treatment of DNA with a reagent that modifies DNA in a methylation-specific manner. Examples of such reagents include, but are not limited to, a methylation-sensitive restriction enzyme, a methylation-dependent restriction enzyme, and a bisulfite reagent.

A frequently used method for analyzing a nucleic acid for the presence of 5-methylcytosine is based upon the bisulfite method described by Frommer, et al. for the detection of 5-methylcytosines in DNA (Frommer et al. (1992) *Proc. Natl. Acad. Sci. USA* 89: 1827-31 explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uracil is desulfonated under alkaline conditions to form uracil. Detection is possible because uracil base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98), methylation-specific PCR (MSP) as is disclosed, e.g., in U.S. Pat. No. 5,786,146, or using an assay comprising sequence-specific probe cleavage, e.g., a QuARTS flap endonuclease assay (see, e.g., Zou et al. (2010) "Sensitive quantification of methylated markers with a novel methylation specific technology" *Clin Chem* 56: A199; and in U.S. Pat. Nos. 8,361,720; 8,715,937; 8,916,344; and 9,212,392.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" *Nucleic Acids Res.* 24: 5064-6). It is thus possible to analyze individual cells for methylation status, illustrating the utility and sensitivity of the method. An overview of conventional methods for detecting 5-methylcytosine is provided by Rein, T., et al. (1998) *Nucleic Acids Res.* 26: 2255.

The bisulfite technique typically involves amplifying short, specific fragments of a known nucleic acid subsequent to a bisulfite treatment, then either assaying the product by sequencing (Olek & Walter (1997) *Nat. Genet.* 17: 275-6) or a primer extension reaction (Gonzalgo & Jones (1997) *Nucleic Acids Res.* 25: 2529-31; WO 95/00669; U.S. Pat. No. 6,251,594) to analyze individual cytosine positions. Some methods use enzymatic digestion (Xiong & Laird (1997) *Nucleic Acids Res.* 25: 2532-4). Detection by hybridization has also been described in the art (Olek et al., WO 99/28498). Additionally, use of the bisulfite technique for methylation detection with respect to individual genes has been described (Grigg & Clark (1994) *Bioessays* 16: 431-6; Zeschnigk et al. (1997) *Hum Mol Genet.* 6: 387-95; Feil et al. (1994) *Nucleic Acids Res.* 22: 695; Martin et al. (1995) *Gene* 157: 261-4; WO 9746705; WO 9515373).

Various methylation assay procedures can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-specific restriction enzymes, e.g., methylation-sensitive or methylation-dependent enzymes.

For example, genomic sequencing has been simplified for analysis of methylation patterns and 5-methylcytosine distributions by using bisulfite treatment (Frommer et al. (1992) *Proc. Natl. Acad. Sci. USA* 89: 1827-1831). Additionally, restriction enzyme digestion of PCR products amplified from bisulfite-converted DNA finds use in assessing methylation state, e.g., as described by Sadri & Hornsby (1997) *Nucl. Acids Res.* 24: 5058-5059 or as embodied in the method known as COBRA (Combined Bisulfite Restriction Analysis) (Xiong & Laird (1997) *Nucleic Acids Res.* 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, DMR, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components. Assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase. MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can be used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to:

PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" *Nat Methods* 7: 133-6; Meissner et al. (2005) "Reduced representation bisulfite sequencing for comparative high-resolution DNA methylation analysis" *Nucleic Acids Res.* 33: 5868-77.

In some embodiments, a quantitative allele-specific real-time target and signal amplification (QuARTS) assay is used to evaluate methylation state. Three reactions sequentially occur in each QuARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes a 5' nuclease, e.g., a FEN-1 endonuclease, to release the flap sequence by cutting between the detection probe and the flap sequence. The flap sequence is complementary to a non-hairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" *Clin Chem* 56: A199), and U.S. Pat. Nos. 8,361,720; 8,715,937; 8,916,344; and 9,212,392, each of which is incorporated herein by reference for all purposes.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkyleneglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8-tetramethylchromane 2-carboxylic acid or trihydroxybenzone acid and derivates thereof, e.g., Gallic acid (see: PCT/EP2004/011715, which is incorporated by reference in its entirety). In certain preferred embodiments, the bisulfite reaction comprises treatment with ammonium hydrogen sulfite, e.g., as described in WO 2013/116375.

In some embodiments, fragments of the treated DNA are amplified using sets of primer oligonucleotides according to the present invention (e.g., see Tables 1C and 6B) and an amplification enzyme. The amplification of several DNA segments can be carried out simultaneously in one and the same reaction vessel. Typically, the amplification is carried out using a polymerase chain reaction (PCR). Amplicons are typically 100 to 2000 base pairs in length.

In another embodiment of the method, the methylation status of CpG positions within or near a marker comprising a DMR (e.g., DMR 1-560, Tables 1A and 6A) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids"), incorporated herein by reference in its entirety.

In some embodiments, the markers described herein find use in QUARTS assays performed on stool samples. In some embodiments, methods for producing DNA samples and, in particular, to methods for producing DNA samples that comprise highly purified, low-abundance nucleic acids in a small volume (e.g., less than 100, less than 60 microliters) and that are substantially and/or effectively free of substances that inhibit assays used to test the DNA samples (e.g., PCR, INVADER, QuARTS assays, etc.) are provided. Such DNA samples find use in diagnostic assays that qualitatively detect the presence of, or quantitatively measure the activity, expression, or amount of, a gene, a gene variant (e.g., an allele), or a gene modification (e.g., methylation) present in a sample taken from a patient. For example, some cancers are correlated with the presence of particular mutant alleles or particular methylation states, and thus detecting and/or quantifying such mutant alleles or methylation states has predictive value in the diagnosis and treatment of cancer. Many valuable genetic markers are present in extremely low amounts in samples and many of the events that produce such markers are rare. Consequently, even sensitive detection methods such as PCR require a large amount of DNA to provide enough of a low-abundance target to meet or supersede the detection threshold of the assay. Moreover, the presence of even low amounts of inhibitory substances compromise the accuracy and precision of these assays directed to detecting such low amounts of a target. Accordingly, provided herein are methods providing the requisite management of volume and concentration to produce such DNA samples.

In some embodiments, the sample comprises blood, serum, leukocytes, plasma, or saliva. In some embodiments, the subject is human. Such samples can be obtained by any number of means known in the art, such as will be apparent to the skilled person. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens. The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Nos. 8,808,990 and 9,169,511, and in WO 2012/155072, or by a related method.

The analysis of markers can be carried out separately or simultaneously with additional markers within one test sample. For example, several markers can be combined into one test for efficient processing of multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events. The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

It is contemplated that embodiments of the technology are provided in the form of a kit. The kits comprise embodiments of the compositions, devices, apparatuses, etc. described herein, and instructions for use of the kit. Such instructions describe appropriate methods for preparing an analyte from a sample, e.g., for collecting a sample and preparing a nucleic acid from the sample. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. It is understood that liquid components (e.g., a buffer) may be provided in a lyophilized form to be reconstituted by the user. Kits may include a control or reference for assessing, validating, and/or assuring the performance of the kit. For example, a kit for assaying the amount of a nucleic acid present in a sample may include a control comprising a known concentration of the same or another nucleic acid for comparison and, in some embodiments, a detection reagent (e.g., a primer) specific for the control nucleic acid. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

Methods

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker comprising a DMR (e.g., DMR 1-560 e.g., as provided in Tables 1A and 6A) and
2) detecting ovarian cancer, clear cell OC, endometrioid OC, mucinous OC, or serous OC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3, and
2) detecting ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1, and
2) detecting ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333, and
2) detecting ovarian cancer (e.g., afforded with a sensitivity of greater than or equal to 80% and a specificity of greater than or equal to 80%).

In some embodiments of the technology, methods are provided that comprise the following steps:

1) measuring the levels of CA-125 within a blood sample (e.g., plasma sample, whole blood sample, leukocyte sample, serum sample) obtained from the subject;
2) contacting a nucleic acid (e.g., genomic DNA, e.g., isolated from a blood sample (e.g., plasma sample, whole blood sample, leukocyte sample, serum sample) obtained from the subject with at least one reagent or series of reagents that distinguishes between methylated and non-methylated CpG dinucleotides within at least one marker selected from a chromosomal region having an annotation selected from the group consisting of ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, and SIM2_A, and
3) detecting ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2, and
2) detecting ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of PALLD, PRDM14, MAX.chr1.147790358-147790381, BCAT1, MAML3_A, SKI, DNMT3A_A, and C2CD4D, and 2) detecting ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of TACC2_A, LRRC41_A, EPS8L2, LBH, LIME1_B, MDFI, FAIM2_A, GYPC_A, AGRN_B, and ZBED4, and 2) detecting clear cell ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D, and 2) detecting clear cell ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D, and 2) detecting clear cell ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of AGRN_8794, BHLHE23_8339, EPS8L2_F, RASSF1_8293, MDFI 6321, SKI, GYPC_C, NKX2-6_4159, LOC100131366, FAIM2_B, GPRIN1_B, LRRC41_B, TACC2_B, LBH, SIM2_B, CDO1_A, and DSCR6, and 2) detecting clear cell ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of PARP15, GPRIN1_A, GYPC1_A, FLJ34208, MAX.chr1.147790358-147790381, FAIM2_A, SH2B3, KCNQ5, IRF4, and BCAT1, and 2) detecting endometrioid ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D, and 2) detecting endometrioid ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D, and 2) detecting endometrioid ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of BCAT1_6015, EPS8L2_F, SKI, NKX2-6_4159, C1QL3_B, GPRIN1_B, PARP15, OXT_C, SIM2_B, DNMT3A_A, and CELF2_A, and
2) detecting endometrioid ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of CMTM3_A, ATP10A_C, TSHZ3, ZMIZ1_B, ATP10A_B, ELMO1_B, TACC2_A, LRRC4, VIM, and ZNF382_A, and
2) detecting mucinous ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2, and
2) detecting mucinous ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, PALLD, TACC2_A, BCAT1, AGRN_B, SKI, SLC12A8, ZMIZ1_B, and BCL2L11, and
2) detecting mucinous ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of BCAT1_6015, ELMO1_9100, KCNA3_7518, KCNA3_7320, MDFI 6321, SKI, VIPR_B, ZNF382_B, ATP10A_E, CMTM3_B, ZMIZ1_D, SRC_B, HDGFRP3, TACC2_B, TSHZ3, LBH, DNMT3A_A, and
2) detecting mucinous ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of MAX.chr1.147790358-147790381, MAML3, NR2F6, DNMT3A_A, SKI, SOBP, UBTF, AGRN_C, MAX.chr12.30975740-30975780, and CAPN2_A, and
2) detecting serous ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D, and
2) detecting serous ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of NCOR2, MAX.chr1.147790358-147790381, MAX.chr6.10382190-10382225, IFFO1_A, GDF6, and C2CD4D, and
2) detecting serous ovarian cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or ovarian tissue) obtained from the subject with at least one reagent or series of reagents that distinguishes between methylated and non-methylated CpG dinucleotides within at least one marker selected from a chromosomal region having an annotation selected from the group consisting of SKI, PEAR1_B, CAPN2_B, SIM2_B, DNMT3A_A, CDO1_A, and NR2F6, and 2) detecting serous ovarian cancer (e.g., afforded with a sensitivity of greater than or equal to 80% and a specificity of greater than or equal to 80%).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:
   - AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A, 6B; Example I);
   - MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I);
   - PALLD, PRDM14, MAX.chr1.147790358-147790381, BCAT1, MAML3_A, SKI, DNMT3A_A, and C2CD4D (see, Table 4A; Example I); and
   - BCAT1_6015, SKI, SIM2_B, DNMT3A_A, CDO1_A, and DSCR6 (see, Table 8A; Example II);

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring a methylation level for one or more genes in a biological sample (e.g., blood sample, plasma sample) of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1;

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring a methylation level for one or more genes in a biological sample (e.g., blood sample, plasma sample) of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, SIM2_A, AGRN 8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333;

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring the levels of CA-125 within a blood sample (e.g., plasma sample, whole blood sample, leukocyte sample, serum sample) obtained from a human individual;

2) measuring a methylation level for one or more genes in a blood sample (e.g., plasma sample, whole blood sample, leukocyte sample, serum sample) of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, and SIM2_A;

3) amplifying the treated genomic DNA using a set of primers for the selected one or more genes; and 4) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:

AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A, 6B; Example I);

MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I);

GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1 (see, Table 9; Example III);

ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III);

PALLD, PRDM14, MAX.chr1.147790358-147790381, BCAT1, MAML3_A, SKI, DNMT3A_A, and C2CD4D (see, Table 4A; Example I); and BCAT1_6015, SKI, SIM2_B, DNMT3A_A, CDO1_A, and DSCR6 (see, Table 8A; Example II);

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

AGRN_A, ATP10A_A, ATP10A_B, ATP10A_C, ATP10A_D, BCAT1, CCND2_D, CMTM3_A, ELMO1_A, ELMO1_B, ELMO1_C, EMX1, EPS8L2_A, EPS8L2_B, EPS8L2_C, EPS8L2_D, FAIM2_A, FLJ34208_A, GPRIN1, GYPC_A, INA_A, ITGA4_B, KCNA3_A, KCNA3_C, LBH, LIME1_A, LIME1_B, LOC646278, LRRC4, LRRC41_A, MAX.chr1.110626771-110626832, MAX.chr1.147790358-147790381, MAX.chr1.161591532-161591608, MAX.chr15.28351937-28352173, MAX.chr15.28352203-28352671, MAX.chr15.29131258-29131734, MAX.chr4.8859995-8860062, MAX.chr5.42952182-42952292, MDFI, NCOR2, NKX2-6, OPLAH_A, PARP15, PDE10A, PPP1R16B, RASSF1_B, SEPTIN9, SKI, SLC12A8, SRC_A, SSBP4_B, ST8SIA1, TACC2_A, TSHZ3, UBTF, VIM, VIPR2_A, ZBED4, ZMIZ1_A, ZMIZ1_B, ZMIZ1_C, ZNF382_A, ZNF469_B, ATP6V1B1_A, BZRAP1, GDF6, IFFO1_A, IFFO1_B, KCNAB2, LIMD2, MAML3_B, MAX.chr14.102172350-102172770, MAX.chr16.85482307-85482494, MAX.chr17.76254728-76254841, MAX.chr5.42993898-42994179, and RASAL3 (see, Tables 1A, 1B, 6A, 6B; Example I);

GPRIN1 (e.g., GPRIN1_A, GPRIN1_B), CDO1 (e.g., CDO1_A, CDO1_B), SRC (e.g., SRC_A, SRC_B), SIM2 (e.g., SIM2_A, SIM2_B), AGRN (e.g., AGRN_A, AGRN_B, AGRN_C, AGRN_8794), FAIM2 (e.g., FAIM2_A, FAIM2_B), CELF2 (e.g., CELF2_A, CELF2_B), DSCR6, GYPC (e.g., GYPC_A, GYPC_B, GYPC_C), CAPN2 (e.g., CAPN2_A, CAPN2_B), and BCAT1 (see, Table 9; Example III);

ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333 (see, Table 10, Example III);

MAX.chr16.85482307-85482494, GDF6, IFFO_A, MAX.chr5.42993898-42994179, MAX.chr17.76254728-76254841, MAX.chr14.102172350-102172770, RASAL3, BZRAP1, and LIMD2 (see, Table 3; Example I);

PALLD, PRDM14, MAX.chr1.147790358-147790381, BCAT1, MAML3_A, SKI, DNMT3A_A, and C2CD4D (see, Table 4A; Example I); and BCAT1_6015, SKI, SIM2_B, DNMT3A_A, CDO1_A, and DSCR6 (see, Table 8A; Example II).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:

TACC2_A, LRRC41_A, EPS8L2, LBH, LIME1_B, MDFI, FAIM2_A, GYPC_A, AGRN_B, and ZBED4 (see, Table 2A; Example I);

MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I);

NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I); and AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II);

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:

TACC2_A, LRRC41_A, EPS8L2, LBH, LIME1_B, MDFI, FAIM2_A, GYPC_A, AGRN_B, and ZBED4 (see, Table 2A; Example I);

MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I);

NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I); and AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II);

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

TACC2_A, LRRC41_A, EPS8L2, LBH, LIME1_B, MDFI, FAIM2_A, GYPC_A, AGRN_B, and ZBED4 (see, Table 2A; Example I);

MT1A_A, CELF2_A, KCNA3_A, MDFI, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, MAX.chr14.105512178-105512224, EPS8L2_E, SKI, GPRIN1_A, MAX.chr8.142215938-142216298, CDO1_A, DNMT3A_A, SIM2_A, SKI, MT1A_B, GYPC_A, BCL2L11, PISD, and C2CD4D (see, Table 4B; Example I);

NCOR2, MT1A_B, CELF2_A, PALLD, PRDM14, PARP15, TACC2_A, MAX.chr1.147790358-147790381, BCAT1, MAX.chr11.14926602-14926671, AGRN_B, MAX.chr6.10382190-10382225, DSCR6, MAML3_A, SKI, GPRIN1_A, CDO1_A, SIM2_A, IFFO1_A, MT1A_B, GYPC_A, BCL2L11, GDF6, and C2CD4D (see, Table 5B; Example I); and AGRN_8794, BHLHE23_8339, EPS8L2_F, RASSF1_8293, MDFI_6321, SKI, GYPC_C, NKX2-6_4159, LOC100131366, FAIM2_B, GPRIN1_B, LRRC41_B, TACC2_B, LBH, SIM2_B, CDO1_A, and DSCR6 (see, Table 8B; Example II).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:

PARP15, GPRIN1_A, GYPC1_A, FLJ34208, MAX.chr1.147790358-147790381, FAIM2_A, SH2B3, KCNQ5, IRF4, and BCAT1 (see, Table 2B; Example I);

NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I);

NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I); and BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II);

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:

PARP15, GPRIN1_A, GYPC1_A, FLJ34208, MAX.chr1.147790358-147790381, FAIM2_A, SH2B3, KCNQ5, IRF4, and BCAT1 (see, Table 2B; Example I);

NCOR2, CELF2_A, PALLD, PRDM14, MAX.chr1.147790358-147790381, BCAT1, MAX.chr11.14926602-14926671, MAML3_A, SKI, GPRIN1_A, SKI, BCL2L11, and C2CD4D (see, Table 4C; Example I);

NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I); and BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II);

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

PARP15, GPRIN1_A, GYPC1_A, FLJ34208, MAX.chr1.147790358-147790381, FAIM2_A, SH2B3, KCNQ5, IRF4, and BCAT1 (see, Table 2B; Example I);

NCOR2, CELF2_A, PALLD, PRDM14, MAX.chr1.147790358-147790381, BCAT1,

MAX.chr11.14926602-14926671, MAML3_A, SKI, GPRIN1_A, SKI, BCL2L11, and C2CD4D (see, Table 4C; Example I);

NCOR2, PALLD, PRDM14, MAX.chr1.147790358-147790381, MAX.chr11.14926602-14926671, DSCR6, GPRIN1_A, CDO1_A, SIM2_A, IFFO1_A, and C2CD4D (see, Table 5C; Example I); and BCAT1_6015, EPS8L2_F, SKI, NKX2-6_4159, C1QL3_B, GPRIN1_B, PARP15, OXT_C, SIM2_B, DNMT3A_A, and CELF2_A (see, Table 8C; Example II).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:
   CMTM3_A, ATP10A_C, TSHZ3, ZMIZ1_B, ATP10A_B, ELMO1_B, TACC2_A, LRRC4, VIM, and ZNF382_A (see, Table 2C; Example I);
   NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I);
   NCOR2, PALLD, TACC2_A, BCAT1, AGRN_B, SKI, SLC12A8, ZMIZ1_B, and BCL2L11 (see, Table 5D; Example I); and
   BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II);
2) amplifying the treated genomic DNA using a set of primers for the selected one or more genes; and
3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:
   CMTM3_A, ATP10A_C, TSHZ3, ZMIZ1_B, ATP10A_B, ELMO1_B, TACC2_A, LRRC4, VIM, and ZNF382_A (see, Table 2C; Example I);
   NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I);
   NCOR2, PALLD, TACC2_A, BCAT1, AGRN_B, SKI, SLC12A8, ZMIZ1_B, and BCL2L11 (see, Table 5D; Example I); and
   BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II);
2) measuring the amount of at least one reference marker in the DNA; and
3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);
2) amplifying the modified genomic DNA using a set of primers for the selected one or more genes; and
3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;
   wherein the one or more genes is selected from one of the following groups:
   CMTM3_A, ATP10A_C, TSHZ3, ZMIZ1_B, ATP10A_B, ELMO1_B, TACC2_A, LRRC4, VIM, and ZNF382_A (see, Table 2C; Example I);
   NCOR2, MT1A_A, KCNA3_A, ZMIZ1_C, TACC2_A, MAX.chr1.147790358-147790381, BCAT1, AGRN_B, SKI, SLC12A8, ZMIZ1_B, BCL2L11, and GATA2 (see, Table 4D; Example I);
   NCOR2, PALLD, TACC2_A, BCAT1, AGRN_B, SKI, SLC12A8, ZMIZ1_B, and BCL2L11 (see, Table 5D; Example I); and
   BCAT1_6015, ELMO1_9100, KCNA3_7518, KCNA3_7320, MDFI_6321, SKI, VIPR_B, ZNF382_B, ATP10A_E, CMTM3_B, ZMIZ1_D, SRC_B, HDGFRP3, TACC2_B, TSHZ3, LBH, DNMT3A_A (see, Table 8D; Example II).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:
   MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I);
   PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I);
   NCOR2, MAX.chr1.147790358-147790381, MAX.chr6.10382190-10382225, IFFO1_A, GDF6, and C2CD4D (see, Table 5A; Example I); and
   SKI, PEAR1_B, CAPN2_B, SIM2_B, DNMT3A_A, CDO1_A, and NR2F6 (see, Table 8E; Example II);
2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:
   MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I);
   PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I);
   NCOR2, MAX.chr1.147790358-147790381, MAX.chr6.10382190-10382225, IFFO1_A, GDF6, and C2CD4D (see, Table 5A; Example I); and
   SKI, PEAR1_B, CAPN2_B, SIM2_B, DNMT3A_A, CDO1_A, and NR2F6 (see, Table 8E; Example II);
2) measuring the amount of at least one reference marker in the DNA; and
3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);
2) amplifying the modified genomic DNA using a set of primers for the selected one or more genes; and
3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;
   wherein the one or more genes is selected from one of the following groups:
   MAX.chr1.147790358-147790381, MAML3, NR2F6, DNMT3A_A, SKI, SOBP, UBTF, AGRN_C, MAX.chr12.30975740-30975780, and CAPN2_A (see, Table 2D; Example I);
   PALLD, PRDM14, MAX.chr1.147790358-147790381, CAPN2_A, MAX.chr6.10382190-10382225, SKI, NR2F6, IFFO1_A, MT1A_B, IFFO1_B, GDF6, and C2CD4D (see, Table 4E; Example I);
   NCOR2, MAX.chr1.147790358-147790381, MAX.chr6.10382190-10382225, IFFO1_A, GDF6, and C2CD4D (see, Table 5A; Example I); and
   SKI, PEAR1_B, CAPN2_B, SIM2_B, DNMT3A_A, CDO1_A, and NR2F6 (see, Table 8E; Example II).

Within any of such methods, determining the methylation level for any of such markers is accomplished with the primers recited in Tables 1C or 6B.

Preferably, the sensitivity for such methods is from about 70% to about 100%, or from about 80% to about 90%, or from about 80% to about 85%. Preferably, the specificity is from about 70% to about 100%, or from about 80% to about 90%, or from about 80% to about 85%.

Genomic DNA may be isolated by any means, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types comprising neoplastic matter or pre-neoplastic matter are suitable for use in the present method, e.g., cell lines, histological slides, biopsies, paraffin-embedded tissue, body fluids, stool, ovarian tissue, colonic effluent, urine, blood plasma, blood serum, whole blood, isolated blood cells, cells isolated from the blood, and combinations thereof.

The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Appl. Ser. No. 61/485,386 or by a related method.

The genomic DNA sample is then treated with at least one reagent, or series of reagents, that distinguishes between methylated and non-methylated CpG dinucleotides within at least one marker comprising a DMR (e.g., DMR 1-560, e.g., as provided by Tables 1A and 6A).

In some embodiments, the reagent converts cytosine bases which are unmethylated at the 5'-position to uracil, thymine, or another base which is dissimilar to cytosine in terms of hybridization behavior. However in some embodiments, the reagent may be a methylation sensitive restriction enzyme.

In some embodiments, the genomic DNA sample is treated in such a manner that cytosine bases that are unmethylated at the 5' position are converted to uracil, thymine, or another base that is dissimilar to cytosine in terms of hybridization behavior. In some embodiments, this treatment is carried out with bisulfite (hydrogen sulfite, disulfite) followed by alkaline hydrolysis.

The treated nucleic acid is then analyzed to determine the methylation state of the target gene sequences (at least one gene, genomic sequence, or nucleotide from a marker comprising a DMR, e.g., at least one DMR chosen from DMR 1-560, e.g., as provided in Tables 1A and 6A). The method of analysis may be selected from those known in the art, including those listed herein, e.g., QuARTS and MSP as described herein.

Aberrant methylation, more specifically hypermethylation of a marker comprising a DMR (e.g., DMR 1-560, e.g., as provided by Tables 1A and 6A) is associated with an ovarian cancer.

The technology relates to the analysis of any sample associated with an ovarian cancer. For example, in some embodiments the sample comprises a tissue and/or biological fluid obtained from a patient. In some embodiments, the sample comprises a secretion. In some embodiments, the sample comprises blood, serum, plasma, gastric secretions, pancreatic juice, a gastrointestinal biopsy sample, microdissected cells from an ovarian tissue biopsy, and/or cells recovered from stool. In some embodiments, the sample comprises ovarian tissue. In some embodiments, the subject is human. The sample may include cells, secretions, or tissues from the ovary, breast, liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample.

Such samples can be obtained by any number of means known in the art, such as will be apparent to the skilled person. For instance, urine and fecal samples are easily attainable, while blood, ascites, serum, or pancreatic fluid samples can be obtained parenterally by using a needle and syringe, for instance. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens In some embodiments, the technology relates to a method for treating a patient (e.g., a patient with ovarian cancer) (e.g., a patient with one or more of clear cell OC, endometrioid OC, mucinous OC, serous OC), the method comprising determining the methylation state of one or more DMR as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments of the technology, a method for diagnosing an ovarian cancer in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker (e.g., a DMR as disclosed herein), the methylation state of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers (e.g., DMR) disclosed herein. Further, in some embodiments of the presently disclosed subject matter, multiple determination of the biomarkers over time can be made to facilitate diagnosis and/or prognosis. A temporal change in the biomarker can be used to predict a clinical outcome, monitor the progression of ovarian cancer, and/or monitor the efficacy of appropriate therapies directed against the cancer. In such an embodiment for example, one might expect to see a change in the methylation state of one or more biomarkers (e.g., DMR) disclosed herein (and potentially one or more additional biomarker(s), if monitored) in a biological sample over time during the course of an effective therapy.

The presently disclosed subject matter further provides in some embodiments a method for determining whether to initiate or continue prophylaxis or treatment of a cancer in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with ovarian cancer risk, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker (e.g., a DMR). Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., having a normal methylation state of one or more DMR), the chance of a given outcome (e.g., suffering from an ovarian cancer) may be very low.

In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein (e.g., a DMR) can be established, and the degree of change in the methylation state of the biomarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with an ovarian cancer. In certain embodiments of the method, a subject is identified as having metaplasia upon identifying an aberrant methylation state of one or more DMR provided herein in a biological sample obtained from the subject. In other embodiments of the method, the detection of an aberrant methylation state of one or more of such biomarkers in a biological sample obtained from the subject results in the subject being identified as having cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having an ovarian cancer if, when compared to a control methylation state, there is a measurable difference in the methylation state of at least one biomarker in the sample. Conversely, when no change in methylation state is identified in the biological sample, the subject can be identified as not having ovarian cancer, not being at risk for the cancer, or as having a low risk of the cancer. In this regard, subjects having the cancer or risk thereof can be differentiated from subjects having low to substantially no cancer or risk thereof. Those subjects having a risk of developing an ovarina cancer can be placed on a more intensive and/or regular screening schedule, including endoscopic surveillance. On the other hand, those subjects having low to substantially no risk may avoid being subjected to additional testing for ovarian cancer (e.g., invasive procedure), until such time as a future screening, for example, a screening conducted in accordance with the present technology, indicates that a risk of ovarian cancer has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, an ovarian cancer indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like.

The presently-disclosed subject matter further includes a system for diagnosing an ovarian cancer and/or a specific form of ovarian cancer (e.g., clear cell OC, endometrioid OC, mucinous OC, serous OC) in a subject. The system can be provided, for example, as a commercial kit that can be used to screen for a risk of ovarian cancer or diagnose an ovarian cancer in a subject from whom a biological sample has been collected. An exemplary system provided in accordance with the present technology includes assessing the methylation state of a DMR as provided in Tables 1A and 6A.

EXAMPLES

Example I

Tissue and blood was obtained from Mayo Clinic biospecimen repositories with institutional IRB oversight. Samples were chosen with strict adherence to subject research authorization and inclusion/exclusion criteria. Cancer sub-types included 1) serous OC, 2) clear cell OC, 3) mucinous OC, and 4) endometrioid OC. Controls included non-neoplastic fallopian tissue and whole blood derived leukocytes. Tissues were macro-dissected and histology reviewed by an expert gynecological pathologist. Samples were age matched, randomized, and blinded. Sample DNA from 77 frozen tissues (18 serous OC, 15 clear cell OC, 6 mucinous OC, 18 endometrioid OC, 6 benign fallopian tube, 14 benign fallopian tube brushings) and 19 buffy coats from cancer-free females was purified using the QIAamp DNA Tissue Mini kit and QIAamp DNA Blood Mini kit (Qiagen, Valencia CA), respectively. DNA was re-purified with AMPure XP beads (Beckman-Coulter, Brea CA) and quantified by PicoGreen (Thermo-Fisher, Waltham MA). DNA integrity was assessed using qPCR. 4 ovarian cancer cell lines were also sequenced (TOV21G, SKOV3, OVCAR3, CAOV3).

RRBS sequencing libraries were prepared following the Meissner protocol (Gu et al. Nature Protocols 2011 April; 6(4):468-81) with modifications. Samples were combined in a 4-plex format and sequenced by the Mayo Genomics Facility on the Illumina HiSeq 2500 instrument (Illumina, San Diego CA). Reads were processed by Illumina pipeline modules for image analysis and base calling. Secondary analysis was performed using SAAP-RRBS, a Mayo developed bioinformatics suite. Briefly, reads were cleaned-up using Trim-Galore and aligned to the GRCh37/hg19 reference genome build with BSMAP. Methylation ratios were determined by calculating C/(C+T) or conversely, G/(G+A) for reads mapping to reverse strand, for CpGs with coverage ≥10× and base quality score ≥20.

Individual CpGs were ranked by hypermethylation ratio, namely the number of methylated cytosines at a given locus over the total cytosine count at that site. For cases, the ratios were required to be ≥0.20 (20%); for tissue controls, ≤0.05 (5%); for buffy coat controls, ≤0.01 (1%). CpGs which did not meet these criteria were discarded. Subsequently, candidate CpGs were binned by genomic location into DMRs (differentially methylated regions) ranging from approximately 60-200 bp with a minimum cut-off of 5 CpGs per region. DMRs with excessively high CpG density (>30%) were excluded to avoid GC-related amplification problems in the validation phase. For each candidate region, a 2-D matrix was created which compared individual CpGs in a sample to sample fashion for both cases and controls. Overall OC vs all benign ovarian tissue and/or no-cancer buffy coat was analyzed, as well as subtype comparisons. These CpG matrices were then compared back to the reference sequence to assess whether genomically contiguous methylation sites had been discarded during the initial filtering. From this subset of regions, final selections required coordinated and contiguous hypermethylation (in cases) of individual CpGs across the DMR sequence on a per sample level. Conversely, control samples had to have at least 10-fold less methylation than cases and the CpG pattern had to be more random and less coordinated. At least 10% of cancer samples within a subtype cohort were required to have at least a 50% hypermethylation ratio for every CpG site within the DMR.

In a separate analysis, a proprietary DMR identification pipeline and regression package was utilized to derive DMRs based on average methylation values of the CpG. The difference in average methylation percentage was compared between OC cases, tissue controls and buffy coat controls; a tiled reading frame within 100 base pairs of each mapped CpG was used to identify DMRs where control methylation was <5%; DMRs were only analyzed if the total depth of coverage was 10 reads per subject on average and the variance across subgroups was >0. Assuming a biologically relevant increase in the odds ratio of >3× and a coverage depth of 10 reads, ≥18 samples per group were required to achieve 80% power with a two-sided test at a significance level of 5% and assuming binomial variance inflation factor of 1.

Following regression, DMRs were ranked by p-value, area under the receiver operating characteristic curve (AUC) and fold-change difference between cases and all controls. No adjustments for false discovery were made during this phase as independent validation was planned a priori.

A proprietary methodology of sample preparation, sequencing, analyses pipelines, and filters was utilized to identify and narrow differentially methylated regions (DMRs) to those which would pinpoint these gynecological cancers and excel in a clinical testing environment. From the tissue-to-tissue analysis, 471 hypermethylated ovarian cancer (OC) DMRs were identified (Table 1A and 1B). They included OC specific regions, OC subtype specific regions, as well as those regions that targeted a more universal cancer spectrum. The top subtype ranked DMRs are listed in Tables 2A, 2B, 2C, and 2D. The tissue to leukocyte (buffy coat) analysis yielded 55 hypermethylated ovarian tissue DMRs with less than 1% noise in WBCs (DMRs 472-525 shown in Tables 1A and 1B). The top overall buffy DMRs are listed in Table 3. From the tissue and buffy marker groups, 68 candidates were chosen for an initial pilot. Methylation-specific PCR assays were developed and tested on two rounds of tissue samples; those that were sequenced (frozen) and larger independent cohorts (FFPE). Short amplicon primers (<150 bp) were designed to target the most discriminant CpGs with in a DMR and tested on controls to ensure that fully methylated fragments amplified robustly and in a linear fashion; that unmethylated and/or unconverted fragments did not amplify. The 136 primer sequences are listed in Table 1C. Ultimately, 54 assays were taken forward (14 assays failed QC and were dropped).

The results from stage one validation were analyzed logistically to determine AUC and fold change. From previous work it was recognized that the epigenetics of cancer subtypes within an organ differ and that the best panels are derived from combinations of subtype markers. The analyses for the tissue and buffy coat controls were run separately. Results are highlighted in Tables 4A, 4B, 4C, 4D and 4E. A number of assays were 100% discriminant in OC from buffy coat samples and approaching 100% in the OC vs benign fallopian tube comparison.

These results provided a rich source of highly performing candidates to take into independent sample testing. Of the original 54 assays, 33 were selected. Most fell within the AUC range of 0.90-1.00, but others were included which had extremely high FC numbers (very little background) and/or those which exhibited complementarity with other methylated DNA markers (MDMS). All assays demonstrated high analytical performance—linearity, efficiency, sequence specificity (assessed using melt curve analysis), and strong amplification.

In round 2 validation, as in the previous step, the entire sample and marker set was run in one batch. ~10 ng of FFPE-derived sample DNA was run per marker—350 total. OC subtype vs normal tissue and buffy coat results for individual MDMs are listed in Table 5A, 5B, 5C, and 5D. Multiple MDMs showed marked methylation fold changes vs controls (10 to >1000) across all OC histologies.

The data was plotted in a heat matrix format, which allows one to visualize complementarity. A cross-validated 2-MDM panel was derived from rPART modeling: (C2CD4D, NCOR2) discriminated overall OC from benign fallopian tissue with 99% sensitivity and 97% specificity. Subtype rPART and random forest modeling yielded perfect discrimination in all histologies (AUC=1).

Whole methylome sequencing, stringent filtering criteria, and biological validation yielded outstanding candidate MDMs for ovarian cancer. Some MDMs discriminate all OC histologies from controls with comparably high sensitivity, while others accurately distinguish among histologies. Given high discrimination and ease of assay, such MDMs merit further exploration for clinical application as early detection markers.

Table RA provides DMR information including chromosome number, gene annotation, and DMR start/stop position for such markers. Table 1B provides p-value, area under the receiver operating characteristic curve (AUC) and fold-change difference between OC cases and all controls. Table 1C provides the primer sequence information for various markers provided in Tables 1A and 1B.

TABLE 1A

| DMR No. | Gene Annotation | Chromosome No. | DMR Start-End Positions |
|---|---|---|---|
| 1 | A1BG | 19 | 58858941-58858983 |
| 2 | ABLIM3 | 5 | 148521010-148521347 |
| 3 | ADAM8 | 10 | 135090085-135090491 |
| 4 | ADRB1 | 10 | 115803122-115803270 |
| 5 | AEBP1 | 7 | 44143993-44144057 |
| 6 | AGRN_A | 1 | 968398-968861 |
| 7 | AGRN_B | 1 | 969237-969426 |
| 8 | AGRN_C | 1 | 975860-976046 |
| 9 | AJAP1 | 1 | 4715931-4716109 |
| 10 | AMIGO3 | 3 | 49756614-49757016 |
| 11 | ANKLE1 | 19 | 17392948-17393075 |
| 12 | ANKRD29 | 18 | 21199479-21199692 |
| 13 | ANO8 | 19 | 17439360-17439541 |
| 14 | ANPEP | 15 | 90358365-90358451 |
| 15 | ARHGEF1 | 19 | 42386936-42386997 |
| 16 | ARL10 | 5 | 175792149-175792960 |
| 17 | ARL5C | 17 | 37321417-37321631 |
| 18 | ATP10A_A | 15 | 26107757-26107986 |
| 19 | ATP10A_B | 15 | 26107990-26108203 |
| 20 | ATP10A_C | 15 | 26108433-26108524 |
| 21 | ATP10A_D | 15 | 26108550-26108818 |
| 22 | ATP2A3_A | 17 | 3867152-3867216 |
| 23 | ATP2A3_B | 17 | 3867435-3867536 |
| 24 | BCAN | 1 | 156611761-156611950 |
| 25 | BCAT1 | 12 | 25055793-25056189 |
| 26 | BCL11B_A | 14 | 99736361-99736463 |
| 27 | BCL11B_B | 14 | 99736933-99737063 |
| 28 | BCL11B_C | 14 | 99737497-99737609 |
| 29 | BEND4 | 4 | 42153526-42153625 |
| 30 | BEST4 | 1 | 45249967-45250240 |

TABLE 1A-continued

| DMR No. | Gene Annotation | Chromosome No. | DMR Start-End Positions |
|---|---|---|---|
| 31 | BHLHE23_A | 20 | 61638021-61638117 |
| 32 | BHLHE23_B | 20 | 61638192-61638565 |
| 33 | BOLA1 | 1 | 149871496-149871610 |
| 34 | C12orf42 | 12 | 103889256-103889370 |
| 35 | C14orf184 | 14 | 92040736-92040870 |
| 36 | C14orf38_A | 14 | 60043243-60043329 |
| 37 | C14orf38_B | 14 | 60043455-60043565 |
| 38 | C17orf107 | 17 | 4802571-4802889 |
| 39 | C17orf46 | 17 | 43339216-43339594 |
| 40 | C17orf64_A | 17 | 58498720-58498794 |
| 41 | C17orf64_B | 17 | 58499005-58499095 |
| 42 | C19orf35_A | 19 | 2282272-2282493 |
| 43 | C19orf35_B | 19 | 2282568-2282640 |
| 44 | C1orf200 | 1 | 9712789-9712900 |
| 45 | C1QL3_A | 10 | 16563117-16563891 |
| 46 | C3orf72 | 3 | 138663788-138663885 |
| 47 | C6orf147 | 6 | 74019480-74019585 |
| 48 | CACNA1G | 17 | 48639699-48639734 |
| 49 | CACNA2D4 | 12 | 1906505-1906559 |
| 50 | CAPN2_A | 1 | 223936868-223937004 |
| 51 | CARD11 | 7 | 3083446-3083541 |
| 52 | CCND2_A | 12 | 4381398-4381485 |
| 53 | CCND2_B | 12 | 4381789-4381895 |
| 54 | CCND2_C | 12 | 4381964-4382142 |
| 55 | CCND2_D | 12 | 4383820-4384113 |
| 56 | CD151 | 11 | 830191-830499 |
| 57 | CD38 | 4 | 15780224-15780290 |
| 58 | CD70 | 19 | 6590980-6591072 |
| 59 | CD8A_A | 2 | 87017985-87018012 |
| 60 | CD8A_B | 2 | 87018067-87018126 |
| 61 | CDO1_A | 5 | 115152022-115152432 |
| 62 | CDO1_B | 5 | 115152466-115152505 |
| 63 | CELF2_A | 10 | 11207221-11207812 |
| 64 | CELF2_B | 10 | 11207796-11207938 |
| 65 | CLIC6 | 21 | 36041908-36042182 |
| 66 | CMTM3_A | 16 | 66638182-66638341 |
| 67 | CNR1_A | 6 | 88876927-88877128 |
| 68 | CNR1_B | 6 | 88877220-88877275 |
| 69 | CNRIP1 | 2 | 68546519-68546627 |
| 70 | COL14A1 | 8 | 121137165-121137326 |
| 71 | CPT1A | 11 | 68610548-68610744 |
| 72 | CSDAP1 | 16 | 31580718-31580899 |
| 73 | CYP11A1 | 15 | 74658391-74658453 |
| 74 | CYTH2 | 19 | 48984042-48984183 |
| 75 | DAB2IP | 9 | 124462035-124462178 |
| 76 | DDN | 12 | 49391147-49391271 |
| 77 | DGKZ | 11 | 46389264-46389321 |
| 78 | DIDO1 | 20 | 61560520-61560934 |
| 79 | DLG4 | 17 | 7108434-7108738 |
| 80 | DLL4 | 15 | 41218265-41218582 |
| 81 | DNMT3A_A | 2 | 25500046-25500305 |
| 82 | DOCK2_A | 5 | 169064274-169064312 |
| 83 | DOCK2_B | 5 | 169064321-169064452 |
| 84 | DSCR6 | 21 | 38378492-38378858 |
| 85 | ELAVL3 | 19 | 11593130-11593200 |
| 86 | ELMO1_A | 7 | 37487417-37487633 |
| 87 | ELMO1_B | 7 | 37487695-37488671 |
| 88 | ELMO1_C | 7 | 37488818-37488882 |
| 89 | EMB | 5 | 49736794-49737178 |
| 90 | EMX1 | 2 | 73147710-73147772 |
| 91 | ENO3 | 17 | 4853764-4853800 |
| 92 | EPS8L2_A | 11 | 725829-725907 |
| 93 | EPS8L2_B | 11 | 726000-726061 |
| 94 | EPS8L2_C | 11 | 726066-726121 |
| 95 | EPS8L2_D | 11 | 726129-726188 |
| 96 | EPS8L2_E | 11 | 726202-726557 |
| 97 | ESPN | 1 | 6508635-6508742 |
| 98 | EVI5L | 19 | 7927507-7927609 |
| 99 | FAIM2_A | 12 | 50297610-50297988 |
| 100 | FAM69B | 9 | 139606494-139606544 |
| 101 | FEV | 2 | 219849187-219849229 |
| 102 | FLJ22536 | 6 | 21666391-21666587 |
| 103 | FLJ34208_A | 3 | 194208242-194208346 |
| 104 | FLJ34208_B | 3 | 194208392-194208424 |
| 105 | FLJ42875 | 1 | 2987463-2987488 |
| 106 | FLJ45983_A | 10 | 8097087-8097163 |
| 107 | FLJ45983_B | 10 | 8097491-8097541 |

TABLE 1A-continued

| DMR No. | Gene Annotation | Chromosome No. | DMR Start-End Positions |
|---|---|---|---|
| 108 | FOXE1 | 9 | 100616468-100616545 |
| 109 | FZD2 | 17 | 42635471-42635540 |
| 110 | GAPDHS | 19 | 36025078-36025197 |
| 111 | GATA2 | 3 | 128209003-128209339 |
| 112 | GBGT1 | 9 | 136038933-136039446 |
| 113 | GDF7 | 2 | 20866066-20866362 |
| 114 | GFI1_A | 1 | 92948353-92948494 |
| 115 | GFI1_B | 1 | 92948564-92948643 |
| 116 | GJA4 | 1 | 35258460-35258657 |
| 117 | GOLGA8A_A | 15 | 34728868-34729108 |
| 118 | GOLGA8A_B | 15 | 34729569-34729627 |
| 119 | GP5 | 3 | 194118822-194118924 |
| 120 | GPR144 | 9 | 127212625-127212653 |
| 121 | GPRIN1_A | 5 | 176023883-176024195 |
| 122 | GSX1 | 13 | 28363905-28363973 |
| 123 | GYPC_A | 2 | 127413591-127413988 |
| 124 | GYPC_B | 2 | 127414040-127414189 |
| 125 | HAAO | 2 | 43019960-43020076 |
| 126 | HCG4P6_A | 6 | 29894629-29894706 |
| 127 | HCG4P6_B | 6 | 29894728-29895060 |
| 128 | HDGFRP3 | 15 | 83875827-83875946 |
| 129 | HIC1_A | 17 | 1958916-1959035 |
| 130 | HIC1_B | 17 | 1959271-1959370 |
| 131 | HIST1H2BE | 6 | 26184228-26184336 |
| 132 | HIST1H3G | 6 | 26273744-26273884 |
| 133 | HMX3 | 10 | 124895638-124895782 |
| 134 | HOPX | 4 | 57522384-57522421 |
| 135 | HOXA6 | 7 | 27191540-27191631 |
| 136 | HOXA7 | 7 | 27196032-27196120 |
| 137 | HOXB3 | 17 | 46655280-46655642 |
| 138 | HPDL | 1 | 45792729-45792887 |
| 139 | HPSE2 | 10 | 100994002-100994115 |
| 140 | HRH2 | 5 | 175085230-175085493 |
| 141 | ICAM4 | 19 | 10398100-10398242 |
| 142 | IGFBP7 | 4 | 57976729-57976874 |
| 143 | IKZF1 | 7 | 50343339-50343420 |
| 144 | IL17C_A | 16 | 88701004-88701036 |
| 145 | IL17C_B | 16 | 88701240-88701422 |
| 146 | INA_A | 10 | 105036646-105036836 |
| 147 | IRAK2 | 3 | 10206783-10206832 |
| 148 | IRF4_A | 6 | 391420-391465 |
| 149 | IRF4_B | 6 | 391489-391525 |
| 150 | IRF4_C | 6 | 391630-391913 |
| 151 | IRF4_D | 6 | 393508-393550 |
| 152 | IRF4_E | 6 | 393636-393700 |
| 153 | ITGA4_A | 2 | 182321830-182322222 |
| 154 | ITGA4_B | 2 | 182322260-182322569 |
| 155 | ITGA5 | 12 | 54812397-54812487 |
| 156 | ITGB2 | 21 | 46352783-46352834 |
| 157 | ITPKB_A | 1 | 226924944-226925001 |
| 158 | ITPRIPL1 | 2 | 96991110-96991303 |
| 159 | JAK3_A | 19 | 17958411-17958512 |
| 160 | JAM3_A | 11 | 133938954-133939134 |
| 161 | JSRP1 | 19 | 2253171-2253346 |
| 162 | KCNA1_A | 12 | 5018819-5019101 |
| 163 | KCNA1_B | 12 | 5019343-5019751 |
| 164 | KCNA3_A | 1 | 111217012-111217118 |
| 165 | KCNA3_B | 1 | 111217162-111217358 |
| 166 | KCNA3_C | 1 | 111217478-111217843 |
| 167 | KCNA3_D | 1 | 111217621-111217793 |
| 168 | KCNK12 | 2 | 47748450-47748743 |
| 169 | KCNK4 | 11 | 64059938-64059994 |
| 170 | KCNK9_A | 8 | 140715067-140715136 |
| 171 | KCNK9_B | 8 | 140715169-140715272 |
| 172 | KCNK9_C | 8 | 140715402-140715463 |
| 173 | KCNQ5_A | 6 | 73331057-73331808 |
| 174 | KCNQ5_B | 6 | 73331977-73332327 |
| 175 | KCNQ5_C | 6 | 73332569-73332850 |
| 176 | KCTD15 | 19 | 34288332-34288538 |
| 177 | KIAA1383 | 1 | 232941174-232941363 |
| 178 | KL | 13 | 33591064-33591101 |
| 179 | KLF16 | 19 | 1857112-1857272 |
| 180 | KLHL21 | 1 | 6663497-6663739 |
| 181 | LAPTM4B | 8 | 98788068-98788302 |
| 182 | LBH | 2 | 30453651-30453973 |
| 183 | LCNL1 | 9 | 139880005-139880043 |
| 184 | LIME1_A | 20 | 62369116-62369184 |

TABLE 1A-continued

| DMR No. | Gene Annotation | Chromosome No. | DMR Start-End Positions |
|---|---|---|---|
| 185 | LIME1_B | 20 | 62369366-62369505 |
| 186 | LIMK1 | 7 | 73509063-73509133 |
| 187 | LMX1B | 9 | 129377593-129377885 |
| 188 | LOC100132891 | 8 | 72756370-72756468 |
| 189 | LOC151174 | 2 | 239140297-239140360 |
| 190 | LOC339674 | 22 | 42353684-42353820 |
| 191 | LOC440461 | 17 | 66195680-66195779 |
| 192 | LOC646278 | 15 | 29077327-29077630 |
| 193 | LOC648809 | 15 | 84748786-84749007 |
| 194 | LPHN1 | 19 | 14260451-14260665 |
| 195 | LRRC10B | 11 | 61277048-61277085 |
| 196 | LRRC32 | 11 | 76382075-76382101 |
| 197 | LRRC4 | 7 | 127671885-127672583 |
| 198 | LRRC41_A | 1 | 46767372-46769064 |
| 199 | LRRC41_B | 1 | 46769340-46769650 |
| 200 | LRRC8D | 1 | 90309263-90309378 |
| 201 | LTB | 6 | 31548580-31548608 |
| 202 | LTK | 15 | 41805316-41805441 |
| 203 | LY75 | 2 | 160760789-160760845 |
| 204 | MAML3_A | 4 | 140656481-140656692 |
| 205 | MAX.chr1.110626771-110626832 | 1 | 110626771-110626832 |
| 206 | MAX.chr1.147775386-147775483 | 1 | 147775386-147775483 |
| 207 | MAX.chr1.147790358-147790381 | 1 | 147790250-147790489 |
| 208 | MAX.chr1.148598377-148598471 | 1 | 148598377-148598471 |
| 209 | MAX.chr1.161591532-161591608 | 1 | 161591532-161591608 |
| 210 | MAX.chr1.21917279-21917313 | 1 | 21917279-21917313 |
| 211 | MAX.chr1.2472236-2472504 | 1 | 2472236-2472504 |
| 212 | MAX.chr1.2472508-2472586 | 1 | 2472508-2472586 |
| 213 | MAX.chr1.32237654-32237674 | 1 | 32237654-32237674 |
| 214 | MAX.chr1.32238032-32238105 | 1 | 32238032-32238105 |
| 215 | MAX.chr1.32238359-32238419 | 1 | 32238359-32238419 |
| 216 | MAX.chr1.32410292-32410428 | 1 | 32410292-32410428 |
| 217 | MAX.chr1.46632623-46632858 | 1 | 46632623-46632858 |
| 218 | MAX.chr1.48058986-48059074 | 1 | 48058986-48059074 |
| 219 | MAX.chr1.98510937-98511077 | 1 | 98510937-98511077 |
| 220 | MAX.chr1.98511049-98511077 | 1 | 98511049-98511077 |
| 221 | MAX.chr1.98519485-98519592 | 1 | 98519485-98519592 |
| 222 | MAX.chr10.22541609-22541719 | 10 | 22541609-22541719 |
| 223 | MAX.chr10.22541684-22541719 | 10 | 22541684-22541719 |
| 224 | MAX.chr10.22541986-22542037 | 10 | 22541986-22542037 |
| 225 | MAX.chr10.22765282-22765351 | 10 | 22765282-22765351 |
| 226 | MAX.chr11.14926602-14926671 | 11 | 14926602-14926671 |
| 227 | MAX.chr11.14926840-14926955 | 11 | 14926840-14926955 |
| 228 | MAX.chr11.45376949-45377082 | 11 | 45376949-45377082 |
| 229 | MAX.chr11.45376949-45377204 | 11 | 45376949-45377204 |
| 230 | MAX.chr11.57250516-57250847 | 11 | 57250516-57250847 |
| 231 | MAX.chr12.29302564-29302695 | 12 | 29302564-29302695 |
| 232 | MAX.chr12.30975740-30975780 | 12 | 30975740-30975780 |
| 233 | MAX.chr12.4273826-4274239 | 12 | 4273826-4274239 |
| 234 | MAX.chr14.100784600-100784781 | 14 | 100784600-100784781 |
| 235 | MAX.chr14.103557836-103558188 | 14 | 103557836-103558188 |
| 236 | MAX.chr14.105512178-105512224 | 14 | 105512131-105512271 |
| 237 | MAX.chr14.60386315-60386417 | 14 | 60386315-60386417 |
| 238 | MAX.chr14.97685168-97685437 | 14 | 97685168-97685437 |
| 239 | MAX.chr14.97685552-97685839 | 14 | 97685552-97685839 |
| 240 | MAX.chr15.28351937-28352173 | 15 | 28351937-28352173 |
| 241 | MAX.chr15.28352203-28352671 | 15 | 28352203-28352671 |
| 242 | MAX.chr15.29131258-29131734 | 15 | 29131258-29131734 |
| 243 | MAX.chr15.31685160-31685245 | 15 | 31685160-31685245 |
| 244 | MAX.chr15.65186050-65186150 | 15 | 65186050-65186150 |
| 245 | MAX.chr15.74891008-74891138 | 15 | 74891008-74891138 |
| 246 | MAX.chr15.75471061-75471202 | 15 | 75471061-75471202 |
| 247 | MAX.chr16.50875166-50875262 | 16 | 50875166-50875262 |
| 248 | MAX.chr16.50875166-50875301 | 16 | 50875166-50875301 |
| 249 | MAX.chr17.37366022-37366321 | 17 | 37366022-37366321 |
| 250 | MAX.chr19.2273768-2273823 | 19 | 2273768-2273823 |
| 251 | MAX.chr19.30716607-30716756 | 19 | 30716607-30716756 |
| 252 | MAX.chr19.37288390-37288811 | 19 | 37288390-37288811 |
| 253 | MAX.chr19.42444222-42444334 | 19 | 42444222-42444334 |
| 254 | MAX.chr19.55962661-55962773 | 19 | 55962661-55962773 |
| 255 | MAX.chr19.5828277-5828498 | 19 | 5828277-5828498 |
| 256 | MAX.chr2.118981858-118981934 | 2 | 118981858-118981934 |
| 257 | MAX.chr2.118982007-118982089 | 2 | 118982007-118982089 |
| 258 | MAX.chr2.119067767-119068112 | 2 | 119067767-119068112 |
| 259 | MAX.chr2.127783351-127783403 | 2 | 127783351-127783403 |
| 260 | MAX.chr2.175191004-175191127 | 2 | 175191004-175191127 |
| 261 | MAX.chr2.241855537-241855585 | 2 | 241855537-241855585 |

TABLE 1A-continued

| DMR No. | Gene Annotation | Chromosome No. | DMR Start-End Positions |
|---|---|---|---|
| 262 | MAX.chr2.25438959-25439001 | 2 | 25438959-25439001 |
| 263 | MAX.chr2.25439173-25439276 | 2 | 25439173-25439276 |
| 264 | MAX.chr2.66653544-66653582 | 2 | 66653544-66653582 |
| 265 | MAX.chr2.66653881-66653935 | 2 | 66653881-66653935 |
| 266 | MAX.chr2.97193155-97193524 | 2 | 97193155-97193524 |
| 267 | MAX.chr2.97193478-97193562 | 2 | 97193478-97193562 |
| 268 | MAX.chr20.30175888-30175927 | 20 | 30175888-30175927 |
| 269 | MAX.chr20.3073377-3073486 | 20 | 3073377-3073486 |
| 270 | MAX.chr20.49308029-49308083 | 20 | 49308029-49308083 |
| 271 | MAX.chr3.107148795-107148869 | 3 | 107148795-107148869 |
| 272 | MAX.chr3.128274281-128274519 | 3 | 128274281-128274519 |
| 273 | MAX.chr3.138679378-138679414 | 3 | 138679378-138679414 |
| 274 | MAX.chr3.18485437-18485723 | 3 | 18485437-18485723 |
| 275 | MAX.chr3.186490624-186490778 | 3 | 186490624-186490778 |
| 276 | MAX.chr3.69591053-69591097 | 3 | 69591053-69591097 |
| 277 | MAX.chr4.174430671-174430719 | 4 | 174430671-174430719 |
| 278 | MAX.chr4.174430751-174430776 | 4 | 174430751-174430776 |
| 279 | MAX.chr4.41869404-41869433 | 4 | 41869404-41869433 |
| 280 | MAX.chr4.8859707-8859944 | 4 | 8859707-8859944 |
| 281 | MAX.chr4.8859995-8860062 | 4 | 8859995-8860062 |
| 282 | MAX.chr4.8860076-8860122 | 4 | 8860076-8860122 |
| 283 | MAX.chr5.178957539-178957851 | 5 | 178957539-178957851 |
| 284 | MAX.chr5.2038771-2038990 | 5 | 2038771-2038990 |
| 285 | MAX.chr5.42951482-42951568 | 5 | 42951482-42951568 |
| 286 | MAX.chr5.42952182-42952292 | 5 | 42952182-42952292 |
| 287 | MAX.chr6.10382190-10382225 | 6 | 10382154-10382261 |
| 288 | MAX.chr6.108440553-108440720 | 6 | 108440553-108440720 |
| 289 | MAX.chr6.157557273-157557374 | 6 | 157557273-157557374 |
| 290 | MAX.chr6.28175549-28175579 | 6 | 28175549-28175579 |
| 291 | MAX.chr6.42738979-42739055 | 6 | 42738979-42739055 |
| 292 | MAX.chr7.127744282-127744490 | 7 | 127744282-127744490 |
| 293 | MAX.chr7.142494643-142495353 | 7 | 142494643-142495353 |
| 294 | MAX.chr7.1706293-1706418 | 7 | 1706293-1706418 |
| 295 | MAX.chr7.99595234-99595474 | 7 | 99595234-99595474 |
| 296 | MAX.chr8.124173231-124173268 | 8 | 124173231-124173268 |
| 297 | MAX.chr8.142215938-142216298 | 8 | 142215938-142216298 |
| 298 | MAX.chr8.145103855-145103943 | 8 | 145103855-145103943 |
| 299 | MAX.chr8.145104058-145104455 | 8 | 145104058-145104455 |
| 300 | MAX.chr8.145105537-145105891 | 8 | 145105537-145105891 |
| 301 | MAX.chr8.145105977-145106067 | 8 | 145105977-145106067 |
| 302 | MAX.chr8.6658405-6658443 | 8 | 6658405-6658443 |
| 303 | MAX.chr8.688047-688103 | 8 | 688047-688103 |
| 304 | MAX.chr9.113594-113689 | 9 | 113594-113689 |
| 305 | MAX.chr9.129485515-129485818 | 9 | 129485515-129485818 |
| 306 | MDFI | 6 | 41605839-41606346 |
| 307 | MFSD2B | 2 | 24233083-24233209 |
| 308 | MGC16275 | 17 | 72210023-72210198 |
| 309 | MPZ | 1 | 161275472-161275996 |
| 310 | MSX2 | 5 | 174152507-174152713 |
| 311 | MT1A_A | 16 | 56669159-56669211 |
| 312 | MT1A_B | 16 | 56669458-56669636 |
| 313 | MYO15B_A | 17 | 73584228-73584557 |
| 314 | MYO15B_B | 17 | 73584560-73584600 |
| 315 | MYO15B_C | 17 | 73585026-73585115 |
| 316 | MYOZ3 | 5 | 150051282-150051406 |
| 317 | NBPF3 | 1 | 21767084-21767293 |
| 318 | NCOR2 | 12 | 124941831-124942044 |
| 319 | NEFL | 8 | 24814074-24814163 |
| 320 | NFATC1 | 18 | 77159828-77159857 |
| 321 | NFATC4 | 14 | 24837473-24838153 |
| 322 | NFIC_A | 19 | 3358520-3358591 |
| 323 | NFIC_B | 19 | 3360968-3361330 |
| 324 | NFIC_C | 19 | 3435098-3435351 |
| 325 | NFIX | 19 | 13124203-13124307 |
| 326 | NID2 | 14 | 52535746-52536302 |
| 327 | NKX2-3 | 10 | 101290864-101290938 |
| 328 | NKX2-6 | 8 | 23564076-23564181 |
| 329 | NR2F6 | 19 | 17346347-17346780 |
| 330 | NRTN | 19 | 5828107-5828231 |
| 331 | NTN1 | 17 | 9143253-9143499 |
| 332 | NTRK3_A | 15 | 88799927-88799988 |
| 333 | NTRK3_B | 15 | 88800193-88800380 |
| 334 | OBSCN | 1 | 228463593-228463779 |
| 335 | OLIG1 | 21 | 34443688-34443868 |
| 336 | OLIG2 | 21 | 34399771-34399916 |
| 337 | OPLAH_A | 8 | 145106349-145106488 |
| 338 | OPLAH_B | 8 | 145106672-145106921 |

TABLE 1A-continued

| DMR No. | Gene Annotation | Chromosome No. | DMR Start-End Positions |
|---|---|---|---|
| 339 | OPRL1 | 20 | 62711578-62711704 |
| 340 | OSR2 | 8 | 99954516-99954637 |
| 341 | OXT_A | 20 | 3052709-3052813 |
| 342 | OXT_B | 20 | 3052884-3052977 |
| 343 | PALLD | 4 | 169799211-169799372 |
| 344 | PALM3 | 19 | 14168328-14168446 |
| 345 | PARP15 | 3 | 122296692-122296851 |
| 346 | PAX6 | 11 | 31825838-31825879 |
| 347 | PDE6B | 4 | 657799-658022 |
| 348 | PDE10A | 6 | 166076546-166077074 |
| 349 | PDX1 | 13 | 28498334-28498404 |
| 350 | PEAR1_A | 1 | 156863509-156863554 |
| 351 | PIF1 | 15 | 65116269-65116639 |
| 352 | PIP5KL1 | 9 | 130689558-130689627 |
| 353 | PISD | 22 | 32026204-32026773 |
| 354 | PLEKHA6 | 1 | 204328789-204328989 |
| 355 | PLEKHO1 | 1 | 150123028-150123073 |
| 356 | PLXNC1 | 12 | 94543384-94543621 |
| 357 | PNMAL2 | 19 | 46996713-46996787 |
| 358 | PPFIA4_A | 1 | 203044930-203045036 |
| 359 | PPP1R16B | 20 | 37435478-37435773 |
| 360 | PRDM14 | 8 | 70981925-70982133 |
| 361 | PRKAG2 | 7 | 151480148-151480267 |
| 362 | PRKAR1B_A | 7 | 641712-641771 |
| 363 | PRKCB_A | 16 | 23847557-23847586 |
| 364 | PRKCB_B | 16 | 23847659-23847699 |
| 365 | PRKCB_C | 16 | 23847825-23847924 |
| 366 | PRKCB_D | 16 | 23847935-23848025 |
| 367 | PROCA1 | 17 | 27038756-27038861 |
| 368 | PROKR2 | 20 | 5297178-5297272 |
| 369 | PTGDR | 14 | 52735279-52735395 |
| 370 | PTP4A3_A | 8 | 142427934-142428065 |
| 371 | PTP4A3_B | 8 | 142428209-142428278 |
| 372 | PTPRS | 19 | 5338930-5339005 |
| 373 | PTPRU | 1 | 29586282-29586672 |
| 374 | PYCARD | 16 | 31213961-31214287 |
| 375 | RAI1_A | 17 | 17626939-17627256 |
| 376 | RAI1_B | 17 | 17627449-17627542 |
| 377 | RASGEF1A | 10 | 43697946-43698226 |
| 378 | RASSF1_A | 3 | 50378163-50378232 |
| 379 | RASSF1_B | 3 | 50378242-50378506 |
| 380 | RBFOX3 | 17 | 77216036-77216108 |
| 381 | RET | 10 | 43600358-43600417 |
| 382 | RFTN1_A | 3 | 16554307-16554544 |
| 383 | RILPL2 | 12 | 123920605-123920783 |
| 384 | RNF220 | 1 | 44873859-44874011 |
| 385 | RTN4RL2 | 11 | 57244133-57244310 |
| 386 | RUNX3 | 1 | 25256939-25256984 |
| 387 | SALL3 | 18 | 76739367-76739410 |
| 388 | SCGB3A1 | 5 | 180017894-180018010 |
| 389 | SEPTIN9 | 17 | 75447349-75448208 |
| 390 | SFMBT2_A | 10 | 7450245-7450492 |
| 391 | SFMBT2_B | 10 | 7451000-7451219 |
| 392 | SFMBT2_C | 10 | 7451122-7451185 |
| 393 | SH2B3 | 12 | 111844616-111844676 |
| 394 | SH3PXD2A | 10 | 105452732-105452854 |
| 395 | SHH_A | 7 | 155596622-155596834 |
| 396 | SHH_B | 7 | 155597896-155598039 |
| 397 | SIM2_A | 21 | 38076892-38077026 |
| 398 | SKI | 1 | 2222218-2222508 |
| 399 | SLC12A8 | 3 | 124860558-124861019 |
| 400 | SLC25A47 | 14 | 100784600-100784767 |
| 401 | SLC4A11 | 20 | 3218820-3218937 |
| 402 | SLC5A5_A | 19 | 17983502-17983586 |
| 403 | SLC5A5_B | 19 | 17983598-17983715 |
| 404 | SLC8A3 | 14 | 70654428-70654774 |
| 405 | SLFN12L | 17 | 33814255-33814301 |
| 406 | SMTN | 22 | 31480775-31481518 |
| 407 | SOBP_A | 6 | 107956180-107956211 |
| 408 | SP9 | 2 | 175202051-175202128 |
| 409 | SPATA18 | 4 | 52917781-52918182 |
| 410 | SPDYA | 2 | 29033199-29033781 |
| 411 | SPEF1 | 20 | 3758385-3758848 |
| 412 | SPOCK2_A | 10 | 73847053-73847086 |
| 413 | SPOCK2_B | 10 | 73847235-73847539 |
| 414 | SPON2_A | 4 | 1165210-1165299 |
| 415 | SPON2_B | 4 | 1165343-1165543 |

TABLE 1A-continued

| DMR No. | Gene Annotation | Chromosome No. | DMR Start-End Positions |
|---|---|---|---|
| 416 | SRC_A | 20 | 36013131-36013293 |
| 417 | SSBP4_A | 19 | 18539898-18539951 |
| 418 | SSBP4_B | 19 | 18540000-18540094 |
| 419 | SSBP4_C | 19 | 18540229-18540318 |
| 420 | ST8SIA1 | 12 | 22487798-22487868 |
| 421 | STX16 | 20 | 57225361-57225498 |
| 422 | TACC1 | 8 | 38645352-38645822 |
| 423 | TACC2_A | 10 | 123922953-123923142 |
| 424 | TBKBP1 | 17 | 45772630-45772754 |
| 425 | TBX20 | 7 | 35293783-35293840 |
| 426 | TCF3 | 19 | 1651228-1651464 |
| 427 | TEAD3 | 6 | 35465820-35465933 |
| 428 | TET2 | 4 | 106067300-106067367 |
| 429 | TGFB1 | 19 | 41860019-41860100 |
| 430 | TJP2 | 9 | 71788680-71789619 |
| 431 | TMC4 | 19 | 54668457-54668534 |
| 432 | TMC6 | 17 | 76123694-76123758 |
| 433 | TMEFF2 | 2 | 193059694-193059802 |
| 434 | TMEM101 | 17 | 42092155-42092451 |
| 435 | TMEM106A | 17 | 41364038-41364262 |
| 436 | TNFRSF10C | 8 | 22960622-22960682 |
| 437 | TNFRSF8 | 1 | 12123499-12123582 |
| 438 | TRIM15 | 6 | 30139641-30139719 |
| 439 | TRIM71 | 3 | 32859445-32859594 |
| 440 | TRIM9_A | 14 | 51561036-51561087 |
| 441 | TRIM9_B | 14 | 51561136-51561442 |
| 442 | TRPV2 | 17 | 16319144-16319187 |
| 443 | TSC22D4 | 7 | 100075240-100075445 |
| 444 | TSHZ3 | 19 | 31839415-31840120 |
| 445 | TSPY26P | 20 | 30777758-30778400 |
| 446 | TXNRD1 | 12 | 104609676-104609867 |
| 447 | UBTF | 17 | 42287818-42288018 |
| 448 | ULBP1 | 6 | 150286136-150286230 |
| 449 | UST | 6 | 149069280-149069352 |
| 450 | VASP | 19 | 46012679-46012761 |
| 451 | VILL | 3 | 38035507-38035975 |
| 452 | VIM | 10 | 17271136-17272017 |
| 453 | VIPR2_A | 7 | 158937338-158937701 |
| 454 | WNT7B | 22 | 46367055-46367110 |
| 455 | XKR6 | 8 | 11059151-11059333 |
| 456 | XYLT1 | 16 | 17563754-17564236 |
| 457 | ZBED4 | 22 | 50243124-50243470 |
| 458 | ZEB2_A | 2 | 145273503-145273611 |
| 459 | ZEB2_B | 2 | 145273632-145273799 |
| 460 | ZFP3 | 17 | 4981325-4981972 |
| 461 | ZMIZ1_A | 10 | 81001957-81002169 |
| 462 | ZMIZ1_B | 10 | 81002179-81002856 |
| 463 | ZMIZ1_C | 10 | 81002774-81003124 |
| 464 | ZNF132 | 19 | 58951346-58951858 |
| 465 | ZNF382_A | 19 | 37095829-37096330 |
| 466 | ZNF469_A | 16 | 88496936-88497068 |
| 467 | ZNF469_B | 16 | 88497173-88497294 |
| 468 | ZNF703 | 8 | 37554309-37554811 |
| 469 | ZNF781 | 19 | 38182950-38183200 |
| 470 | ZSCAN12 | 6 | 28367509-28367628 |
| 471 | ZSCAN23 | 6 | 28411060-28411316 |
| 472 | ATP6V1B1_A | 2 | 71192303-71192387 |
| 473 | ATP6V1B1_B | 2 | 71192391-71192453 |
| 474 | BANK1 | 4 | 102712067-102712226 |
| 475 | BCL2L11 | 2 | 111876417-111876495 |
| 476 | BZRAP1 | 17 | 56405949-56406457 |
| 477 | C17orf64_C | 17 | 58498720-58499190 |
| 478 | C19orf35_C | 19 | 2282230-2282493 |
| 479 | C2CD4D | 1 | 151810778-151810945 |
| 480 | CCDC88C | 14 | 91790479-91790734 |
| 481 | TRIM9_C | 14 | 51560749-51561240 |
| 482 | CORO1A | 16 | 30195584-30195646 |
| 483 | DNMT3A_B | 2 | 25499898-25500026 |
| 484 | DNMT3A_C | 2 | 25500061-25500236 |
| 485 | FAM189B | 1 | 155220306-155220461 |
| 486 | FCHO1 | 19 | 17862130-17862551 |
| 487 | FXYD5 | 19 | 35646113-35646632 |
| 488 | GDF6 | 8 | 97157560-97158030 |
| 489 | GMDS | 6 | 1624813-1624862 |
| 490 | IFFO1_A | 12 | 6664906-6665023 |
| 491 | IFFO1_B | 12 | 6665135-6665425 |
| 492 | INA_B | 10 | 105036559-105036778 |

TABLE 1A-continued

| DMR No. | Gene Annotation | Chromosome No. | DMR Start-End Positions |
|---|---|---|---|
| 493 | ITPKB_B | 1 | 226862888-226863048 |
| 494 | ITPKB_C | 1 | 226924740-226924976 |
| 495 | JAK3_B | 19 | 17958411-17958961 |
| 496 | KANK3 | 19 | 8407580-8407717 |
| 497 | KCNAB2 | 1 | 6053564-6053753 |
| 498 | LIMD2 | 17 | 61778317-61778400 |
| 499 | MAML3_B | 4 | 140656559-140656624 |
| 500 | MAX.chr1.9689803-9690241 | 1 | 9689803-9690241 |
| 501 | MAX.chr10.101300125-101300155 | 10 | 101300125-101300155 |
| 502 | MAX.chr11.14926756-14927227 | 11 | 14926756-14927227 |
| 503 | MAX.chr12.30975740-30975961 | 12 | 30975740-30975961 |
| 504 | MAX.chr14.102172350-102172770 | 14 | 102172350-102172770 |
| 505 | MAX.chr16.85482307-85482494 | 16 | 85482307-85482494 |
| 506 | MAX.chr17.76254728-76254841 | 17 | 76254728-76254841 |
| 507 | MAX.chr20.56008090-56008227 | 20 | 56008090-56008227 |
| 508 | MAX.chr4.174430662-174430790 | 4 | 174430662-174430790 |
| 509 | MAX.chr5.42993898-42994179 | 5 | 42993898-42994179 |
| 510 | MAX.chr6.1379890-1379965 | 6 | 1379890-1379965 |
| 511 | MAX.chr7.2569526-2569650 | 7 | 2569526-2569650 |
| 512 | MAX.chr8.124173112-124173541 | 8 | 124173112-124173541 |
| 513 | PPFIA4_B | 1 | 203044753-203044863 |
| 514 | PPFIA4_C | 1 | 203044899-203044961 |
| 515 | PRKAR1B_B | 7 | 641251-641544 |
| 516 | PRKAR1B_C | 7 | 641566-641742 |
| 517 | PTGER4_A | 5 | 40681137-40681372 |
| 518 | PTGER4_B | 5 | 40681717-40682193 |
| 519 | PTPRCAP | 11 | 67204667-67204747 |
| 520 | RASAL3 | 19 | 15574876-15575148 |
| 521 | RASSF1_C | 3 | 50378163-50378750 |
| 522 | RUNX1 | 21 | 36398973-36399247 |
| 523 | SLC29A4 | 7 | 5336631-5336744 |
| 524 | SLC35D3 | 6 | 137244314-137244409 |
| 525 | SOBP_B | 6 | 107956152-107956211 |

TABLE 1B

| DMR No. | Gene Annotation | Area Under Curve | Fold-Change | p-value |
|---|---|---|---|---|
| 1 | A1BG | 0.6544 | 8.881 | 0.0006461 |
| 2 | ABLIM3 | 0.7567 | 14.96 | 0.000006848 |
| 3 | ADAM8 | 0.75 | 22.84 | 0.003361 |
| 4 | ADRB1 | 0.6933 | 10.87 | 0.002295 |
| 5 | AEBP1 | 0.8933 | 42.27 | 0.0002977 |
| 6 | AGRN_A | 0.99 | 80 | 0.006998 |
| 7 | AGRN_B | 0.7986 | 11.38 | 0.0006022 |
| 8 | AGRN_C | 0.8903 | 19.04 | 0.002814 |
| 9 | AJAP1 | 0.8382 | 21.54 | 0.000009943 |
| 10 | AMIGO3 | 0.9567 | 28.8 | 7.815E−08 |
| 11 | ANKLE1 | 0.7118 | 7.758 | 0.006422 |
| 12 | ANKRD29 | 0.7233 | 13.1 | 0.005132 |
| 13 | ANO8 | 0.7683 | 7.53 | 0.004867 |
| 14 | ANPEP | 0.6853 | 5.584 | 0.0001538 |
| 15 | ARHGEF1 | 0.7267 | 18.41 | 0.009129 |
| 16 | ARL10 | 0.94 | 28.12 | 0.00002384 |
| 17 | ARL5C | 0.7528 | 27.61 | 0.0001708 |
| 18 | ATP10A_A | 1 | 30.73 | 6.249E−09 |
| 19 | ATP10A_B | 1 | 245.4 | 1.1E−09 |
| 20 | ATP10A_C | 1 | 341.2 | 0.00007308 |
| 21 | ATP10A_D | 1 | 34.16 | 1.608E−11 |
| 22 | ATP2A3_A | 0.8583 | 14.21 | 0.00000201 |
| 23 | ATP2A3_B | 0.6867 | 17.2 | 0.003838 |
| 24 | BCAN | 0.9583 | 13.08 | 0.000001579 |
| 25 | BCAT1 | 1 | 79.37 | 5.014E−12 |
| 26 | BCL11B_A | 0.9867 | 6.934 | 6.682E−07 |
| 27 | BCL11B_B | 0.9833 | 57.45 | 0.0001541 |
| 28 | BCL11B_C | 0.8283 | 10.78 | 0.00004186 |
| 29 | BEND4 | 0.7941 | 7.411 | 0.0001528 |
| 30 | BEST4 | 0.66 | 24.18 | 0.0003696 |
| 31 | BHLHE23_A | 0.97 | 28.06 | 0.000001769 |
| 32 | BHLHE23_B | 0.9533 | 28.66 | 8.302E−07 |
| 33 | BOLA1 | 0.8133 | 5.7 | 0.00739 |
| 34 | C12orf42 | 0.6912 | 7.798 | 0.003686 |
| 35 | C14orf184 | 0.8567 | 46.56 | 0.001492 |

TABLE 1B-continued

| DMR No. | Gene Annotation | Area Under Curve | Fold-Change | p-value |
|---|---|---|---|---|
| 36 | C14orf38_A | 0.7333 | 8.048 | 0.000008448 |
| 37 | C14orf38_B | 0.6824 | 10.58 | 0.002335 |
| 38 | C17orf107 | 0.9206 | 19.7 | 0.0035 |
| 39 | C17orf46 | 0.8806 | 93.94 | 0.00008659 |
| 40 | C17orf64_A | 0.7456 | 19.39 | 0.000006859 |
| 41 | C17orf64_B | 0.8556 | 15.67 | 0.000002679 |
| 42 | C19orf35_A | 0.7485 | 8.741 | 0.0003768 |
| 43 | C19orf35_B | 0.8826 | 14.91 | 0.00001519 |
| 44 | C1orf200 | 0.9533 | 12.6 | 3.491E−07 |
| 45 | C1QL3_A | 0.8133 | 19.06 | 0.0001654 |
| 46 | C3orf72 | 0.6833 | 8.511 | 0.0001902 |
| 47 | C6orf147 | 0.6596 | 3.923 | 0.002154 |
| 48 | CACNA1G | 0.8267 | 18.84 | 0.0004358 |
| 49 | CACNA2D4 | 0.8867 | 19.07 | 0.0001017 |
| 50 | CAPN2_A | 0.8806 | 49.97 | 0.004007 |
| 51 | CARD11 | 0.9015 | 28.11 | 0.001149 |
| 52 | CCND2_A | 0.8765 | 12.62 | 0.00004201 |
| 53 | CCND2_B | 0.8033 | 6.981 | 0.0004369 |
| 54 | CCND2_C | 0.9853 | 28.97 | 0.00005149 |
| 55 | CCND2_D | 0.9967 | 38.38 | 0.0001518 |
| 56 | CD151 | 0.6853 | 16.18 | 0.007558 |
| 57 | CD38 | 0.7309 | 5.398 | 0.0001178 |
| 58 | CD70 | 0.7118 | 9.494 | 0.0001615 |
| 59 | CD8A_A | 0.8183 | 5.041 | 0.0002965 |
| 60 | CD8A_B | 0.6867 | 4.417 | 0.003114 |
| 61 | CDO1_A | 0.9167 | 27.11 | 0.000002148 |
| 62 | CDO1_B | 0.8987 | 12.31 | 2.355E−07 |
| 63 | CELF2_A | 0.9706 | 55.52 | 0.000000824 |
| 64 | CELF2_B | 0.9235 | 69.19 | 0.000000867 |
| 65 | CLIC6 | 0.88 | 37.52 | 0.00001932 |
| 66 | CMTM3_A | 1 | 379.6 | 0.000004797 |
| 67 | CNR1_A | 0.8333 | 11.08 | 0.0002641 |
| 68 | CNR1_B | 0.8986 | 6.632 | 2.378E−08 |
| 68 | CNR1_B | 0.965 | 47.74 | 0.008 |
| 69 | CNRIP1 | 0.7083 | 8.175 | 0.004742 |
| 70 | COL14A1 | 0.7194 | 7.588 | 0.00346 |
| 71 | CPT1A | 0.6985 | 5.504 | 0.0004104 |
| 72 | CSDAP1 | 0.8564 | 8.104 | 0.000002696 |
| 73 | CYP11A1 | 0.785 | 174.8 | 0.006516 |
| 74 | CYTH2 | 0.7147 | 11.12 | 0.001887 |
| 75 | DAB2IP | 0.7633 | 8.707 | 0.0005873 |
| 76 | DDN | 0.8361 | 13.65 | 0.00001727 |
| 77 | DGKZ | 0.8147 | 8.819 | 0.00001577 |
| 78 | DIDO1 | 0.9033 | 19.96 | 0.001844 |
| 79 | DLG4 | 0.685 | 10.81 | 0.0004877 |
| 80 | DLL4 | 0.7767 | 6.585 | 0.005444 |
| 81 | DNMT3A_A | 0.9333 | 29.9 | 0.0003524 |
| 82 | DOCK2_A | 0.6765 | 4.147 | 0.001841 |
| 83 | DOCK2_B | 0.6794 | 7.295 | 0.00009245 |
| 84 | DSCR6 | 0.9241 | 24.78 | 0.000005174 |
| 85 | ELAVL3 | 0.74 | 11.23 | 0.00009692 |
| 86 | ELMO1_A | 1 | 132.1 | 2.564E−08 |
| 87 | ELMO1_B | 1 | 203.7 | 0.0000838 |
| 88 | ELMO1_C | 1 | 59.3 | 7.298E−07 |
| 89 | EMB | 0.93 | 35.78 | 0.0003639 |
| 90 | EMX1 | 1 | 20.6 | 3.807E−09 |
| 91 | ENO3 | 0.8683 | 16.03 | 0.000003145 |
| 92 | EPS8L2_A | 1 | 57.73 | 9.647E−12 |
| 93 | EPS8L2_B | 1 | 68.16 | 0.000006863 |
| 94 | EPS8L2_C | 1 | 160.2 | 0.000005736 |
| 95 | EPS8L2_D | 1 | 52.76 | 0.00009573 |
| 96 | EPS8L2_E | 0.9567 | 102.7 | 9.648E−07 |
| 97 | ESPN | 0.6132 | 6.202 | 0.00143 |
| 98 | EVI5L | 0.8933 | 11.73 | 0.0004139 |
| 99 | FAIM2_A | 1 | 47 | 2.702E−09 |
| 100 | FAM69B | 0.7471 | 27.75 | 0.005765 |
| 101 | FEV | 0.7368 | 10.38 | 0.0007329 |
| 102 | FLJ22536 | 0.8833 | 15.99 | 0.002614 |
| 103 | FLJ34208_A | 0.9912 | 28 | 3.514E−08 |
| 104 | FLJ34208_B | 0.8806 | 18.98 | 0.00001492 |
| 105 | FLJ42875 | 0.7838 | 6.465 | 0.003577 |
| 106 | FLJ45983_A | 0.7812 | 8.717 | 0.00002707 |
| 107 | FLJ45983_B | 0.8699 | 10.64 | 0.000005396 |
| 108 | FOXE1 | 0.7639 | 6.357 | 0.00338 |
| 109 | FZD2 | 0.7083 | 99.24 | 0.009477 |
| 110 | GAPDHS | 0.7667 | 29.01 | 0.003253 |
| 111 | GATA2 | 0.9833 | 6.062 | 2.356E−08 |

TABLE 1B-continued

| DMR No. | Gene Annotation | Area Under Curve | Fold-Change | p-value |
|---|---|---|---|---|
| 112 | GBGT1 | 0.8567 | 28.95 | 0.0005991 |
| 113 | GDF7 | 0.8433 | 34.55 | 0.00002293 |
| 114 | GFI1_A | 0.8147 | 4.787 | 6.398E−07 |
| 115 | GFI1_B | 0.9367 | 13.76 | 0.000001453 |
| 116 | GJA4 | 0.8067 | 51.6 | 0.002206 |
| 117 | GOLGA8A_A | 0.67 | 7.573 | 0.0004803 |
| 118 | GOLGA8A_B | 0.6853 | 8.917 | 0.003308 |
| 119 | GP5 | 0.8941 | 13.92 | 0.000009619 |
| 120 | GPR144 | 0.8 | 21.8 | 0.001782 |
| 121 | GPRIN1_A | 1 | 56.59 | 1.866E−07 |
| 122 | GSX1 | 0.6926 | 4.784 | 0.002045 |
| 123 | GYPC_A | 1 | 46.94 | 1.207E−08 |
| 124 | GYPC_B | 0.9598 | 25.93 | 0.000000743 |
| 125 | HAAO | 0.6875 | 14.23 | 0.00987 |
| 126 | HCG4P6_A | 0.8559 | 19.03 | 0.00004768 |
| 127 | HCG4P6_B | 0.8643 | 53.23 | 0.00001682 |
| 128 | HDGFRP3 | 0.9083 | 264.6 | 0.005772 |
| 129 | HIC1_A | 0.82 | 15.78 | 0.008269 |
| 130 | HIC1_B | 0.84 | 8.745 | 0.009024 |
| 131 | HIST1H2BE | 0.7583 | 20.23 | 0.0003459 |
| 132 | HIST1H3G | 0.7559 | 8.885 | 0.0008868 |
| 133 | HMX3 | 0.7765 | 5.382 | 0.001231 |
| 134 | HOPX | 0.8279 | 6.978 | 0.0002184 |
| 135 | HOXA6 | 0.8745 | 8.803 | 0.00222 |
| 136 | HOXA7 | 0.7235 | 7.266 | 0.0001254 |
| 137 | HOXB3 | 0.8792 | 255.3 | 0.0009786 |
| 138 | HPDL | 0.7867 | 7.105 | 0.00005945 |
| 139 | HPSE2 | 0.67 | 9.805 | 0.005669 |
| 140 | HRH2 | 0.9333 | 11.87 | 5.858E−10 |
| 141 | ICAM4 | 0.8625 | 7.528 | 0.00002389 |
| 142 | IGFBP7 | 0.7639 | 16.19 | 0.002099 |
| 143 | IKZF1 | 0.7735 | 6.009 | 0.007191 |
| 144 | IL17C_A | 0.6574 | 10.14 | 0.006494 |
| 145 | IL17C_B | 0.7647 | 42.2 | 0.009096 |
| 146 | INA_A | 0.9933 | 11.07 | 0.000002026 |
| 147 | IRAK2 | 0.6632 | 16.61 | 0.00237 |
| 148 | IRF4_A | 0.8309 | 27.17 | 0.00009321 |
| 149 | IRF4_B | 0.9765 | 36.51 | 9.513E−07 |
| 150 | IRF4_C | 0.9824 | 25.5 | 0.000017 |
| 151 | IRF4_D | 0.7324 | 9.383 | 0.008479 |
| 152 | IRF4_E | 0.7456 | 8.068 | 0.002086 |
| 153 | ITGA4_A | 0.95 | 23.1 | 0.000003344 |
| 154 | ITGA4_B | 0.9917 | 17.91 | 0.000001087 |
| 155 | ITGA5 | 0.8375 | 9.488 | 0.00007725 |
| 156 | ITGB2 | 0.7306 | 4.286 | 0.001626 |
| 157 | ITPKB_A | 0.7167 | 15.83 | 0.002895 |
| 158 | ITPRIPL1 | 0.6567 | 8.02 | 0.004609 |
| 159 | JAK3_A | 0.8441 | 37.73 | 0.00007119 |
| 160 | JAM3_A | 0.8117 | 9.335 | 0.00002176 |
| 161 | JSRP1 | 0.8533 | 30 | 0.0000128 |
| 162 | KCNA1_A | 0.8456 | 18.55 | 0.00002068 |
| 163 | KCNA1_B | 0.9222 | 27.8 | 0.00001255 |
| 164 | KCNA3_A | 1 | 11.77 | 0.000000026 |
| 165 | KCNA3_B | 0.975 | 14.21 | 4.593E−08 |
| 166 | KCNA3_C | 1 | 27.74 | 0.000000133 |
| 167 | KCNA3_D | 0.6778 | 14.56 | 0.002861 |
| 168 | KCNK12 | 0.8233 | 13.36 | 0.0001527 |
| 169 | KCNK4 | 0.8412 | 10.95 | 0.001631 |
| 170 | KCNK9_A | 0.6967 | 9.458 | 0.0009651 |
| 171 | KCNK9_B | 0.6833 | 11.69 | 0.008939 |
| 172 | KCNK9_C | 0.7833 | 13.34 | 0.00008646 |
| 173 | KCNQ5_A | 0.9206 | 36.2 | 0.0002181 |
| 174 | KCNQ5_B | 0.8278 | 29.53 | 0.002382 |
| 175 | KCNQ5_C | 0.9853 | 25.67 | 0.0002584 |
| 176 | KCTD15 | 0.93 | 75.32 | 0.005265 |
| 177 | KIAA1383 | 0.6639 | 13.01 | 0.0003342 |
| 178 | KL | 0.7471 | 5.618 | 0.00007553 |
| 179 | KLF16 | 0.8867 | 43.9 | 0.0002147 |
| 180 | KLHL21 | 0.7042 | 14.21 | 0.000305 |
| 181 | LAPTM4B | 0.6667 | 93190000 | 0.9955 |
| 182 | LBH | 1 | 158.1 | 0.0000823 |
| 183 | LCNL1 | 0.8204 | 13.69 | 0.0005437 |
| 184 | LIME1_A | 0.99 | 53.73 | 1.862E−08 |
| 185 | LIME1_B | 1 | 80.14 | 8.084E−07 |
| 186 | LIMK1 | 0.9118 | 13.08 | 0.00005383 |
| 187 | LMX1B | 0.8667 | 17.28 | 0.0004894 |
| 188 | LOC100132891 | 0.7319 | 7.814 | 0.001522 |

TABLE 1B-continued

| DMR No. | Gene Annotation | Area Under Curve | Fold-Change | p-value |
|---|---|---|---|---|
| 189 | LOC151174 | 0.7324 | 10.59 | 0.00003981 |
| 190 | LOC339674 | 0.7029 | 12.95 | 0.00007156 |
| 191 | LOC440461 | 0.6633 | 10.07 | 0.005412 |
| 192 | LOC646278 | 1 | 13.65 | 3.871E−08 |
| 193 | LOC648809 | 0.6633 | 8.992 | 0.0002679 |
| 194 | LPHN1 | 0.8982 | 18.43 | 0.00004102 |
| 195 | LRRC10B | 0.8 | 5.359 | 0.000004834 |
| 196 | LRRC32 | 0.7412 | 11.54 | 0.0002366 |
| 197 | LRRC4 | 1 | 177.2 | 0.0002576 |
| 198 | LRRC41_A | 1 | 189.9 | 0.000006696 |
| 199 | LRRC41_B | 0.9233 | 331.1 | 0.00001455 |
| 200 | LRRC8D | 0.67 | 3.422 | 0.006004 |
| 201 | LTB | 0.8132 | 3.637 | 0.000402 |
| 202 | LTK | 0.8033 | 8.959 | 0.00003262 |
| 203 | LY75 | 0.7556 | 7.301 | 0.002031 |
| 204 | MAML3_A | 0.9583 | 14.34 | 5.424E−08 |
| 205 | MAX.chr1.110626771-110626832 | 1 | 36.78 | 1.847E−07 |
| 206 | MAX.chr1.147775386-147775483 | 0.7286 | 39.08 | 0.001102 |
| 207 | MAX.chr1.147790358-147790381 | 0.9917 | 21.51 | 5.145E−07 |
| 208 | MAX.chr1.148598377-148598471 | 0.6559 | 8.982 | 0.008606 |
| 209 | MAX.chr1.161591532-161591608 | 1 | 17.5 | 1.128E−07 |
| 210 | MAX.chr1.21917279-21917313 | 0.8778 | 9.553 | 0.00001685 |
| 211 | MAX.chr1.2472236-2472504 | 0.92 | 18.64 | 0.0004799 |
| 212 | MAX.chr1.2472508-2472586 | 0.8267 | 26.72 | 0.002689 |
| 213 | MAX.chr1.32237654-32237674 | 0.7542 | 7.453 | 0.0004997 |
| 214 | MAX.chr1.32238032-32238105 | 0.7778 | 16.66 | 0.0007896 |
| 215 | MAX.chr1.32238359-32238419 | 0.7056 | 9.275 | 0.004603 |
| 216 | MAX.chr1.32410292-32410428 | 0.7118 | 10.9 | 0.009478 |
| 217 | MAX.chr1.46632623-46632858 | 0.8533 | 34.46 | 0.00004827 |
| 218 | MAX.chr1.48058986-48059074 | 0.9 | 12.01 | 2.751E−08 |
| 219 | MAX.chr1.98510937-98511077 | 0.8412 | 11.62 | 0.00001779 |
| 220 | MAX.chr1.98511049-98511077 | 0.6833 | 17.37 | 0.002974 |
| 221 | MAX.chr1.98519485-98519592 | 0.6517 | 28.32 | 0.001259 |
| 222 | MAX.chr10.22541609-22541719 | 0.675 | 8.215 | 0.00122 |
| 223 | MAX.chr10.22541684-22541719 | 0.7083 | 4.839 | 0.004316 |
| 224 | MAX.chr10.22541986-22542037 | 0.91 | 12.16 | 5.242E−07 |
| 225 | MAX.chr10.22765282-22765351 | 0.84 | 14.52 | 0.0001487 |
| 226 | MAX.chr11.14926602-14926671 | 0.8467 | 12.76 | 0.000004841 |
| 227 | MAX.chr11.14926840-14926955 | 0.97 | 16.98 | 9.164E−09 |
| 228 | MAX.chr11.45376949-45377082 | 0.9517 | 115.3 | 0.000004361 |
| 229 | MAX.chr11.45376949-45377204 | 0.9221 | 46.27 | 0.0003883 |
| 230 | MAX.chr11.57250516-57250847 | 0.9333 | 80.85 | 0.000003486 |
| 231 | MAX.chr12.29302564-29302695 | 0.7338 | 10.06 | 0.0000429 |
| 232 | MAX.chr12.30975740-30975780 | 0.8861 | 13.36 | 2.012E−07 |
| 233 | MAX.chr12.4273826-4274239 | 0.8647 | 69 | 0.0002053 |
| 234 | MAX.chr14.100784600-100784781 | 0.7847 | 31.75 | 0.0008823 |
| 235 | MAX.chr14.103557836-103558188 | 0.73 | 45.31 | 0.002456 |
| 236 | MAX.chr14.105512178-105512224 | 0.9367 | 7.222 | 0.00002564 |
| 237 | MAX.chr14.60386315-60386417 | 0.8817 | 35.08 | 0.00287 |
| 238 | MAX.chr14.97685168-97685437 | 0.85 | 12.5 | 0.00002023 |
| 239 | MAX.chr14.97685552-97685839 | 0.8786 | 14.81 | 3.795E−08 |
| 240 | MAX.chr15.28351937-28352173 | 0.9917 | 147.2 | 0.0002627 |
| 241 | MAX.chr15.28352203-28352671 | 1 | 67.39 | 0.00005411 |
| 242 | MAX.chr15.29131258-29131734 | 1 | 86.77 | 0.000000195 |
| 243 | MAX.chr15.31685160-31685245 | 0.7407 | 21.19 | 0.005291 |
| 244 | MAX.chr15.65186050-65186150 | 0.8853 | 10.04 | 0.00008134 |
| 245 | MAX.chr15.74891008-74891138 | 0.7267 | 10.41 | 0.006328 |
| 246 | MAX.chr15.75471061-75471202 | 0.8929 | 21.23 | 0.001064 |
| 247 | MAX.chr16.50875166-50875262 | 0.7059 | 7.995 | 0.0008048 |
| 248 | MAX.chr16.50875166-50875301 | 0.765 | 5.509 | 0.00009394 |
| 249 | MAX.chr17.37366022-37366321 | 0.84 | 61.52 | 0.00969 |
| 250 | MAX.chr19.2273768-2273823 | 0.6931 | 9.226 | 0.0002203 |
| 251 | MAX.chr19.30716607-30716756 | 0.9324 | 30.77 | 0.001229 |
| 252 | MAX.chr19.37288390-37288811 | 0.7971 | 68.63 | 0.007985 |
| 253 | MAX.chr19.42444222-42444334 | 0.8767 | 19.68 | 0.0007796 |
| 254 | MAX.chr19.55962661-55962773 | 0.8633 | 13.64 | 0.002362 |
| 255 | MAX.chr19.5828277-5828498 | 0.6412 | 53.01 | 0.0001286 |
| 256 | MAX.chr2.118981858-118981934 | 0.8467 | 9.919 | 0.0002715 |
| 257 | MAX.chr2.118982007-118982089 | 0.89 | 12.5 | 0.000007672 |
| 258 | MAX.chr2.119067767-119068112 | 0.9267 | 9.924 | 2.498E−07 |
| 259 | MAX.chr2.127783351-127783403 | 0.6853 | 16.1 | 0.006544 |
| 260 | MAX.chr2.175191004-175191127 | 0.68 | 5.084 | 0.002279 |
| 261 | MAX.chr2.241855537-241855585 | 0.8319 | 5.466 | 0.00001195 |
| 262 | MAX.chr2.25438959-25439001 | 0.7361 | 8.401 | 0.0003554 |
| 263 | MAX.chr2.25439173-25439276 | 0.655 | 15.85 | 0.006701 |
| 264 | MAX.chr2.66653544-66653582 | 0.8724 | 16.31 | 0.0003529 |
| 265 | MAX.chr2.66653881-66653935 | 0.9062 | 16.45 | 0.00002628 |

TABLE 1B-continued

| DMR No. | Gene Annotation | Area Under Curve | Fold-Change | p-value |
|---|---|---|---|---|
| 266 | MAX.chr2.97193155-97193524 | 0.6764 | 11.81 | 0.009997 |
| 267 | MAX.chr2.97193478-97193562 | 0.8819 | 15.24 | 0.0000772 |
| 268 | MAX.chr20.30175888-30175927 | 0.9333 | 13.48 | 0.000008072 |
| 269 | MAX.chr20.3073377-3073486 | 0.7567 | 5.665 | 0.0006037 |
| 270 | MAX.chr20.49308029-49308083 | 0.8719 | 20.88 | 0.0003897 |
| 271 | MAX.chr3.107148795-107148869 | 0.7569 | 46.05 | 0.004906 |
| 272 | MAX.chr3.128274281-128274519 | 0.9133 | 16.16 | 0.000007595 |
| 273 | MAX.chr3.138679378-138679414 | 0.8667 | 29.07 | 0.000004821 |
| 274 | MAX.chr3.18485437-18485723 | 0.8533 | 20.2 | 0.0001419 |
| 275 | MAX.chr3.186490624-186490778 | 0.6733 | 8.495 | 0.009519 |
| 276 | MAX.chr3.69591053-69591097 | 0.9518 | 21.05 | 0.00000792 |
| 277 | MAX.chr4.174430671-174430719 | 0.9441 | 13.81 | 5.443E−08 |
| 278 | MAX.chr4.174430751-174430776 | 0.6694 | 9.455 | 0.001239 |
| 279 | MAX.chr4.41869404-41869433 | 0.8639 | 8.957 | 7.459E−07 |
| 280 | MAX.chr4.8859707-8859944 | 0.9304 | 11.03 | 0.00001052 |
| 281 | MAX.chr4.8859995-8860062 | 1 | 15.92 | 6.853E−09 |
| 282 | MAX.chr4.8860076-8860122 | 0.725 | 7.894 | 0.0001833 |
| 283 | MAX.chr5.178957539-178957851 | 0.7267 | 9.425 | 0.0001272 |
| 284 | MAX.chr5.2038771-2038990 | 0.9 | 28.04 | 7.505E−07 |
| 285 | MAX.chr5.42951482-42951568 | 0.8983 | 8.985 | 7.898E−07 |
| 286 | MAX.chr5.42952182-42952292 | 1 | 12.51 | 7.848E−09 |
| 287 | MAX.chr6.10382190-10382225 | 0.9412 | 17.5 | 7.771E−10 |
| 288 | MAX.chr6.108440553-108440720 | 0.8866 | 13.62 | 0.00004107 |
| 289 | MAX.chr6.157557273-157557374 | 0.8583 | 9.341 | 0.00009311 |
| 290 | MAX.chr6.28175549-28175579 | 0.9 | 8.988 | 0.00002146 |
| 291 | MAX.chr6.42738979-42739055 | 0.7807 | 11.24 | 0.0006332 |
| 292 | MAX.chr7.127744282-127744490 | 0.65 | 11.98 | 0.0001731 |
| 293 | MAX.chr7.142494643-142495353 | 0.9433 | 45.64 | 0.0005619 |
| 294 | MAX.chr7.1706293-1706418 | 0.8485 | 5.619 | 0.0001293 |
| 295 | MAX.chr7.99595234-99595474 | 0.6667 | 8.374 | 0.0001195 |
| 296 | MAX.chr8.124173231-124173268 | 0.7722 | 4.552 | 0.001168 |
| 297 | MAX.chr8.142215938-142216298 | 0.9567 | 87.27 | 3.469E−07 |
| 298 | MAX.chr8.145103855-145103943 | 0.6882 | 6.976 | 0.007105 |
| 299 | MAX.chr8.145104058-145104455 | 0.9267 | 50.22 | 0.001557 |
| 300 | MAX.chr8.145105537-145105891 | 0.8777 | 20.95 | 0.003006 |
| 301 | MAX.chr8.145105977-145106067 | 0.9196 | 18.25 | 0.0001214 |
| 302 | MAX.chr8.6658405-6658443 | 0.6833 | 6.011 | 0.003327 |
| 303 | MAX.chr8.688047-688103 | 0.8817 | 28 | 0.001064 |
| 304 | MAX.chr9.113594-113689 | 0.8971 | 5.339 | 0.00004707 |
| 305 | MAX.chr9.129485515-129485818 | 0.9133 | 106 | 0.006038 |
| 306 | MDFI | 1 | 73.57 | 0.000004885 |
| 307 | MFSD2B | 0.7933 | 37.02 | 0.001475 |
| 308 | MGC16275 | 0.9333 | 10.26 | 0.00006057 |
| 309 | MPZ | 0.8417 | 23.23 | 0.0005555 |
| 310 | MSX2 | 0.7639 | 5.593 | 0.0001681 |
| 311 | MT1A_A | 0.7678 | 10.91 | 0.0000658 |
| 312 | MT1A_B | 0.9339 | 12.34 | 0.000001177 |
| 313 | MYO15B_A | 0.93 | 43.36 | 0.0001431 |
| 314 | MYO15B_B | 0.8433 | 17.27 | 0.003642 |
| 315 | MYO15B_C | 0.9 | 14.9 | 0.007671 |
| 316 | MYOZ3 | 0.7912 | 5.008 | 0.0001528 |
| 317 | NBPF3 | 0.6706 | 8.853 | 0.005487 |
| 318 | NCOR2 | 0.9955 | 38.93 | 2.476E−10 |
| 319 | NEFL | 0.8825 | 25.46 | 0.0006411 |
| 320 | NFATC1 | 0.82 | 8.974 | 0.0003065 |
| 321 | NFATC4 | 0.91 | 22.36 | 0.006938 |
| 322 | NFIC_A | 0.96 | 27.22 | 0.000488 |
| 323 | NFIC_B | 0.9367 | 84.11 | 0.00185 |
| 324 | NFIC_C | 0.6972 | 32.63 | 0.0001043 |
| 325 | NFIX | 0.8234 | 14.95 | 0.00007753 |
| 326 | NID2 | 0.9278 | 7.711 | 3.206E−07 |
| 327 | NKX2-3 | 0.8579 | 8.629 | 0.00000336 |
| 328 | NKX2-6 | 1 | 14.31 | 9.91E−11 |
| 329 | NR2F6 | 0.9417 | 67.65 | 0.0001251 |
| 330 | NRTN | 0.6997 | 89.44 | 0.002364 |
| 331 | NTN1 | 0.6676 | 21.88 | 0.0001142 |
| 332 | NTRK3_A | 0.8553 | 31.75 | 0.005009 |
| 333 | NTRK3_B | 0.9529 | 39.83 | 0.003353 |
| 334 | OBSCN | 0.7347 | 35.22 | 0.002406 |
| 335 | OLIG1 | 0.6767 | 6.84 | 0.003567 |
| 336 | OLIG2 | 0.9107 | 11.58 | 0.000001446 |
| 337 | OPLAH_A | 0.9917 | 15.82 | 0.000007607 |
| 338 | OPLAH_B | 0.9235 | 29.03 | 0.0001982 |
| 339 | OPRL1 | 0.8317 | 6.596 | 0.0004722 |
| 340 | OSR2 | 0.6176 | 5.538 | 0.003435 |
| 341 | OXT_A | 0.9233 | 17.05 | 0.000002882 |
| 342 | OXT_B | 0.9467 | 63.26 | 0.0002042 |

TABLE 1B-continued

| DMR No. | Gene Annotation | Area Under Curve | Fold-Change | p-value |
|---|---|---|---|---|
| 343 | PALLD | 0.9656 | 19.54 | 1.219E−10 |
| 344 | PALM3 | 0.88 | 168.5 | 0.006656 |
| 345 | PARP15 | 1 | 62.6 | 1.898E−08 |
| 346 | PAX6 | 0.8728 | 9.994 | 0.000000247 |
| 347 | PDE6B | 0.9118 | 19.01 | 0.00001524 |
| 348 | PDE10A | 1 | 45.15 | 0.000009912 |
| 349 | PDX1 | 0.9167 | 30.83 | 0.0000925 |
| 350 | PEAR1_A | 0.8786 | 6.704 | 0.00007155 |
| 351 | PIF1 | 0.9633 | 13.9 | 1.939E−09 |
| 352 | PIP5KL1 | 0.6933 | 6.343 | 0.008768 |
| 353 | PISD | 0.93 | 465.4 | 0.03728 |
| 354 | PLEKHA6 | 0.9393 | 21.27 | 0.000001155 |
| 355 | PLEKHO1 | 0.7567 | 4.877 | 0.008098 |
| 356 | PLXNC1 | 0.8162 | 7.564 | 0.0006475 |
| 357 | PNMAL2 | 0.6574 | 9.419 | 0.001336 |
| 358 | PPFIA4_A | 0.9054 | 22.96 | 0.000005626 |
| 359 | PPP1R16B | 1 | 16.73 | 9.679E−10 |
| 360 | PRDM14 | 0.9295 | 13.12 | 0.000002319 |
| 361 | PRKAG2 | 0.7722 | 31.49 | 0.00008639 |
| 362 | PRKAR1B_A | 0.8972 | 25.88 | 0.00003686 |
| 363 | PRKCB_A | 0.7706 | 8.209 | 0.0002441 |
| 364 | PRKCB_B | 0.9167 | 7.564 | 0.00003846 |
| 365 | PRKCB_C | 0.7508 | 8.802 | 0.0003597 |
| 366 | PRKCB_D | 0.8279 | 10.52 | 0.000001553 |
| 367 | PROCA1 | 0.8706 | 27.19 | 0.00001691 |
| 368 | PROKR2 | 0.7088 | 16.37 | 0.00005348 |
| 369 | PTGDR | 0.875 | 15.13 | 0.000001258 |
| 370 | PTP4A3_A | 0.6389 | 81100000 | 0.9931 |
| 371 | PTP4A3_B | 0.95 | 19.27 | 0.000007774 |
| 372 | PTPRS | 0.8556 | 15.35 | 0.000009913 |
| 373 | PTPRU | 0.8433 | 19.24 | 0.001639 |
| 374 | PYCARD | 0.9833 | 66.56 | 0.0002255 |
| 375 | RAI1_A | 0.87 | 114 | 0.000005652 |
| 376 | RAI1_B | 0.955 | 163.4 | 0.00001528 |
| 377 | RASGEF1A | 0.83 | 17.9 | 0.0001497 |
| 378 | RASSF1_A | 0.9833 | 41.85 | 0.000002522 |
| 379 | RASSF1_B | 0.9933 | 24.8 | 9.235E−09 |
| 380 | RBFOX3 | 0.7681 | 7.262 | 0.00104 |
| 381 | RET | 0.7838 | 9.604 | 0.0004724 |
| 382 | RFTN1_A | 0.8389 | 18.25 | 0.0002672 |
| 383 | RILPL2 | 0.9083 | 89.71 | 0.0009295 |
| 384 | RNF220 | 0.9364 | 7.609 | 7.141E−07 |
| 385 | RTN4RL2 | 0.7183 | 12.52 | 0.004958 |
| 386 | RUNX3 | 0.805 | 10.17 | 0.0007233 |
| 387 | SALL3 | 0.8309 | 27.66 | 0.0005659 |
| 388 | SCGB3A1 | 0.8042 | 14.23 | 0.00007877 |
| 389 | SEPTIN9 | 0.9933 | 87.79 | 0.0007871 |
| 390 | SFMBT2_A | 0.7353 | 17.61 | 0.00299 |
| 391 | SFMBT2_B | 0.7681 | 30.47 | 0.002173 |
| 392 | SFMBT2_C | 0.9133 | 36.08 | 0.00007163 |
| 393 | SH2B3 | 0.9868 | 17.79 | 0.00003501 |
| 394 | SH3PXD2A | 0.7603 | 12.73 | 0.006045 |
| 395 | SHH_A | 0.7933 | 86.22 | 0.0009818 |
| 396 | SHH_B | 0.725 | 17.6 | 0.004096 |
| 397 | SIM2_A | 0.9152 | 14.67 | 1.523E−07 |
| 398 | SKI | 1 | 79.27 | 1.098E−07 |
| 399 | SLC12A8 | 1 | 77.66 | 3.571E−08 |
| 400 | SLC25A47 | 0.9733 | 66.69 | 0.001407 |
| 401 | SLC4A11 | 0.8833 | 13.13 | 0.0001207 |
| 402 | SLC5A5_A | 0.8767 | 9.298 | 0.000003536 |
| 403 | SLC5A5_B | 0.7767 | 9.372 | 0.002392 |
| 404 | SLC8A3 | 0.9353 | 38.43 | 0.0001207 |
| 405 | SLFN12L | 0.8421 | 43.3 | 0.0001534 |
| 406 | SMTN | 0.91 | 16.65 | 0.00177 |
| 407 | SOBP_A | 0.9333 | 8.568 | 4.472E−08 |
| 408 | SP9 | 0.6676 | 3.771 | 0.0008535 |
| 409 | SPATA18 | 0.6833 | 11.52 | 0.0003341 |
| 410 | SPDYA | 0.8324 | 22.84 | 0.000003646 |
| 411 | SPEF1 | 0.81 | 44.2 | 0.001272 |
| 412 | SPOCK2_A | 0.9467 | 56.14 | 0.0001242 |
| 413 | SPOCK2_B | 0.9733 | 18.93 | 0.00001608 |
| 414 | SPON2_A | 0.8333 | 9.385 | 0.00001783 |
| 415 | SPON2_B | 0.8667 | 7.556 | 0.000009146 |
| 416 | SRC_A | 0.9933 | 364.7 | 0.002044 |
| 417 | SSBP4_A | 0.9433 | 12.18 | 2.734E−09 |
| 418 | SSBP4_B | 0.99 | 33.82 | 4.907E−10 |
| 419 | SSBP4_C | 0.9404 | 17.04 | 2.022E−08 |

TABLE 1B-continued

| DMR No. | Gene Annotation | Area Under Curve | Fold-Change | p-value |
|---|---|---|---|---|
| 420 | ST8SIA1 | 0.9917 | 34.46 | 2.652E−09 |
| 421 | STX16 | 0.8735 | 25.58 | 0.0002471 |
| 422 | TACC1 | 0.9583 | 30.34 | 0.00001213 |
| 423 | TACC2_A | 1 | 217.2 | 0.0003304 |
| 424 | TBKBP1 | 0.94 | 35.27 | 2.28E−10 |
| 425 | TBX20 | 0.93 | 28.72 | 0.00199 |
| 426 | TCF3 | 0.9267 | 18.76 | 0.000004029 |
| 427 | TEAD3 | 0.8633 | 11.71 | 0.00002807 |
| 428 | TET2 | 0.7778 | 5.054 | 0.0006353 |
| 429 | TGFB1 | 0.8917 | 17.59 | 0.0006773 |
| 430 | TJP2 | 0.9765 | 56.47 | 0.002008 |
| 431 | TMC4 | 0.6667 | 5.203 | 0.004701 |
| 432 | TMC6 | 0.89 | 8.028 | 0.0002984 |
| 433 | TMEFF2 | 0.7735 | 7.797 | 0.0001361 |
| 434 | TMEM101 | 0.93 | 51.4 | 0.00001231 |
| 435 | TMEM106A | 0.7417 | 14.14 | 0.0004017 |
| 436 | TNFRSF10C | 0.6647 | 7.404 | 0.001976 |
| 437 | TNFRSF8 | 0.678 | 14.86 | 0.002477 |
| 438 | TRIM15 | 0.9737 | 25.3 | 0.00002151 |
| 439 | TRIM71 | 0.6912 | 17.62 | 0.004034 |
| 440 | TRIM9_A | 0.7867 | 9.348 | 0.00001029 |
| 441 | TRIM9_B | 0.9412 | 7.746 | 0.000001165 |
| 442 | TRPV2 | 0.7983 | 5.552 | 0.001986 |
| 443 | TSC22D4 | 0.8667 | 45.25 | 0.0002631 |
| 444 | TSHZ3 | 1 | 330.4 | 0.002852 |
| 445 | TSPY26P | 0.72 | 13.24 | 0.005337 |
| 446 | TXNRD1 | 0.7779 | 29.56 | 0.00005732 |
| 447 | UBTF | 0.99 | 37.3 | 1.175E−07 |
| 448 | ULBP1 | 0.9567 | 21.94 | 0.000001494 |
| 449 | UST | 0.96 | 73.73 | 0.0009294 |
| 450 | VASP | 0.8167 | 25.26 | 0.007948 |
| 451 | VILL | 0.8324 | 26.28 | 0.003267 |
| 452 | VIM | 1 | 128.6 | 3.678E−07 |
| 453 | VIPR2_A | 1 | 49.5 | 0.000003125 |
| 454 | WNT7B | 0.83 | 113.3 | 0.0002042 |
| 455 | XKR6 | 0.7162 | 13.39 | 0.006601 |
| 456 | XYLT1 | 0.7765 | 5.564 | 0.000001447 |
| 457 | ZBED4 | 1 | 33.68 | 0.00003722 |
| 458 | ZEB2_A | 0.9386 | 59.23 | 0.004218 |
| 459 | ZEB2_B | 0.8833 | 17.62 | 0.0001426 |
| 460 | ZFP3 | 0.865 | 94.31 | 0.003443 |
| 461 | ZMIZ1_A | 1 | 43.45 | 2.878E−07 |
| 462 | ZMIZ1_B | 1 | 307.9 | 3.498E−09 |
| 463 | ZMIZ1_C | 1 | 297.4 | 2.396E−09 |
| 464 | ZNF132 | 0.8867 | 56.31 | 0.000001664 |
| 465 | ZNF382_A | 1 | 86.86 | 1.14E−09 |
| 466 | ZNF469_A | 0.9833 | 24.13 | 0.0001099 |
| 467 | ZNF469_B | 1 | 15.78 | 0.000000149 |
| 468 | ZNF703 | 0.98 | 66.04 | 0.005629 |
| 469 | ZNF781 | 0.7191 | 40.16 | 0.0009516 |
| 470 | ZSCAN12 | 0.7426 | 50.98 | 0.009365 |
| 471 | ZSCAN23 | 0.7309 | 26.36 | 0.0004899 |
| 472 | ATP6V1B1_A | 0.999 | 169.2 | 0.003 |
| 473 | ATP6V1B1_B | 0.984 | 116.5 | 0.002 |
| 474 | BANK1 | 0.813 | 10.77 | 0.048 |
| 475 | BCL2L11 | 0.979 | 63.01 | 0.003 |
| 476 | BZRAP1 | 0.994 | 77.62 | 0.00001416 |
| 477 | C17orf64_C | 0.983 | 101.6 | 0.009 |
| 478 | C19orf35_C | 0.951 | 40.84 | 0.007 |
| 479 | C2CD4D | 0.982 | 103.7 | 3E−04 |
| 480 | CCDC88C | 0.965 | 124.5 | 0.005 |
| 481 | TRIM9_C | 0.956 | 32.22 | 0.01 |
| 482 | CORO1A | 0.958 | 33.47 | 0.002 |
| 483 | DNMT3A_B | 0.958 | 44.81 | 0.004 |
| 484 | DNMT3A_C | 0.987 | 57.07 | 0.002 |
| 485 | FAM189B | 0.982 | 41.54 | 0.002 |
| 486 | FCHO1 | 0.979 | 54.92 | 0.002 |
| 487 | FXYD5 | 0.963 | 43.45 | 7E−04 |
| 488 | GDF6 | 1 | 80.2 | 0.003 |
| 489 | GMDS | 0.967 | 91.6 | 0.01 |
| 490 | IFFO1_A | 0.999 | 285.5 | 1E−03 |
| 491 | IFFO1_B | 0.998 | 164.8 | 1E−04 |
| 492 | INA_B | 0.969 | 38.89 | 0.004 |
| 493 | ITPKB_B | 0.978 | 207.9 | 0.00002857 |
| 494 | ITPKB_C | 0.981 | 97.94 | 0.006 |
| 495 | JAK3_B | 0.981 | 41.07 | 0.002 |
| 496 | KANK3 | 0.984 | 41.48 | 0.002 |

TABLE 1B-continued

| DMR No. | Gene Annotation | Area Under Curve | Fold-Change | p-value |
|---|---|---|---|---|
| 497 | KCNAB2 | 0.991 | 50.86 | 0.003 |
| 498 | LIMD2 | 0.992 | 153.6 | 6E−04 |
| 499 | MAML3_B | 0.991 | 39.57 | 0.002 |
| 500 | MAX.chr1.9689803-9690241 | 0.984 | 86.99 | 0.00001809 |
| 501 | MAX.chr10.101300125-101300155 | 0.962 | 30.08 | 0.002 |
| 502 | MAX.chr11.14926756-14927227 | 0.97 | 64.79 | 0.004 |
| 503 | MAX.chr12.30975740-30975961 | 0.966 | 71.51 | 0.004 |
| 504 | MAX.chr14.102172350-102172770 | 0.998 | 60.04 | 0.003 |
| 505 | MAX.chr16.85482307-85482494 | 1 | 110.5 | 0.001 |
| 506 | MAX.chr17.76254728-76254841 | 0.998 | 79.79 | 0.003 |
| 507 | MAX.chr20.56008090-56008227 | 0.973 | 62.96 | 8E−04 |
| 508 | MAX.chr4.174430662-174430790 | 0.963 | 90.75 | 0.009 |
| 509 | MAX.chr5.42993898-42994179 | 0.999 | 103.2 | 0.000006147 |
| 510 | MAX.chr6.1379890-1379965 | 0.964 | 42.04 | 0.002 |
| 511 | MAX.chr7.2569526-2569650 | 0.983 | 40.92 | 0.004 |
| 512 | MAX.chr8.124173112-124173541 | 0.966 | 54.57 | 0.003 |
| 513 | PPFIA4_B | 0.969 | 56.41 | 5E−04 |
| 514 | PPFIA4_C | 0.961 | 54.65 | 0.002 |
| 515 | PRKAR1B_B | 0.981 | 110.1 | 0.004 |
| 516 | PRKAR1B_C | 0.953 | 73.58 | 0.004 |
| 517 | PTGER4_A | 0.965 | 66.17 | 0.006 |
| 518 | PTGER4_B | 0.983 | 75.21 | 0.004 |
| 519 | PTPRCAP | 0.985 | 80.48 | 2E−04 |
| 520 | RASAL3 | 0.995 | 115.7 | 0.00001693 |
| 521 | RASSF1_C | 0.984 | 106.3 | 0.009 |
| 522 | RUNX1 | 0.987 | 152.2 | 0.007 |
| 523 | SLC29A4 | 0.96 | 45.59 | 0.001 |
| 524 | SLC35D3 | 0.961 | 56.18 | 0.003 |
| 525 | SOBP_B | 0.98 | 61.02 | 0.002 |

TABLE 1C

| DMR # | Name | 5'-3' Sequence (hg19) | SEQ ID NO. |
|---|---|---|---|
| 318 | NCOR2 | Forward: GAGGAGTTTTAATATTTTTATAGCGG | 1 |
| 318 | NCOR2 | Reverse: AACAAACTTCAATAAACCCGACGCA | 2 |
| 343 | PALLD | Forward: GGCGACGGCGAGGAGGAGTTTTAC | 3 |
| 343 | PALLD | Reverse: GCAACCCTTCGACGCTAAACCCG | 4 |
| 207 | MAX.chr1.147790358-147790381 | Forward: GATATGTTGTCGGGGTTCGTTACGA | 5 |
| 207 | MAX.chr1.147790358-147790381 | Reverse: CAAAATACCCGATAAAACAATCGAA | 6 |
| 287 | MAX.chr6.10382190-10382225 | Forward: CGTTAGTCGTTTTTATTTTTAATTTATCGT | 7 |
| 287 | MAX.chr6.10382190-10382225 | Reverse: CTTCAAAAACTCCAACGCGTC | 8 |
| 354 | PLEKHA6 | Forward: GATTAGATTAGATTCGGAGTTTCGT | 9 |
| 354 | PLEKHA6 | Reverse: ACCAACTAAAATCCTCCTCCCCCGC | 10 |
| 384 | RNF220 | Forward: TAGTTTGGTTAAAGGGTGCGAATTCGA | 11 |
| 384 | RNF220 | Reverse: CGAAACTCTTCCGAACTAAATAATACACCCGCT | 12 |
| 81 | DNMT3A_A | Forward: TTTGTTGGGAGTTCGGGGTTTTATC | 13 |
| 81 | DNMT3A_A | Reverse: AACCTATCCGAAACCTCCCCGTT | 14 |
| 312 | MT1A_B | Forward: TTGCGTATAGGTTAGTTTAGGATCGT | 15 |
| 312 | MT1A_B | Reverse: CTTACACCCGCCCCGCTAAATTCG | 16 |
| 311 | MT1A_A | Forward: TCGTTGGTTATCGTACGTTTTTCGT | 17 |
| 311 | MT1A_A | Reverse: ACTAAACCTATCCCGAAATCCCGAT | 18 |
| 360 | PRDM14 | Forward: GGTTGTTTTTGTAGTGTTTATAGGACGG | 19 |

TABLE 1C-continued

| DMR # | Name | 5'-3' Sequence (hg19) | SEQ ID NO. |
|---|---|---|---|
| 360 | PRDM14 | Reverse: AAAACAAAATATACTACCCGCCGAA | 20 |
| 25 | BCAT1 | Forward: GGGGAGGAGTTTTTAATCGTTTCGT | 21 |
| 25 | BCAT1 | Reverse: AAACAACCGCTTCGATTTTAACGAC | 22 |
| 84 | DSCR6 | Forward: CGGTAGGGGAAGTTTAGTAGGTGAGCGT | 23 |
| 84 | DSCR6 | Reverse: GAACTAAAAACGTTTCCGTCGAACGCA | 24 |
| 398 | SKI | Forward: GGTAGTTAGGCGGTTATTACGGGTCGC | 25 |
| 398 | SKI | Reverse: AAAATCTACTCCCTCCCCGAACGCT | 26 |
| 61 | CDO1_A | Forward: CGCGCGTTTTATTGTTGGGTTGC | 27 |
| 61 | CDO1_A | Reverse: AACGAACTATTAAACTCCCTCGCC | 28 |
| 397 | SIM2_A | Forward: GTTAGTAGTTGTTGGGGCGGCGTTC | 29 |
| 397 | SIM2_A | Reverse: AACCCGATACCCCCATTACCGTACG | 30 |
| 185 | LIME1_B | Forward: CGCGTAGTAGTAGGGGTGAGTAGAGGGC | 31 |
| 185 | LIME1_B | Reverse: GAATCTAACCCAAAAATTAACACGCGCT | 32 |
| 63 | CELF2_A | Forward: CGGGATCGGAGTTAGAATTTTTCGT | 33 |
| 63 | CELF2_A | Reverse: ACCTAAACGCCTAACGACCCCCG | 34 |
| 99 | FAIM2_A | Forward: TATTTCGGGGGAGGGTTAAGGGCG | 35 |
| 99 | FAIM2_A | Reverse: GCTACGAATTCGCGAACCCGAA | 36 |
| 64 | CELF2_B | Forward: GGGTTGTTTAGAAAGTGATTTTTCGGGAGC | 37 |
| 64 | CELF2_B | Reverse: AAAACCGAAACAAAACGAAAACGCA | 38 |
| 204 | MAML3_A | Forward: TGTTTTTTTATTTTATTTTTAGTTTTTTCGT | 39 |
| 204 | MAML3_A | Reverse: AATTTCTCATTACCGACTTTTCTTCCAACCGAA | 40 |
| 329 | NR2F6 | Forward: GGCGCGTATTTGGTTTATGAAAGTTACGG | 41 |
| 329 | NR2F6 | Reverse: CAAACGACGCTACCCCTACACACGA | 42 |
| 447 | UBTF | Forward: GGCGTTAGTTTTTTATTTATTTTTAGGGGGCGC | |
| 447 | UBTF | Reverse: CCAACCCATACTTCTACCCGCCGAC | 44 |
| 398 | SKI | Forward: ACGAAATATTTTTAATTGAGTTCGA | 45 |
| 398 | SKI | Reverse: AAAAAATACGAAACACAAAAACGAC | 46 |
| 131 | HIST1H2BE | Forward: TTGGCGTATTATATAATAAGCGTTCGA | 47 |
| 131 | HIST1H2BE | Reverse: GAAAAACAACAAACGCACGACCGTC | 48 |
| 164 | KCNA3_A | Forward: ACGTAGTTGAAGATTTTTTGTTAGTTTTTCGA | 49 |
| 164 | KCNA3_A | Reverse: ACCTCATACGCCGCTTAAAATCGCC | 50 |
| 345 | PARP15 | Forward: TAGTAGGGTTGAGTTTGGGGTTCGT | 51 |
| 345 | PARP15 | Reverse: GTAAAATCTCTACGCCCGCTCGAA | 52 |
| 50 | CAPN2_A | Forward: CGTTCGAGTTGCGAAAGGGACGT | 53 |
| 50 | CAPN2_A | Reverse: GCACTCCTAAAATTCCGCGCGAA | 54 |
| 334 | OBSCN | Forward: GGTAAAATTTACGTTGTGTAGAATTAGGCGG | 55 |
| 334 | OBSCN | Reverse: ACGTAAAAATCCACGCCGAAAACGC | 56 |
| 399 | SLC12A8 | Forward: TTATTTTTGGATTAGCGATCGACGA | 57 |

TABLE 1C-continued

| DMR # | Name | 5'-3' Sequence (hg19) | SEQ ID NO. |
|---|---|---|---|
| 399 | SLC12A8 | Reverse: GCGCTAACTATTCTCGATTACGCC | 58 |
| 452 | VIM | Forward: CGTTTAGGTTATCGTTATTTTTCGT | 59 |
| 452 | VIM | Reverse: GAACCGCCGAACATCCTACGAT | 60 |
| 462 | ZMIZ1_B | Forward: GGGGGCGGGAGATATTCGAAGTTATTTATC | 61 |
| 462 | ZMIZ1_B | Reverse: AAACGCTATCGCCCGAAAAAAACCG | 62 |
| 19 | ATP10A_B | Forward: TTTTGGGTAGGAAGGATAGTAGCGT | 63 |
| 19 | ATP10A_B | Reverse: CAAAAACGAACGACGACGAC | 64 |
| 463 | ZMIZ1 C | Forward: GCGAGTCGGGGTTTTTTGGAGAC | 65 |
| 463 | ZMIZ1_C | Reverse: CACCCACCCTACGTATACCCGCGT | 66 |
| 444 | TSHZ3 | Forward: GATTTGGCGCGGTTTAGCGC | 67 |
| 444 | TSHZ3 | Reverse: CCCTCTCGCACCCATTTAAAAAACCG | 68 |
| 226 | MAX.chr11.14926602-14926671 | Forward: TGAATGTTAATTAAGATTGCGTTCG | 69 |
| 226 | MAX.chr11.14926602-14926671 | Reverse: AACACCCTCACGAAAAACCCGCG | 70 |
| 236 | MAX.chr14.105512178-105512224 | Forward: TTGTAGTTGTTGTTTTTTGGCGGTCGC | 71 |
| 236 | MAX.chr14.105512178-105512224 | Reverse: AAACCGAACGAATTTCGCTTTCCCG | 72 |
| 121 | GPRIN1_A | Forward: TGGCGGCGTCGTATATTTTTTACGT | 73 |
| 121 | GPRIN1_A | Reverse: ACCGCTATAACGCCCCCGAA | 74 |
| 39 | C17orf46 | Forward: TAGTTAAAGAGTATATTGGAGGCGG | 75 |
| 39 | C17orf46 | Reverse: CTCTATCCTAAAAACGAAAAACGAA | 76 |
| 434 | TMEM101 | Forward: AGGGGTAGCGTGTGAGTAGTATCGA | 77 |
| 434 | TMEM101 | Reverse: TACCCTTTCCCAAAATAACGTCGAA | 78 |
| 123 | GYPC_A | Forward: GTTAGTTTTCGCGGTTTTTGTTCGG | 79 |
| 123 | GYPC_A | Reverse: CGCCGTACTATTAAAACTTCTCGTCGAC | 80 |
| 306 | MDFI | Forward: TTTTTGGTTGGGTTAAGTTCGGCGC | 81 |
| 306 | MDFI | Reverse: GCCTTCTCAATCGCCCCTCTACGAA | 82 |
| 423 | TACC2_A | Forward: TTAGTTTCGTTTTCGGAGTTCGCGA | 83 |
| 423 | TACC2_A | Reverse: CTCCTATATATAACACGATAATATCATCATCGCC | 84 |
| 7 | AGRN_B | Forward: TTTTTAGTTTTTTTCGTTTTCGCGG | 85 |
| 7 | AGRN_B | Reverse: ACGACTTCCTTTATCTCTACTCCCGCC | 86 |
| 96 | EPS8L2_E | Forward: CGGAAAATTAGTAATATTAGGGCGT | 87 |
| 96 | EPS8L2_E | Reverse: CGAACCCGACTCGTAAATAAACGAC | 88 |
| 297 | MAX.chr8.142215938-142216298 | Forward: GTCGTACGTATCGGGTGGACGA | 89 |
| 297 | MAX.chr8.142215938-142216298 | Reverse: CCCTAACTAACGCGAACCCG | 90 |
| 418 | SSBP4_B | Forward: GGAGGGGCGAATAGAGTTTTTTTCG | 91 |
| 418 | SSBP4 B | Reverse: AAAACGACCCCTTCCTCTCTCGCC | 92 |
| 490 | IFFO1_A | Forward: TTTGGTTAGGAAGTAGCGGAATCGG | 93 |
| 490 | IFFO1_A | Reverse: GCAATAACCTAAACTCCAACATCAACGTA | 94 |
| 493 | ITPKB_B | Forward: ATAATTTTAAGGGGGAAACGTTCGT | 95 |

TABLE 1C-continued

| DMR # | Name | 5'-3' Sequence (hg19) | SEQ ID NO. |
|---|---|---|---|
| 493 | ITPKB_B | Reverse: CCAATATAACCGACTTCTTAAACGCT | 96 |
| 491 | IFF01_B | Forward: GATTAATTAGGCGGTTCGGTAGCGG | 97 |
| 491 | IFF01_B | Reverse: CAATTAAAACCTATCATTAACTTCCCCTCGAC | 98 |
| 475 | BCL2L11 | Forward: GGTTGTAAGGGTTTTTGGTTTTCGACGC | 99 |
| 475 | BCL2L11 | Reverse: AACGAATTCATACGTCCCCCGAA | 100 |
| 488 | GDF6 | Forward: CGTTTCGTTAGTAGTTATCGATTTTCGT | 101 |
| 488 | GDF6 | Reverse: AAACGAACCCCCTCCTTCGCGT | 102 |
| 479 | C2CD4D | Forward: GTTTACGCGCGAGAGCGTGTTGC | 103 |
| 479 | C2CD4D | Reverse: GCCCGAACCCGACCTAATATTCGAT | 104 |
| 250 | MAX.chr19.2273768-2273823 | Forward: GGATGTTTGTGTTTTTAATTTAATTTTTGAGTTC | 105 |
| 250 | MAX.chrl9.2273768-2273823 | Reverse: AAATACTACTACCCCGAACGACGCT | 106 |
| 409 | SPATA18 | Forward: ACATATACACACATATCCTTCCTTCCCCAACGAT | 107 |
| 409 | SPATA18 | Reverse: TTTTGTAAAGTTTTCGCGGTTGCGA | 108 |
| 370 | PTP4A3_A | Forward: TCGTCGGTTACGTTTTTTACGTGAC | 109 |
| 370 | PTP4A3_A | Reverse: CGAAACCGACTCCAAACGCT | 110 |
| 310 | MSX2 | Forward: GGGTGTCGAAGTCGGATTTTACGA | 111 |
| 310 | MSX2 | Reverse: AACCACAAAAAAACATTTCCTCCCCGC | 112 |
| 348 | PDE10A | Forward: GAGTTTCGGCGGTTTTTCGAAAGTAGC | 113 |
| 348 | PDE10A | Reverse: CCACGAACAACGACACTACGACGCT | 114 |
| 137 | HOXB3 | Forward: TGTTTTTTCGTTTTTGGTCGTCGGC | 115 |
| 137 | HOXB3 | Reverse: AACCCCAAATTCCCTCCATACGAA | 116 |
| 388 | SCGB3A1 | Forward: GGGAGGCGTTTAGGAATCGTCGC | 117 |
| 388 | SCGB3A1 | Reverse: CCTATATCCCGAAAACTCGCA | 118 |
| 111 | GATA2 | Forward: AGGAGTGTTTGAGTAGGGGTTTCGG | 119 |
| 111 | GATA2 | Reverse: TTTTTCCTCTACACCGAATTACGAA | 120 |
| 340 | OSR2 | Forward: TAGGGTTAGTAGGCGGTTTAGGCGC | 121 |
| 340 | OSR2 | Reverse: CGAACTCCAACTTTAAAAAATACCGCGTA | 122 |
| 255 | MAX.chr19.5828277-5828498 | Forward: GATTTATTTTCGGCGAGGGGTTCGC | 123 |
| 255 | MAX.chr19.5828277-5828498 | Reverse: CGCTTTCCCGATAAAAACGACGACGTA | 124 |
| 181 | LAPTM4B | Forward: AGTAGTAGTTGTTGGAGTAGAATCGCGT | 125 |
| 181 | LAPTM4B | Reverse: GCCCGAAACGATAAAAATAATCGCGC | 126 |
| 317 | NBPF3 | Forward: TTTTATTTTCGAGGTCGGAAATCGG | 127 |
| 317 | NBPF3 | Reverse: CAAATCAAAAACGCGAACGCTCTCG | 128 |
| 97 | ESPN | Forward: TTAGTTGCGGGAAGATAGTGATCGG | 129 |
| 97 | ESPN | Reverse: AACGCCTACCGAACAAATACCCGAA | 130 |
| 353 | PISD | Forward: TCGTGTTTACGTGGGGACGG | 131 |
| 353 | PISD | Reverse: CGCGAACAAAATTAAACGAATCGTA | 132 |

TABLE 1C-continued

| DMR # | Name | 5'-3' Sequence (hg19) | SEQ ID NO. |
|---|---|---|---|
| 33 | BOLA1 | Forward: TAGACGTTAGGAGTGAGGGTCGGGGC | 133 |
| 33 | BOLA1 | Reverse: TAAAACGAATACGAAAATCGCGAAACGAA | 134 |
| 474 | BANK1 | Forward: TTTAGGTGGGTAGTCGCGTATTCGG | 135 |
| 474 | BANK1 | Reverse: CTAACGATAACCCGTAATCTCCGCA | 136 |

A subset of the DMRs was chosen for further development. The criteria were primarily the logistic-derived area under the ROC curve metric which provides a performance assessment of the discriminant potential of the region. An AUC of 0.85 was chosen as the cut-off. In addition, the methylation fold-change ratio (average cancer hypermethylation ratio/average control hypermethylation ratio) was calculated and a lower limit of 10 was employed for tissue vs tissue comparisons and 20 for the tissue vs buffy coat comparisons. P values were required to be less than 0.01. DMRs had to be listed in both the average and individual CpG selection processes. Quantitative methylation specific PCR (qMSP) primers were designed for candidate regions using MethPrimer (Li L C and Dahiya R. Bioinformatics 2002 November; 18(11):1427-31) and QC checked on 20 ng (6250 equivalents) of positive and negative genomic methylation controls. Multiple annealing temperatures were tested for optimal discrimination. Validation was performed in two stages of qMSP. The first consisted of re-testing the sequenced DNA samples. This was done to verify that the DMRs were truly discriminant and not the result of over-fitting the extremely large next generation datasets. The second utilized a larger set of independent samples (Serous OC—36 samples; Clear Cell OC—21 samples; Mucinous OC—14 samples; Endometrioid OC—23 samples; Control Fallopian Tube Benign—29 samples; Control Buffy Coat—28 samples).

Tissues were identified as before, with expert clinical and pathological review. DNA purification was performed as previously described. The EZ-96 DNA Methylation kit (Zymo Research, Irvine CA) was used for the bisulfite conversion step. 10 ng of converted DNA (per marker) was amplified using SYBR Green detection on Roche 480 Light-Cyclers (Roche, Basel Switzerland). Serially diluted universal methylated genomic DNA (Zymo Research) was used as a quantitation standard. A CpG agnostic ACTB (0-actin) assay was used as an input reference and normalization control. Results were expressed as methylated copies (specific marker)/copies of ACTB.

Results were analyzed logistically for individual MDMs (methylated DNA marker) performance. For combinations of markers, two techniques were used. First, the rPart technique was applied to the entire MDM set and limited to combinations of 3 MDMs, upon which an rPart predicted probability of cancer was calculated. The second approach used random forest regression (rForest) which generated 500 individual rPart models that were fit to boot strap samples of the original data (roughly ⅔ of the data for training) and used to estimate the cross-validation error (⅓ of the data for testing) of the entire MDM panel and was repeated 500 times. to avoid spurious splits that either under- or overestimate the true cross-validation metrics. Results were then averaged across the 500 iterations.

Table 2A shows ten methylated regions that distinguished clear cell OC tissue from buffy coat control and control fallopian tube tissue (percentage methylation for control buffy coat, control fallopian tube tissue, and clear cell OC tissue) (AUC and p-value between % methylation clear cell tissue and % methylation control fallopian tube).

TABLE 2A

Ten methylated regions that distinguished clear cell OC tissue from buffy coat control, control fallopian tube tissue, clear cell ovarian cancer tissue.

| DMR# | Gene | % M Buffy Coat | % M Fallopian Tube | % M Clear Cell OC | AUC | Fold Change | pvalue |
|---|---|---|---|---|---|---|---|
| 423 | TACC2_A | 0.99% | 0.40% | 46.37% | 1 | 217 | 0.0003304 |
| 198 | LRRC41_A | 0.46% | 0.30% | 36.28% | 1 | 190 | 6.696E−06 |
| 94 | EPS8L2_C | 0.56% | 0.96% | 60.94% | 1 | 160 | 5.736E−06 |
| 182 | LBH | 0.40% | 0.25% | 28.17% | 1 | 158 | 0.0000823 |
| 185 | LIME1_B | 0.27% | 1.32% | 51.66% | 1 | 80 | 8.084E−07 |
| 306 | MDFI | 0.51% | 0.78% | 36.78% | 1 | 74 | 4.885E−06 |
| 99 | FAIM2_A | 0.59% | 1.58% | 42.93% | 1 | 47 | 2.702E−09 |
| 123 | GYPC_A | 0.37% | 1.52% | 41.92% | 1 | 47 | 1.207E−08 |
| 7 | AGRN_B | 0.73% | 2.39% | 51.24% | 1 | 43 | 6.792E−10 |
| 457 | ZBED4 | 0.70% | 1.13% | 27.85% | 1 | 34 | 3.722E−05 |

Table 2B shows ten methylated regions that distinguished endometrioid OC tissue from buffy coat control and control fallopian tube tissue (percentage methylation for control buffy coat, control fallopian tube tissue, and endometrioid OC tissue) (AUC and p-value between 0% methylation endometrioid tissue and 0% methylation control fallopian tube).

TABLE 2B

Ten methylated regions that distinguished endometrioid OC tissue from buffy coat control, control fallopian tube tissue, endometrioid ovarian cancer tissue.

| DMR# | Gene | % M Buffy Coat | % M Fallopian Tube | % M endometrioid OC | AUC | Fold Change | pvalue |
|---|---|---|---|---|---|---|---|
| 345 | PARP15 | 0.44% | 1.27% | 44.65% | 1 | 63 | 1.898E−08 |
| 121 | GPRIN1_A | 0.58% | 1.41% | 44.79% | 1 | 57 | 1.866E−07 |
| 123 | GYPC_A | 0.37% | 1.52% | 39.96% | 0.9912 | 43 | 7.342E−07 |
| 103 | FLJ34208 | 0.16% | 2.51% | 41.87% | 0.9912 | 28 | 3.514E−08 |
| 207 | MAX.chr1. 147790358-147790381 | 0.62% | 4.41% | 48.42% | 0.9912 | 20 | 2.389E−08 |
| 99 | FAIM2_A | 0.59% | 1.58% | 42.27% | 0.9889 | 46 | 7.617E−07 |
| 393 | SH2B3 | 0.86% | 1.62% | 22.66% | 0.9868 | 18 | 3.501E−05 |
| 175 | KCNQ5 | 0.24% | 1.14% | 22.85% | 0.9853 | 26 | 0.0002584 |
| 150 | IRF4 | 0.17% | 1.57% | 28.91% | 0.9824 | 26 | 0.000017 |
| 25 | BCAT1 | 0.30% | 1.25% | 24.95% | 0.9722 | 26 | 0.0001114 |

Table 2C shows ten methylated regions that distinguished mucinous OC tissue from buffy coat control and control fallopian tube tissue (percentage methylation for control buffy coat, control fallopian tube tissue, and mucinous OC tissue) (AUC and p-value between % methylation mucinous tissue and 0% methylation control fallopian tube).

TABLE 2C

Ten methylated regions that distinguished mucinous OC tissue from buffy coat control, control fallopian tube tissue, and mucinous ovarian cancer tissue.

| DMR# | Gene | % M Buffy Coat | % M Fallopian Tube | % M mucinous OC | AUC | Fold Change | pvalue |
|---|---|---|---|---|---|---|---|
| 66 | CMTM3_A | 0.32% | 0.22% | 45.24% | 1 | 380 | 4.80E−06 |
| 20 | ATP10A_C | 0.35% | 0.27% | 47.77% | 1 | 341 | 7.31E−05 |
| 444 | TSHZ3 | 0.68% | 0.27% | 47.30% | 1 | 330 | 0.002852 |
| 462 | ZMIZ1_B | 0.19% | 0.23% | 41.58% | 1 | 308 | 3.50E−09 |
| 19 | ATP10A_B | 0.69% | 0.20% | 32.41% | 1 | 245 | 1.10E−09 |
| 87 | ELMO1_B | 0.11% | 0.16% | 24.45% | 1 | 204 | 8.38E−05 |
| 423 | TACC2_A | 0.99% | 0.40% | 44.62% | 1 | 202 | 3.82E−08 |
| 197 | LRRC4 | 0.37% | 0.21% | 26.81% | 1 | 177 | 0.0002576 |
| 452 | VIM | 0.11% | 0.27% | 25.61% | 1 | 129 | 3.68E−07 |
| 465 | ZNF382_A | 0.47% | 0.51% | 30.72% | 1 | 87 | 1.14E−09 |

Table 2D shows ten methylated regions that distinguished serous OC tissue from buffy coat control and control fallopian tube tissue (percentage methylation for control buffy coat, control fallopian tube tissue, and serous OC tissue) (AUC and p-value between 00 methylation serous tissue and 00 methylation control fallopian tube).

TABLE 2D

Ten methylated regions that distinguished serous OC tissue from buffy coat control, control fallopian tube tissue, ovarian cancer tissue.

| DMR# | Gene | % M Buffy Coat | % M Fallopian Tube | % M serous OC | AUC | Fold Change | pvalue |
|---|---|---|---|---|---|---|---|
| 207 | MAX.chr1. 147790358-147790381 | 0.62% | 4.41% | 49.78% | 0.9917 | 22 | 5.145E−07 |
| 204 | MAML3 | 0.75% | 2.88% | 17.15% | 0.9583 | 7 | 1.176E−07 |
| 329 | NR2F6 | 0.23% | 0.73% | 33.21% | 0.9417 | 68 | 0.0001251 |
| 81 | DNMT3A_A | 0.44% | 0.90% | 21.39% | 0.9333 | 30 | 0.0003524 |
| 398 | SKI | 0.31% | 1.03% | 32.03% | 0.9284 | 45 | 6.022E−07 |
| 407 | SOBP | 0.56% | 4.19% | 28.61% | 0.925 | 9 | 3.089E−06 |
| 447 | UBTF | 0.49% | 1.57% | 39.00% | 0.8972 | 40 | 1.662E−07 |
| 8 | AGRN_C | 0.46% | 0.74% | 12.44% | 0.8903 | 19 | 0.002814 |

TABLE 2D-continued

Ten methylated regions that distinguished serous OC tissue from buffy coat control, control fallopian tube tissue, ovarian cancer tissue.

| DMR# | Gene | % M Buffy Coat | % M Fallopian Tube | % M serous OC | AUC | Fold Change | pvalue |
|---|---|---|---|---|---|---|---|
| 232 | MAX.chr12.30975740-30975780 | 0.18% | 4.76% | 40.01% | 0.8861 | 13 | 2.012E−07 |
| 50 | CAPN2_A | 0.21% | 0.79% | 28.39% | 0.8806 | 50 | 0.004007 |

Table 3 shows the top ten methylated regions that distinguished OC tissue from buffy coat control (percentage methylation difference between OC and control buffy coat provided; percentage methylation difference between OC and control fallopian tube provided; AUC provided; fold-change difference provided; and p-value provided.

TABLE 3

| DMR# | Gene | % M Buffy Coat | % M Fallopian Tube | % M OC | AUC | Fold Change | pvalue |
|---|---|---|---|---|---|---|---|
| MAX.chr16.85482307-85482494 | 505 | 0.52% | 19.64% | 36.76% | 1 | 111 | 0.001246 |
| GDF6 | 488 | 0.52% | 17.12% | 29.59% | 1 | 80 | 0.002582 |
| IFFO1_A | 490 | 0.49% | 15.96% | 58.34% | 0.999 | 286 | 0.0009795 |
| ATP6V1B1_A | 472 | 0.60% | 21.70% | 50.68% | 0.9989 | 169 | 0.002853 |
| MAX.chr5.42993898-42994179 | 509 | 0.94% | 21.49% | 49.41% | 0.9989 | 103 | 0.000006147 |
| MAX.chr17.76254728-76254841 | 506 | 0.53% | 13.96% | 29.83% | 0.9979 | 80 | 0.003074 |
| MAX.chr14.102172350-102172770 | 504 | 0.46% | 14.88% | 21.82% | 0.9979 | 60 | 0.003098 |
| RASAL3 | 520 | 0.68% | 35.36% | 44.23% | 0.9954 | 116 | 0.00001693 |
| BZRAP1 | 476 | 0.72% | 25.52% | 36.09% | 0.9937 | 78 | 0.00001416 |
| LIMD2 | 498 | 0.45% | 12.86% | 40.78% | 0.9919 | 154 | 0.000554 |

Tables 4A-E are results from an initial tissue validation where upwards of 60 top DMRs were chosen from the sequencing data, and designed qMSP assays. These DMRs were run on OC tissue, clear cell OC tissue, endometrioid OC tissue, mucinous OC tissue, serous OC tissue, and control fallopian tube tissue. Next, a larger, independent tissue validation was performed where new untested cases and controls are tested (see, Table 5).

TABLE 4A

| DMR No. | Marker | AUC (all OC vs all benign tissue) | AUC (all OC vs buffy) |
|---|---|---|---|
| 318 | NCOR2 | 0.88377 | 0.99908 |
| 311 | MT1A_A | 0.88816 | 0.988 |
| 63 | CELF2_A | 0.89232 | 0.97599 |
| 164 | KCNA3_A | 0.87259 | 0.94598 |
| 463 | ZMIZ1_C | 0.55789 | 0.71191 |
| 306 | MDFI | 0.62719 | 0.77101 |
| 343 | PALLD | 0.93114 | 1 |
| 360 | PRDM14 | 0.91667 | 1 |
| 345 | PARP15 | 0.8057 | 0.91782 |
| 423 | TACC2_A | 0.68969 | 0.88458 |
| 207 | MAX.chr1.147790358-147790381 | 0.97675 | 1 |
| 25 | BCAT1 | 0.93991 | 0.98199 |
| 64 | CELF2_B | 0.84649 | 0.93629 |
| 50 | CAPN2_A | 0.79671 | 0.89612 |
| 226 | MAX.chr11.14926602-14926671 | 0.86886 | 0.97922 |
| 7 | AGRN_B | 0.77325 | 0.95199 |
| 287 | MAX.chr6.10382190-10382225 | 0.88158 | 0.97692 |
| 84 | DSCR6 | 0.86667 | 0.94183 |
| 204 | MAML3_A | 0.92412 | 0.94737 |
| 334 | OBSCN | 0.69561 | 0.90028 |
| 236 | MAX.chr14.105512178-105512224 | 0.78026 | 0.91782 |

TABLE 4A-continued

| DMR No. | Marker | AUC (all OC vs all benign tissue) | AUC (all OC vs buffy) |
|---|---|---|---|
| 96 | EPS8L2_E | 0.76404 | 0.84765 |
| 398 | SKI | 0.96579 | 1 |
| 329 | NR2F6 | 0.70614 | 0.91413 |
| 399 | SLC12A8 | 0.74386 | 0.90859 |
| 121 | GPRIN1_A | 0.87018 | 0.89751 |
| 297 | MAX.chr8.142215938-142216298 | 0.6557 | 0.8144 |
| 61 | CDO1_A | 0.86228 | 0.91043 |
| 81 | DNMT3A_A | 0.90132 | 0.98615 |
| 397 | SIM2_A | 0.88026 | 0.98615 |
| 398 | SKI | 0.95482 | 0.99815 |
| 462 | ZMIZ1_B | 0.60439 | 0.70083 |
| 434 | TMEM101 | 0.62939 | 0.84765 |
| 490 | IFFO1_A | 0.81404 | 1 |
| 312 | MT1A_B | 0.89825 | 0.99169 |
| 19 | ATP10A_B | 0.46009 | 0.64774 |
| 123 | GYPC_A | 0.77281 | 0.91136 |
| 491 | IFFO1_B | 0.80175 | 0.99354 |
| 348 | PDE10A | 0.58333 | 0.72946 |
| 475 | BCL2L11 | 0.86228 | 1 |
| 137 | HOXB3 | 0.46711 | 0.27239 |
| 353 | PISD | 0.63684 | 0.62512 |
| 488 | GDF6 | 0.82982 | 1 |
| 388 | SCGB3A1 | 0.47193 | 0.54663 |
| 33 | BOLA1 | 0.67544 | 0.65374 |
| 479 | C2CD4D | 0.92982 | 0.99123 |
| 111 | GATA2 | 0.59298 | 0.89104 |
| 474 | BANK1 | 0.63114 | 0.89935 |
| 250 | MAX.chr19.2273768-2273823 | 0.58596 | 0.85134 |
| 340 | OSR2 | 0.775 | 0.90397 |
| 370 | PTP4A3_A | 0.62522 | 0.7627 |
| 181 | LAPTM4B | 0.48289 | 0.49354 |
| 310 | MSX2 | 0.44781 | 0.5337 |
| 317 | NBPF3 | 0.4943 | 0.46491 |

TABLE 4B

| DMR No. | Marker | AUC (clear cell vs all benign tissue) |
|---|---|---|
| 318 | NCOR2 | 0.89333 |
| 311 | MT1A_A | 0.96833 |
| 63 | CELF2_A | 0.91833 |
| 164 | KCNA3_A | 0.9225 |
| 463 | ZMIZ1_C | 0.48167 |
| 306 | MDFI | 0.90333 |
| 343 | PALLD | 0.96333 |
| 360 | PRDM14 | 0.95333 |
| 345 | PARP15 | 0.965 |
| 423 | TACC2_A | 0.985 |
| 207 | MAX.chr1.147790358-147790381 | 0.97667 |
| 25 | BCAT1 | 0.93 |
| 64 | CELF2_B | 0.89667 |
| 50 | CAPN2_A | 0.85417 |
| 226 | MAX.chr11.14926602-14926671 | 0.96167 |
| 7 | AGRN_B | 0.94333 |
| 287 | MAX.chr6.10382190-10382225 | 0.9425 |
| 84 | DSCR6 | 1 |
| 204 | MAML3_A | 0.94583 |
| 334 | OBSCN | 0.84333 |
| 236 | MAX.chr14.105512178-105512224 | 0.91667 |
| 96 | EPS8L2_E | 0.99833 |
| 398 | SKI | 0.99833 |
| 329 | NR2F6 | 0.675 |
| 399 | SLC12A8 | 0.73 |
| 121 | GPRIN1_A | 0.99833 |
| 297 | MAX.chr8.142215938-142216298 | 0.97833 |
| 61 | CDO1_A | 1 |
| 81 | DNMT3A_A | 0.95667 |
| 397 | SIM2_A | 1 |
| 398 | SKI | 0.98667 |
| 462 | ZMIZ1_B | 0.49167 |
| 434 | TMEM101 | 0.88583 |

TABLE 4B-continued

| DMR No. | Marker | AUC (clear cell vs all benign tissue) |
|---|---|---|
| 490 | IFFO1_A | 0.83 |
| 312 | MT1A_B | 0.995 |
| 19 | ATP10A_B | 0.58667 |
| 123 | GYPC_A | 0.98667 |
| 491 | IFFO1_B | 0.81333 |
| 348 | PDE10A | 0.66 |
| 475 | BCL2L11 | 0.94833 |
| 137 | HOXB3 | 0.39333 |
| 353 | PISD | 0.995 |
| 488 | GDF6 | 0.86333 |
| 388 | SCGB3A1 | 0.41833 |
| 33 | BOLA1 | 0.87833 |
| 479 | C2CD4D | 0.95833 |
| 111 | GATA2 | 0.50167 |
| 474 | BANK1 | 0.54667 |
| 250 | MAX.chr19.2273768-2273823 | 0.62667 |
| 340 | OSR2 | 0.83333 |
| 370 | PTP4A3_A | 0.74167 |
| 181 | LAPTM4B | 0.57333 |
| 310 | MSX2 | 0.34167 |
| 317 | NBPF3 | 0.44167 |

TABLE 4C

| DMR No. | Marker | AUC (endometrioid vs all benign tissue) |
|---|---|---|
| 318 | NCOR2 | 0.90278 |
| 311 | MT1A_A | 0.81111 |

TABLE 4C-continued

| DMR No. | Marker | AUC (endometrioid vs all benign tissue) |
|---|---|---|
| 63 | CELF2_A | 0.97639 |
| 164 | KCNA3_A | 0.84097 |
| 463 | ZMIZ1_C | 0.45139 |
| 306 | MDFI | 0.45278 |
| 343 | PALLD | 0.91667 |
| 360 | PRDM14 | 0.90278 |
| 345 | PARP15 | 0.89722 |
| 423 | TACC2_A | 0.65694 |
| 207 | MAX.chr1.147790358-147790381 | 0.9875 |
| 25 | BCAT1 | 0.98611 |
| 64 | CELF2_B | 0.89514 |
| 50 | CAPN2_A | 0.75556 |
| 226 | MAX.chr11.14926602-14926671 | 0.93889 |
| 7 | AGRN_B | 0.67639 |
| 287 | MAX.chr6.10382190-10382225 | 0.75903 |
| 84 | DSCR6 | 0.7875 |
| 204 | MAML3_A | 0.96042 |
| 334 | OBSCN | 0.49306 |
| 236 | MAX.chr14.105512178-105512224 | 0.84583 |
| 96 | EPS8L2_E | 0.725 |
| 398 | SKI | 0.95 |
| 329 | NR2F6 | 0.6875 |
| 399 | SLC12A8 | 0.66944 |
| 121 | GPRIN1_A | 0.99722 |
| 297 | MAX.chr8.142215938-142216298 | 0.58889 |
| 61 | CDO1_A | 0.81111 |
| 81 | DNMT3A_A | 0.88472 |
| 397 | SIM2_A | 0.88472 |
| 398 | SKI | 0.93472 |
| 462 | ZMIZ1_B | 0.57083 |
| 434 | TMEM101 | 0.86736 |
| 490 | IFFO1_A | 0.77917 |
| 312 | MT1A_B | 0.81667 |
| 19 | ATP10A_B | 0.39722 |
| 123 | GYPC_A | 0.78194 |
| 491 | IFFO1_B | 0.7625 |
| 348 | PDE10A | 0.64306 |
| 475 | BCL2L11 | 0.90972 |
| 137 | HOXB3 | 0.6375 |
| 353 | PISD | 0.49653 |
| 488 | GDF6 | 0.7375 |
| 388 | SCGB3A1 | 0.62361 |
| 33 | BOLA1 | 0.41667 |
| 479 | C2CD4D | 0.96528 |
| 111 | GATA2 | 0.53194 |
| 474 | BANK1 | 0.58472 |
| 250 | MAX.chr19.2273768-2273823 | 0.40833 |
| 340 | OSR2 | 0.73056 |
| 370 | PTP4A3_A | 0.58264 |
| 181 | LAPTM4B | 0.43611 |
| 310 | MSX2 | 0.30417 |
| 317 | NBPF3 | 0.42917 |

TABLE 4D

| DMR No. | Marker | AUC (mucinous vs all benign tissue) |
|---|---|---|
| 318 | NCOR2 | 0.925 |
| 311 | MT1A_A | 1 |
| 63 | CELF2_A | 0.71667 |
| 164 | KCNA3_A | 0.99583 |
| 463 | ZMIZ1_C | 1 |
| 306 | MDFI | 0.23333 |
| 343 | PALLD | 0.80833 |
| 360 | PRDM14 | 0.83333 |
| 345 | PARP15 | 0.42917 |
| 423 | TACC2_A | 1 |
| 207 | MAX.chr1.147790358-147790381 | 0.90417 |
| 25 | BCAT1 | 1 |
| 64 | CELF2_B | 0.6625 |

TABLE 4D-continued

| DMR No. | Marker | AUC (mucinous vs all benign tissue) |
|---|---|---|
| 50 | CAPN2_A | 0.56667 |
| 226 | MAX.chr11.14926602-14926671 | 0.62083 |
| 7 | AGRN_B | 0.9125 |
| 287 | MAX.chr6.10382190-10382225 | 0.7875 |
| 84 | DSCR6 | 0.775 |
| 204 | MAML3_A | 0.88125 |
| 334 | OBSCN | 0.49167 |
| 236 | MAX.chr14.105512178-105512224 | 0.8625 |
| 96 | EPS8L2_E | 0.49583 |
| 398 | SKI | 0.95 |
| 329 | NR2F6 | 0.83333 |
| 399 | SLC12A8 | 0.97917 |
| 121 | GPRIN1_A | 0.5125 |
| 297 | MAX.chr8.142215938-142216298 | 0.57083 |
| 61 | CDO1_A | 0.8375 |
| 81 | DNMT3A_A | 0.89583 |
| 397 | SIM2_A | 0.8625 |
| 398 | SKI | 0.97917 |
| 462 | ZMIZ1_B | 1 |
| 434 | TMEM101 | 0.81875 |
| 490 | IFFO1_A | 0.47083 |
| 312 | MT1A_B | 0.87917 |
| 19 | ATP10A_B | 0.8375 |
| 123 | GYPC_A | 0.74167 |
| 491 | IFFO1_B | 0.54583 |
| 348 | PDE10A | 0.47083 |
| 475 | BCL2L11 | 0.99583 |
| 137 | HOXB3 | 0.80417 |
| 353 | PISD | 0.69375 |
| 488 | GDF6 | 0.62917 |
| 388 | SCGB3A1 | 0.72917 |
| 33 | BOLA1 | 0.5375 |
| 479 | C2CD4D | 0.725 |
| 111 | GATA2 | 0.9125 |
| 474 | BANK1 | 0.525 |
| 250 | MAX.chr19.2273768-2273823 | 0.52083 |
| 340 | OSR2 | 0.8375 |
| 370 | PTP4A3_A | 0.70417 |
| 181 | LAPTM4B | 0.36458 |
| 310 | MSX2 | 0.70417 |
| 317 | NBPF3 | 0.64167 |

TABLE 4E

| DMR No. | Marker | AUC (serous vs all benign tissue) |
|---|---|---|
| 318 | NCOR2 | 0.84306 |
| 311 | MT1A_A | 0.86111 |
| 63 | CELF2_A | 0.84514 |
| 164 | KCNA3_A | 0.82153 |
| 463 | ZMIZ1_C | 0.58056 |
| 306 | MDFI | 0.56875 |
| 343 | PALLD | 0.95972 |
| 360 | PRDM14 | 0.92778 |
| 345 | PARP15 | 0.70694 |
| 423 | TACC2_A | 0.37292 |
| 207 | MAX.chr1.147790358-147790381 | 0.99028 |
| 25 | BCAT1 | 0.88194 |
| 64 | CELF2_B | 0.81736 |
| 50 | CAPN2_A | 0.91111 |
| 226 | MAX.chr11.14926602-14926671 | 0.80417 |
| 7 | AGRN_B | 0.68194 |
| 287 | MAX.chr6.10382190-10382225 | 0.98472 |
| 84 | DSCR6 | 0.86528 |
| 204 | MAML3_A | 0.88403 |
| 334 | OBSCN | 0.8375 |
| 236 | MAX.chr14.105512178-105512224 | 0.81528 |
| 96 | EPS8L2_E | 0.69722 |
| 398 | SKI | 0.95972 |
| 329 | NR2F6 | 0.93056 |
| 399 | SLC12A8 | 0.75139 |
| 121 | GPRIN1_A | 0.76389 |

TABLE 4E-continued

| DMR No. | Marker | AUC (serous vs all benign tissue) |
|---|---|---|
| 297 | MAX.chr8.142215938-142216298 | 0.70694 |
| 61 | CDO1_A | 0.80694 |
| 81 | DNMT3A_A | 0.87361 |
| 397 | SIM2_A | 0.78194 |
| 398 | SKI | 0.94028 |
| 462 | ZMIZ1_B | 0.6 |
| 434 | TMEM101 | 0.32708 |
| 490 | IFFO1_A | 0.93056 |
| 312 | MT1A_B | 0.90556 |
| 19 | ATP10A_B | 0.56389 |
| 123 | GYPC_A | 0.59583 |
| 491 | IFFO1_B | 0.91667 |
| 348 | PDE10A | 0.50278 |
| 475 | BCL2L11 | 0.69861 |
| 137 | HOXB3 | 0.44861 |
| 353 | PISD | 0.58889 |
| 488 | GDF6 | 0.96111 |
| 388 | SCGB3A1 | 0.47361 |
| 33 | BOLA1 | 0.66944 |
| 479 | C2CD4D | 0.93889 |
| 111 | GATA2 | 0.37361 |
| 474 | BANK1 | 0.78333 |
| 250 | MAX.chr19.2273768-2273823 | 0.76528 |
| 340 | OSR2 | 0.75 |
| 370 | PTP4A3_A | 0.70972 |
| 181 | LAPTM4B | 0.475 |
| 310 | MSX2 | 0.73056 |
| 317 | NBPF3 | 0.50694 |

Table 5A shows area under the curve for various markers from Table 1 that distinguished serous OC tissue from benign ovarian tissue and buffy coat.

TABLE 5A

| DMR No. | Marker | tissue AUC | buffy AUC |
|---|---|---|---|
| 318 | NCOR2 | 0.90805 | 0.96329 |
| 312 | MT1A_B | 0.71169 | 0.94147 |
| 63 | CELF2_A | 0.70642 | 0.83333 |
| 164 | KCNA3_A | 0.78065 | 0.79663 |
| 343 | PALLD | 0.87931 | 0.93452 |
| 360 | PRDM14 | 0.85441 | 0.78671 |
| 345 | PARP15 | 0.77395 | 0.77579 |
| 423 | TACC2_A | 0.76054 | 0.70139 |
| 207 | MAX.chr1.147790358-147790381 | 0.91092 | 0.98413 |
| 25 | BCAT1 | 0.88697 | 0.85417 |
| 50 | CAPN2_A | 0.84674 | 0.89484 |
| 226 | MAX.chr11.14926602-14926671 | 0.7931 | 0.85516 |
| 7 | AGRN_B | 0.83238 | 0.93056 |
| 287 | MAX.chr6.10382190-10382225 | 0.92816 | 0.92063 |
| 84 | DSCR6 | 0.84195 | 0.78869 |
| 204 | MAML3_A | 0.81466 | 0.92758 |
| 236 | MAX.chr14.105512178-105512224 | 0.70259 | 0.84474 |
| 398 | SKI | 0.87452 | 0.99802 |
| 329 | NR2F6 | 0.86973 | 0.95437 |
| 399 | SLC12A8 | 0.79502 | 1 |
| 121 | GPRIN1_A | 0.65134 | 0.5129 |
| 61 | CDO1_A | 0.7318 | 0.71825 |
| 81 | DNMT3A_A | 0.67529 | 0.60863 |
| 397 | SIM2_A | 0.81609 | 0.90278 |
| 462 | ZMIZ1_B | 0.55077 | 0.46528 |
| 490 | IFFO1_A | 0.91954 | 1 |
| 312 | MT1A_B | 0.78161 | 0.97321 |
| 123 | GYPC_A | 0.62165 | 0.87599 |
| 475 | BCL2L11 | 0.64847 | 0.9375 |
| 488 | GDF6 | 0.93487 | 1 |
| 479 | C2CD4D | 0.91284 | 0.98413 |
| 111 | GATA2 | 0.48755 | 0.39583 |
| 474 | BANK1 | 0.57375 | 0.94444 |

Table 5B shows area under the curve for various markers from Table 1 that distinguished clear cell OC tissue from benign ovarian tissue and buffy coat.

TABLE 5B

| DMR No. | Marker | tissue AUC | buffy AUC |
|---|---|---|---|
| 318 | NCOR2 | 0.99343 | 1 |
| 312 | MT1A_B | 0.99015 | 1 |
| 63 | CELF2_A | 0.94828 | 0.97279 |
| 164 | KCNA3_A | 0.89491 | 0.90136 |
| 343 | PALLD | 1 | 1 |
| 360 | PRDM14 | 0.99507 | 0.9966 |
| 345 | PARP15 | 1 | 1 |
| 423 | TACC2_A | 0.96388 | 0.95068 |
| 207 | MAX.chr1.147790358-147790381 | 1 | 1 |
| 25 | BCAT1 | 0.99343 | 0.9966 |
| 50 | CAPN2_A | 0.83251 | 0.90646 |
| 226 | MAX.chr11.14926602-14926671 | 0.95567 | 0.95493 |
| 7 | AGRN_B | 0.99507 | 0.9966 |
| 287 | MAX.chr6.10382190-10382225 | 1 | 1 |
| 84 | DSCR6 | 1 | 1 |
| 204 | MAML3_A | 0.96388 | 1 |
| 236 | MAX.chr14.105512178-105512224 | 0.79228 | 0.91241 |
| 398 | SKI | 0.96223 | 0.98639 |
| 329 | NR2F6 | 0.83333 | 0.91412 |
| 399 | SLC12A8 | 0.86535 | 1 |
| 121 | GPRIN1_A | 1 | 1 |
| 61 | CDO1_A | 1 | 1 |
| 81 | DNMT3A_A | 0.89491 | 0.87245 |
| 397 | SIM2_A | 1 | 1 |
| 462 | ZMIZ1_B | 0.54187 | 0.46429 |
| 490 | IFFO1_A | 0.95402 | 1 |
| 312 | MT1A_B | 1 | 1 |
| 123 | GYPC_A | 1 | 1 |
| 475 | BCL2L11 | 0.96059 | 1 |
| 488 | GDF6 | 0.95895 | 1 |
| 479 | C2CD4D | 1 | 1 |
| 111 | GATA2 | 0.42529 | 0.39116 |
| 474 | BANK1 | 0.77668 | 0.93367 |

Table 5C shows area under the curve for various markers from Table 1 that distinguished endometrioid OC tissue from benign ovarian tissue and buffy coat.

TABLE 5C

| DMR No. | Marker | tissue AUC | buffy AUC |
|---|---|---|---|
| 318 | NCOR2 | 0.94003 | 0.95807 |
| 312 | MT1A_B | 0.78711 | 0.93323 |
| 63 | CELF2_A | 0.85007 | 0.90683 |
| 164 | KCNA3_A | 0.8051 | 0.81832 |
| 343 | PALLD | 1 | 1 |
| 360 | PRDM14 | 0.90555 | 0.87267 |
| 345 | PARP15 | 0.86132 | 0.85714 |
| 423 | TACC2_A | 0.84558 | 0.79814 |
| 207 | MAX.chr1.147790358-147790381 | 0.997 | 1 |
| 25 | BCAT1 | 0.89805 | 0.88509 |
| 50 | CAPN2_A | 0.73013 | 0.79969 |
| 226 | MAX.chr11.14926602-14926671 | 0.92804 | 0.95807 |
| 7 | AGRN_B | 0.7099 | 0.78882 |
| 287 | MAX.chr6.10382190-10382225 | 0.86807 | 0.86491 |
| 84 | DSCR6 | 0.96252 | 0.91925 |
| 204 | MAML3_A | 0.86057 | 0.94099 |
| 236 | MAX.chr14.105512178-105512224 | 0.85907 | 0.9441 |
| 398 | SKI | 0.73988 | 0.93944 |
| 329 | NR2F6 | 0.61694 | 0.76941 |
| 399 | SLC12A8 | 0.8021 | 1 |
| 121 | GPRIN1_A | 0.92054 | 0.87811 |
| 61 | CDO1_A | 0.93778 | 0.93634 |
| 81 | DNMT3A_A | 0.71514 | 0.64596 |

TABLE 5C-continued

| DMR No. | Marker | tissue AUC | buffy AUC |
|---|---|---|---|
| 397 | SIM2_A | 0.93553 | 0.99845 |
| 462 | ZMIZ1 B | 0.53523 | 0.45497 |
| 490 | IFFO1_A | 0.90105 | 0.99845 |
| 312 | MT1A_B | 0.85607 | 0.92857 |
| 123 | GYPC_A | 0.89205 | 0.96661 |
| 475 | BCL2L11 | 0.81934 | 0.93012 |
| 488 | GDF6 | 0.61169 | 1 |
| 479 | C2CD4D | 0.997 | 1 |
| 111 | GATA2 | 0.33358 | 0.2764 |
| 474 | BANK1 | 0.30735 | 0.87422 |

Table 5D shows area under the curve for various markers from Table 1 that distinguished mucinous OC tissue from benign ovarian tissue and buffy coat.

TABLE 5D

| DMR No. | Marker | tissue AUC | buffy AUC |
|---|---|---|---|
| 318 | NCOR2 | 0.98768 | 1 |
| 312 | MT1A_B | 0.82759 | 1 |
| 63 | CELF2_A | 0.68596 | 0.80867 |
| 164 | KCNA3_A | 0.88177 | 0.88903 |
| 343 | PALLD | 0.91626 | 0.95663 |
| 360 | PRDM14 | 0.82759 | 0.75 |
| 345 | PARP15 | 0.77833 | 0.78061 |
| 423 | TACC2_A | 0.9803 | 0.96173 |
| 207 | MAX.chr1.147790358-147790381 | 0.87685 | 0.97194 |
| 25 | BCAT1 | 0.99754 | 0.9949 |
| 50 | CAPN2_A | 0.6601 | 0.77806 |
| 226 | MAX.chr11.14926602-14926671 | 0.85961 | 0.90689 |
| 7 | AGRN_B | 0.92118 | 0.95408 |
| 287 | MAX.chr6.10382190-10382225 | 0.86207 | 0.85969 |
| 84 | DSCR6 | 0.62808 | 0.55102 |
| 204 | MAML3_A | 0.85961 | 0.9898 |
| 236 | MAX.chr14.105512178-105512224 | 0.75739 | 0.67474 |
| 398 | SKI | 1 | 1 |
| 329 | NR2F6 | 0.47167 | 0.70281 |
| 399 | SLC12A8 | 0.90887 | 1 |
| 121 | GPRIN1_A | 0.63793 | 0.49617 |
| 61 | CDO1_A | 0.84975 | 0.85459 |
| 81 | DNMT3A_A | 0.78325 | 0.70536 |
| 397 | SIM2_A | 0.8399 | 0.96173 |
| 462 | ZMIZ1_B | 0.92365 | 0.90816 |
| 490 | IFFO1_A | 0.84729 | 1 |
| 312 | MT1A_B | 0.84606 | 0.93878 |
| 123 | GYPC_A | 0.76108 | 0.98469 |
| 475 | BCL2L11 | 0.94828 | 1 |
| 488 | GDF6 | 0.69458 | 1 |
| 479 | C2CD4D | 0.73153 | 1 |
| 111 | GATA2 | 0.85714 | 0.84184 |
| 474 | BANK1 | 0.4532 | 0.93367 |

Example II

This example describes identification of ovarian cancer tissue markers, clear cell ovarian cancer tissue markers, endometrioid ovarian cancer tissue markers, mucinous ovarian cancer tissue markers, and serous ovarian cancer tissue markers.

Candidate methylation markers for the detection of ovarian cancer, clear cell OC, endometrioid OC, mucinous OC, and serous OC were identified by RRBS of ovarian tissue samples, clear cell OC tissue samples, endometrioid OC tissue samples, mucinous OC tissue samples, serous OC tissue samples, and normal ovarian tissue samples. To identify methylated DNA markers, 149 samples per patient group (see Table 7) underwent an RRBS process followed by an alignment to a bisulfite converted human genome. CpG regions of high ratios of methylation in ovarian cancer, clear cell OC, endometrioid OC, mucinous OC, and serous OC relative to normal ovarian tissue and buffy coat were selected and mapped to their gene names

TABLE 7

| | Number | Stage I | Stage II | Stage III | Stage IV |
|---|---|---|---|---|---|
| Sample type | | | | | |
| Normal | 35 | NA | NA | NA | NA |
| Cancer | 57 | 25 | 8 | 19 | 5 |
| Cancer Subtype | | | | | |
| Clear Cell | 15 | 8 | 4 | 3 | 0 |
| Endometrioid | 18 | 12 | 3 | 3 | 0 |
| Mucinous | 6 | 4 | 1 | 0 | 1 |
| Serous | 18 | 1 | 0 | 13 | 4 |

After markers were selected by RRBS, a total of 49 methylation markers were identified and target enrichment long-probe quantitative amplified signal assays were designed and ordered (see, e.g., WO2017/075061 and U.S. patent application Ser. No. 15/841,006 for general techniques). Table 6A shows the marker chromosomal regions used for the 49 methylation markers. Table 6B shows primer information and probe information for the markers. FIG. 1 further provides marker chromosomal regions used for the 49 methylation markers and related primer and probe information.

TABLE 6A

| DMR No. | Gene Annotation | Chromosome No. | DMR Start-End Positions |
|---|---|---|---|
| 526 | AGRN_8794 | 1 | 968670-968849 |
| 527 | BCAT1_6015 | 12 | 25055940-25056138 |
| 528 | BHLHE23_8339 | 20 | 61638294-61638506 |
| 529 | ELMO1_9100 | 7 | 37488054-37488165 |
| 530 | EPS8L2_F | 11 | 726397-726519 |
| 531 | JAM3_B | 11 | 133938908-133939011 |
| 532 | KCNA3_7320 | 1 | 111217250-111217357 |
| 533 | KCNA3_7518 | 1 | 111217487-111217673 |
| 534 | MDFI_6321 | 6 | 41606064-41606357 |
| 545 | RASSF1_8293 | 3 | 50378182-50378372 |
| 536 | SFMBT2_2363 | 10 | 7451790-7452428 |
| 398 | SKI | 1 | 2222218-2222508 |
| 537 | SPOCK2_7433 | 10 | 73847355-73847446 |
| 538 | VIPR2_B | 7 | 158937203-158937476 |
| 539 | ZMIZ1_D | 8 | 81002589-81002797 |
| 540 | ZNF382_B | 19 | 37096085-37096209 |
| 541 | GYPC_3753 | 2 | 127413592-127413887 |
| 542 | GYPC_C | 2 | 127413898-127413988 |
| 543 | RFTN1_B | 3 | 16554329-16554496 |
| 345 | PARP15 | 3 | 122296692-122296851 |
| 119 | GP5 | 3 | 194118822-194118924 |
| 544 | GPRIN1_B | 5 | 176023887-176023974 |
| 545 | HCG4_0331 | 6 | 29760284-29760410 |
| 546 | HCG4_0556 | 6 | 29760436-29760577 |
| 547 | NKX2-6_4159 | 8 | 23564076-23564193 |
| 548 | C1QL3_B | 10 | 16562562-16562645 |
| 549 | FAIM2_B | 12 | 50297643-50297814 |
| 550 | LOC100131366 | 14 | 103655515-103655633 |
| 551 | NTN1 | 17 | 9143164-9143445 |
| 552 | ARL5C_1519 | 17 | 37321484-37321627 |
| 40 | C17orf64_A | 17 | 58498720-58498794 |
| 553 | OXT_C | 20 | 3052753-3052884 |
| 554 | PEAR1_B | 1 | 156863357-156863488 |
| 555 | ATP10A_E | 15 | 26108540-26108828 |
| 63 | CELF2_A | 10 | 11207221-11207812 |

TABLE 6A-continued

| DMR No. | Gene Annotation | Chromosome No. | DMR Start-End Positions |
|---|---|---|---|
| 556 | CAPN2_B | 1 | 223936858-223937009 |
| 84 | DSCR6 | 21 | 38378492-38378858 |
| 329 | NR2F6 | 19 | 17346347-17346780 |
| 61 | CDO1_A | 5 | 115152022-115152432 |
| 81 | DNMT3A_A | 2 | 25500046-25500305 |
| 557 | SIM2_B | 21 | 38076882-38077036 |
| 558 | CMTM3_B | 16 | 66638172-66638351 |
| 559 | SRC_B | 20 | 36013121-36013303 |
| 199 | LRRC41_B | 1 | 46769340-46769650 |
| 444 | TSHZ3 | 19 | 31839415-31840120 |
| 128 | HDGFRP3 | 15 | 83875827-83875946 |
| 560 | TACC2_B | 10 | 123922953-123923142 |
| 182 | LBH | 2 | 30453651-30453973 |

TABLE 6B

| Gene Annotation | DMR No. | Forward Primer 5'-3' | SEQ ID NO: | Reverse Primer 5'-3' | SEQ ID NO: | Probe Sequence | SEQ ID NO: |
|---|---|---|---|---|---|---|---|
| AGRN_8794 | 526 | GCGGTTTTTCGAGTTTTTTGCG | 137 | GAACGAATCCGCGCC | 138 | AGGCCACGGACGGGCGATTTCGATTTATTTTCG/3C6/ | 235 |
| BCAT1_6015 | 527 | GCGGTGTGGTTAAGTTTCGG | 139 | CGCGACCCCAAATCGTA | 140 | CGCGCCGAGGGCGTACGGTTTATAGGGC/3C6/ | 236 |
| BHLHE23_8339 | 528 | CGGGTTTTATTTTTTTTCGTTTTCGTTTC | 141 | AACGAAATCCCACCGAACG | 142 | CGCGCCGAGGCGGTTTTAAGTCGCGGA/3C6/ | 237 |
| ELMO1_9100 | 529 | GTAGAGCGTTTCGACGCG | 143 | TCGAACGAAAATAACCGCCG | 144 | AGGCCACGGACGGCGCTCGACAAAATAAAAAC/3C6/ | 238 |
| EPS8L2_F | 530 | GTTTTTAGTTAGGCGCGGATTTC | 145 | AACCCGTAAACCAACCGC | 146 | CGCGCCGAGGCGTTCGGATTCGATTCGT/3C6/ | 239 |
| JAM3_B | 531 | TGGTCGTTTTAGCGTTATGTCG | 147 | CGAAAACTACAAACCGCGC | 148 | AGGCCACGGACGCCGCGCTACCGCTA/3C6/ | 240 |
| KCNA3_7320 | 532 | CGGTTATGTCGGGCGG | 149 | CAACGACGATACCCACACG | 150 | CGCGCCGAGGGCTAATAAACCACGACTACG/3C6/ | 241 |
| KCNA3_7518 | 533 | TCGTTTTTTCGTCGTTTTCGTTTTC | 151 | CCCGTACGAAAACCCGA | 152 | AGGCCACGGACGCGAGTCGAGTTTATCGTTTG/3C6/ | 242 |
| MDF1_6321 | 534 | GTTCGTTATGCGCGTTTGTTTC | 153 | GAACACCCGAAAACCAACGA | 154 | CGCGCCGAGGCGGGCGTTTTTGTTTAGG/3C6/ | 243 |

TABLE 6B-continued

| Gene Annotation | DMR No. | Forward Primer 5'-3' | SEQ ID NO: | Reverse Primer 5'-3' | SEQ ID NO: | Probe Sequence | SEQ ID NO: |
|---|---|---|---|---|---|---|---|
| RASSF1_8293 | 545 | GTTTTGTGGTTTCGTTCGGTTC | 155 | CCGATTAAACCCGTACTTCGC | 156 | AGGCCACGGACGCGCGTTTGTTAGCGTTTAAA/3C6/ | 244 |
| SFMBT2_2363 | 536 | TTTCGTTTTTGTATTTATTTTAGCGACGT | 157 | ACGCGAAAAAAACGCGAAAACG | 158 | CGCGCCGAGGGCGAAATAAATAACAACGACGA/3C6/ | 245 |
| SKI | 398 | GTTAGGCGGTTATTACGGGTC | 159 | GAAATCTACTCCCTCCCCGA | 160 | AGGCCACGGACGCGCGTTTTTTATTAGTTAGTCGTT/3C6/ | 246 |
| SPOCK2_7433 | 537 | TATGTTGTTTTTTTTTCGTAAAGTTTACGGT | 161 | CCGACAATAAAAATAACATCGACTCG | 162 | CGCGCCGAGGGCGCGATACCCTCTATTC/3C6/ | 247 |
| VIPR2_B | 538 | TCGTTCGCGTTTTAGTATTCGG | 163 | CGAAAAAAACGCTCCTCCCG | 164 | AGGCCACGGACGGCCGATCTTCGCCTT/3C6/ | 248 |
| ZMIZ1_D | 539 | GTTCGTTCGGTAGCGGC | 165 | ACCACTTCGCTACGAAAAAACG | 166 | CGCGCCGAGGGCGAACGAATATAAATCGAAAAC/3C6/ | 249 |
| ZNF382_B | 540 | TAGTCGTAATAGGGCGGTCG | 167 | CCGAAACGACCCGTTAATCG | 168 | AGGCCACGGACGGCCGCGCGATACTAA/3C6/ | 250 |
| GYPC_3753 | 541 | TGATTTAGGTGTCGTTTTTTTTCGTC | 169 | GAAAAAAAATCGCGCTCCCG | 170 | AGGCCACGGACGCGTCGAGGGTTAGGAGT/3C6/ | 251 |
| GYPC_C | 542 | ATTTATTGGAGGTCGCGGTTC | 171 | CCGAAACACCAAAACGTCCG | 172 | CGCGCCGAGGGTAACCGTAACTCGACCC/3C6/ | 252 |
| RFTN1_B | 543 | GTGTTTTTGGTGGTTTCGGC | 173 | ATACTAAACGTATAAAAACAAACATACCGC | 174 | AGGCCACGGACGCGCGCTCCGAAAAAAC/3C6/ | 253 |
| PARP15 | 345 | GGTTCGTAAGATTTAGTAGTTCGA | 175 | CGAAACAAAAAAATCAATATAATCGACGC | 176 | CGCGCCGAGGCGGGCGTAGAGA | 254 |

TABLE 6B-continued

| Gene Annotation | DMR No. | Forward Primer 5'-3' | SEQ ID NO: | Reverse Primer 5'-3' | SEQ ID NO: | Probe Sequence | SEQ ID NO: |
|---|---|---|---|---|---|---|---|
| | | GC | | | | TTTTACG/ 3C6/ | |
| GPS | 119 | TAGGAC GTCGC GGTTTA TTTC | 177 | CGCAATAC TCGAAAAA CGACG | 178 | AGGCCA CGGACG GTAACG CGCATC TCCG/ 3C6/ | 255 |
| GPRIN1_B | 544 | TCGCGT CGTCGT TCGT | 179 | GACGCCAT CTAAAAAC GCGA | 180 | CGCGCC GAGG TCGTTC GTGTCG GTTTC/ 3C6/ | 256 |
| HCG4_0331 | 545 | GGCGA CGTGGA CGATAC | 181 | CTAAAACT CGTAACGT CGCTATCG | 182 | AGGCCA CGGACG GAACCG CACGCA CTA/3C6/ | 257 |
| HCG4_0556 | 546 | GGTTTG TGAGTG ATATCG GTCG | 183 | CGAACCCA AAAACTCG AAAAAACC | 184 | CGCGCC GAGG CCGAAC GATCCG TAAAAAA TATAA/ 3C6/ | 258 |
| NKX2-6_4159 | 547 | GGGTTT AGTAGT ATTTCG AAGGC G | 185 | GAAAAATT CAAAATAC CGCTCCTC AC | 186 | AGGCCA CGGACG CCCGAA CCTCCT CGA/3C6/ | 259 |
| C1QL3_B | 548 | GAAGGT TACGAG GTGTTT AAGTTC G | 187 | AACAAATA AACTTACC GATAATAA AATCGTAA TAATTTC | 188 | CGCGCC GAGG GACGAC GTGGTT ATTAATT TCG/3C6/ | 260 |
| FAIM2_B | 549 | TTGCGG AGGAC GTTGC | 189 | GAAAAAAA ACGATACG CCGCC | 190 | CGCGCC GAGG CGGATT CGCGAG TTCG/ 3C6/ | 261 |
| LOC100131366 | 550 | TTTCGA TTTCGT AGTTTC GCGG | 191 | CTCGCGAA ACGTAACG AAAAC | 192 | AGGCCA CGGACG GCGCGT TTTTTGA GGC/3C6/ | 262 |
| NTN1 | 551 | CGTTCG TTTTCG TTCGGT TTC | 193 | ACCTAACG CCGAAACA ACG | 194 | CGCGCC GAGG CGTTTTG GCGTTC GTTC/ 3C6/ | 263 |
| ARL5C_1519 | 552 | GTTGTT TTTTTTA TCGTTT CGGAGT G | 195 | CCTCTACC CACCGTAC CG | 196 | AGGCCA CGGACG GCGTCT ACTTCC CACC/ 3C6/ | 264 |
| C17orf64_A | 40 | GTTTTC GGGTTA TTTTTAT | 197 | TCCCCTAC CACCCAAC G | 198 | CGCGCC GAGG GACCAC | 265 |

TABLE 6B-continued

| Gene Annotation | DMR No. | Forward Primer 5'-3' | SEQ ID NO: | Reverse Primer 5'-3' | SEQ ID NO: | Probe Sequence | SEQ ID NO: |
|---|---|---|---|---|---|---|---|
| | | TTGAAGTCG | | | | CTCGAACACAAA/3C6/ | |
| OXT_C | 553 | GGGTTTAATATTTGTTGCGCGG | 199 | CGAAGCGTTGCGTTGTTAG | 200 | AGGCCACGGACGGACGATACCCACGAAACAA/3C6/ | 266 |
| PEAR1_B | 554 | TTGGCGAGGGTTCGAGT | 201 | CTAATCGCAAAACCGAAAAAAACG | 202 | CGCGCCGAGGGCCGAAAAACGAAAAACAAAAA/3C6/ | 267 |
| ATP10A_E | 555 | GAGAGGAAATCGCGAAGCG | 203 | CCCCTAAAAAAACGCGCGA | 204 | AGGCCACGGACGGCGAGAAAAGGCGTTTTC/3C6/ | 268 |
| CELF2_A | 63 | GACGTTTATTTGGACGTTTGGC | 205 | ACCGAAATCAAAACCCTCCG | 206 | CGCGCCGAGGCGATTTTCGTTTCGCGTT/3C6/ | 269 |
| CELF2_A | 63 | GTTTCGCGACGTTTATTTGGAC | 207 | ACCGAAATCAAAACCCTCCG | 208 | CGCGCCGAGGCGTTTGGCGATTTTCGTT/3C6/ | 270 |
| CAPN2_B | 556 | GCGCGGAATTTTAGGAGTGC | 209 | CGCGACCCCACGATAATC | 210 | AGGCCACGGACGCGGGGTTCGAGTGTAAAT/3C6/ | 271 |
| DSCR6 | 84 | GTTTTCGAGGGAGTGCGTTC | 211 | CGAAAAAAAAAAACGAAACCCGC | 212 | CGCGCCGAGGCGACGGAAACGTTTTTAGTTC/3C6/ | 272 |
| NR2F6 | 329 | GGTGTTGAAGAGTAGTCGCGT | 213 | CGACGCAAAAAACGACGC | 214 | AGGCCACGGACGTCGTTAGTTCGTATACGTTGTC/3C6/ | 273 |
| CDO1_A | 61 | CGAAACGTAAGGATGTCGTCG | 215 | AATTTATATATACACCGCGTCTCCAAC | 216 | CGCGCCGAGGCGATCCCGAATCCACTAC/3C6/ | 274 |
| DNMT3A_A | 81 | TGTTTTGTTCGGTGAGGTTTCG | 217 | CAAACCGCCACCTAATCGC | 218 | AGGCCACGGACGCGAACAAACGCCCCC/3C6/ | 275 |
| SIM2_B | 557 | AAAGGGAGTTTTCGGGC | 219 | ACCCGATACCCCCATTACC | 220 | CGCGCCGAGGCGTACG | 276 |

TABLE 6B-continued

| Gene Annotation | DMR No. | Forward Primer 5'-3' | SEQ ID NO: | Reverse Primer 5'-3' | SEQ ID NO: | Probe Sequence | SEQ ID NO: |
|---|---|---|---|---|---|---|---|
| | | G | | | | CAAACC TAAAAAA TTC/3C6/ | |
| CMTM3_B | 558 | GGTGGT TAAGAA AGTCGT AAGAAA ATTTCG | 221 | TCTAAACA ACAAAAAC CCCGACC | 222 | AGGCCA CGGACG CGTAATA TCGACT CCGCAA/ 3C6/ | 277 |
| SRC_B | 559 | GGATG GTTTCG GTTGGG TTC | 223 | GCAAAACG CCAACAAA AAACG | 224 | AGGCCA CGGACG CGCGTT AGGATG CGT/3C6/ | 278 |
| LRRC41_B | 199 | GGTCGA GGGAAT TAGAGT TTTCG | 225 | AACCTAAC CCGCCAAA ACAC | 226 | CGCGCC GAGG CGCACG AAACCC TCTTA/ 3C6/ | 279 |
| TSHZ3 | 444 | GGGATC GGTTCG TTTATT CGTTC | 227 | CCCGAAAC ATCTTCCG CG | 228 | AGGCCA CGGACG CGCGTT TTTTGGT TCGG/ 3C6/ | 280 |
| HDGFRP3 | 128 | GATTCG TTTTCG AAAGTG GGC | 229 | TAAAACAA AAACTCCC GACCTCG | 230 | CGCGCC GAGG CGGAAG GATGGT CGTTTT/ 3C6/ | 281 |
| TACC2_B | 560 | GTTTTT GTGTGT GATACG ATGATG TTATTA TC | 231 | GTTTCCGA AACCCGC GA | 232 | AGGCCA CGGACG CGTCGA GTAGTTT TAACGTT TG/3C6/ | 282 |
| LBH | 182 | TAGTTT TTCGTA AGTTAA CGCGTT TC | 233 | CCCGCAA CCTTACGA TCAAC | 234 | CGCGCC GAGG CGTGGG TATTCG GTTTTTC/ 3C6/ | 283 |

Sensitivities for each methylation marker were calculated at a 959% cutoff per subtype and listed in Tables 8A (ovarian cancer), 8B (clear cell OC), 8C (endometrioid OC), 8D (mucinous OC), and 8E (serous OC). Table 8A-E shows the ovarian cancer and sub-type tissue sensitivity at 95% specificity for the markers shown in Table 6A for OC, clear cell OC, endometrioid OC, mucinous, and serous OC.

TABLE 8A

| DMR No. | Marker | OC Sensitivity @95% specificity |
|---|---|---|
| 526 | AGRN_8794 | 49.1% |
| 527 | BCAT1_6015 | 80.7% |
| 529 | ELMO1_9100 | 24.6% |
| 528 | BHLHE23_8339 | 63.2% |
| 531 | JAM3_B | 26.3% |
| 530 | EPS8L2_F | 77.2% |
| 533 | KCNA3_7518 | 33.3% |

TABLE 8A-continued

| DMR No. | Marker | OC Sensitivity @95% specificity |
|---|---|---|
| 532 | KCNA3_7320 | 52.6% |
| 545 | RASSF1_8293 | 61.4% |
| 534 | MDFI_6321 | 70.2% |
| 398 | SKI | 89.5% |
| 536 | SFMBT2_2363 | 59.6% |
| 538 | VIPR_B | 56.1% |
| 537 | SPOCK2_7433 | 42.1% |
| 540 | ZNF382_B | 15.8% |
| 551 | NTN1 | 56.1% |
| 541 | GYPC_3753 | 63.2% |
| 542 | GYPC_C | 70.2% |
| 545 | HCG4_0331 | 43.9% |
| 546 | HCG4_0556 | 40.4% |
| 547 | NKX2-6_4159 | 77.2% |
| 548 | C1QL3_B | 64.9% |
| 550 | LOC100131366 | 71.9% |

TABLE 8A-continued

| DMR No. | Marker | OC Sensitivity @95% specificity |
|---|---|---|
| 549 | FAIM2_B | 71.9% |
| 555 | ATP10A_E | 45.6% |
| 544 | GPRIN1_B | 73.7% |
| 558 | CMTM3_B | 56.1% |
| 199 | LRRC41_B | 56.1% |
| 119 | GP5 | 61.4% |
| 345 | PARP15 | 70.2% |
| 552 | ARL5C_1519 | 64.9% |
| 539 | ZMIZ1_D | 38.6% |
| 553 | OXT_C | 68.4% |
| 40 | C17orf64_A | 45.6% |
| 557 | SRC_B | 66.7% |
| 128 | HDGFRP3 | 26.3% |
| 560 | TACC2_B | 68.4% |
| 543 | RFTN1_B | 33.3% |
| 554 | PEAR1_B | 73.7% |
| 444 | TSHZ3 | 70.2% |
| 182 | LBH | 63.2% |
| 556 | CAPN2_B | 68.4% |
| 557 | SIM2_B | 87.7% |
| 81 | DNMT3A_A | 82.5% |
| 61 | CDO1_A | 84.2% |
| 329 | NR2F6 | 61.4% |
| 84 | DSCR6 | 80.7% |
| 63 | CELF2_A | 70.2% |

TABLE 8B

| DMR No. | Marker | Clear cell OC sensitivity @95% spec. |
|---|---|---|
| 526 | AGRN_8794 | 100.0% |
| 527 | BCAT1_6015 | 73.3% |
| 529 | ELMO1_9100 | 6.7% |
| 528 | BHLHE23_8339 | 100.0% |
| 531 | JAM3_B | 53.3% |
| 530 | EPS8L2_F | 100.0% |
| 533 | KCNA3_7518 | 40.0% |
| 532 | KCNA3_7320 | 53.3% |
| 545 | RASSF1_8293 | 100.0% |
| 534 | MDFI_6321 | 100.0% |
| 398 | SKI | 100.0% |
| 536 | SFMBT2_2363 | 66.7% |
| 538 | VIPR_B | 66.7% |
| 537 | SPOCK2_7433 | 73.3% |
| 540 | ZNF382_B | 0.0% |
| 551 | NTN1 | 80.0% |
| 541 | GYPC_3753 | 93.3% |
| 542 | GYPC_C | 100.0% |
| 545 | HCG4_0331 | 46.7% |
| 546 | HCG4_0556 | 53.3% |
| 547 | NKX2-6_4159 | 100.0% |
| 548 | C1QL3_B | 93.3% |
| 550 | LOC100131366 | 100.0% |
| 549 | FAIM2_B | 100.0% |
| 555 | ATP10A_E | 20.0% |
| 544 | GPRIN1_B | 100.0% |
| 558 | CMTM3_B | 80.0% |
| 199 | LRRC41_B | 100.0% |
| 119 | GP5 | 93.3% |
| 345 | PARP15 | 93.3% |
| 552 | ARL5C_1519 | 93.3% |
| 539 | ZMIZ1_D | 46.7% |
| 553 | OXT_C | 93.3% |
| 40 | C17orf64_A | 46.7% |
| 557 | SRC_B | 86.7% |
| 128 | HDGFRP3 | 20.0% |
| 560 | TACC2_B | 100.0% |
| 543 | RFTN1_B | 40.0% |
| 554 | PEAR1_B | 93.3% |
| 444 | TSHZ3 | 93.3% |
| 182 | LBH | 100.0% |
| 556 | CAPN2_B | 73.3% |
| 557 | SIM2_B | 100.0% |

TABLE 8B-continued

| DMR No. | Marker | Clear cell OC sensitivity @95% spec. |
|---|---|---|
| 81 | DNMT3A_A | 86.7% |
| 61 | CDO1_A | 100.0% |
| 329 | NR2F6 | 60.0% |
| 84 | DSCR6 | 100.0% |
| 63 | CELF2_A | 73.3% |

TABLE 8C

| DMR No. | Marker | Endometrioid OC sensitivity @95% spec. |
|---|---|---|
| 526 | AGRN_8794 | 22.2% |
| 527 | BCAT1_6015 | 88.9% |
| 529 | ELMO1_9100 | 22.2% |
| 528 | BHLHE23_8339 | 77.8% |
| 531 | JAM3_B | 27.8% |
| 530 | EPS8L2_F | 83.3% |
| 533 | KCNA3_7518 | 44.4% |
| 532 | KCNA3_7320 | 55.6% |
| 545 | RASSF1_8293 | 72.2% |
| 534 | MDFI_6321 | 66.7% |
| 398 | SKI | 83.3% |
| 536 | SFMBT2_2363 | 55.6% |
| 538 | VIPR_B | 66.7% |
| 537 | SPOCK2_7433 | 55.6% |
| 540 | ZNF382_B | 11.1% |
| 551 | NTN1 | 61.1% |
| 541 | GYPC_3753 | 72.2% |
| 542 | GYPC_C | 77.8% |
| 545 | HCG4_0331 | 50.0% |
| 546 | HCG4_0556 | 55.6% |
| 547 | NKX2-6_4159 | 88.9% |
| 548 | C1QL3_B | 83.3% |
| 550 | LOC100131366 | 77.8% |
| 549 | FAIM2_B | 77.8% |
| 555 | ATP10A_E | 50.0% |
| 544 | GPRIN1_B | 100.0% |
| 558 | CMTM3_B | 55.6% |
| 199 | LRRC41_B | 38.9% |
| 119 | GP5 | 50.0% |
| 345 | PARP15 | 88.9% |
| 552 | ARL5C_1519 | 72.2% |
| 539 | ZMIZ1_D | 27.8% |
| 553 | OXT_C | 88.9% |
| 40 | C17orf64_A | 50.0% |
| 557 | SRC_B | 55.6% |
| 128 | HDGFRP3 | 22.2% |
| 560 | TACC2_B | 61.1% |
| 543 | RFTN1_B | 44.4% |
| 554 | PEAR1_B | 61.1% |
| 444 | TSHZ3 | 66.7% |
| 182 | LBH | 66.7% |
| 556 | CAPN2_B | 66.7% |
| 557 | SIM2_B | 88.9% |
| 81 | DNMT3A_A | 83.3% |
| 61 | CDO1_A | 77.8% |
| 329 | NR2F6 | 55.6% |
| 84 | DSCR6 | 72.2% |
| 63 | CELF2_A | 94.4% |

TABLE 8D

| DMR No. | Marker | Mucinous OC sensitivity @95% spec. |
|---|---|---|
| 526 | AGRN_8794 | 16.7% |
| 527 | BCAT1_6015 | 100.0% |
| 529 | ELMO1_9100 | 83.3% |
| 528 | BHLHE23_8339 | 66.7% |
| 531 | JAM3_B | 16.7% |
| 530 | EPS8L2_F | 50.0% |
| 533 | KCNA3_7518 | 83.3% |

TABLE 8D-continued

| DMR No. | Marker | Mucinous OC sensitivity @95% spec. |
|---|---|---|
| 532 | KCNA3_7320 | 83.3% |
| 545 | RASSF1_8293 | 33.3% |
| 534 | MDFI_6321 | 100.0% |
| 398 | SKI | 83.3% |
| 536 | SFMBT2_2363 | 66.7% |
| 538 | VIPR_B | 100.0% |
| 537 | SPOCK2_7433 | 0.0% |
| 540 | ZNF382_B | 100.0% |
| 551 | NTN1 | 0.0% |
| 541 | GYPC_3753 | 33.3% |
| 542 | GYPC_C | 33.3% |
| 545 | HCG4_0331 | 16.7% |
| 546 | HCG4_0556 | 0.0% |
| 547 | NKX2-6_4159 | 66.7% |
| 548 | C1QL3_B | 66.7% |
| 550 | LOC100131366 | 33.3% |
| 549 | FAIM2_B | 50.0% |
| 555 | ATP10A_E | 100.0% |
| 544 | GPRIN1_B | 0.0% |
| 558 | CMTM3_B | 100.0% |
| 199 | LRRC41_B | 0.0% |
| 119 | GP5 | 50.0% |
| 345 | PARP15 | 33.3% |
| 552 | ARL5C_1519 | 33.3% |
| 539 | ZMIZ1_D | 100.0% |
| 553 | OXT_C | 0.0% |
| 40 | C17orf64_A | 0.0% |
| 557 | SRC_B | 83.3% |
| 128 | HDGFRP3 | 83.3% |
| 560 | TACC2_B | 100.0% |
| 543 | RFTN1_B | 16.7% |
| 554 | PEAR1_B | 33.3% |
| 444 | TSHZ3 | 83.3% |
| 182 | LBH | 100.0% |
| 556 | CAPN2_B | 16.7% |
| 557 | SIM2_B | 66.7% |
| 81 | DNMT3A_A | 83.3% |
| 61 | CDO1_A | 66.7% |
| 329 | NR2F6 | 0.0% |
| 84 | DSCR6 | 66.7% |
| 63 | CELF2_A | 16.7% |

TABLE 8E

| DMR No. | Marker | Serous OC sensitivity @95% spec. |
|---|---|---|
| 526 | AGRN_8794 | 44.4% |
| 527 | BCAT1_6015 | 72.2% |
| 529 | ELMO1_9100 | 22.2% |
| 528 | BHLHE23_8339 | 16.7% |
| 531 | JAM3_B | 5.6% |
| 530 | EPS8L2_F | 61.1% |
| 533 | KCNA3_7518 | 0.0% |
| 532 | KCNA3_7320 | 38.9% |
| 545 | RASSF1_8293 | 27.8% |
| 534 | MDFI_6321 | 38.9% |
| 398 | SKI | 88.9% |
| 536 | SFMBT2_2363 | 55.6% |
| 538 | VIPR_B | 22.2% |
| 537 | SPOCK2_7433 | 16.7% |
| 540 | ZNF382_B | 5.6% |
| 551 | NTN1 | 50.0% |
| 541 | GYPC_3753 | 38.9% |
| 542 | GYPC_C | 50.0% |
| 545 | HCG4_0331 | 44.4% |
| 546 | HCG4_0556 | 27.8% |
| 547 | NKX2-6_4159 | 50.0% |
| 548 | C1QL3_B | 22.2% |
| 550 | LOC100131366 | 55.6% |
| 549 | FAIM2_B | 50.0% |
| 555 | ATP10A_E | 44.4% |
| 544 | GPRIN1_B | 50.0% |
| 558 | CMTM3_B | 22.2% |

TABLE 8E-continued

| DMR No. | Marker | Serous OC sensitivity @95% spec. |
|---|---|---|
| 199 | LRRC41_B | 55.6% |
| 119 | GP5 | 50.0% |
| 345 | PARP15 | 44.4% |
| 552 | ARL5C_1519 | 44.4% |
| 539 | ZMIZ1_D | 22.2% |
| 553 | OXT_C | 50.0% |
| 40 | C17orf64_A | 55.6% |
| 557 | SRC_B | 55.6% |
| 128 | HDGFRP3 | 16.7% |
| 560 | TACC2_B | 38.9% |
| 543 | RFTN1_B | 22.2% |
| 554 | PEAR1_B | 83.3% |
| 444 | TSHZ3 | 50.0% |
| 182 | LBH | 16.7% |
| 556 | CAPN2_B | 83.3% |
| 557 | SIM2_B | 83.3% |
| 81 | DNMT3A_A | 77.8% |
| 61 | CDO1_A | 83.3% |
| 329 | NR2F6 | 88.9% |
| 84 | DSCR6 | 77.8% |
| 63 | CELF2_A | 61.1% |

Example III

This example describes the identification of plasma markers for detecting ovarian cancer (OC).

DNA methylation is an early event in carcinogenesis and can be detected in blood plasma samples from cancer patients. In DNA extracted from tissues, experiments (described in Examples I and II) first discovered, then validated discriminant methylated DNA marker (MDM) candidates for OC within tissue samples. Subsequent experiments independently tested plasma from women with and without OC and identified, validated, and demonstrated clinical feasibility for methylated DNA markers for plasma detection of OC.

For discovery, DNA from 67 frozen tissues (18 high grade serous (HGS), 18 endometrioid, 15 clear cell (CC), 6 mucinous OCs; 10 benign fallopian tube epithelium (FTE); and 19 buffy coats from cancer-free women underwent reduced representation bisulfite sequencing (RRBS) to identify MDMs associated with OC. Candidate MDM selection was based on receiver operating characteristic (ROC) discrimination, methylation fold change, and low background methylation among controls. Blinded biological validation was performed using MSP on DNA extracted from independent FFPE tissues from OCs (36 HGS, 22 endometrioid, 21 CC, and 14 mucinous) and 29 FTE. Top performing MDMs in tissue were tested using long-probe quantitative signal assays in independent pre-treatment plasma samples from women newly-diagnosed with OC and population-sampled healthy women. A random forest modeling analysis was performed to generate predictive probability of disease; results were 500-fold in silico cross-validated.

After RRBS discovery and biological validation, 33 MDMs showed marked methylation fold changes (10 to >1000) across all OC histologies vs FTE. The top 11 MDMs (GPRIN1, CDO1, SRC, SIM2, AGRN, FAIM2, CELF2, DSCR6, GYPC, CAPN2, BCAT1) were tested on plasma from 91 women with OC (76 (84%) HGS) and 91 without OC; the cross-validated 11-MDM panel highly discriminated OC from controls (95% specificity; 79% sensitivity, and AUC 0.91 (0.86-0.96)). Among HGS, the panel correctly identified 83%, including 5/6 stage I/II, and the majority of other subtypes (Table 9).

Whole methylome sequencing, stringent filtering criteria, and biological validation yielded outstanding candidate MDMs for OC that performed with promisingly high sensitivity and specificity in plasma.

TABLE 9

| OC histology | Serous | Clear cell | Endome-trioid | Mucinous | Mixed |
|---|---|---|---|---|---|
| Sample Size | 76 | 4 | 8 | 2 | 1 |
| Sensitivity at 95% specificity % (95% CI) | 83% (73-90%) | 75% (19-99%) | 50% (16-84%) | 50% (13-99%) | 100% (3-100%) |

The following markers MDMs were additionally tested with 66 plasma samples from patient's with OC (e.g., 6 Stage I OC, 3 Stage II OC, 27 Stage III OC, 12 Stage IV OC, 18 ND) and compared with 237 control plasma from patients not having OC: ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, SIM2_A, AGRN_8794, BCAT1_6015, KCNA3_7518, KCNA3_7320, LOC10013136, GYPC_C, SRC (e.g., SRC_A, SRC_B), NR2F6, TSHZ3, CELF2 (e.g., CELF2_A, CELF2_B), TACC2 (e.g., TACC2_A, TACC2_B), VIPR2 (e.g., VIPR2_A, VIPR2_B), and SPOCK2_74333. Table 10 shows the sensitivity and specificity percentages for each marker for detecting OC.

TABLE 10

| Marker | Sensitivity | Specificity |
|---|---|---|
| ATP10A | 30 | 98 |
| EP8SL2 | 30 | 100 |
| CIQL3 | 30 | 95 |
| FAIM2 | 55 | 99 |
| CAPN2_B | 60 | 96 |
| LBH | 10 | 100 |
| CMTM3 | 10 | 100 |
| ZMIZ1_A | 15 | 100 |
| GPRIN2 | 50 | 94 |
| CDO1 | 70 | 95 |
| GP5_8905 | 30 | 95 |
| DSCR6 | 60 | 95 |
| SKI | 40 | 95 |
| SIM2_A | 75 | 95 |
| AGRN_8794 | 70 | 90 |
| BCAT1_6105 | 60 | 90 |
| KCNA3_7518 | 10 | 100 |
| KCNA3_7320 | 20 | 100 |
| LOC10013136 | 40 | 100 |
| GYPC_C | 63 | 95 |
| SRC_A | 32 | 98 |
| NR2F6 | 45 | 95 |
| TSHZ3 | 40 | 90 |
| CELF2 | 71 | 95 |
| TACC2 | 40 | 90 |
| VIPR | 47 | 93 |
| SPOCK2_7433 | 25 | 98 |

Subsequent experiments demonstrated clinical feasibility for identifying OC through detection of a combination of 1) increased cancer antigen 125 (CA-125) levels in comparison to normal non-cancerous levels, and 2) measured methylation level changes in comparison to normal non-cancerous methylation levels for the following markers: ATP10A (e.g., ATP10A_A, ATP10A_B, ATP10A_C, ATP10A_D, ATP10A_E), EPS8L2 (e.g., EPS8L2_A, EPS8L2_B, EPS8L2_C, EPS8L2_D), C1QL3 (e.g., C1QL3_A, C1QL3_B), FAIM2 (e.g., FAIM2_A, FAIM2_B), CAPN2_B, LBH, CMTM3 (e.g., CMTM3_A, CMTM3_B), ZMIZ1 (e.g., ZMIZ1_A, ZMIZ1_B, ZMIZ1_C, ZMIZ1_D), GPRIN1 (e.g., GPRIN1_A, GPRIN1_B), CDO1 (e.g., CDO1_A, CDO1_B), GP5, DSCR6, SKI, and SIM2_A.

Such markers MDMs were tested with 66 plasma samples from patient's with OC (e.g., 6 Stage I OC, 3 Stage II OC, 27 Stage III OC, 12 Stage IV OC, 18 ND) and compared with 237 control plasma from patients not having OC. The levels of CA-125 was also measured in the 66 plasma samples and 237 control plasma samples. Table 11 shows 90% specificity for detecting OC for the MDMs. Table 12 shows 90% specificity for detecting OC for CA-125. Table 13 shows 90% specificity for detecting OC for both the MDMs and CA-125.

TABLE 11

| Tabulate | | |
|---|---|---|
| | MDM Call@90% Spec. | |
| | Neg Row % | Pos Row % |
| Disease Type | | |
| Healthy Normal | 90.06% | 9.94% |
| Ovarian | 19.70% | 80.30% |
| Overall Stage | | |
| I | 16.67% | 83.33% |
| II | 0.00% | 100.00% |
| III | 11.11% | 88.89% |
| IV | 0.00% | 100.00% |
| ND | 50.00% | 50.00% |

TABLE 12

| Tabulate | | |
|---|---|---|
| | CA-125 Call@90% Spec. | |
| | Neg Row % | Pos Row % |
| Disease Type | | |
| Healthy Normal | 89.47% | 10.53% |
| Ovarian | 9.09% | 90.91% |
| Overall Stage | | |
| I | 0.00% | 100.00% |
| II | 0.00% | 100.00% |
| III | 3.70% | 96.30% |
| IV | 0.00% | 100.00% |
| ND | 27.78% | 72.22% |

TABLE 13

| Tabulate | MDM + CA125 Call@90% Spec. | |
|---|---|---|
| | Neg Row % | Pos Row % |
| Disease Type | | |
| Healthy Normal | 90.06% | 9.94% |
| Ovarian | 7.58% | 92.42% |
| Overall Stage | | |
| I | 0.00% | 100.00% |
| II | 0.00% | 100.00% |
| III | 3.70% | 96.30% |
| IV | 0.00% | 100.00% |
| ND | 22.22% | 77.78% |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method comprising:

treating genomic DNA from a sample from a subject having or suspected of having ovarian cancer with a reagent that modifies DNA in a methylation-specific manner;

amplifying the treated genomic DNA using a set of primers specific for each of CDO1 and SIM2; and determining a methylation level of at least one differentially methylated region (DMR) in each of CDO1 and SIM2 using polymerase chain reaction (PCR), nucleic acid sequencing, mass spectrometry, restriction enzyme analysis, mass-based separation, and/or target capture.

2. The method of claim 1, wherein the sample comprises one or more of a plasma sample, a whole blood sample, a leukocyte sample, a serum sample, and/or a tissue sample.

3. The method of claim 1, wherein:

the at least one DMR in CDO1 is selected from CDO1_A and CDO1_B; and the at least one DMR in SIM2 is selected from SIM2_A and SIM2_B.

4. The method of claim 1, further comprising measuring a level of cancer antigen 125 (CA-125) in the sample.

5. The method of claim 1, wherein the reagent that modifies DNA in a methylation-specific manner is a bisulfite reagent.

6. The method of claim 1, wherein determining the methylation level of the at least one DMR in each of CDO1 and SIM2 comprises using one or more methods selected from the group consisting of methylation-specific PCR, quantitative methylation-specific PCR, methylation-specific DNA restriction enzyme analysis, quantitative bisulfite pyrosequencing, flap endonuclease assay analysis, PCR-flap assay analysis, and/or bisulfite genomic sequencing PCR.

7. The method of claim 1, wherein amplifying the treated genomic DNA comprises:

using primers specific for a CpG site in CDO1, wherein the primers specifically bind at least a portion of a genetic region comprising chromosome 5 coordinates 115152022-115152432 or chromosome 5 coordinates 115152466-115152505; and using primers specific for a CpG site in SIM2, wherein the primers specifically bind at least a portion of a genetic region comprising chromosome 21 coordinates 38076892-38077026 or chromosome 21 coordinates 38076882-38077036.

8. The method of claim 1, wherein the at least one DMR is present in a coding region or a regulatory region of CDO1 and SIM2.

9. The method of claim 1, wherein the ovarian cancer is at least one of clear cell ovarian cancer, endometrioid ovarian cancer, mucinous ovarian cancer, and/or serous ovarian cancer.

10. The method of claim 1, wherein the method further comprises amplifying the treated genomic DNA using a set of primers for one or more genes selected from FAIM2, CAPN2, and/or IFFO1.

11. The method of claim 10, wherein the one or more genes is FAIM2.

12. The method of claim 10, wherein the one or more genes is CAPN2.

13. The method of claim 10, wherein the one or more genes is IFFO1.

* * * * *